United States Patent
Mitra et al.

(10) Patent No.: US 11,938,138 B2
(45) Date of Patent: Mar. 26, 2024

(54) METHODS FOR IMPROVED TREATMENT OF CANCER

(71) Applicants: Robi Mitra, St. Louis, MO (US); Arnav Moudgil, St. Louis, MO (US); Michael Nathaniel Wilkinson, St. Louis, MO (US)

(72) Inventors: Robi Mitra, St. Louis, MO (US); Arnav Moudgil, St. Louis, MO (US); Michael Nathaniel Wilkinson, St. Louis, MO (US)

(73) Assignee: Washington University, St. Louis, MO (US)

( * ) Notice: Subject to any disclaimer, the term of this patent is extended or adjusted under 35 U.S.C. 154(b) by 150 days.

(21) Appl. No.: 17/371,750

(22) Filed: Jul. 9, 2021

(65) Prior Publication Data
US 2022/0016131 A1  Jan. 20, 2022

Related U.S. Application Data

(60) Provisional application No. 63/049,658, filed on Jul. 9, 2020.

(51) Int. Cl.
*A61P 35/00* (2006.01)
*A61K 31/506* (2006.01)
*A61K 31/551* (2006.01)

(52) U.S. Cl.
CPC .......... *A61K 31/551* (2013.01); *A61K 31/506* (2013.01); *A61P 35/00* (2018.01)

(58) Field of Classification Search
CPC ....................................... A61P 35/00
See application file for complete search history.

(56) References Cited

PUBLICATIONS

Abramson J.S. et al. (2015) BET Inhibitor CPI-0610 Is Well Tolerated and Induces Responses in Diffuse Large B-Cell Lymphoma and Follicular Lymphoma: Preliminary Analysis of an Ongoing Phase 1 Study. Blood. vol. 126, No. 23, p. 1491.
Adeegbe D.O. et al. (2018) BET Bromodomain Inhibition Cooperates with PD-1 Blockade to Facilitate Antitumor Response in Kras-Mutant Non-Small Cell Lung Cancer. Cancer Immunol Res. vol. 6, No. 10, pp. 1234-1245.
Alqahtani A. et al. (2019) Bromodomain and extra-terminal motif inhibitors: a review of preclinical and clinical advances in cancer therapy. Future Sci OA. vol. 5, No. 3, FSO372, 20 pages.
Amorim S. et al. (2016) Bromodomain inhibitor OTX015 in patients with lymphoma or multiple myeloma: a dose-escalation, open-label, pharmacokinetic, phase 1 study. Lancet Haematol. vol. 3, No. 4, pp. e196-e204.
Angermueller C. et al. (2016). Parallel single-cell sequencing links transcriptional and epigenetic heterogeneity. Nat Methods. vol. 13, No. 3, pp. 229-232.
Avey D. et al. (2018). Single-Cell RNA-Seq Uncovers a Robust Transcriptional Response to Morphine by Glia. Cell Rep. vol. 24, No. 13, pp. 3619-3629.e4.
Benjamini Y. and Hochberg, Y. (1995). Controlling the False Discovery Rate: A Practical and Powerful Approach to Multiple Testing. J. R. Statist. Soc. B. vol. 57, No. 1, pp. 289-300.
Berthon C. et al. (2016). Bromodomain inhibitor OTX015 in patients with acute leukaemia: a dose-escalation, phase 1 study. Lancet Haematol. vol. 3, No. 4, pp. e186-e195.
Bhadury J. et al. (2014). BET and HDAC inhibitors induce similar genes and biological effects and synergize to kill in Myc-induced murine lymphoma. Proc Natl Acad Sci U S A. vol. 111, No. 26, pp. E2721-E2730.
Bolin S. et al. (2018) Combined BET bromodomain and CDK2 inhibition in MYC-driven medulloblastoma. Oncogene. vol. 37, No. 21, pp. 2850-2862.
Brandeis M. et al. (1994). Sp1 elements protect a CpG island from de novo methylation. Nature. vol. 371, No. 6496, pp. 435-438.
Brooks E.E. et al. (1997). CVT-313, a Specific and Potent Inhibitor of CDK2 That Prevents Neointimal Proliferation. J. Biol. Chem. vol. 272, No. 46, pp. 29207-29211.
Brunner A.L. et al. (2009). Distinct DNA methylation patterns characterize differentiated human embryonic stem cells and developing human fetal liver. Genome Res. vol. 19, No. 6, pp. 1044-1056.
Buenrostro J.D. et al. (2013). Transposition of native chromatin for fast and sensitive epigenomic profiling of open chromatin, DNA-binding proteins and nucleosome position. Nat Methods vol. 10, No. 12, pp. 1213-1218.
Buenrostro J.D. et al. (2015). Single-cell chromatin accessibility reveals principles of regulatory variation. Nature vol. 523, pp. 486-490.
Bui M. H. et al. (2017) Preclinical Characterization of BET Family Bromodomain Inhibitor ABBV-075 Suggests Combination Therapeutic Strategies. Cancer Res. vol. 77, No. 11, pp. 2976-2989.
Cadinanos J., and Bradley A. (2007). Generation of an inducible and optimized piggyBac transposon system. Nucleic Acids Res. vol. 35, No. 12, e87, 8 pages.
Cammack A.J. et al. (2020). A viral toolkit for recording transcription factor-DNA interactions in live mouse tissues. Proc Natl Acad Sci USA, vol. 117, No. 18, pp. 10003-10014.
Campagne A. et al. (2019). BAP1 complex promotes transcription by opposing PRC1-mediated H2A ubiquitylation. Nat Commun. vol. 10, No. 348, 15 pages.
Campbell J.N. et al. (2017). A molecular census of arcuate hypothalamus and median eminence cell types. Nat Neurosci. vol. 20, No. 3, pp. 484-496.
Cao J. et al. (2017). Comprehensive single-cell transcriptional profiling of a multicellular organism. Science vol. 357, No. 6352, pp. 661-667.
Cao J. et al. (2018). Joint profiling of chromatin accessibility and gene expression in thousands of single cells. Science vol. 361, No. 6409, pp. 1380-1385.
Carbone M. et al. (2013). BAP1 and cancer. Nat Rev Cancer vol. 13, No. 3, pp. 153-159.
Carter B. et al. (2019). Mapping histone modifications in low cell number and single cells using antibody-guided chromatin tagmentation (ACTseq). Nat Commun vol. 10, No. 3747, 5 pages.

(Continued)

*Primary Examiner* — Bruck Kifle

(57) ABSTRACT

Among the various aspects of the present disclosure is the provision of a methods for increasing chemotherapy sensitivity or decreasing chemotherapy resistance using BET inhibitors.

15 Claims, 83 Drawing Sheets

Specification includes a Sequence Listing.

(56) References Cited

PUBLICATIONS

Castillo-Hair S.M. et al. (2016). FlowCal: A User-Friendly, Open Source Software Tool for Automatically Converting Flow Cytometry Data from Arbitrary to Calibrated Units. ACS Synth Biol. vol. 5, No. 7, pp. 774-780.

Chen W. et al. (2017). Alternative Polyadenylation: Methods, Findings, and Impacts. Genomics, Proteomics & Bioinformatics vol. 15, No. 5, pp. 287-300.

Chiu A.C. et al. (2018). Transcriptional Pause Sites Delineate Stable Nucleosome-Associated Premature Polyadenylation Suppressed by U1 snRNP. Mol Cell. vol. 69, No. 4, pp. 648-663.e7.

Cho S.W. et al. (2018). Promoter of lncRNA Gene PVT1 Is a Tumor-Suppressor DNA Boundary Element. Cell vol. 173, No. 6, pp. 1398-1412.e22.

Clark S.J. et al. (2018). scNMT-seq enables joint profiling of chromatin accessibility DNA methylation and transcription in single cells. Nature Commun. vol. 9, No. 781, 9 pages.

Datlinger P. et al. (2017). Pooled CRISPR screening with single-cell transcriptome readout. Nat Methods vol. 14, No. 3, pp. 297-301.

Davis R.L., Weintraub H., and Lassar A.B. (1987). Expression of a single transfected cDNA converts fibroblasts to myoblasts. Cell vol. 51, No. 6, pp. 987-1000.

Delmore J.E. et al. (2011). BET Bromodomain Inhibition as a Therapeutic Strategy to Target c-Myc. Cell vol. 146, No. 6, pp. 904-917.

Dey A. et al. (2012). Loss of the Tumor Suppressor BAP1 Causes Myeloid Transformation. Science vol. 337, No. 6101, pp. 1541-1546.

Dey S.S. et al. (2015). Integrated genome and transcriptome sequencing of the same cell. Nature Biotechnology vol. 33, No. 3, pp. 285-289.

Di Micco R. et al. (2014). Control of Embryonic Stem Cell Identity by BRD4-Dependent Transcriptional Elongation of Super-Enhancer-Associated Pluripotency Genes. Cell Reports vol. 9, No. 1, pp. 234-247.

Ding S. et al. (2005). Efficient transposition of the piggyBac (PB) transposon in mammalian cells and mice. Cell vol. 122, No. 3, pp. 473-483.

Dixit A. et al. (2016). Perturb-Seq: Dissecting Molecular Circuits with Scalable Single-Cell RNA Profiling of Pooled Genetic Screens. Cell vol. 167, No. 7, pp. 1853-1866.e17.

Dombret H. et al. (2014) A Phase 1 Study of the BET-Bromodomain Inhibitor OTX015 in Patients with Advanced Acute Leukemia. Blood. vol. 124, No. 21, p. 117.

Ernst J. et al. (2011). Mapping and analysis of chromatin state dynamics in nine human cell types. Nature vol. 473, pp. 43-49.

Fan X. et al. (2008). Expression of liver X receptor β is essential for formation of superficial cortical layers and migration of later-born neurons. Proc. Natl. Acad. Sci. U.S.A. vol. 105, No. 36, pp. 13445-13450.

Feng Q. et al. (2014). An epigenomic approach to therapy for tamoxifen-resistant breast cancer. Cell Res. vol. 24, No. 7, pp. 809-819.

Filippakopoulos P. et al. (2010). Selective inhibition of BET bromodomains. Nature vol. 468, No. 7327, pp. 1067-1073.

Fincher C.T. et al. (2018). Cell type transcriptome atlas for the planarian Schmidtea mediterranea. Science vol. 360, No. 6391, eaaq1736, 14 pages.

Fiskus W. et al. (2014) Highly active combination of BRD4 antagonist and histone deacetylase inhibitor against human acute myelogenous leukemia cells. Mol Cancer Ther. vol. 13, No. 5, pp. 1142-1154.

Fogarty N.M.E. et al. (2017). Genome editing reveals a role for OCT4 in human embryogenesis. Nature vol. 55, No. 7674, pp. 67-73.

Folkerts H. et al. (2019). Elevated VMP1 expression in acute myeloid leukemia amplifies autophagy and is protective against venetoclax-induced apoptosis. Cell Death Dis. vol. 10, No. 6, 421, 12 pages.

Fournier M. et al. (2016). FOXA and master transcription factors recruit Mediator and Cohesin to the core transcriptional regulatory circuitry of cancer cells. Sci Rep. vol. 6, No. 34962, 11 pages.

Fulco C.P. et al. (2016). Systematic mapping of functional enhancer-promoter connections. Science. vol. 354, No. 6313, pp. 769-773.

Fullwood M.J. et al. (2009). An oestrogen-receptor-a-bound human chromatin interactome. Nature vol. 462, No. 7269, pp. 58-64.

Garcia-Carpizo V. et al. (2018). CREBBP/EP300 bromodomains are critical to sustain the GATA1/MYC regulatory axis in proliferation. Epigenetics & Chromatin vol. 11, No. 1, 30, 15 pages.

Gasperini M. et al. (2019). A Genome-wide Framework for Mapping Gene Regulation via Cellular Genetic Screens. Cell. vol. 176, No. 1-2, pp. 377-390.

Gogol-Doring A. et al. (2016). Genome-wide Profiling Reveals Remarkable Parallels Between Insertion Site Selection Properties of the MLV Retrovirus and the piggyBac Transposon in Primary Human CD4+ T Cells. Mol Ther. vol. 24, No. 3, pp. 592-606.

Gonen N. et al. (2018). Sex reversal following deletion of a single distal enhancer of Sox9. Science vol. 360, No. 6396, pp. 1469-1471.

Gopalakrishnan R. et al. (2016). Immunomodulatory drugs target IKZF1-IRF4-MYC axis in primary effusion lymphoma in a cereblon-dependent manner and display synergistic cytotoxicity with BRD4 inhibitors. Oncogene. vol. 35, No. 14, pp. 1797-1810.

Greil F., Moorman C., and Van Steensel B. (2006). DamID: Mapping of In Vivo Protein-Genome Interactions Using Tethered DNA Adenine Methyltransferase. In DNA Microarrays, Part A: Array Platforms and Wet-Bench Protocols, (Elsevier), pp. 342-359.

Grosselin K. et al. (2019). High-throughput single-cell ChIP-seq identifies heterogeneity of chromatin states in breast cancer. Nat Genet. vol. 51, pp. 1060-1066.

Gupta S. et al. (2007). Quantifying similarity between motifs. Genome Biol. vol. 8, No. 2, R24, 9 pages.

Gurdon J.B. (2016). Cell Fate Determination by Transcription Factors. In Essays on Developmental Biology, Part A, (Elsevier), pp. 445-454.

Hafler B.P. et al. (2012). Transcription factor Olig2 defines subpopulations of retinal progenitor cells biased toward specific cell fates. Proc Natl Acad Sci U S A. vol. 109, No. 20, pp. 7882-7887.

Hainer S.J. et al. (2019). Profiling of Pluripotency Factors in Single Cells and Early Embryos. Cell vol. 177, No. 5, pp. 1319-1329.e11.

Han X. et al. (2018). Mapping the Mouse Cell Atlas by Microwell-Seq. Cell vol. 172, No. 5, pp. 1091-1107.e17.

Harada A. et al. (2019). A chromatin integration labelling method enables epigenomic profiling with lower input. Nat Cell Biol. vol. 21, pp. 287-296.

Heinemann A. et al. (2015) Combining BET and HDAC inhibitors synergistically induces apoptosis of melanoma and suppresses AKT and YAP signaling. Oncotarget. vol. 6, No. 25., pp. 21507-21521.

Hinrichs A.S. et al. (2006). The UCSC Genome Browser Database: update 2006. Nucleic Acids Res. vol. 34, pp. D590-D598.

Hnisz D. et al. (2013). Super-Enhancers in the Control of Cell Identity and Disease. Cell vol. 155, No. 4, pp. 934-947.

Ho T.T. et al. (2017). Autophagy maintains the metabolism and function of young and old stem cells. Nature vol. 543, pp. 205-210.

Hothorn T., Bretz F., and Westfall P. (2008). Simultaneous Inference in General Parametric Models. Biom. J. vol. 50, No. 3, pp. 346-363.

Hunter, J.D. (2007). Matplotlib: A 2D Graphics Environment. Comput. Sci. Eng. vol. 9, No. 3, pp. 90-95.

Hwang B., Lee J.H., and Bang D. (2018). Single-cell RNA sequencing technologies and bioinformatics pipelines. Exp Mol Med. vol. 50, No. 96, 14 pages.

Ivics Z. et al. (1997). Molecular Reconstruction of Sleeping Beauty, a Tc1-like Transposon from Fish, and Its Transposition in Human Cells. Cell vol. 91, No. 4, pp. 501-510.

Jackman J., and O'Connor P.M. (1998). Methods for Synchronizing Cells at Specific Stages of the Cell Cycle. Curr Protoc in Cell Biol. pp. 8.3.1-8.3.20.

Jing Y. et al. (2016) Concomitant BET and MAPK blockade for effective treatment of ovarian cancer. Oncotarget. vol. 7, No. 3, pp. 2545-2554.

Johnson D.S. et al. (2007). Genome-Wide Mapping of in Vivo Protein-DNA Interactions. Science vol. 316, No. 5830, pp. 1497-1502.

(56) References Cited

PUBLICATIONS

Jostes S. et al. (2017) The bromodomain inhibitor JQ1 triggers growth arrest and apoptosis in testicular germ cell tumours in vitro and in vivo. J Cell Mol Med. vol. 21, No. 7, pp. 1300-1314.

Kalhor R. et al. (2018). Developmental barcoding of whole mouse via homing CRISPR. Science vol. 361, No. 6405, eaat9804, 14 pages.

Karaiskos N. et al. (2017). The *Drosophila* embryo at single-cell transcriptome resolution. Science vol. 358, No. 6360, pp. 194-199.

Kaya-Okur H.S. et al. (2019). CUT&Tag for efficient epigenomic profiling of small samples and single cells. Nat Commun. vol. 10, No. 1930, 10 pages.

Kettlun C. et al. (2011). Manipulating piggyBac transposon chromosomal integration site selection in human cells. Mol Ther. vol. 19, No. 9, pp. 1636-1644.

Kfoury N. et al. (2017). Brd4-bound enhancers drive critical sex differences in glioblastoma. bioRxiv 199059, 29 pages.

Kind J. et al. (2013). Single-Cell Dynamics of Genome-Nuclear Lamina Interactions. Cell vol. 153, No. 1, pp. 178-192.

Kind J. et al. (2015). Genome-wide Maps of Nuclear Lamina Interactions in Single Human Cells. Cell vol. 163, No. 1, pp. 134-147.

Klein A.M. et al. (2015). Droplet Barcoding for Single-Cell Transcriptomics Applied to Embryonic Stem Cells. Cell vol. 161, No. 5, pp. 1187-1201.

Knoechel, B. et al. (2014). An epigenetic mechanism of resistance to targeted therapy in T cell acute lymphoblastic leukemia. Nat Genet. vol. 46, No. 4, pp. 364-370.

Koblish H.K. et al. (2016) The BET inhibitor INCB054329 enhances the activity of checkpoint modulation in syngeneic tumor models. Cancer Res. vol. 76, No. 4 Supp, 4904, 4 pages.

Kvon E.Z. et al. (2016). Progressive Loss of Function in a Limb Enhancer during Snake Evolution. Cell. vol. 167, No. 3, pp. 633-642.e11.

Lalli M.A. et al. (2019). High-throughput single-cell functional elucidation of neurodevelopmental disease-associated genes reveals convergent mechanisms altering neuronal differentiation. bioRxiv 862680, 48 pages.

Lawrence M., Daujat S., and Schneider R. (2016). Lateral Thinking: How Histone Modifications Regulate Gene Expression. Trends Genet. vol. 32, No. 1, pp. 42-56.

Lee C.S. et al. (2005). The initiation of liver development is dependent on Foxa transcription factors. Nature vol. 435, pp. 944-947.

Lee T.I., and Young R.A. (2013). Transcriptional Regulation and Its Misregulation in Disease. Cell vol. 152, No. 6, pp. 1237-1251.

Lee D.H. et al. (2015) Synergistic effect of JQ1 and rapamycin for treatment of human osteosarcoma. Int J Cancer. vol. 136, No. 9, pp. 2055-2064.

Litzenburger U.M. et al. (2017). Single-cell epigenomic variability reveals functional cancer heterogeneity. Genome Biol vol. 18, No. 15, 12 pages.

Liu X. et al. (2008). Yamanaka factors critically regulate the developmental signaling network in mouse embryonic stem cells. Cell Res. vol. 18, No. 12, pp. 1177-1189.

Liu X. et al. (2016) Combination of BET inhibitor INCB054329 and LSD1 inhibitor INCB059872 is synergistic for the treatment of AML in vitro and in vivo. Cancer Res. vol. 76, No. 14, Supp., 2 pages.

Loven J. et al. (2013). Selective Inhibition of Tumor Oncogenes by Disruption of Super-Enhancers. Cell. vol. 153, No. 2, pp. 320-334.

Lozzio C. and Lozzio B. (1975). Human chronic myelogenous leukemia cell-line with positive Philadelphia chromosome. Blood. vol. 45, No. 3, pp. 321-334.

Macaulay I.C. et al. (2015). G&T-seq: parallel sequencing of single-cell genomes and transcriptomes. Nat Methods. vol. 12, No. 6, pp. 519-522.

Machanick P. and Bailey T.L. (2011). MEME-ChIP: motif analysis of large DNA datasets. Bioinformatics vol. 27, No. 12, pp. 1696-1697.

Macleod D. et al. (1994). Sp1 sites in the mouse aprt gene promoter are required to prevent methylation of the CpG island. Genes Dev. vol. 8, No. 19, pp. 2282-2292.

Macosko E.Z. et al. (2015). Highly Parallel Genome-wide Expression Profiling of Individual Cells Using Nanoliter Droplets. Cell. vol. 161, No. 5, pp. 1202-1214.

Martin M. (2011). Cutadapt removes adapter sequences from high-throughput sequencing reads. EMBnet. Journal. vol. 17, No. 1, pp. 10-12.

Martins A.L. et al. (2018). Universal correction of enzymatic sequence bias reveals molecular signatures of protein/DNA interactions. Nucleic Acids Res. vol. 46, No. 2, e9, 12 pages.

Massard C. et al. (2016). 3LBA—A phase Ib trial with MK-8628/OTX015, a small molecule inhibitor of bromodomain (BRD) and extra-terminal (BET) proteins, in patients with selected advanced solid tumors. European Journal of Cancer. vol. 69, pp. S2-S3.

Matatall K.A. et al. (2013). BAP1 deficiency causes loss of melanocytic cell identity in uveal melanoma. BMC Cancer. vol. 13, No. 371, 12 pages.

Mates L. et al. (2009). Molecular evolution of a novel hyperactive *Sleeping Beauty* transposase enables robust stable gene transfer in vertebrates. Nature Genetics. vol. 41, pp. 753-761.

Matkar S. et al. (2015) An Epigenetic Pathway Regulates Sensitivity of Breast Cancer Cells to HER2 Inhibition via FOXO/c-Myc Axis. Cancer Cell. vol. 28, No. 4, pp. 472-485.

Matkar S. et al. (2017) Kinase inhibitors of HER2/AKT pathway induce ERK phosphorylation via a FOXO-dependent feedback loop. Am J Cancer Res. vol. 7, No. 7, pp. 1476-1485.

McCleland M.L. et al. (2016). CCAT1 is an enhancer-templated RNA that predicts BET sensitivity in colorectal cancer. J Clin Invest. vol. 126, No. 2, pp. 639-652.

Meir Y.-J.J. et al. (2011). Genome-wide target profiling of piggyBac and Tol2in HEK 293: pros and cons for gene discovery and gene therapy. BMC Biotechnol. vol. 11, No. 28, 19 pages.

Mi H. et al. (2017). PANTHER version 11: expanded annotation data from Gene Ontology and Reactome pathways, and data analysis tool enhancements. Nucleic Acids Res. vol. 45, No. D1, pp. D183-D189.

Mizuguchi R. et al. (2001). Combinatorial Roles of Olig2 and Neurogenin2 in the Coordinated Induction of Pan-Neuronal and Subtype-Specific Properties of Motoneurons. Neuron. vol. 31, No. 5, pp. 757-771.

Molyneaux B.J. et al. (2007). Neuronal subtype specification in the cerebral cortex. Nat. Rev. Neurosci. vol. 8, No. 6, pp. 427-437.

Muralidharan S.V. et al. (2017). BET bromodomain inhibitors synergize with ATR inhibitors in melanoma. Cell Death Dis. vol. 8, e2981, 7 pages.

Najafova Z. et al. (2017). BRD4 localization to lineage-specific enhancers is associated with a distinct transcription factor repertoire. Nucleic Acids Res. vol. 45, No. 1, pp. 127-141.

O'Dwyer P.J et al. (2016). GSK525762, a selective bromodomain (BRD) and extra terminal protein (BET) inhibitor: results from part 1 of a phase I/II open-label single-agent study in patients with NUT midline carcinoma (NMC) and other cancers. Cancer Rex. vol. 76, No. 14, Supp., 2 pages.

Paoluzzi L. et al. (2016). BET and BRAF inhibitors act synergistically against BRAF-mutant melanoma. Cancer Med. vol. 5, No. 6, pp. 1183-1193.

Peterson V.M. et al. (2017). Multiplexed quantification of proteins and transcripts in single cells. Nat Biotechnol. vol. 35, No. 10, pp. 936-939.

Philipsen S. and Suske G. (1999). A tale of three fingers: the family of mammalian Sp/XKLF transcription factors. Nucleic Acids Res. vol. 27, No. 15, pp. 2991-3000.

Picelli S. et al. (2014). Tn5 transposase and tagmentation procedures for massively scaled sequencing projects. Genome Res. vol. 24, No. 12, pp. 2033-2040.

Ponnaluri V.K.C. et al. (2017). NicE-seq: high resolution open chromatin profiling. Genome Biol. vol. 18, No. 122, 15 pages.

(56) References Cited

PUBLICATIONS

Postel-Vinay S. et al. (2019). First-in-human phase I study of the bromodomain and extraterminal motif inhibitor BAY 1238097: emerging pharmacokinetic/pharmacodynamic relationship and early termination due to unexpected toxicity. Eur J Cancer. vol. 109, pp. 103-110.

Pott S. and Lieb J.D. (2014). What are super-enhancers? Nat Genet. vol. 47, No. 1, pp. 8-12.

Pucilowska J. et al. (2012). Disrupted ERK Signaling during Cortical Development Leads to Abnormal Progenitor Proliferation, Neuronal and Network Excitability and Behavior, Modeling Human Neuro-Cardio-Facial-Cutaneous and Related Syndromes. J Neurosci. vol. 32, No. 25, pp. 8663-8677.

Qi Z. et al. (2017). An optimized, broadly applicable piggyBac transposon induction system. Nucleic Acids Res. vol. 45, No. 7, e55, 13 pages.

Quinlan A.R. and Hall I.M. (2010). BEDTools: a flexible suite of utilities for comparing genomic features. Bioinformatics vol. 26, No. 6, pp. 841-842.

Raff T. et al. (1997). Design and Testing of β-Actin Primers for RT-PCR that Do Not Co-amplify Processed Pseudogenes. BioTechniques vol. 23, No. 3, pp. 456-460.

Ramirez F. et al. (2016). deepTools2: a next generation web server for deep-sequencing data analysis. Nucleic Acids Res. vol. 44, No. W1, pp. W160-W165.

Rašin M.-R. et al. (2007). Numb and Numbl are required for maintenance of cadherin-based adhesion and polarity of neural progenitors. Nat Neurosci. vol. 10, No. 7, pp. 819-827.

Rathert P. et al. (2015). Transcriptional plasticity promotes primary and acquired resistance to BET inhibition. Nature vol. 525, No. 7570, pp. 543-547.

Robitaille T.P. et al. (2013). Astropy: A community Python package for astronomy. A&A. vol. 558, No. A33, 9 pages.

Rodriguez-Fraticelli A.E. et al. (2018). Clonal analysis of lineage fate in native haematopoiesis. Nature vol. 553, No. 7687, pp. 212-216.

Rooijers K. et al. (2019). Simultaneous quantification of protein-DNA contacts and transcriptomes in single cells. Nat Biotechnol. vol. 37, pp. 766-772.

Ropolo A. et al. (2007). The Pancreatitis-induced Vacuole Membrane Protein 1 Triggers Autophagy in Mammalian Cells. J. Biol. Chem. vol. 282, No. 51, pp. 37124-37133.

Rosenberg A.B. et al. (2018). Single-cell profiling of the developing mouse brain and spinal cord with split-pool barcoding. Science vol. 360, No. 6385, pp. 176-182.

Rotem A. et al. (2015). Single-cell ChIP-seq reveals cell subpopulations defined by chromatin state. Nat Biotechnol. vol. 33, No. 11, pp. 1165-1172.

Rouillard A.D. et al. (2016). The harmonizome: a collection of processed datasets gathered to serve and mine knowledge about genes and proteins. Database. vol. 2016, baw100, 16 pages.

Sabari B.R. et al. (2018). Coactivator condensation at super-enhancers links phase separation and gene control. vol. 361, No. 6400, eaar3958, 13 pages.

Sanson K.R. et al. (2018). Optimized libraries for CRISPR-Cas9 genetic screens with multiple modalities. Nat Commun. vol. 9, No. 5416, 15 pages.

Saridey S.K. et al. (2009). PiggyBac transposon-based inducible gene expression in vivo after somatic cell gene transfer. Mol Ther. vol. 17, No. 12, pp. 2115-2120.

Saunders A. et al. (2018). Molecular Diversity and Specializations among the Cells of the Adult Mouse Brain. Cell vol. 174, No. 4, pp. 1015-1030.e16.

Saxena A. et al. (2012). Trehalose-enhanced isolation of neuronal sub-types from adult mouse brain. BioTechniques vol. 52, No. 6, pp. 381-385.

Scargle J.D. et al. (2013). Studies in Astronomical Time Series Analysis. VI. Bayesian Block Representations. APJ. vol. 764, No. 167, 26 pages.

Scheiber I.F. and Dringen R. (2013). Astrocyte functions in the copper homeostasis of the brain. Neurochem Int. vol. 62, No. 5, pp. 556-565.

Schuster D.J. et al. (2014). Biodistribution of adeno-associated virus serotype 9 (AAV9) vector after intrathecal and intravenous delivery in mouse. Front in Neuroanat. vol. 8, No. 42, 14 pages.

Sdelci S. et al. (2019). MTHFD1 interaction with BRD4 links folate metabolism to transcriptional regulation. Nat Genet. vol. 51, pp. 990-998.

Seabold S. and Perktold J. (2010). statsmodels: Econometric and statistical modeling with python. In $9^{th}$ Python in Science Conference, pp. 92-96.

Shahbazi J. et al. (2016) The Bromodomain Inhibitor JQ1 and the Histone Deacetylase Inhibitor Panobinostat Synergistically Reduce N-Myc Expression and Induce Anticancer Effects. Clin Cancer Res. vol. 22, No. 10, pp. 2534-2544.

Shapiro E., Biezuner T., and Linnarsson S. (2013). Single-cell sequencing-based technologies will revolutionize whole-organism science. Nat Rev Genet. vol. 14, No. 9, pp. 618-630.

Shapiro G.I. et al. (2020) A Phase 1 study of RO6870810, a novel bromodomain and extra-terminal protein inhibitor, in patients with NUT carcinoma, other solid tumours, or diffuse large B-cell lymphoma. Br J Cancer. vol. 124, No. 4, pp. 744-753.

Shema E., Bernstein B.E., and Buenrostro J.D. (2019). Single-cell and single-molecule epigenomics to uncover genome regulation at unprecedented resolution. Nat Genet. vol. 51, No. 1, pp. 19-25.

Shively C.A. et al. (2019). Homotypic cooperativity and collective binding are determinants of bHLH specificity and function. Proc Natl Acad Sci USA. vol. 116, No. 32, pp. 16143-16152.

Sloan C.A. et al. (2016). ENCODE data at the ENCODE portal. Nucleic Acids Res. vol. 44, No. D1, pp. D726-D732.

Stathis A. et al. (2016). Clinical Response of Carcinomas Harboring the BRD4-NUT Oncoprotein to the Targeted Bromodomain Inhibitor OTX015/MK-8628. Cancer Discov. vol. 6, No. 5, pp. 492-500.

Stoeckius M. et al. (2017). Simultaneous epitope and transcriptome measurement in single cells. Nat Methods vol. 14, No. 9, pp. 865-868.

Stoeckius M. et al. (2018). Cell Hashing with barcoded antibodies enables multiplexing and doublet detection for single cell genomics. Genome Biology vol. 19, No. 224, 12 pages.

Stroud H. et al. (2017). Early-Life Gene Expression in Neurons Modulates Lasting Epigenetic States. Cell vol. 171, No. 5, pp. 1151-1164.e16.

Stubbs M. et al. (2016). Abstract 3780: Activity of the BET inhibitor INCB054329 in models of lymphoma. Cancer Res. vol. 76, No. 14, Supp., 2 pages.

Stubbs M.C. et al. (2019) The Novel Bromodomain and Extraterminal Domain Inhibitor INCB054329 Induces Vulnerabilities in Myeloma Cells That Inform Rational Combination Strategies. Clin Cancer Res. vol. 25, No. 1, pp. 300-311.

Sun J. et al. (2014). Clonal dynamics of native haematopoiesis. Nature vol. 514, No. 7522, pp. 322-327.

Svensson V., Vento-Tormo R., and Teichmann S.A. (2018). Exponential scaling of single-cell RNA-seq in the past decade. Nature Protocols vol. 13, No. 4, pp. 599-604.

Takahashi K. and Yamanaka S. (2006). Induction of Pluripotent Stem Cells from Mouse Embryonic and Adult Fibroblast Cultures by Defined Factors. Cell vol. 126, No. 4, pp. 663-676.

Tasic B. et al. (2018). Shared and distinct transcriptomic cell types across neocortical areas. Nature vol. 563, No. 7729, pp. 72-78.

The Astropy Collaboration et al. (2018). The Astropy Project: Building an inclusive, open-science project and status of the v2.0 core package. AJ vol. 156, No. 3, 123, 19 pages.

The ENCODE Project Consortium (2012). An integrated encyclopedia of DNA elements in the human genome. Nature 489, 57-74.

Tontsch-Grunt U. et al. (2018) Synergistic activity of BET inhibitor BI 894999 with PLK inhibitor volasertib in AML in vitro and in vivo. Cancer Lett. vol. 421, pp. 112-120.

Vassilev L.T. et al. (2006). Selective small-molecule inhibitor reveals critical mitotic functions of human CDK1. Proc Nat Acad Sci. vol. 103, No. 28, pp. 10660-10665.

Virtanen P. et al. (2020). SciPy 1.0: fundamental algorithms for scientific computing in Python. Nat Methods. vol. 17, pp. 261-272.

(56) References Cited

PUBLICATIONS

Vogel M.J., Peric-Hupkes D., and Van Steensel B. (2007). Detection of in vivo protein-DNA interactions using DamID in mammalian cells. Nat Protoc. vol. 2, No. 6, pp. 1467-1478.

Wang H., Johnston M., and Mitra R.D. (2007). Calling cards for DNA-binding proteins. Genome Res. vol. 17, pp. 1202-1209.

Wang W. et al. (2008). Chromosomal transposition of PiggyBac in mouse embryonic stem cells. Proc Nat Acad Sci. vol. 105, No. 27, pp. 9290-9295.

Wang H. et al. (2011). Calling Cards enable multiplexed identification of the genomic targets of DNA-binding proteins. Genome Res. vol. 21, No. 5, pp. 748-755.

Wang H. (2012). "Calling Cards" for DNA-Binding Proteins in Mammalian Cells. Genetics. vol. 190, No. 3, pp. 941-949.

Wang X. et al. (2012). PrimerBank: a PCR primer database for quantitative gene expression analysis, 2012 update. Nucleic Acids Res. vol. 40, pp. D1144-D1149.

Wang Q. et al. (2019). CoBATCH for High-Throughput Single-Cell Epigenomic Profiling. Mol Cell. vol. 76, No. 1, pp. 206-216.e7.

Whyte W.A. et al. (2013). Master Transcription Factors and Mediator Establish Super-Enhancers at Key Cell Identity Genes. Cell. vol. 153, No. 2, pp. 307-319.

Wilson M.H., Coates C.J., and George A.L. (2007). PiggyBac transposon-mediated gene transfer in human cells. Mol Ther. vol. 15, No. 1, pp. 139-145.

Wolf F.A., Angerer P., and Theis F.J. (2018). SCANPY : large-scale single-cell gene expression data analysis. Genome Biol. vol. 19, No. 1, 15, 5 pages.

Wong C. et al. (2014) The bromodomain and extra-terminal inhibitor CPI203 enhances the antiproliferative effects of rapamycin on human neuroendocrine tumors. Cell Death Dis. vol. 5, No. 10, e1450, 14 pages.

Wu S.C.-Y. et al. (2006). piggyBac is a flexible and highly active transposon as compared to sleeping beauty, Tol2, and Mos1 in mammalian cells. Proc Nat Acad. vol. 103, No. 41, pp. 15008-15013.

Xie S. et al. (2017). Multiplexed Engineering and Analysis of Combinatorial Enhancer Activity in Single Cells. Mol Cell. vol. 66, No. 2, pp. 285-299.e5.

Yen L. et al. (2004). Exogenous control of mammalian gene expression through modulation of RNA self-cleavage. Nature. vol. 431, pp. 471-476.

Yen M. et al. (2018). Transposase mapping identifies the genomic targets of BAP1 in uveal melanoma. BMC Med Genomics. vol. 11, No. 1, 97, 11 pages.

Yoshida J. et al. (2017). Chromatin states shape insertion profiles of the piggyBac, Tol2 and Sleeping Beauty transposons and murine leukemia virus. Scientific Reports. vol. 7, 43613, 18 pages.

Yu H. et al. (2010). The Ubiquitin Carboxyl Hydrolase BAP1 Forms a Ternary Complex with YY1 and HCF-1 and Is a Critical Regulator of Gene Expression. Mol Cell Biol. vol. 30, No. 21, pp. 5071-5085.

Yusa K. et al. (2011). A hyperactive piggyBac transposase for mammalian applications. Proc Nat Acad Sci. vol. 108, No. 4, pp. 1531-1536.

Zeisel A. et al. (2015). Cell types in the mouse cortex and hippocampus revealed by single-cell RNA-seq. Science. vol. 347, No. 6226, pp. 1138-1142.

Zeisel A. et al. (2018). Molecular Architecture of the Mouse Nervous System. Cell. vol. 174, No. 4, pp. 999-1014.e22.

Zhang Y. et al. (2008). Model-based Analysis of ChIP-Seq (MACS). Genome Biol. vol. 9, No. 9, R137, 9 pages.

Zhang Y. et al. (2014). An RNA-Sequencing Transcriptome and Splicing Database of Glia, Neurons, and Vascular Cells of the Cerebral Cortex. J Neurosci. vol. 34, No. 36, pp. 11929-11947.

Zhao W. et al. (2017) Stemness-Related Markers in Cancer. Cancer Transl Med. vol. 3, No. 3, pp. 87-95.

Zheng G.X.Y. et al. (2017). Massively parallel digital transcriptional profiling of single cells, Nat Commun. vol. 8, 14049, 12 pages.

Zheng D., Liu X., and Tian B. (2016). 3'READS+, a sensitive and accurate method for 3' end sequencing of polyadenylated RNA. RNA. vol. 22, No. 10, pp. 1631-1639.

Zhou B. et al. (2019). Comprehensive, integrated, and phased whole-genome analysis of the primary ENCODE cell line K562. Genome Res. vol. 29, No. 3, pp. 472-484.

Zhou X. et al. (2011). The Human Epigenome Browser at Washington University. Nat Methods. vol. 8, No. 12, pp. 989-990.

Zhu X. et al. (2012). Olig2-dependent developmental fate switch of NG2 cells. Development vol. 139, No. 13, pp. 2299-2307.

Zuber J. et al. (2011). RNAi screen identifies Brd4 as a therapeutic target in acute myeloid leukaemia. Nature vol. 478, No. 7370, pp. 524-528.

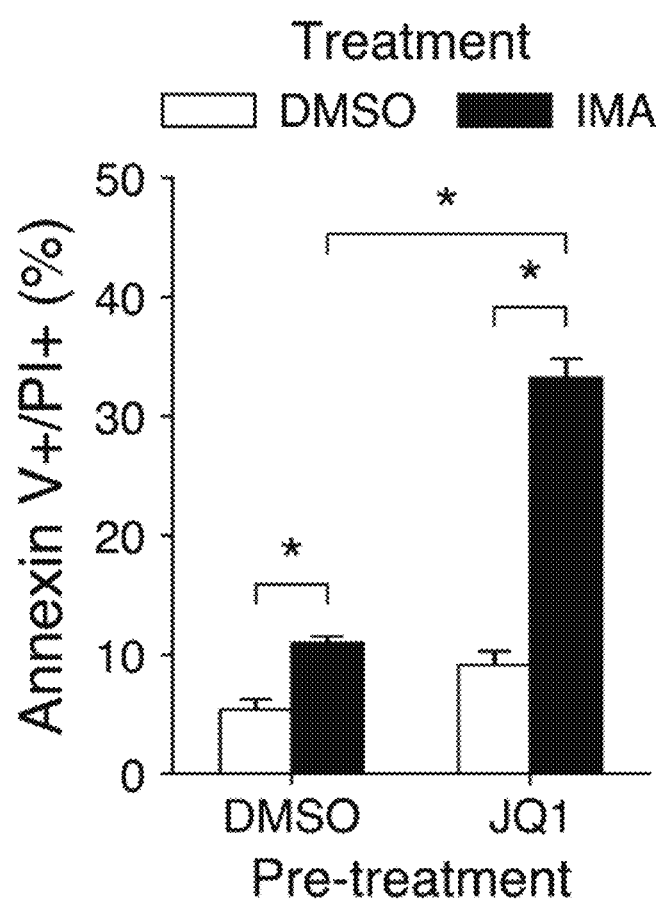

METHODS FOR IMPROVED TREATMENT OF CANCER

CROSS-REFERENCE TO RELATED APPLICATIONS

This application claims priority from U.S. Provisional Application Ser. No. 63/049,658 filed on 9 Jul. 2020, which is incorporated herein by reference in its entirety.

STATEMENT REGARDING FEDERALLY SPONSORED RESEARCH OR DEVELOPMENT

This invention was made with government support under HG009750, MH109133, MH117070, GM007200, HG000045, and HG009986 awarded by the National Institutes of Health. The government has certain rights in the invention.

MATERIAL INCORPORATED-BY-REFERENCE

The Sequence Listing, which is a part of the present disclosure, includes a computer-readable form comprising nucleotide and/or amino acid sequences of the present invention (file name "019486-US-NP_Replacement_Sequence_Listing_ST25.txt" created Tuesday, Sep. 21, 2021; 11,414 bytes). The subject matter of the Sequence Listing is incorporated herein by reference in its entirety.

FIELD OF THE INVENTION

The present disclosure generally relates to treating leukemias.

SUMMARY OF THE INVENTION

Among the various aspects of the present disclosure is the provision of methods for increasing chemotherapy sensitivity or decreasing chemotherapy resistance using BET inhibitors.

An aspect of the present disclosure provides for a method of treating a subject having cancer comprising: administering a BET inhibitor in an amount sufficient to (i) convert tumor-initiating cancer cells into a more chemotherapeutically-sensitive state; or (ii) reduce an amount of stem-like or CD24high cells compared to the amount of stem-like or CD24high cells prior to BET treatment.

In some embodiments, the subject has cancer cells and the cancer cells have a high proportion of stem-like cells (e.g., a greater than or equal proportion CD24high cells to CD24low cells).

In some embodiments, a percentage of chemoresistant (stem-like) cells decreases and a percentage of differentiated, chemosensitive, erythroleukemic cells increases compared to the cells prior to BET inhibiting agent treatment.

In some embodiments, reducing an amount of chemoresistant (stem-like) cells results in the cancer cells becoming more sensitive to treatment with a chemotherapeutic agent.

In some embodiments, the subject is treated with the BET inhibitor prior to receiving a chemotherapeutic treatment (e.g., imatinib).

In some embodiments, the BET inhibitor and chemotherapeutic agent are administered simultaneously with the chemotherapeutic agent.

In some embodiments, the BET inhibitor and chemotherapeutic agent are administered after the chemotherapeutic agent.

In some embodiments, administering the BET inhibitor to the subject increases potency of any chemotherapeutic that targets a differentiated cell state more efficiently than a stem-like cell state.

In some embodiments, the chemotherapeutic is selected from a chemotherapy agent that targets the differentiated cell state more efficiently than a stem-like cell state.

In some embodiments, the cancer cells are leukemia cells, or any cancer having chemo-resistant stem-like cell states regulated by BRD4.

Another aspect of the present disclosure provides for a method of detecting stem-like cells and detecting differentiated, erythroleukemic cells in cancer cells comprising: measuring a level CD24high and CD24low using fluorescent activated cell sorting (FACS); wherein if the subject has a high proportion of stem-like cells (CD24high) compared to differentiated, erythroleukemic cells (CD24low), the subject is treated with a BET inhibiting agent before, during, or after chemotherapy.

Another aspect of the present disclosure provides for a method of monitoring a subject receiving cancer treatment comprising: measuring a level CD24high and CD24low using fluorescent activated cell sorting (FACS); and determining if the subject has an increased proportion of stem-like cells (CD24high) compared to differentiated, erythroleukemic cells (CD24low); or determining if the subject has an increased proportion of stem-like cells (CD24high) to the proportion of stem-like cells (CD24high) prior to treatment (e.g., chemotherapy or BET inhibiting agent treatment).

In some embodiments, if the subject has an increased proportion of stem-like cells (CD24high) compared to differentiated, erythroleukemic cells (CD24low), the subject is not responding to treatment.

In some embodiments, if the subject has an increased proportion of stem-like cells (CD24high) to the proportion of stem-like cells (CD24high) prior to treatment (e.g., chemotherapy or BET inhibiting agent treatment), the subject is not responding to treatment.

In some embodiments, the subject is treated with a BET inhibiting agent.

Another aspect of the present disclosure provides for a method of monitoring a subject at risk for relapse comprising: measuring a level CD24high and CD24low using fluorescent activated cell sorting (FACS); and determining if the subject has an increased proportion of stem-like cells (CD24high) compared to differentiated, erythroleukemic cells (CD24low); or determining if the subject has an increased proportion of stem-like cells (CD24high) to the proportion of differentiated, erythroleukemic cells (CD24low) compared to a prior measurement of the proportion of CD24high and the proportion of CD24low cells.

In some embodiments, if the subject has an increased proportion of stem-like cells (CD24high) compared to differentiated, erythroleukemic cells (CD24low), the subject is at risk for relapse.

In some embodiments, if the subject has an increased proportion of stem-like cells (CD24high) to the proportion of differentiated, erythroleukemic cells (CD24low) compared to a prior measurement of the proportion of CD24high and the proportion of CD24low cells, the subject is at risk for relapse.

In some embodiments, the subject is administered between about 1-10 days of BET inhibitor treatment prior to being administered a chemotherapeutic agent (e.g., imatinib).

In some embodiments, the chemotherapeutic agent is imatinib.

In some embodiments, the BET inhibiting agent is JQ1.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 6A-FIG. 6G. scCC Uncovers Bromodomain-Dependent Cell-State Dynamics in K562 Cells. (A) Gradient of cell states from scRNA-seq analysis of K562 cells. (B) Differential BRD4 binding analysis of undirected HyPBase peaks in K562 cells. (C) Representative distributions of $CD24^{high}$ nd $CD24^{low}$ cells after either 96 h of DMSO (top) or JQ1 (bottom) treatment. (D) Proportion of $CD24^{high}$ cells over a 7-day time course of JQ1 treatment (three-way ANOVA p<0.01). (E) Proportion of $CD24^{high}$ cells after BRD4 CRISPRi (Welch's t test p<0.01). (F) Representative plots of annexin V and PI staining in K562 cells pretreated with either DMSO or JQ1 (250 nM) and subsequently treated for 48 h with either DMSO or imatinib (1 µM). (G) Quantification of (F) (two-way ANOVA p<0.01). See also FIG. 13 and FIG. 14. Bars represent means; error bars denote standard deviations. Experiments were performed in triplicate. DMSO, dimethyl sulfoxide; SSC, side scatter; CRISPRi, CRISPR interference; NT, non-targeting; gRNA, guide RNA; IMA, imatinib; PI, propidium iodide.

DETAILED DESCRIPTION OF THE INVENTION

Figure 1:
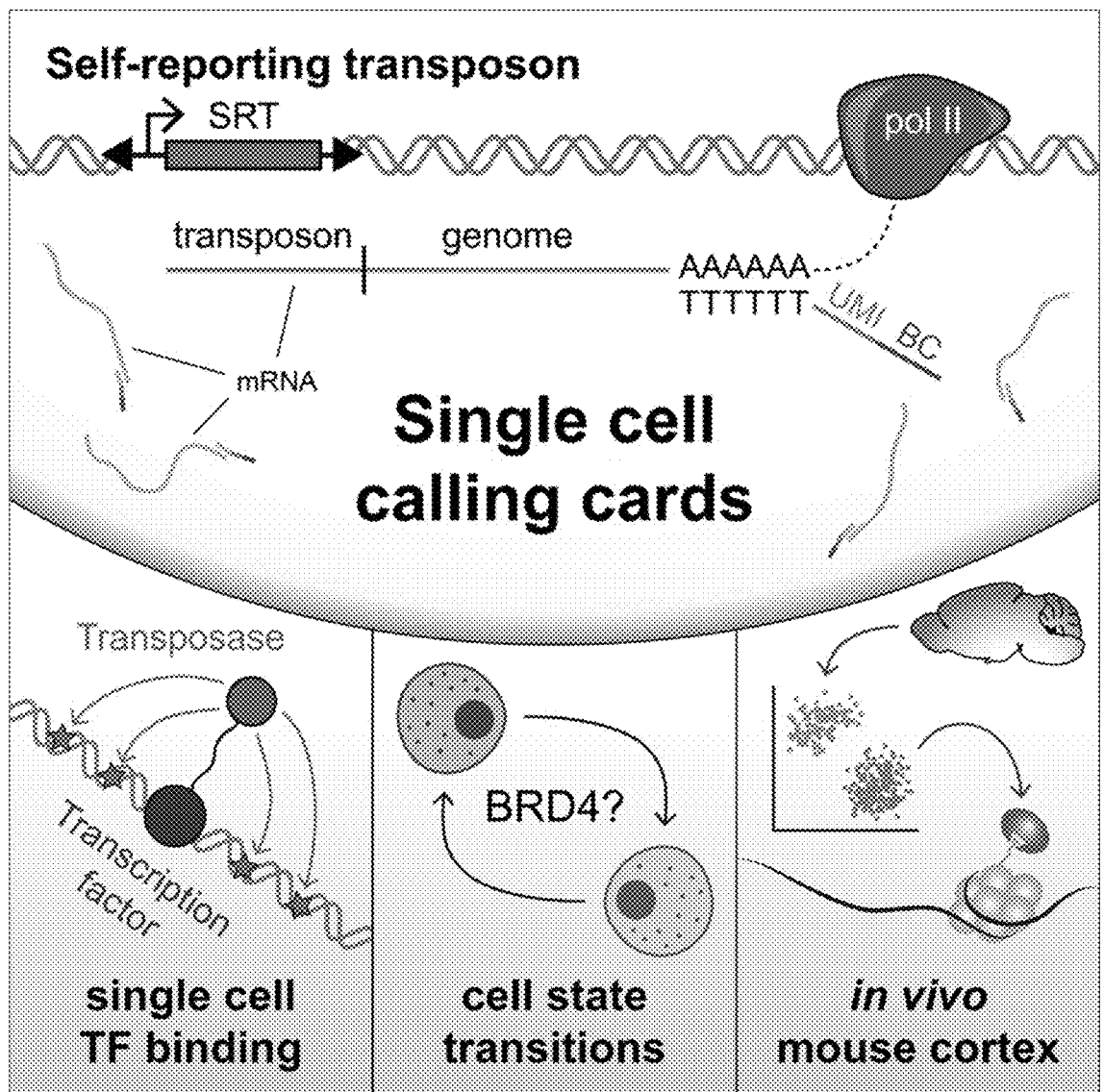
FIG. 1. Graphical abstract.

The present disclosure is based, at least in part, on the discovery that the stem-like cell state in leukemia is regulated by BRD4, an epigenetic reader that is associated with enhancers. As shown herein, it was found that small molecules that inhibit this protein's function, BET inhibitors, can cause the stem-like cells to transition to the more differentiated, erythroleukemic cells, making the population of cells more sensitive to the chemotherapeutic agent, imatinib.

The cure rate of leukemia has improved substantially in the last few decades, and now up to 90% of children can expect to achieve long term remission. However, only 40% of adults achieve remission, and even for children there can be long term effects associated with treatment. As a result, an improved therapeutic strategy for leukemia remains an important goal. Recently, it has become apparent that leukemias are not homogenous populations of cells—there is considerable genetic and epigenetic cell-to-cell variability among cancer cells, and this can have important consequences on response to therapy. For example, experiments using an in vitro cell line model of leukemia demonstrated that this cancer is composed of stem-like cells as well as more differentiated, erythroleukemic cells, and these two cell states were found to have different chemo-sensitivities, with the stem-like cells being more resistant to treatment. We recently found that the stem-like cell state in leukemia is regulated by BRD4, an epigenetic reader that is associated with enhancers. Furthermore, we found that small molecules that inhibit this protein's function, BET inhibitors, can cause the stem-like cells to transition to the more differentiated, erythroleukemic cells, making the population of cells more sensitive to imatinib. Based on these results, the technology comprises the following:

1. Treat patients with a bromodomain and extra-terminal (BET) inhibitor to convert tumor initiating leukemic cells to a more chemotherapeutic-sensitive state. There are a number of different BET inhibitors that are currently undergoing clinical trials and for which safe dosing regimens have been established. Treatment of patients with these inhibitors will cause their leukemias to undergo a cell-state transition so that the percentage of chemoresistant (stem-like) cells will decrease and the percentage of differentiated, chemosensitive, erythroleukemic cells will increase. As a result, the leukemia will be more sensitive to treatment with a chemotherapeutic agent.

2. After about 1-10 days of BET inhibitor treatment, commence treatment of patient with a chemotherapeutic agent (e.g., imatinib). The presently disclosed experiments showed that BET inhibitor pre-treatment increased the sensitivity of K562 leukemia cells to imatinib. However, it is expected that BET inhibitor pre-treatment will increase the potency of any chemotherapeutic that targets the differentiated cell state more efficiently than the stem-like cell state.

Examples of stemness-related markers in different cancer types are known in the art and can be used as markers for the methods described herein (see Zhao et al. Cancer Trans Med. 2017; 3(3): 87-95, incorporated herein by reference).

Stemness-Related Transcriptional Factor (TF) Markers in Cancer:

| Marker | Other names | Function in stem cell | Characteristics | Expressed in Tumor types | Poor prognosis for tumor types |
|---|---|---|---|---|---|
| OCT4 | Oct3/4 or POU5F1 | Stem cell self-renew and poluropotency maintenance | Oct family of POU transcription factor. | Leukemia, Brain, Lung, Bladder, Ovarian, | Esophageal squamous cell carcinoma Medulloblastoma |

-continued

| Marker | Other names | Function in stem cell | Characteristics | Expressed in Tumor types | Poor prognosis for tumor types |
|---|---|---|---|---|---|
| SOX2 | | Stem cell self-renew and poluropotency maintenance | POU family binder transcription factor | Pancreas, Prostate, Renal, Seminoma, Testis Brain, Breast, Lung, Liver, Prostate, Seminoma, Testis | Prostate cancer Blader cancer Stage I lung adenocarcinoma Squamous cell carcinoma Gastric carcinoma Small cell lung cancer Ovarian carcinoma |
| KLF4 | | Stem cell self-renew and poluropotency maintenance | Zinc-finger transcription factor | Leukemia, Myeloma, Brain, Breast, Head and neck, Oral, Prostate, Testis | Breast cancer Nasopharyngeal carcinoma Colon cancer Head and neck squamous cell carcinoma Oral cancer |
| C-MYC | | Stem cell self-renewal | Transcription factor and an oncogene | Leukemia, Lymphoma, Myoloma, Brain, Breast, Colon, Head and Neck, Pancreas, Prostate, Renal, Salivary-gland, testis | Hepatocellular carcinoma Early carcinoma of uterine cervix |
| Nanog | | Stem cell self-renew and poluropotency maintenance | Transcription factor | Brain, Breast, Prostate, colon, liver, Ovarian, | Breast cancer Colorectal cancer Gastric adenocarcinoma Non-small cell lung cancer Ovarian Serous Carcinoma Liver cancer |
| SALL4 | | Stem cell self-renew and poluropotency maintenance Differentiation regulation | Zinc finger transcription factor and an oncogene | Leukemia, Breast, Liver, Colon, Ovarian, testis | Hepatocellular carcinoma Gliomas Myelodysplastic syndromes |

Sternness-Related Markers in Different Cancer Types:

| Leukemia | Bladder | Breast | Colon | Gastric |
|---|---|---|---|---|
| | ALDH1A1 | ALDH1A1 | ALDH1A1 | ALDH1A1 |
| CD34 | CD47 | CD49f/Integrin alpha 6 | CD166 | |
| CD38 | | CD24 | CD24 | |
| CD44 | CD44 | CD44 | CD44 | CD44 |
| | | CD133 | CD133 | |
| CD47 | | CD90 | CD26 | CD15/Lewis X |
| CD96 | | | CD29 | |
| CD117/c-kit | | | | |
| CD123/IL-3 R alpha | CEACAM-6/CD66c | | | |
| | | EpCAM/TROP1 CXCR4 CXCR1/IL-8 RA | Lgr5/GPR49 EpCAM/TROP1 | Lgr5/GPR49 |

-continued

| Leukemia | Bladder | Breast | Colon | Gastric |
|---|---|---|---|---|
| BMI-1 |  | BMI-1 | BMI-1 |  |
|  |  |  | Musashi-1 |  |
| c-Myc |  | c-Myc | c-Myc |  |
|  |  | SOX2 |  |  |
| OCT4 | OCT4 |  |  |  |
| KLF4 |  | KLF4 |  |  |
|  |  | Nanog | Nanog |  |
| SALL4 |  | SALL4 | SALL4 |  |
| TIM3 |  |  |  |  |

| Glioma/Medulloblastoma | Head and Neck | Liver | Lung | Melanoma |
|---|---|---|---|---|
|  | ALDH1A1 |  | ALDH1A1 |  |
| CD49f/Integrin alpha 6 |  | CD45 |  | TNFRSF16 |
|  |  | CD24 |  |  |
| CD44 | CD44 |  |  |  |
| CD133 |  | CD133 | CD133 | CD133 |
| CD15/Lewis X |  | CD13 |  |  |
| CD90/Thy1 |  | CD90/Thy1 | CD90/Thy1 |  |
|  |  |  | CD117/c-kit |  |
|  |  | Aminopeptidase N/CD13 |  | CD166/ALCAM |
|  | Lgr5/GPR49 |  |  |  |
|  |  |  | EpCAM/TROP1 |  |
| CXCR4 |  |  |  |  |
| CX3CR1 |  |  |  |  |
|  | BMI-1 |  |  |  |
| Nestin |  |  |  | Nestin |
| Musashi-1 |  |  |  |  |
| c-Myc |  |  |  |  |
| SOX2 |  | SOX2 | SOX2 |  |
|  |  | Nanog |  |  |
|  |  | SALL4 |  |  |

| Myeloma | Osteosarcoma | Ovarian | Pancreatic | Prostate |
|---|---|---|---|---|
|  |  |  | ALDH1A1 | ALDH1A1 |
| CD27/TNFRSF7 |  | Endoglin/CD105 | CD24 | CD49f/Integrin alpha 6 |
| CD38 |  | CD24 | CD24 | CD151 |
|  | CD44 | CD44 | CD44 | CD44 |
|  |  | CD133 | CD133 | CD133 |
|  |  |  |  | CD166 |
| CD20/MS4A1 |  |  |  | TRA-1-60(R) |
| CD19 |  |  |  |  |
|  |  | CD117/c-kit |  |  |
| CD138Syndecan-1 |  |  |  | ALCAM/CD166 |
|  |  |  | EpCAM/TROP1 |  |
|  |  |  | CXCR4 |  |
|  |  |  | BMI-1 | BMI-1 |
|  | Nestin |  | Nestin |  |
|  |  |  | c-Myc | c-Myc |
|  |  |  |  | SOX2 |
|  |  | OCT4 | OCT4 | OCT4 |
|  |  |  |  | KLF4 |
|  |  | Nanog |  | Nanog |
|  |  | SALL4 |  | SALL4 |
|  |  |  |  | Rex1 |

Modifications can include:
1. The BET inhibitor and chemotherapeutic agent can be administered simultaneously rather than serially or sequentially.
2. Any chemotherapeutic that targets the differentiated cell state more efficiently than the stem-like cell state is likely to see a benefit from BET inhibitor pre-treatment.
3. The disclosed results were obtained using leukemia cells, but many cancers have chemo-resistant stem-like cell states. Stem-like cell states regulated by BRD4 will benefit from BET pre-treatment or treatment. There is evidence to suggest that BRD4 is a master regulator of cell state, so this is likely.
4. Patients could be stratified for treatment by using fluorescent activated cell sorting (FACS) to identify which cancers have a high proportion of stem-like cells. The stem-like cells express high levels of the surface marker CD24, whereas the more differentiated, erythroleukemic cells are marked by low CD24 expression. Patients with a high proportion of stem-like cells are good candidates for this treatment.
5. Use FACS for stem-like cell markers to monitor a patient's progress during treatment.
6. Use FACS for stem-like cell markers to follow-up on a patient during remission, with the aim of potentially detecting relapse earlier.

Bromodomain and Extraterminal Domain (BET) Inhibiting Agent

One aspect of the present disclosure provides for targeting of BET (e.g., BRD4, particularly, but can also target BRD2, BRD3, testis-ovary specific BRDT), its receptor, or its downstream signaling. The present disclosure provides methods of treating or preventing cancer based on the discovery that BET inhibitors tumor initiating cells into a more chemotherapeutically-sensitive state.

As described herein, inhibitors of BET (e.g., antibodies, fusion proteins, small molecules) can reduce or prevent chemotherapy resistance in cancers with stem-like cell states regulated by BRD4.

A BET inhibiting agent can be any agent that can inhibit BET, downregulate BET, or knockdown BET.

For example, the BET inhibiting agent can be JQ1, commonly used to disrupt BRD4 binding and alter target gene expression. Other BET inhibiting agents can be I-BET, PFI-1, I-BET151, MS417, etc.

These BET inhibitors target tumor cells and do not affect normal tissues. This selectivity appears to be mediated by the inhibitors' preferential binding to superenhancers, which are noncoding regions of DNA which bind multiple transcription factors and are critical to the expression of a cell's identity. In the laboratory, researchers have found that Brd4 normally localizes to superenhancers; (it appears JQ1 does the same) limiting Brd4 binding in these critical regions and contributing to the drug's tumor-specific effects.

Other BET inhibiting agents currently known and those being studied in clinical trials can be used (see e.g., Alqahtani et al. Future Sci OA. 2019 March; 5(3): FSO372, incorporated herein by reference).

BET inhibitors are a class of drugs that reversibly bind the bromodomains of Bromodomain and Extra-Terminal motif (BET) proteins BRD2, BRD3, BRD4, and BRDT, and prevent protein-protein interaction between BET proteins and acetylated histones and transcription factors.

BET inhibitors currently in clinical trials:

| Agent | Sponsor | Target | Tumor type | Phase of development | ClinicalTrials.gov identifier |
|---|---|---|---|---|---|
| ABBV-075 | AbbVie | BRD2/3/4, BRDT | Solid tumors; expansion cohorts in AML, multiple myeloma, breast cancer, NSCLC | I | NCT02391480 |
| BAY1238097 | Bayer | Undisclosed | Solid tumors and lymphoma | I (terminated) | NCT02369029 |
| BI 894999 | Boehringer Ingelheim | Undisclosed | Solid tumors and NHL | I | NCT02516553 |
| BMS-986158 | Bristol-Myers Squibb | Undisclosed | Solid tumors | I/II | NCT02419417 |
| CPI-0610 | Constellation Pharmaceuticals/ Roche | BRD4 | Lymphoma | I | NCT01949883 |
| | | | Multiple myeloma | I | NCT02157636 |
| | | | AML, ALL, CML in blast crisis, MDS, MPN | I | NCT02158858 |
| | | | Peripheral nerve sheath tumors II (not yet open) | I | NCT02986919 |
| FT-1101 | Forma therapeutics/ Celgene | BRD2/3/4, BRDT | AML, MDS | I | NCT02543879 |
| GS-5829 | Gilead | Undisclosed | DLBCL, peripheral T cell lymphoma, solid tumors | I | NCT02392611 |
| | | | ER+ breast cancer in combination with exemestane or fulvestrant | I/II | NCT02983604 |
| | | | Metastatic CRPC as single agent and in combination with enzalutamide | I/II | NCT02607228 |

-continued

| Agent | Sponsor | Target | Tumor type | Phase of development | ClinicalTrials.gov identifier |
|---|---|---|---|---|---|
| GSK525762/ I-BET762 | GlaxoSmithKline | BRD2/3/4, BRDT | Hematologic malignancies; expansion cohorts with AML, NHL, or multiple myeloma; exploratory MYC/BCL2/ BCL6-driven cohort | I | NCT01943851 |
|  |  |  | SCLC, NSCLC, colorectal cancer, neuroblastoma, TNBC, ER+ breast cancer, CRPC, or other MYC amplified solid tumor | I | NCT01587703 |
|  |  |  | ER+ breast cancer | II (not yet open) | NCT02964507 |
| GSK2820151/ I-BET151 | GlaxoSmithKline | BRD2/3/4 | Solid tumors | I | NCT02630251 |
| INCB054329 | Incyte | Undisclosed | Hematologic malignancies, solid tumors | I/II | NCT02431260 |
| OTX015/MK-8628 | Merck/Mitsubishi Tanabe | BRD2/3/4 | AML, DLBCL | I | NCT02698189 |
|  |  |  | Solid tumors (NMC, TNBC, NSCLC, CRPC) | I | NCT02698176 |
|  |  |  | GBM | Phase II withdrawn | NCT02296476 |
| PLX51107 | Plexxicon | BRD4 | Solid tumors, lymphoma, AML, MDS | I | NCT02683395 |
| RO6870810/ TEN-010 | Hoffman-LaRoche |  | MDS, AML | I | NCT02308761 |
|  |  |  | Solid tumors | I | NCT01987362 |
| ZEN003694 | Zenith Epigenetics | BRD2/3/4, BRDT | Metastatic CRPC | I | NCT02705469 |
|  |  |  | Metastatic CRPC in combination with enzalutamide | I | NCT02711956 |

Phase I clinical data with single agent BET inhibitors

| Author | Agent | Number of patients treated | Tumor type(s) | Dosing range and schedule of administration | DLTs and toxicities of interest | Responses observed |
|---|---|---|---|---|---|---|
| Hematologic malignancies |||||||
| Dombret et al. | MK-8268/OTX-015 | 36 | Relapsed/ refractory leukemia | 10-60 mg q.d.s. × 14/ 21 days, 40 mg b.i.d., 120 mg q.d.s.; MTD 120 mg q.d.s. | DLTs: G3 diarrhea, G3 fatigue, G3 anorexia. Toxicities also included dysgeusia (11%), abdominal pain (11%), | 1 CR; 1 CRi (platelets); 2 with partial blast clearance, 1 with disappearance of hypertrophied gums |

| Author | Agent | Number of patients treated | Tumor type(s) | Dosing range and schedule of administration | DLTs and toxicities of interest | Responses observed |
|---|---|---|---|---|---|---|
| Amorim et al. | MK-8628/OTX015 | 45 | Relapsed/ refractory lymphoma or multiple myeloma | 10-120 mg q.d.s.; 40 mg b.i.d.; RP2D 80 mg q.d.s. × 14/ 21 days | decreased factor VII (21%) DLTs: G4 thrombocytopenia, G4 neutropenia, G3 hyponatremia Other toxicities included diarrhea (47%), dysgeusia (15%), fatigue (27%), anemia (91%) | 3 OR (DLBCL), 1 with improvement of pleural effusion; 2 with resolution of B symptoms; 2 with responses not meeting PR criteria |
| Berthon et al. | MK-8628/OTX015 | 41 | Acute leukemia, MDS | 10-60 mg q.d.s. × 14/ 21 days; RP2D 80 mg q.d.s. × 14/21 days | DLTs: G3 diarrhea, G3 fatigue. Diarrhea (34%), fatigue (27%), and rash (20%) limited compliance | 2 CR, 1 CRi (platelets) × 2 months, 2 partial blast clearance |
| Abramson et al. | CPI-0610 | 44 | Relapsed/ refractory lymphoma | 40-300 mg q.d.s. × 14/ 21 days | MTD not yet established; primary toxicity is dose dependent, reversible thrombocytopenia; 1 patient with G4 thrombocytopenia; 1 patient with G3 diarrhea | 2 CR; 1 PR; 5 with responses not qualifying as PR; 6 SD |
| Solid tumors | | | | | | |
| Shapiro et al. | RO6870810/ TEN-010 | 3 | NMC | 0.1-0.45 mg/ kg q.d.s. × 21/28 days | Not available | 2 PR |
| Stathis et al. | MK-8628/OTX-015 | 4 (case series) | NMC | Not described | G3 thrombocytopenia, G2 nausea, G2 dysgeusia, G2 hyperglycemia, G2 fatigue | 2 PR; 1 SD |
| Massard et al. | MK-8628/OTX-015 | 47 | NMC, CRPC, NSCLC | 80 mg q.d.s., 100 mg q.d.s. × 7 days q 21 days; MTD not reached for the latter | Toxicities: G3-4 thrombocytopenia (20%), G3 anemia (9%), G3 fatigue (7%) | 4 PR; 5 SD for 4-8 months |
| Solid tumors and hematologic malignancies | | | | | | |
| Postel-Vinay et al. | BAY1238097 | 8 | Advanced solid tumors or NHL | 5-40 mg 2×/week in 21 day cycle | DLTs: G3 headache, G3 vomiting, G3 low back pain at 80 mg. | Development halted as DLTs occurred at subtherapeutic doses of |

-continued

| Author | Agent | Number of patients treated | Tumor type(s) | Dosing range and schedule of administration | DLTs and toxicities of interest | Responses observed |
|---|---|---|---|---|---|---|
| O'Dwyer et al. | GSK525762 | 70 | Hematologic and solid malignancies; 17 with NMC | 2-100 mg q.d.s., 20-30 mg b.i.d.; RP2D 80 mg daily | Toxicities: Recurrent headaches in 50% patients at 10 and 40 mg cohorts Toxicities: thrombocytopenia (44%), nausea (40%), vomiting (29%) | drug 2 PR; 4 SD in NMC patients |

In vivo combination studies of BET inhibitors:

| Author | Combination | Xenograft used | Effect observed |
|---|---|---|---|
| BET inhibitors and epigenetic agents | | | |
| Bhadury et al. | RVX2135 and vorinostat | B6 mice transplanted with 2749 lymphoma cell line | Faster reduction of leukocytosis compared with single agent vorinostat; prolonged WBC reduction and improved survival; reduced concentration of vorinostat required compared with that required for similar effect as single agent |
| Fiskus et al. | JQ1 and panobinostat | NOD/SCID mice injected with OCI-AML3 or MOLM13 cells | Improved survival compared with either agent alone; increased reduction in levels of c-MYC, BCL-2, and CDK6 proteins in OCI-AML3 model |
| Heinemann et al. | I-BET151 and panobinostat | NOD/SCID mice injected with patient-derived melanoma cells resistant to vemurafenib | Improved survival compared with I-BET151 alone; synergistically increased expression of BIM, cPARP and reduced expression of XIAP |
| Shahbazi et al. | JQ1 and panobinostat | Balb/c mice, SK-N-BE(2) neuroblastoma cells | Synergistic inhibition of tumor growth compared with either agent alone and reduction of N-MYC expression |
| Jostes et al. | JQ1 and romidepsin | Xenografts of NT2/D1 and NCCIT embryonal carcinoma | Synergistic reduction of tumor burden compared with JQ1 alone, seen with reduced dose of romidepsin and reduced frequency of JQ1 dosing |
| Bui et al. | ABBV-075 and azacitadine | AKM1 AML xenografts | Synergistic effect on tumor regression with better tolerance by xenografts than BET inhibitor monotherapy |

-continued

| Author | Combination | Xenograft used | Effect observed |
|---|---|---|---|
| Liu et al. | INCB054329 and LSD1 inhibitor INCB059872 | Human AML xenografts | Synergistic effect on increasing apoptosis and myeloid differentiation; combination resulted in increased downregulation of MYC compared with either agent alone; synergy most effective with sequential therapy when LSD1 inhibitor administered first |
| BET inhibitors and targeted agents | | | |
| Lee et al. | JQ1 and rapamycin | Nude mice injected with MNNG/HOS osteosarcoma cells | Combination reduced tumor volume and weight compared with rapamycin alone (JQ1 had no effect on either as single agent) |
| Wong et al. | CPI203 and rapamycin | Nude mice injected with BON-1 pancreatic neuroendocrine tumor cells | Synergistic inhibition of tumor growth compared with either agent alone or reduction of MYC protein levels; however, increased apoptosis not seen. Dose reduction required to minimize weight loss. |
| Jing et al. | JQ1 and trametinib | Nude mice injected with ES2 ovarian clear cell carcinoma cells | Combination reduced tumor volume and weight compared with either agent alone; however, increased weight loss observed with combination |
| Paoluzzi et al. | JQ1 and vemurafenib | NOD/SCID mice injected with A375 melanoma cells | Increased survival and reduced tumor growth in combination compared with either agent alone; unique downregulation of apoptotic regulators BCL2, MCL1, BCL-XL, BIRC5, and APAF1 and more than 30 transcriptional regulators with combination; increased weight loss observed with combination |
| Feng et al. | JQ1 and fulvestrant | Ovariectomized nude mice injected with tamoxifen-resistant MCF7 breast cancer cells | Combination demonstrated synergistic inhibition of tumor growth and of ERα protein expression as opposed to either agent alone |
| Matkar et al. | I-BET151 and lapatinib | Nude mice injected with Her2+ BT474 breast cancer cells | Synergistic inhibition of tumor growth compared with either agent alone; no effect on tumor size but reduction in number of tumor cells with increased fibrosis |
| Matkar et al. | I-BET151 and lapatinib | Nude mice injected with Her2+ UACC812 breast cancer cells | Synergistic decrease in tumor size compared with either agent alone |
| Gopalakrishnan et al. | JQ1 and lenalidomide | NOD/SCID mice injected with BC-3 lymphoma cells | Synergistic reduction of weight (measure of ascites) and improved survival compared with either agent alone |
| Stubbs et al. | INCB054329 and PI3Kδ inhibitor INCB050465 | Mice injected with Pfeiffer germinal center diffuse large B cell lymphoma cells | Increased number of partial tumor regressions compared with agents individually |

-continued

| Author | Combination | Xenograft used | Effect observed |
|---|---|---|---|
| BET inhibitors and cell cycle inhibitors | | | |
| Tontsch-Grunt et al. | BI 894999 and CDK9 inhibitors Alvocidib and LDC000067 | Mice injected with MV-4-11, THP-1, and MOLM13 cells | Synergistic inhibition of tumor growth and MYC expression compared with single agent BET inhibitor |
| Bolin et al. | Unidentified BET and CDK2 inhibitors | Mice transplanted with medulloblastoma | Synergistic effect on tumor growth inhibition and improvement of overall survival compared with either agent alone |
| BET inhibitors and cytotoxic chemotherapeutic agents | | | |
| Stubbs et al. | INCB054329 and bendamustine | Mice injected with Pfeiffer germinal center diffuse large B cell lymphoma cells | 'Enhanced tumor efficacy' compared with either agent alone |
| BET inhibitors and immune checkpoint inhibitors | | | |
| Adeegbe et al. | JQ1 and unidentified PD-1 inhibitor | KRASmt NSCLC murine xenograft | Synergistic effect on decreasing tumor burden and improving overall survival |
| Koblish et al. | INCB054329 and IDO1 inhibitor epacadostat or unnamed PD-1 and PD-L1 inhibitors | Multiple unspecified syngeneic tumor models in immunodeficient mice | Synergistic effect on suppression of tumor growth |
| BET inhibitors and inhibitors of DNA damage repair | | | |
| Muralidharan et al. | RVX2135 and ATR inhibitor AZ20 | λ820 and λ2749 murine Myc-induced lymphoma xenografts | Synergistic delay in tumor onset in λ820 xenografts; synergistic WBC reduction and improved survival in λ2749 xenografts |

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing chemotherapy resistance or remission in a subject in need of administration of a therapeutically effective amount of a BET inhibiting agent, so as to increase sensitivity to chemotherapy treatment.

Methods described herein are generally performed on a subject in need thereof. A subject in need of the therapeutic methods described herein can be a subject having, diagnosed with, suspected of having, or at risk for developing cancer or in remission. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of a BET inhibiting agent is, for example, an amount that would cause the desired therapeutic effect in a subject while minimizing undesired side effects. In various embodiments, an effective amount of a BET inhibiting agent described herein can substantially inhibit cancer, slow the progress of cancer, or limit the development of cancer.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a BET inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to increase chemotherapy sensitivity.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a BET inhibiting agent can occur as a single event or over a time course of treatment. For example, a BET inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for cancer.

A BET inhibiting agent can be administered simultaneously or sequentially with another agent, such as a chemotherapeutic agent, an antibiotic, an anti-inflammatory, or another agent. For example, a BET inhibiting agent can be administered simultaneously with another agent, such as a chemotherapeutic agent, an antibiotic or an anti-inflammatory. Simultaneous administration can occur through administration of separate compositions, each containing one or more of a BET inhibiting agent, a chemotherapeutic agent, an antibiotic, an anti-inflammatory, or another agent. Simultaneous administration can occur through administration of one composition containing two or more of a BET inhibiting agent, a chemotherapeutic agent, an antibiotic, an anti-inflammatory, or another agent. A BET inhibiting agent can be administered sequentially with a chemotherapeutic agent, an antibiotic, an anti-inflammatory, or another agent. For example, a BET inhibiting agent can be administered before or after administration of a chemotherapeutic agent, an antibiotic, an anti-inflammatory, or another agent.

Chemotherapeutic Agents

The BET inhibitors described herein can increase a cancer cells sensitivity to a chemotherapeutic agent. As described herein, the BET inhibitors can increase sensitivity to imatinib. Imatinib is specific tyrosine kinase receptor inhibitor that is used in the therapy of Philadelphia chromosome-positive chronic myelogenous leukemia and gastrointestinal stromal tumors, both of which are marked by an abnormal, constitutively expressed tyrosine kinase that causes unregulated cell growth. Imatinib is in a class of medications called kinase inhibitors. It works by blocking the action of the abnormal protein that signals cancer cells to multiply.

A chemotherapeutic agent can be any one or combination of Abiraterone Acetate; Abitrexate (Methotrexate); Abraxane (Paclitaxel Albumin-stabilized Nanoparticle Formulation); ABVE; ABVE-PC; AC; AC-T; Adcetris (Brentuximab Vedotin); ADE; Ado-Trastuzumab Emtansine; Adriamycin (Doxorubicin Hydrochloride); Afatinib Dimaleate; Afinitor (Everolimus); Akynzeo (Netupitant and Palonosetron Hydrochloride); Aldara (Imiquimod); Aldesleukin; Alecensa (Alectinib); Alectinib; Alemtuzumab; Alkeran (Melphalan Hydrochloride); Alkeran (Melphalan); Alimta (Pemetrexed Disodium); Aloxi (Palonosetron Hydrochloride); Ambochlorin/Amboclorin (Chlorambucil); Amifostine; Aminolevulinic Acid; Anastrozole; Aprepitant; Aredia (Pamidronate Disodium); Arimidex (Anastrozole); Aromasin (Exemestane); Arranon (Nelarabine); Arsenic Trioxide; Arzerra (Ofatumumab); Asparaginase Erwinia chrysanthemi; Atezolizumab; Avastin (Bevacizumab); Avelumab; Axitinib; Azacitidine; Bavencio (Avelumab) BEACOPP; Becenum (Carmustine); Beleodaq (Belinostat); Belinostat; Bendamustine Hydrochloride; BEP; Bevacizumab; Bexarotene; Bexxar (Tositumomab and Iodine I 131 Tositumomab); Bicalutamide; BiCNU (Carmustine); Bleomycin; Blinatumomab; Blincyto (Blinatumomab); Bortezomib; Bosulif (Bosutinib); Bosutinib; Brentuximab Vedotin; BuMel; Busulfan; Busulfex (Busulfan); Cabazitaxel; Cabometyx (Cabozantinib-S-Malate); Cabozantinib-S-Malate; CAF; Campath (Alemtuzumab); Camptosar (Irinotecan Hydrochloride); Capecitabine; CAPOX; Carac (Fluorouracil-Topical); Carboplatin; Carboplatin-Taxol; Carfilzomib; Carmubris (Carmustine); Casodex (Bicalutamide); CEM; Ceritinib; Cerubidine (Daunorubicin Hydrochloride); Cervarix (Recombinant HPV Bivalent Vaccine); Cetuximab; CEV; Chlorambucil; Chlorambucil-prednisone; CHOP; Cisplatin; Cladribine; Clafen (Cyclophosphamide); Clofarabine; Clofarex (Clofarabine); Clolar (Clofarabine); CMF; Cobimetinib; Cometriq (Cabozantinib-S-Malate); COPDAC; COPP; COPP-ABV; Cosmegen (Dactinomycin); Cotellic (Cobimetinib); Crizotinib; CVP; Cyclophosphamide; Cyfos (Ifosfamide); Cyramza (Ramucirumab); Cytarabine; Cytarabine Liposome; Cytosar-U (Cytarabine); Cytoxan (Cyclophosphamide); Dabrafenib; Dacarbazine; Dacogen (Decitabine); Dactinomycin; Daratumumab; Darzalex (Daratumumab); Dasatinib; Daunorubicin Hydrochloride; Decitabine; Defibrotide Sodium; Defitelio (Defibrotide Sodium); Degarelix; Denileukin Diftitox; Denosumab; DepoCyt (Cytarabine Liposome); Dexamethasone; Dexrazoxane Hydrochloride; Dinutuximab; Docetaxel; Doxil (Doxorubicin Hydrochloride Liposome); Doxorubicin Hydrochloride; Doxorubicin Hydrochloride Liposome; Dox-SL (Doxorubicin Hydrochloride Liposome); DTIC-Dome (Dacarbazine); Efudex (Fluorouracil-Topical); Elitek (Rasburicase); Ellence (Epirubicin Hydrochloride); Elotuzumab; Eloxatin (Oxaliplatin); Eltrombopag Olamine; Emend (Aprepitant); Empliciti (Elotuzumab); Enzalutamide; Epirubicin Hydrochloride; EPOCH; Erbitux (Cetuximab); Eribulin Mesylate; Erivedge (Vismodegib); Erlotinib Hydrochloride; Erwinaze (Asparaginase Erwinia chrysanthemi); Ethyol (Amifostine); Etopophos (Etoposide Phosphate); Etoposide; Etoposide Phosphate; Evacet (Doxorubicin Hydrochloride Liposome); Everolimus; Evista (Raloxifene Hydrochloride); Evomela (Melphalan Hydrochloride); Exemestane; 5-FU (Fluorouracil Injection); 5-FU (Fluorouracil-Topical); Fareston (Toremifene); Farydak (Panobinostat); Faslodex (Fulvestrant); FEC; Femara (Letrozole); Filgrastim; Fludara (Fludarabine Phosphate); Fludarabine Phosphate; Fluoroplex (Fluorouracil-Topical); Fluorouracil Injection; Fluorouracil-Topical; Flutamide; Folex (Methotrexate); Folex PFS (Methotrexate); FOLFIRI, FOLFIRI-BEVACIZUMA13, FOLFIRI-CETUXIMA13, FOLFIRINOX; FOLFOX; Folotyn (Pralatrexate); FU-LV; Fulvestrant; Gardasil (Recombinant HPV Quadrivalent Vaccine); Gardasil 9 (Recombinant HPV Nonavalent Vaccine); Gazyva (Obinutuzumab); Gefitinib; Gemcitabine Hydrochloride; Gemcitabine-Cisplatin; GEMCITABINE-OXALIPLATIN; Gemtuzumab Ozogamicin; Gemzar (Gemcitabine Hydrochloride); Gilotrif (Afatinib Dimaleate); Gleevec (Imatinib Mesylate); Gliadel (Carmustine Implant); Gliadel wafer (Carmustine Implant); Glucarpidase; Goserelin Acetate; Halaven (Eribulin Mesylate); Hemangeol (Propranolol Hydrochloride); Herceptin (Trastuzumab); HPV Bivalent Vaccine, Recombinant; HPV Nonavalent Vaccine, Recombinant; HPV Quadrivalent Vaccine, Recombinant; Hycamtin (Topotecan Hydrochloride); Hydrea (Hydroxyurea); Hydroxyurea; Hyper-CVAD; Ibrance (Palbociclib); Ibritumomab Tiuxetan; Ibrutinib; ICE; Iclusig (Ponatinib Hydrochloride); Idamycin (Idarubicin Hydrochloride); Idarubicin Hydrochloride; Idelalisib; Ifex (Ifosfamide); Ifosfamide; Ifosfamidum (Ifosfamide); IL-2 (Aldesleukin); Imatinib Mesylate; Imbruvica (Ibrutinib); Imiquimod; Imlygic (Talimogene Laherparepvec); Inlyta (Axitinib); Interferon Alfa-2b, Recombinant; Interleukin-2 (Aldesleukin); Intron A (Recombinant Interferon Alfa-2b); Iodine I 131 Tositumomab and Tositumomab; Ipilimumab; Iressa (Gefitinib); Irinotecan Hydrochloride; Irinotecan Hydrochloride Liposome; Istodax (Romidepsin); Ixabepilone; Ixazomib Citrate; Ixempra (Ixabepilone); Jakafi (Ruxolitinib Phosphate); JEB, Jevtana (Cabazitaxel); Kadcyla (Ado-Trastuzumab Emtansine); Keoxifene (Raloxifene Hydrochloride); Kepivance (Palifermin); Keytruda (Pembrolizumab); Kisgali (Ribociclib); Kyprolis (Carfilzomib); Lanreotide Acetate; Lapatinib Ditosylate; Lartruvo (Olaratumab); Lenalidomide; Lenvatinib Mesylate; Lenvima (Lenvatinib Mesylate); Letrozole; Leucovorin Calcium; Leukeran (Chlorambucil); Leuprolide Acetate; Leustatin (Cladribine); Levulan (Aminolevulinic Acid); Linfolizin (Chlorambucil); LipoDox (Doxorubicin Hydrochloride Liposome); Lomustine; Lonsurf (Trifluridine and Tipiracil Hydrochloride); Lupron (Leuprolide Acetate); Lupron Depot (Leuprolide Acetate); Lupron Depot-Ped (Leuprolide Acetate); Lynparza (Olaparib); Mardibo (Vincristine Sulfate Liposome); Matulane (Procarbazine Hydrochloride); Mechlorethamine Hydrochloride; Megestrol Acetate; Mekinist (Trametinib); Melphalan; Melphalan Hydrochloride; Mercaptopurine; Mesna; Mesnex (Mesna); Methazolastone (Temozolomide); Methotrexate; Methotrexate LPF (Methotrexate); Methylnaltrexone Bromide; Mexate (Methotrexate); Mexate-AQ (Methotrexate); Mitomycin C; Mitoxantrone Hydrochloride; Mitozytrex (Mitomycin C); MOPP; Mozobil (Plerixafor); Mustargen (Mechlorethamine Hydrochloride); Mutamycin (Mitomycin C); Myleran (Busulfan); Mylosar (Azacitidine); Mylotarg (Gemtuzumab Ozogamicin); Nanoparticle Paclitaxel (Paclitaxel Albumin-stabilized Nanoparticle Formulation); Navelbine (Vinorelbine Tartrate); Necitumumab; Nelarabine; Neosar (Cyclophosphamide); Netupitant and Palonosetron Hydrochloride; Neulasta (Pegfilgrastim); Neupogen (Filgrastim); Nexavar (Sorafenib Tosylate); Nilandron (Nilutamide); Nilotinib; Nilutamide; Ninlaro (Ixazomib Citrate); Nivolumab; Nolvadex (Tamoxifen Citrate); Nplate (Romiplostim); Obinutuzumab; Odomzo (Sonidegib); OEPA; Ofatumumab; OFF; Olaparib; Olaratumab; Omacetaxine Mepesuccinate; Oncaspar (Pegaspargase); Ondansetron Hydrochloride; Onivyde (Irinotecan Hydrochloride Liposome); Ontak (Denileukin Diftitox); Opdivo (Nivolumab); OPPA; Osimertinib; Oxaliplatin; Paclitaxel; Paclitaxel Albumin-stabilized Nanoparticle Formulation; PAD; Palbociclib; Palifermin; Palonosetron Hydrochloride; Palonosetron Hydrochloride and Netupitant; Pamidronate Disodium; Panitumumab; Panobinostat; Paraplat (Carboplatin); Paraplatin (Carboplatin); Pazopanib Hydrochloride; PCV; PEB; Pegaspargase; Pegfilgrastim; Peginterferon Alfa-2b; PEG-Intron (Peginterferon Alfa-2b); Pembrolizumab; Pemetrexed Disodium; Perjeta (Pertuzumab); Pertuzumab; Platinol (Cisplatin); Platinol-AQ (Cisplatin); Plerixafor; Pomalidomide; Pomalyst (Pomalidomide); Ponatinib Hydrochloride; Portrazza (Necitumumab); Pralatrexate; Prednisone; Procarbazine Hydrochloride; Proleukin (Aldesleukin); Prolia (Denosumab); Promacta (Eltrombopag Olamine); Propranolol Hydrochloride; Provenge (Sipuleucel-T); Purinethol (Mercaptopurine); Purixan (Mercaptopurine); Radium 223 Dichloride; Raloxifene Hydrochloride; Ramucirumab; Rasburicase; R-CHOP; R-CVP; Recombinant Human Papillomavirus (HPV) Bivalent Vaccine; Recombinant Human Papillomavirus (HPV) Nonavalent Vaccine; Recombinant Human Papillomavirus (HPV) Quadrivalent Vaccine; Recombinant Interferon Alfa-2b; Regorafenib; Relistor (Methylnaltrexone Bromide); R-EPOCH; Revlimid (Lenalidomide); Rheumatrex (Methotrexate); Ribociclib; R-ICE; Rituxan (Rituximab); Rituximab; Rolapitant Hydrochloride; Romidepsin; Romiplostim; Rubidomycin (Daunorubicin Hydrochloride); Rubraca (Rucaparib Camsylate); Rucaparib Camsylate; Ruxolitinib Phosphate; Sclerosol Intrapleural Aerosol (Talc); Siltuximab; Sipuleucel-T; Somatuline Depot (Lanreotide Acetate); Sonidegib; Sorafenib Tosylate; Sprycel (Dasatinib); STANFORD V; Sterile Talc Powder (Talc); Steritalc (Talc); Stivarga (Regorafenib); Sunitinib Malate; Sutent (Sunitinib Malate); Sylatron (Peginterferon Alfa-2b); Sylvant (Siltuximab); Synribo (Omacetaxine Mepesuccinate); Tabloid (Thioguanine); TAC; Tafinlar (Dabrafenib); Tagrisso (Osimertinib); Talc; Talimogene Laherparepvec; Tamoxifen Citrate; Tarabine PFS (Cytarabine); Tarceva (Erlotinib Hydrochloride); Targretin (Bexarotene); Tasigna (Nilotinib); Taxol (Paclitaxel); Taxotere (Docetaxel); Tecentriq (Atezolizumab); Temodar (Temozolomide); Temozolomide; Temsirolimus; Thalidomide; Thalomid (Thalidomide); Thioguanine; Thiotepa; Tolak (Fluorouracil-Topical); Topotecan Hydrochloride; Toremifene; Torisel (Temsirolimus); Tositumomab and Iodine I 131 Tositumomab; Totect (Dexrazoxane Hydrochloride); TPF; Trabectedin; Trametinib; Trastuzumab; Treanda (Bendamustine Hydrochloride); Trifluridine and Tipiracil Hydrochloride; Trisenox (Arsenic Trioxide); Tykerb (Lapatinib Ditosylate); Unituxin (Dinutuximab); Uridine Triacetate; VAC; Vandetanib; VAMP; Varubi (Rolapitant Hydrochloride); Vectibix (Panitumumab); Velban (Vinblastine Sulfate); Velcade (Bortezomib); Velsar (Vinblastine Sulfate); Vemurafenib; Venclexta (Venetoclax); Venetoclax; Viadur (Leuprolide Acetate); Vidaza (Azacitidine); Vinblastine Sulfate; Vincasar PFS (Vincristine Sulfate); Vincristine Sulfate; Vincristine Sulfate Liposome; Vinorelbine Tartrate; VIP; Vismodegib; Vistogard (Uridine Triacetate); Voraxaze (Glucarpidase); Vorinostat; Votrient (Pazopanib Hydrochloride); Wellcovorin (Leucovorin Calcium); Xalkori (Crizotinib); Xeloda (Capecitabine); XELIRI; XELOX; Xgeva (Denosumab); Xofigo (Radium 223 Dichloride); Xtandi (Enzalutamide); Yervoy (Ipilimumab); Yondelis (Trabectedin); Zaltrap (Ziv-Aflibercept); Zarxio (Filgrastim); Zelboraf (Vemurafenib); Zevalin (Ibritumomab Tiuxetan); Zinecard (Dexrazoxane Hydrochloride); Ziv-Aflibercept; Zofran (Ondansetron Hydrochloride); Zoladex (Goserelin Acetate); Zoledronic Acid; Zolinza (Vorinostat); Zometa (Zoledronic Acid); Zydelig (Idelalisib); Zykadia (Ceritinib); or Zytiga (Abiraterone Acetate).

Cancer

Methods and compositions as described herein can be used for the prevention, treatment, or slowing the progression of cancer or tumor growth. For example, the cancer can be Acute Lymphoblastic Leukemia (ALL); Acute Myeloid Leukemia (AML); Adrenocortical Carcinoma; AIDS-Related Cancers; Kaposi Sarcoma (Soft Tissue Sarcoma); AIDS-Related Lymphoma (Lymphoma); Primary CNS Lymphoma (Lymphoma); Anal Cancer; Appendix Cancer; Gastrointestinal Carcinoid Tumors; Astrocytomas; Atypical Teratoid/Rhabdoid Tumor, Childhood, Central Nervous System (Brain Cancer); Basal Cell Carcinoma of the Skin; Bile Duct Cancer; Bladder Cancer; Bone Cancer (including Ewing Sarcoma and Osteosarcoma and Malignant Fibrous Histiocytoma); Brain Tumors; Breast Cancer; Bronchial Tumors; Burkitt Lymphoma; Carcinoid Tumor (Gastrointestinal); Childhood Carcinoid Tumors; Cardiac (Heart) Tumors; Central Nervous System cancer; Atypical Teratoid/

Rhabdoid Tumor, Childhood (Brain Cancer); Embryonal Tumors, Childhood (Brain Cancer); Germ Cell Tumor, Childhood (Brain Cancer); Primary CNS Lymphoma; Cervical Cancer; Cholangiocarcinoma; Bile Duct Cancer Chordoma; Chronic Lymphocytic Leukemia (CLL); Chronic Myelogenous Leukemia (CML); Chronic Myeloproliferative Neoplasms; Colorectal Cancer; Craniopharyngioma (Brain Cancer); Cutaneous T-Cell; Ductal Carcinoma In Situ (DCIS); Embryonal Tumors, Central Nervous System, Childhood (Brain Cancer); Endometrial Cancer (Uterine Cancer); Ependymoma, Childhood (Brain Cancer); Esophageal Cancer; Esthesioneuroblastoma; Ewing Sarcoma (Bone Cancer); Extracranial Germ Cell Tumor; Extragonadal Germ Cell Tumor; Eye Cancer; Intraocular Melanoma; Intraocular Melanoma; Retinoblastoma; Fallopian Tube Cancer; Fibrous Histiocytoma of Bone, Malignant, or Osteosarcoma; Gallbladder Cancer; Gastric (Stomach) Cancer; Gastrointestinal Carcinoid Tumor; Gastrointestinal Stromal Tumors (GIST) (Soft Tissue Sarcoma); Germ Cell Tumors; Central Nervous System Germ Cell Tumors (Brain Cancer); Childhood Extracranial Germ Cell Tumors; Extragonadal Germ Cell Tumors; Ovarian Germ Cell Tumors; Testicular Cancer; Gestational Trophoblastic Disease; Hairy Cell Leukemia; Head and Neck Cancer; Heart Tumors; Hepatocellular (Liver) Cancer; Histiocytosis, Langerhans Cell; Hodgkin Lymphoma; Hypopharyngeal Cancer; Intraocular Melanoma; Islet Cell Tumors; Pancreatic Neuroendocrine Tumors; Kaposi Sarcoma (Soft Tissue Sarcoma); Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Lymphoma; Male Breast Cancer; Malignant Fibrous Histiocytoma of Bone or Osteosarcoma; Melanoma; Melanoma, Intraocular (Eye); Merkel Cell Carcinoma (Skin Cancer); Mesothelioma, Malignant; Metastatic Cancer; Metastatic Squamous Neck Cancer with Occult Primary; Midline Tract Carcinoma Involving NUT Gene; Mouth Cancer; Multiple Endocrine Neoplasia Syndromes; Multiple Myeloma/Plasma Cell Neoplasms; Mycosis Fungoides (Lymphoma); Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip or Oral Cavity Cancer; Oropharyngeal Cancer; Osteosarcoma and Malignant Fibrous Histiocytoma of Bone; Ovarian Cancer Pancreatic Cancer; Pancreatic Neuroendocrine Tumors (Islet Cell Tumors); Papillomatosis; Paraganglioma; Paranasal Sinus and Nasal Cavity Cancer; Parathyroid Cancer; Penile Cancer; Pharyngeal Cancer; Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer Renal Cell (Kidney) Cancer; Retinoblastoma; Rhabdomyosarcoma, Childhood (Soft Tissue Sarcoma); Salivary Gland Cancer; Sarcoma; Childhood Rhabdomyosarcoma (Soft Tissue Sarcoma); Childhood Vascular Tumors (Soft Tissue Sarcoma); Ewing Sarcoma (Bone Cancer); Kaposi Sarcoma (Soft Tissue Sarcoma); Osteosarcoma (Bone Cancer); Uterine Sarcoma; Sezary Syndrome (Lymphoma); Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; T-Cell Lymphoma, Cutaneous; Lymphoma; Mycosis Fungoides and Sezary Syndrome; Testicular Cancer; Throat Cancer; Nasopharyngeal Cancer; Oropharyngeal Cancer; Hypopharyngeal Cancer; Thymoma and Thymic Carcinoma; Thyroid Cancer; Thyroid Tumors; Transitional Cell Cancer of the Renal Pelvis and Ureter (Kidney (Renal Cell) Cancer); Ureter and Renal Pelvis; Transitional Cell Cancer (Kidney (Renal Cell) Cancer; Urethral Cancer; Uterine Cancer, Endometrial; Uterine Sarcoma; Vaginal Cancer; Vascular Tumors (Soft Tissue Sarcoma); Vulvar Cancer; or Wilms Tumor. Brain or spinal cord tumors can be acoustic neuroma; astrocytoma, atypical teratoid rhabdoid tumor (ATRT); brain stem glioma, chordoma; chondrosarcoma; choroid plexus; CNS lymphoma; craniopharyngioma; cysts; ependymoma; ganglioglioma; germ cell tumor; glioblastoma (GBM); glioma, hemangioma; juvenile pilocytic astrocytoma (JPA); lipoma; lymphoma; medulloblastoma; meningioma; metastatic brain tumor; neurilemmomas; neurofibroma; neuronal & mixed neuronal-glial tumors; non-Hodgkin lymphoma; oligoastrocytoma; oligodendroglioma; optic nerve glioma, pineal tumor; pituitary tumor; primitive neuroectodermal (PNET); rhabdoid tumor; or schwannoma. An astrocytoma can be grade I pilocytic astrocytoma, grade II—low-grade astrocytoma, grade III anaplastic astrocytoma, or grade IV glioblastoma (GBM), or a juvenile pilocytic astrocytoma. A glioma can be a brain stem glioma, ependymoma, mixed glioma, optic nerve glioma, or subependymoma.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10:0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Active compounds are administered at a therapeutically effective dosage sufficient to treat a condition associated with a condition in a patient. For example, the efficacy of a compound can be evaluated in an animal model system that may be predictive of efficacy in treating the disease in a human or another animal, such as the model systems shown in the examples and drawings.

An effective dose range of a therapeutic can be extrapolated from effective doses determined in animal studies for a variety of different animals. In general a human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in more accurate HED values, which are based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are peculiar to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a subject may be determined by physical and physiological factors such as type of animal treated, age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

Screening

Also provided are methods for screening for BET inhibitors that increase chemotherapy potency or reduce chemotherapy resistance.

The subject methods find use in the screening of a variety of different candidate molecules (e.g., potentially therapeutic candidate molecules).

Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character xlog P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character xlog P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical successful if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a BET inhibitor and, optionally, a chemotherapeutic agent. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10:0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10:0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has,"

"having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Self-Reporting Transposons Enable Simultaneous Readout of Gene Expression and Transcription Factor Binding in Single Cells This example describes the discovery of bromodomain-dependent cell-state transitions in leukemic cells, a novel genetic element that can be mapped from mRNA and directed by DNA-binding proteins, combined gene expression and transcription factor binding data from single cells, and multiple transcription factors mapped in several cell lines and the mouse cortex.

Figure 6A:
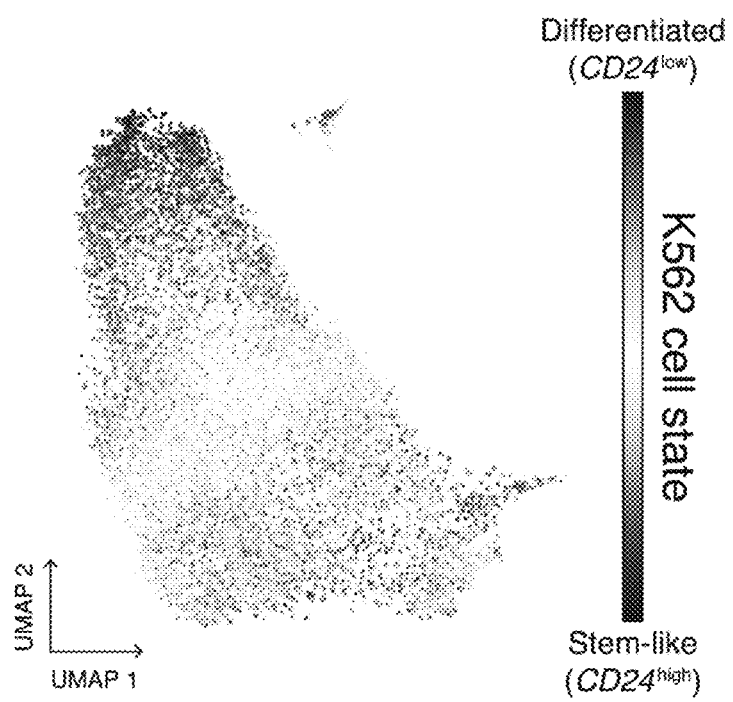
Figure 13A:
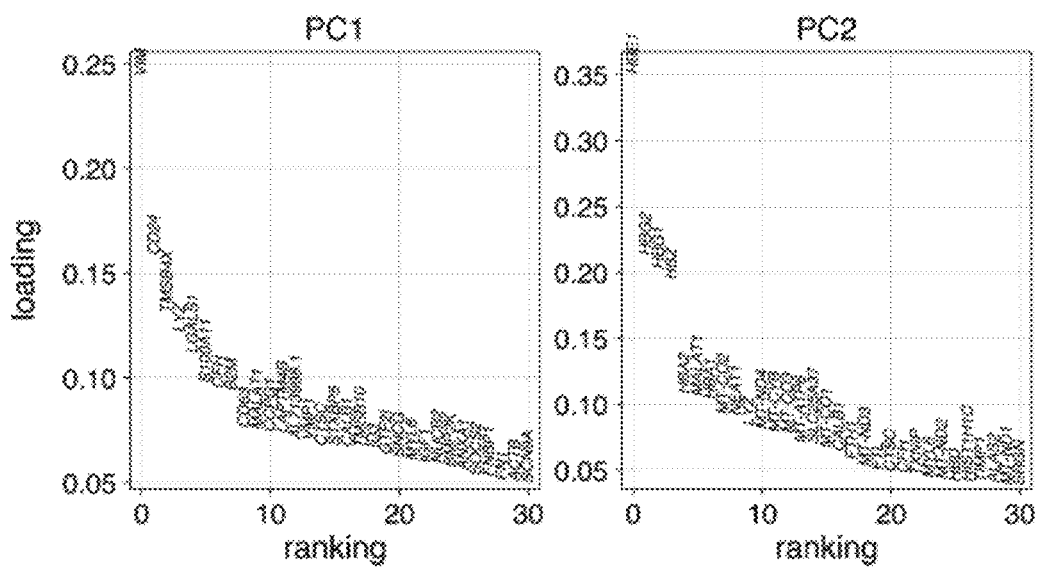
FIG. 13A-FIG. 13G. Clustering of K562 Cells into Stem-like and Differentiated States, Related to FIG. 6. (A) Principal component analysis of K562 scRNA-seq data. (B) Relative expression levels of highest-ranking genes in PC1 (top) and PC2 (bottom). (C) Gaussian mixture modeling of a cell-state score to define stem-like and differentiated K562 clusters. (D) Visualization of assigned cell clusters in the UMAP projection. (E) Specific expression of CD24 and HBZ in the stem-like and differentiated clusters, respectively. (F) Genome browser view of scCC in the stem-like and differentiated clusters alongside bulk BRD4 and H3K27ac ChIP-seq as well as RNA Pol II ChIA-PET. (G) Expression of VMP1 and PVT1 in the stem-like and differentiated clusters. PC: principal component.
Figure 13B:
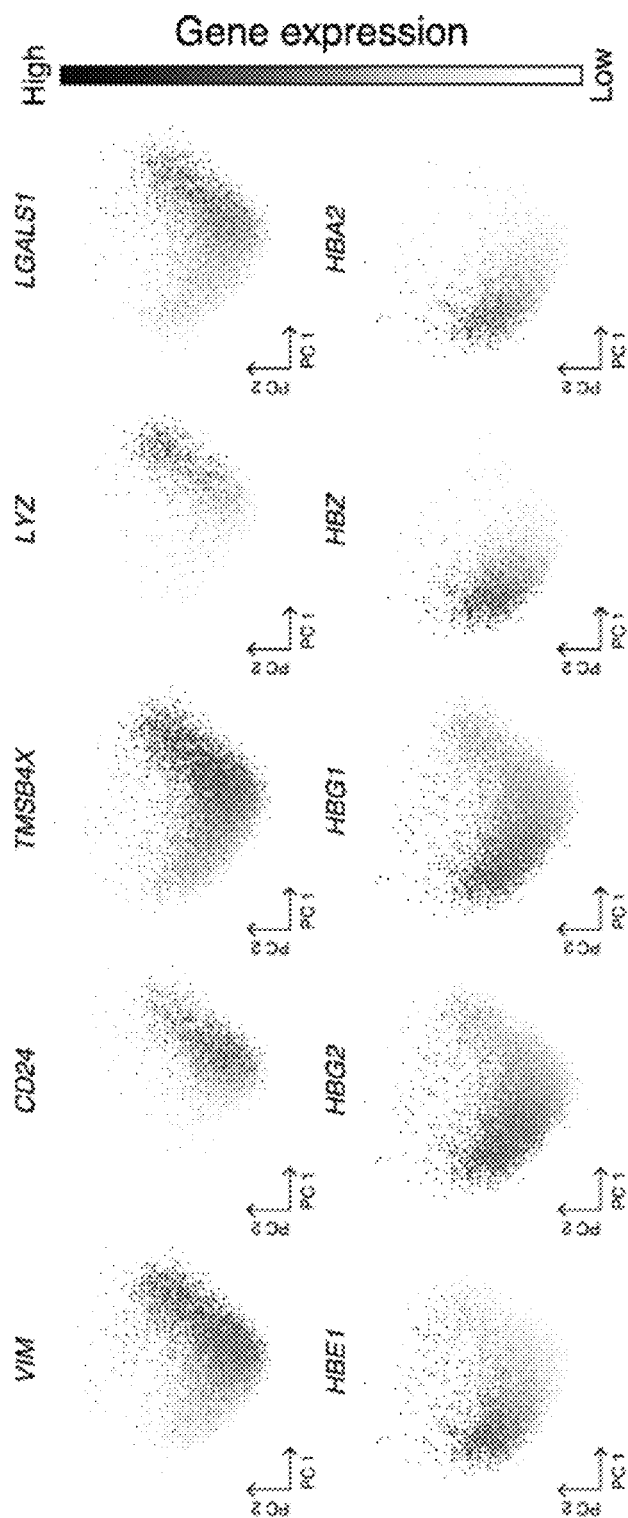
Figure 13C:
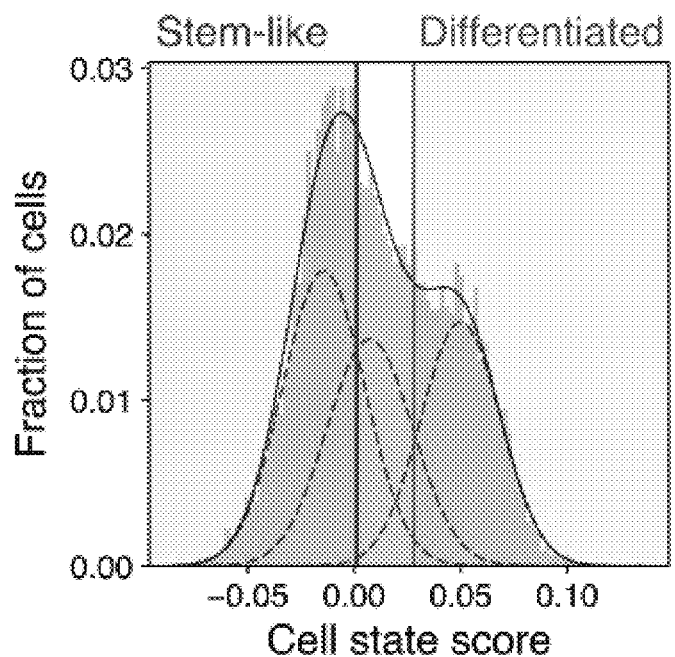
Figure 13D:
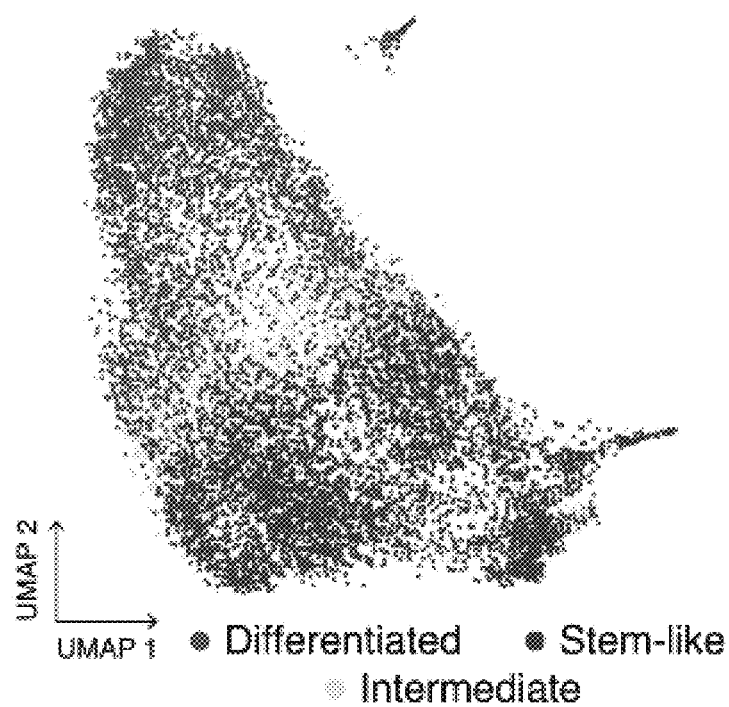
Figure 13E:
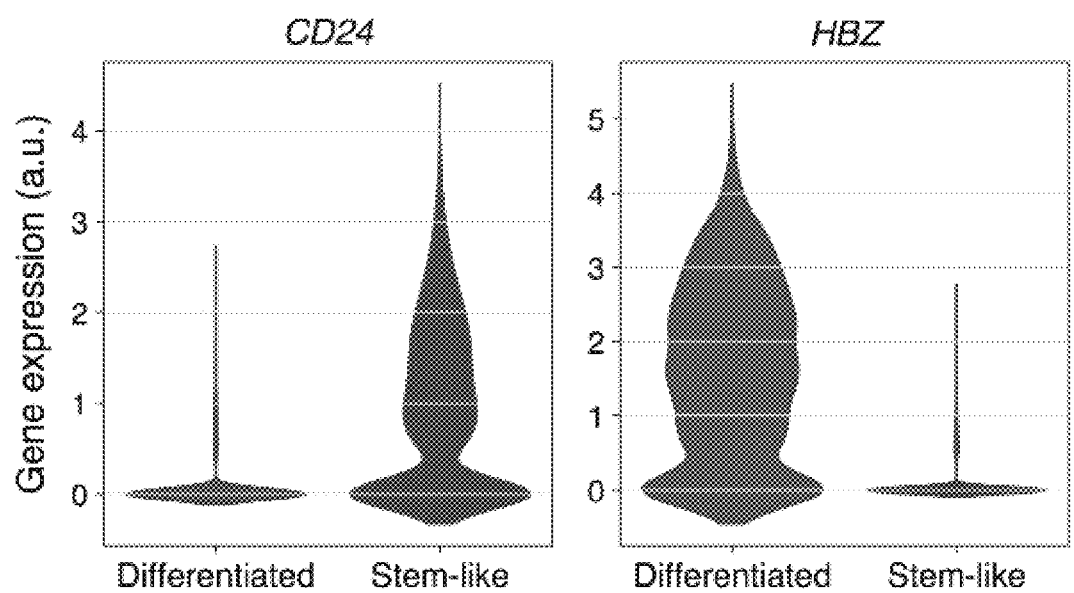

Details of the experiments are detailed in the below Results, Discussion, and Methods sections. Below is a summary of pertinent results. K562 is a chronic myelogenous leukemia (CML) cell line first isolated in 1970 (Lozzio and Lozzio, 1975) and has been a workhorse of molecular biology ever since (Zhou et al., 2019). Recently, K562 cultures have been shown to be mixtures of a stem-like state characterized by high levels of the surface marker CD24, and a more differentiated, erythroleukemic state marked by low CD24 expression, with individual cells dynamically oscillating between these two extremes (Litzenburger et al., 2017). Since we profiled BRD4 binding in K562 cells with scCC, we wondered whether we could see evidence of these two states in the scRNA-seq data. Principal components analysis (PCA) of single cell gene expression (FIG. 13A) revealed CD24 as one of the top genes in PC1, while PC2 was enriched in hemoglobin genes, particularly the fetal-specific markers HBE1 and HBZ. Furthermore, the expression of top PC1 and PC2 genes appear to be anticorrelated: cells that strongly expressed CD24 are not likely to express HBZ, and vice-versa (FIG. 13B), suggesting mutually exclusive states. Scoring single cells on a subset of top PC genes revealed a gradient of cell states along a stem-like-to-differentiated axis (FIG. 6A). We then clustered cells on the basis of this state score to define stem-like and differentiated populations (FIG. 13C-D), which faithfully recapitulate the expression differences detected by PCA (FIG. 13E).

Figure 6B:
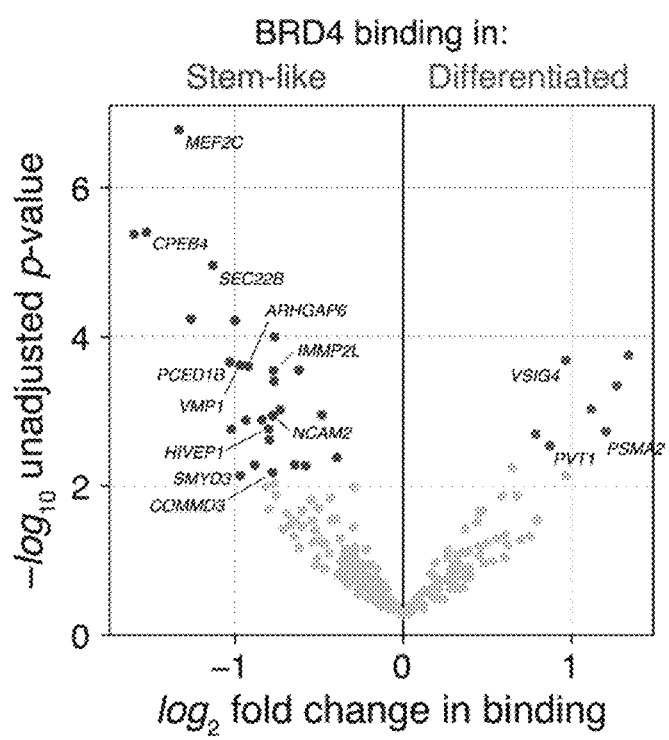
Figure 13F:
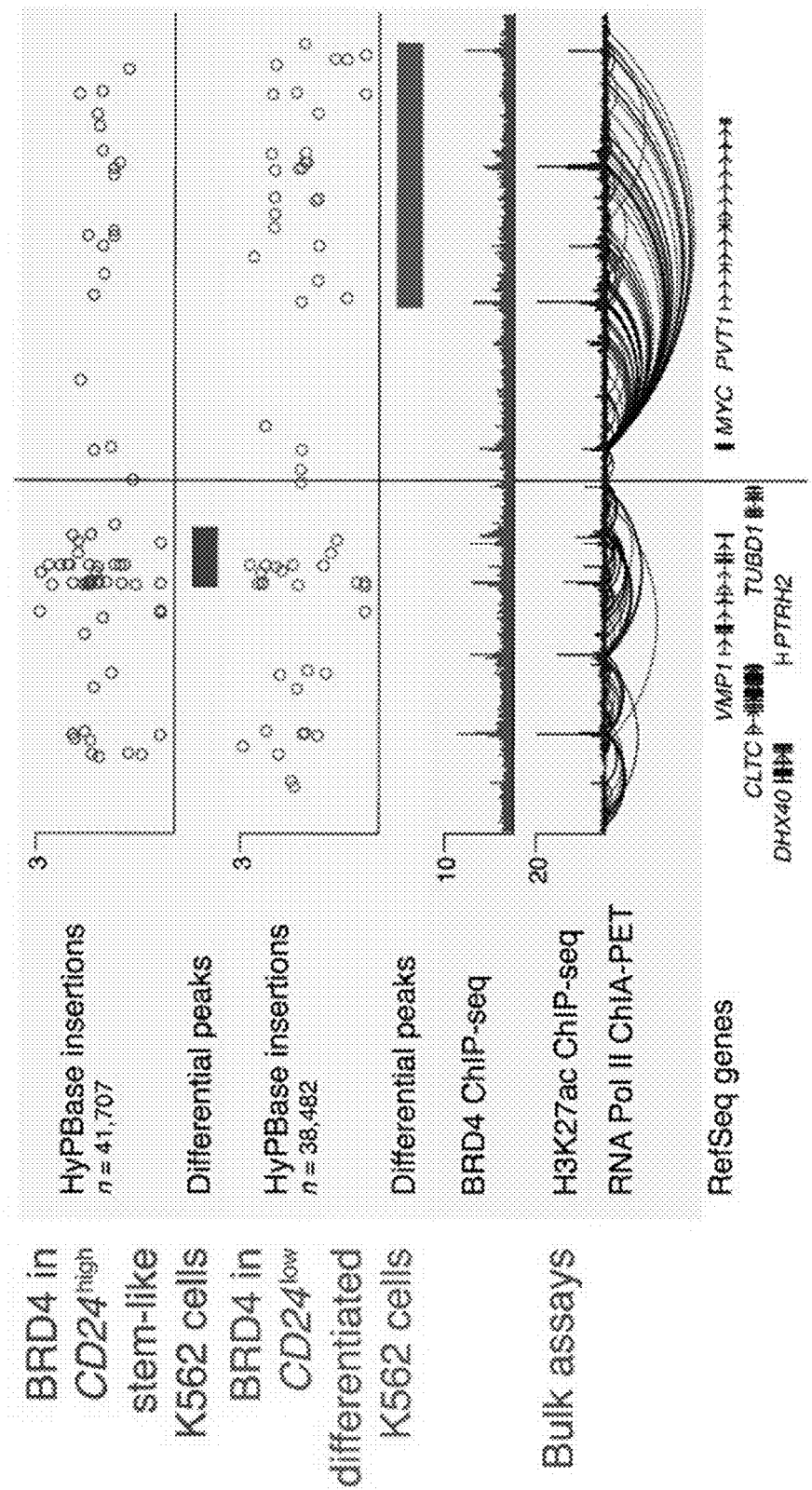
Figure 13G:
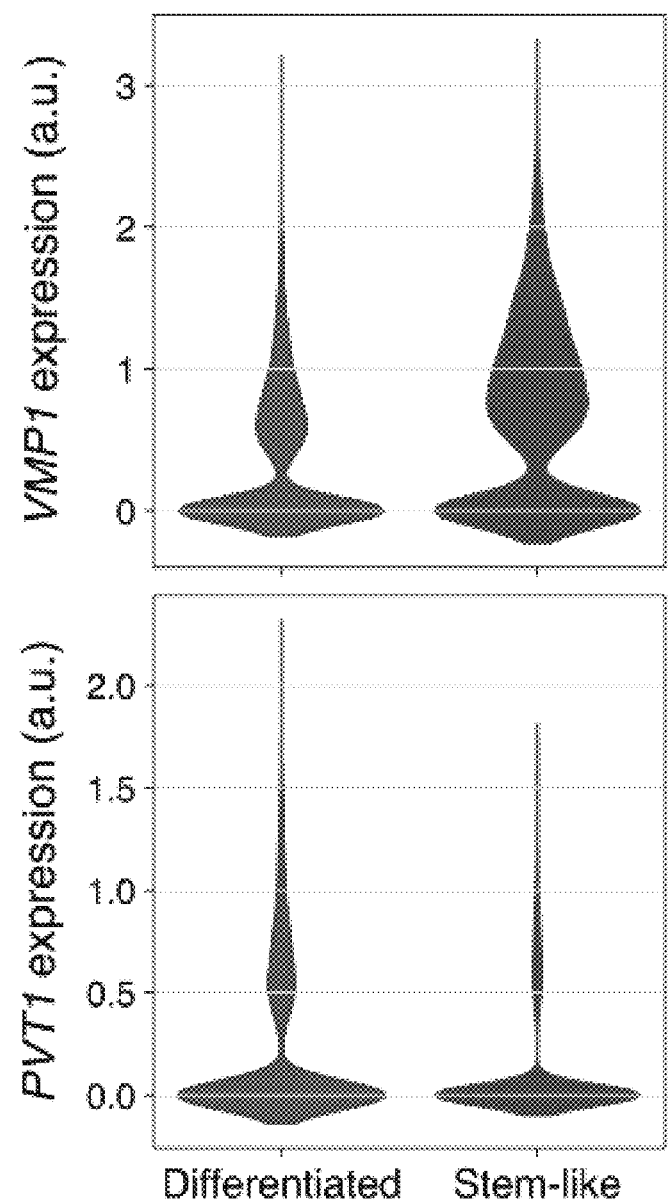
Figure 14A:
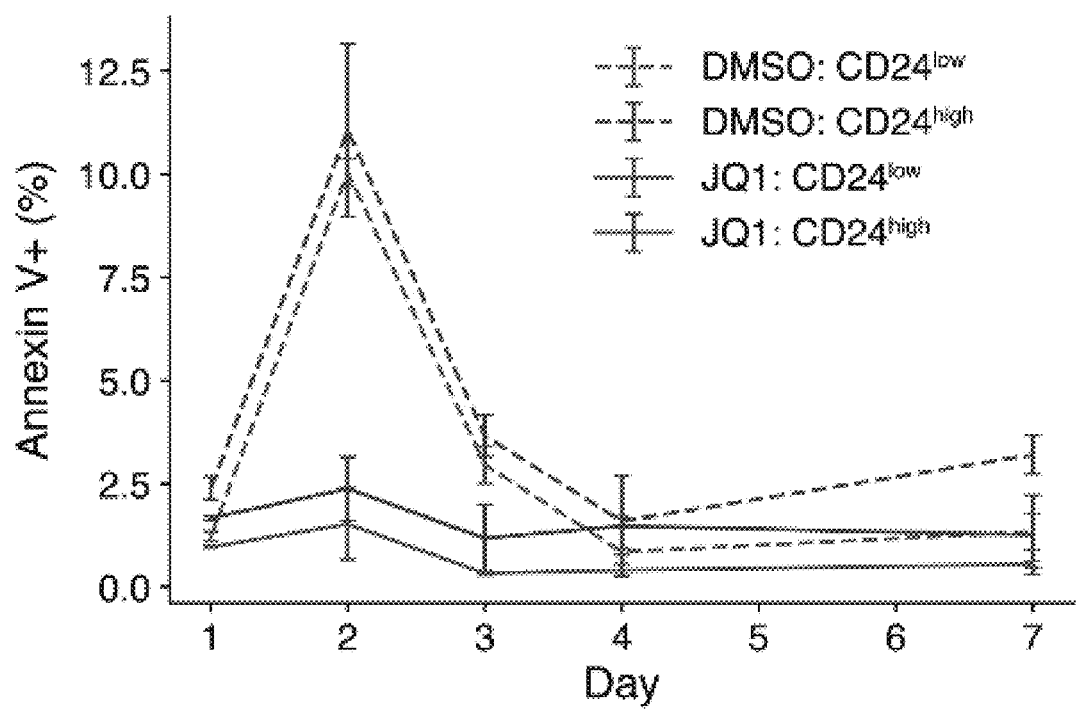
FIG. 14A-FIG. 14H. Validation of Bromodomain-Dependent K562 Cell States, Related to FIG. 6. (A) Annexin V staining in $CD24^{high}$ (red) or $CD24^{low}$ (blue) K562 cells treated with DMSO (dashed line) or JQ1 (solid line) over a seven-day time course. (B) Genome browser view of the CD24 locus. (C) qRT-PCR for MYC and CD24 expression levels in bulk K562 cells treated with JQ1 relative to DMSO-treated controls. (D) Expression changes in BRD2, BRD3, and BRD4 in K562 cells transduced with dCas9-KRAB and BRD4 CRISPRi gRNA (Welch's t test $p<0.05$). (E) Annexin V and PI co-staining in cells subjected to either non-targeting (top) or BRD4 (bottom) CRISPRi followed by either DMSO (left) or imatinib (right) treatment. (F) Average percent of annexin V/PI double positive cells in either the non-targeted or BRD4 CRISPRi replicates, stratified by either DMSO or imatinib exposure (two-way ANOVA $p<0.01$). (G) Percent of K562 cells in either G1 (left) or G2 (right) phase after 36 hours of drug treatment (one-way ANOVA with Dunnett's test *$p<0.05$, **$p<0.01$). (H) Percent of K562 cells in the $CD24^{high}$ state (left) after 5 days, and the percent of annexin V/PI double positive cells (right) at the same time point ($p<0.01$ in each instance, one-way ANOVA with Dunnett's test). Bars/points represent means; error bars denote standard deviations. Experiments were performed in triplicate. DMSO: dimethyl sulfoxide; n.s.: not significant; FC: fold change; SSC: side scatter; CRISPRi: CRISPR interference; NT: non-targeting; gRNA: guide RNA; IMA: imatinib; PI: propidium iodide.
Figure 14B:
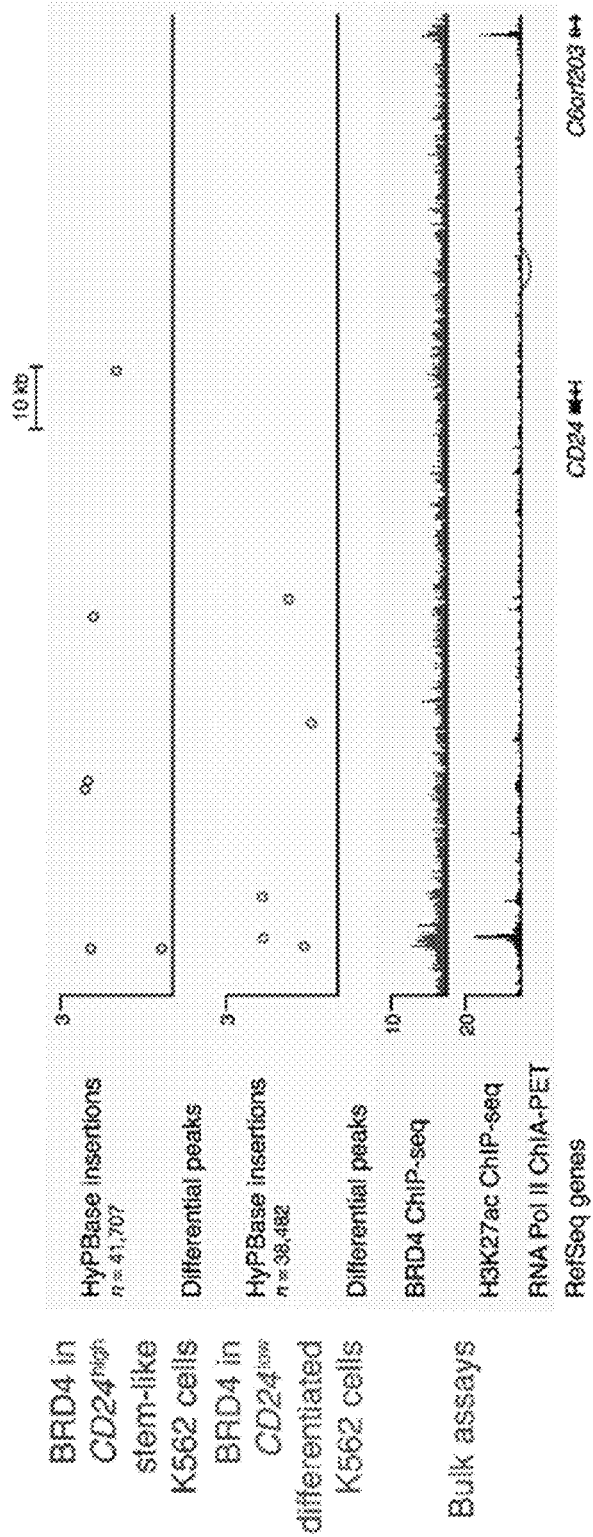
Figure 14C:
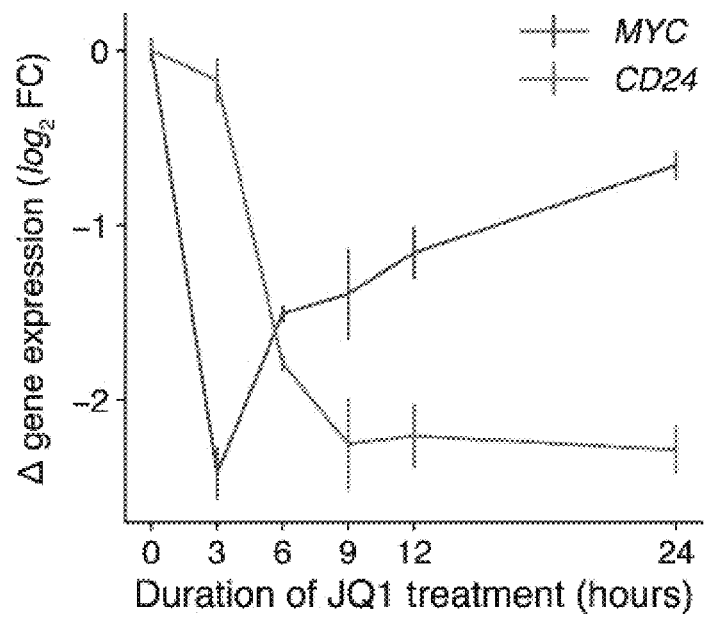
Figure 14D:
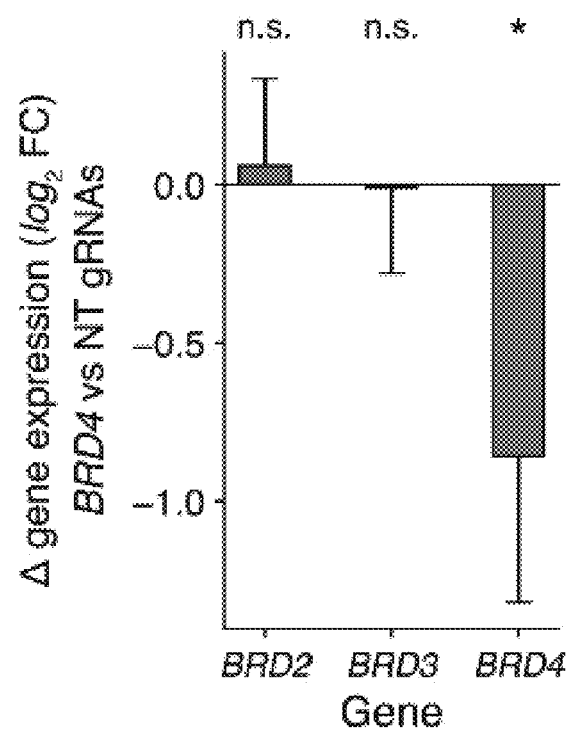
Figure 14E:
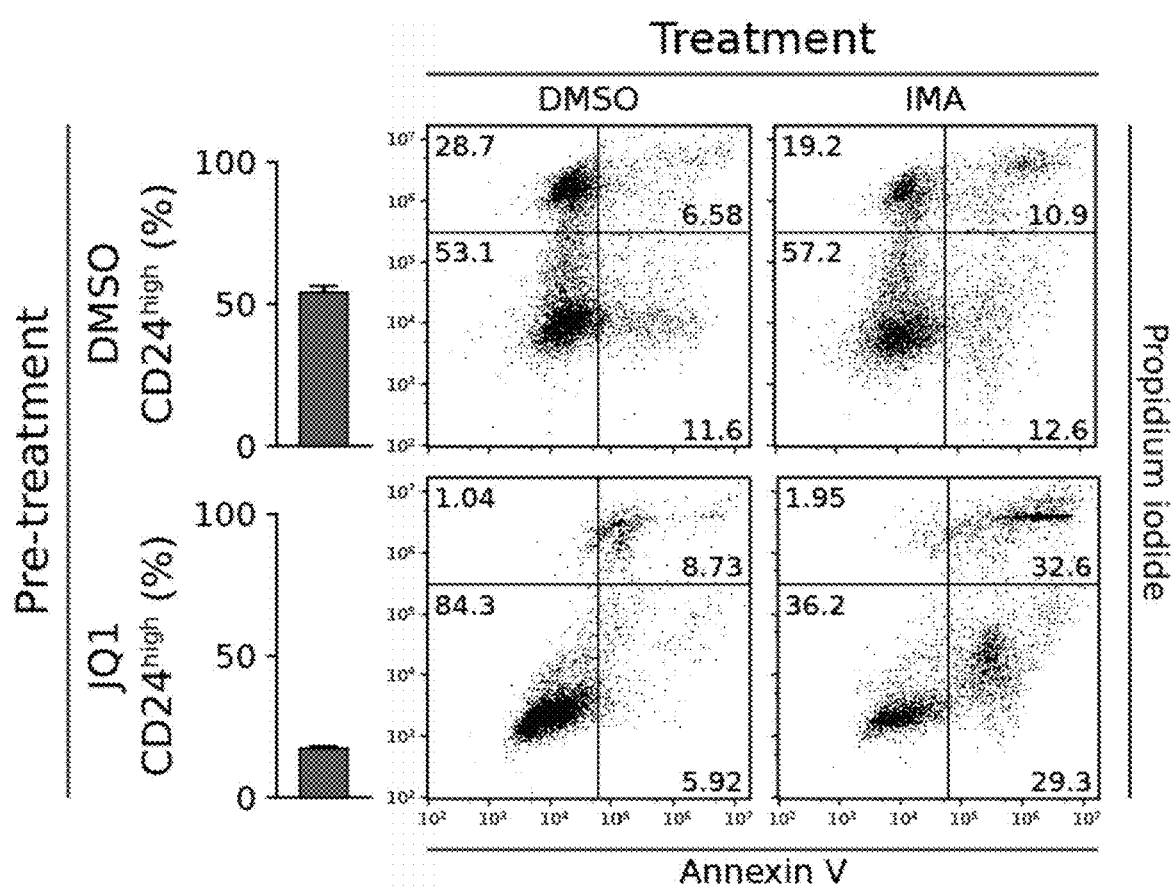
Figure 14F:
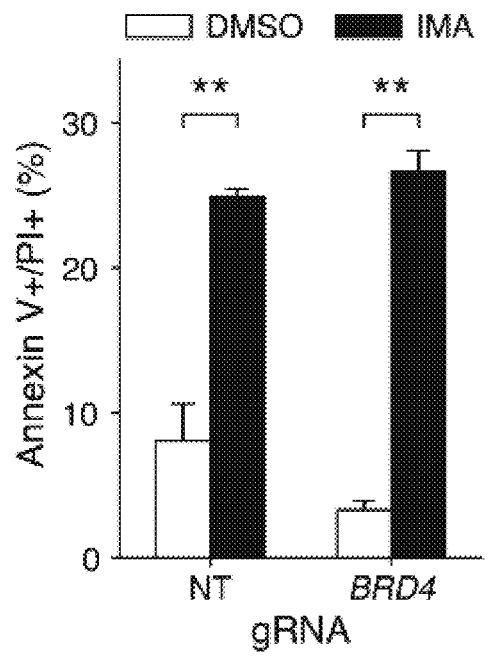

Super-enhancers and BRD4 are thought to mark genes important for specifying cell identity, and while the strongest evidence for this comes from comparisons between organ systems and sharply delineated disease states (Hnisz et al., 2013; Whyte et al., 2013), recent studies have shown that even closely related subpopulations of the same cell type can show subtle changes in BRD4 enrichment and enhancer utilization (Knoechel et al., 2014; Rathert et al., 2015). Therefore, we asked whether we could detect any differences in BRD4 binding between CD24high and CD24low cells. We first stratified scCC insertions by cell state, assigning 41,707 to the stem-like state and 38,482 to the differentiated cluster (FIG. 14F). We then analyzed the peaks generated across all K562 cells and quantified differential binding between the two clusters. Indeed, we found multiple peaks that showed significant differential binding at a false-discovery rate threshold of 10% (FIG. 6B). We corroborated these hits by comparing our peak calls to bulk BRD4 and H3K27ac ChIP-seq data, as well as to RNA pol II ChIA-PET data, which connects putative enhancers to actively transcribed genes (Fullwood et al., 2009). We highlight two genes that showed both differential binding and expression: VMP1, bound more in the CD24high stem-like cells; and PVT1, bound more in the differentiated, CD24low cells FIG. 13F-FIG. 13G). VMP1 overexpression is sufficient to induce autophagy (Ropolo et al., 2007), which is important for hematopoietic stem cell function (Folkerts et al., 2019; Ho et al., 2017) and may be one pathway recruited during these dynamic state transitions. PVT1 can act as both a tumor-suppressor and oncogene, in both instances acting on the MYC locus (Cho et al., 2018).

We next investigated whether the observed differences in BRD4 binding might be causally responsible for establishing these two cell states. Since modulation of this epigenetic reader has been previously shown to influence cell identity across a range of tissues (Di Micco et al., 2014; Kfoury et al., 2017; Najafova et al., 2017), we hypothesized that perturbing BRD4 would change the distribution of cells in the stem-like and differentiated states. Moreover, due to the asymmetric nature of significant hits in FIG. 6B, there is a subset of peaks specific to the CD24high state that are not shared by the CD24low state, suggesting that there may be a gene regulatory network that is recruited as cells transit from the differentiated to stem-like state and lost as they return. Thus, we predicted that not only should the distribution of CD24high/CD24low cells change upon BRD4 perturbation, but also that the stem-like CD24high population should be more susceptible to such a perturbation.

Figure 6C:
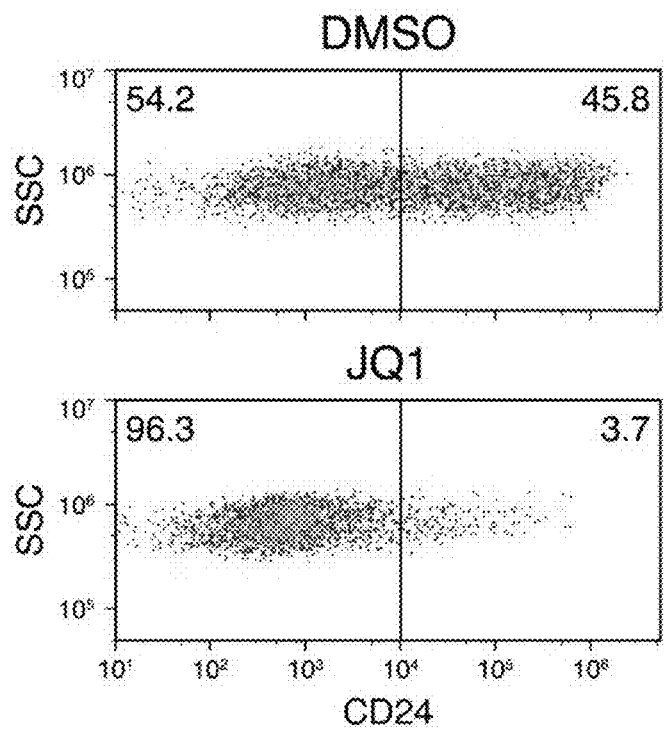
Figure 6D:
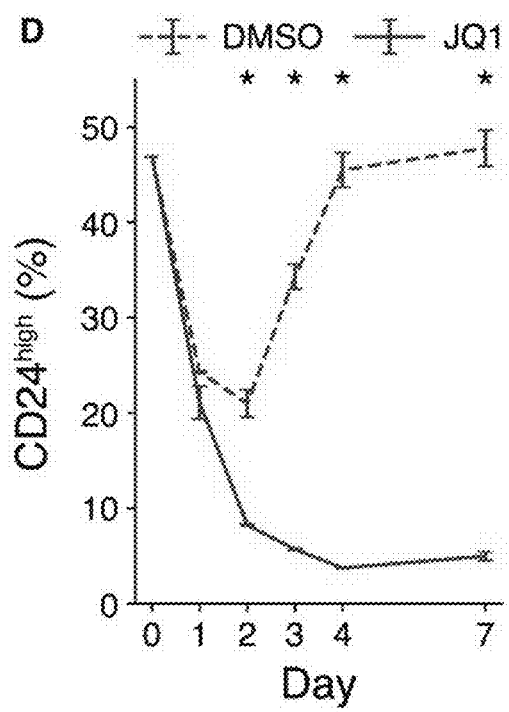

To test this hypothesis, we treated cells with the small molecule bromodomain inhibitor JQ1, commonly used to disrupt BRD4 binding and alter target gene expression (Delmore et al., 2011; Garcia-Carpizo et al., 2018; Lovén et al., 2013; Sdelci et al., 2019). We observed that JQ1 exposure was sufficient to shift the population from one containing equal proportions of CD24high/CD24low cells to one comprised of almost exclusively CD24low cells (>95% CD24low cells, FIG. 6C). A time course analysis showed that this conversion takes place rapidly over the first two days, plateaus at day four, and remains stable one week after treatment; in contrast the control cells remain evenly split between the two states at this timepoint (FIG. 6D; two-way ANOVA p<0.01). We ruled out the possibility that JQ1 is selectively cytotoxic to CD24high cells as there were no significant differences in levels of the early apoptotic marker annexin V between CD24high and CD24low cells, regardless of whether they had been exposed to JQ1 or DMSO (FIG. 14A; three-way ANOVA p=0.84). We also investigated whether CD24 is a direct target of BRD4, which would imply that the loss of CD24high cells does not reflect a true change in cell state but is, instead, a trivial transcriptional consequence of downregulating RD4 by JQ1. To do so, we examined genomic signals at the CD24 locus and did not find any prominent BRD4 binding sites, either by ChIP-seq or calling cards, or elevated levels of H3K27 acetylation in the vicinity of CD24 (FIG. 14B). We also compared the relative changes in mRNA levels of MYC, a known BRD4 target (Knoechel et al., 2014; Lovén et al., 2013; Rathert et al., 2015; Zuber et al., 2011), to that of CD24 during the first 24 hours of JQ1 exposure. Whereas MYC levels fell within the first 3 hours of exposure, transcript levels of CD24 decreased most precipitously somewhere between 3 and 9 hours after JQ1 induction (FIG. 14C). This delayed response suggests that CD24 is not a direct target of BRD4, but instead its expression changes as the result of downstream regulatory factors. These results argue that JQ1 treatment does not simply downregulate a cell surface marker, but rather perturbs transcriptional networks that ultimately include CD24.

Figure 6E:
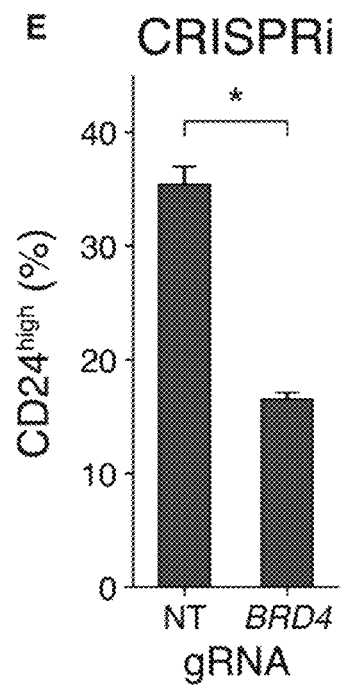

While JQ1 shows greatest affinity for BRD4, it does have some promiscuity toward other bromodomains, such as those of the related bromodomain and extraterminal domain (BET) proteins BRD2 and BRD3 (Filippakopoulos et al., 2010). Thus, it was possible that the observed state shift may be arising through off-target effects and not through BRD4 itself. To address this, we specifically downregulated BRD4 expression with CRISPRi using a dCas9-KRAB (Fulco et al., 2016; Xie et al., 2017) fusion directed to the BRD4 locus. We confirmed, with qRT-PCR, that our BRD4 guide RNA (gRNA) resulted in knockdown of BRD4 and not BRD2 nor BRD3 (FIG. 14D; Welch's t-test p<0.05). As with JQ1, we observed a significant decrease in the proportion of CD24high cells with the BRD4 gRNA compared to the non-targeting (NT) gRNA (FIG. 6E; Welch's t-test p<0.01), though not to the same levels as JQ1. This result suggests that BRD4 is necessary for the observed cell state dynamics between CD24high and CD24low K562 cells, though it is likely that other bromodomains also play a role.

Figure 6F:
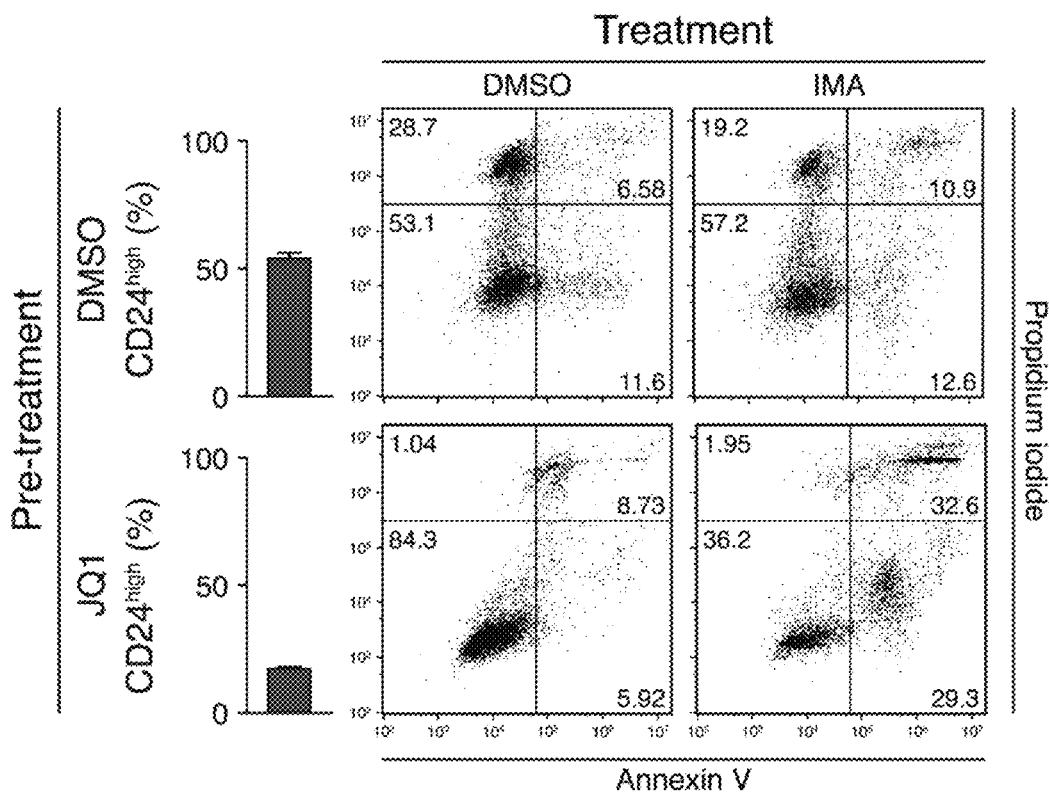

We next sought to obtain further evidence that bromodomain inhibition shifts K562 cell state by performing a direct functional assay. The CD24high/CD24low K562 cell states have been previously shown to have different chemosensitivities, with the latter population showing more apoptosis when exposed to imatinib (Litzenburger et al., 2017). We wondered whether bromodomain perturbation similarly increased imatinib sensitivity, or if its effect was restricted to modulating CD24. We tested this by first pre-treating K562 cells with either DMSO or JQ1 for five days. In the DMSO-treated group, the fraction of CD24high cells rose to 54% on average, while the mean for JQ1-treated cells was 17% (FIG. 6F). We then challenged each pretreatment group with either DMSO or imatinib and measured apoptosis by staining for annexin V and propidium iodide (PI). We observed a significant increase in annexin V/PI double positive cells in imatinib-treated cells over those pre-treated with DMSO (FIG. 6F-FIG. 6G; two-way ANOVA p<0.01), indicating that JQ1 sensitizes K562 cells to imatinib. We also found that BRD4 CRISPRi partially phenocopied this sensitization, though again not to the same effect size as JQ1 (FIG. 14E-FIG. 14F; Tukey's honestly significant difference p=0.68). This phenomenon is likely dosage dependent: in our experiments, CRISPRi reduced BRD4 mRNA levels by less than 50% (FIG. 14D), whereas JQ1, at this concentration, is expected to almost completely abolish BRD4 activity (Filippakopoulos et al., 2010). Thus, while a mild knockdown can reduce CD24 levels, a higher level of inhibition may be necessary to induce imatinib sensitivity. Nevertheless, these results establish that bromodomain inhibition functionally, in addition to phenotypically, shifts the underlying cell state of K562 cells.

Figure 14G:
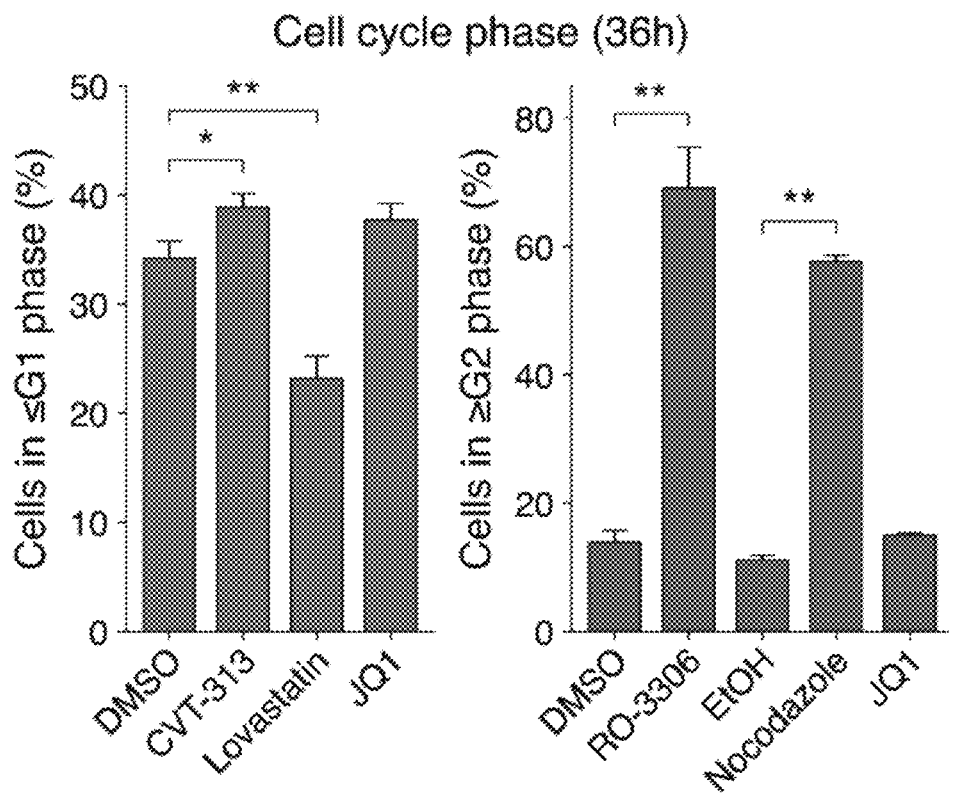
Figure 14H:
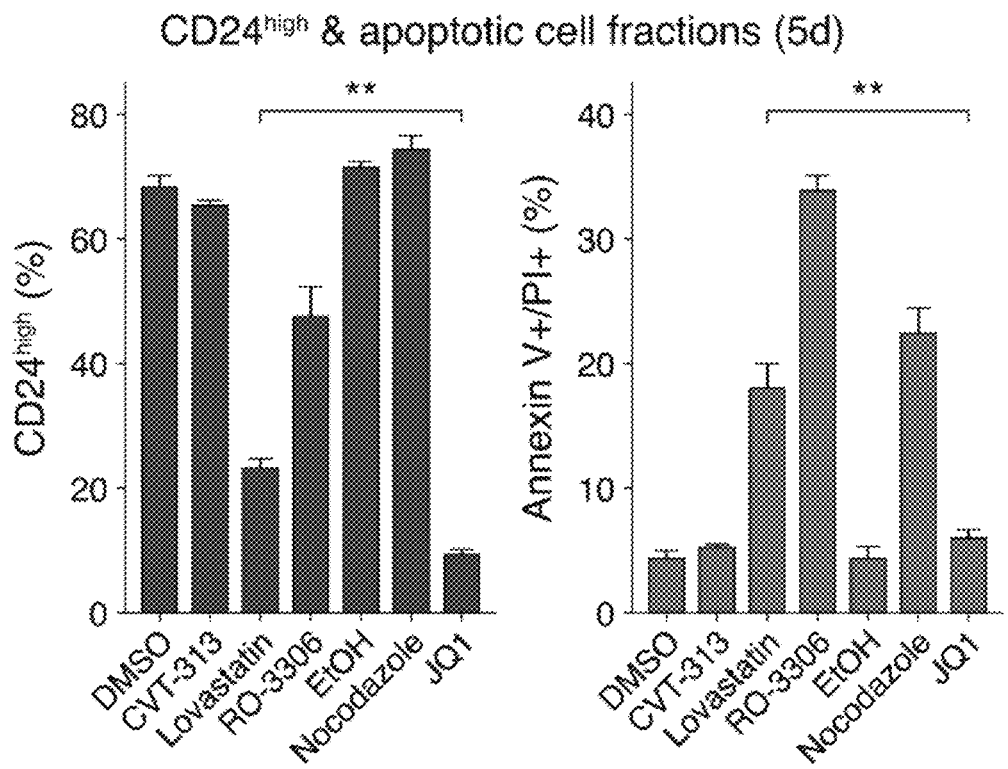

Finally, we asked whether the JQ1-induced K562 cell state shift could be a non-specific response to generic drug treatment. To test this, we treated K562 cultures with cell cycle inhibitors, another class of commonly used antineoplastic agents. We used lovastatin and nocodazole, two drugs classically used to synchronize cells in culture (Jackman and O'Connor, 1998), as well as the cyclin-dependent kinase inhibitors CVT-313 (Brooks et al., 1997) and RO-3306 (Vassilev et al., 2006). We first confirmed that all drugs perturbed cell cycle by altering the proportions of cells in either G1 or G2/M phase (FIG. 14G). CVT-313 caused a significant increase in G1 arrest cells (one-way ANOVA p<0.05) and both nocodazole and RO-3306 caused significant G2 arrest (one-way ANOVA p<0.01). While lovastatin has been reported to arrest cells in G1, in our hands it caused a significant decrease in G1 phase K562 cells (one-way ANOVA p<0.01). Cultures remained under drug treatment until five days had elapsed, at which point we measured CD24 levels and stained for apoptotic activity (FIG. 14H). JQ1 caused the greatest reduction in CD24high cells (one-way ANOVA p<0.01) and induced significantly less apoptosis than its closest competitor, lovastatin (one-way ANOVA p<0.01). While all cell cycle inhibitors caused cell death, the mitotic inhibitors nocodazole and RO-3306 had very few surviving cells after five days of treatment. Thus, JQ1's effect on cell state appears to be mediated by a unique mechanism of action that is not readily replicated by cell cycle perturbation.

SUMMARY

Cellular heterogeneity confounds in situ assays of transcription factor (TF) binding. Single-cell RNA sequencing (scRNA-seq) deconvolves cell types from gene expression, but no technology links cell identity to TF binding sites (TFBS) in those cell types. We present self-reporting transposons (SRTs) and use them in single-cell calling cards (scCC), a novel assay for simultaneously measuring gene expression and mapping TFBS in single cells. The genomic locations of SRTs are recovered from mRNA, and SRTs deposited by exogenous, TF-transposase fusions can be used to map TFBS. We then present scCC, which map SRTs from scRNA-seq libraries, simultaneously identifying cell types and TFBS in those same cells. We benchmark multiple TFs with this technique. Next, we use scCC to discover BRD4-mediated cell-state transitions in K562 cells. Finally, we map BRD4 binding sites in the mouse cortex at single-cell resolution, establishing a new method for studying TF biology in situ.

Introduction

Transcription factors (TFs) regulate the gene expression patterns that specify cell state (Gurdon, 2016; Hafler et al., 2012; Mizuguchi et al., 2001; Zhu et al., 2012). They are central to a number of critical developmental processes including the maintenance of pluripotency (Liu et al., 2008; Takahashi and Yamanaka, 2006), fate choice (Mizuguchi et al., 2001; Zhu et al., 2012), and embryogenesis (Fogarty et al., 2017). Perturbing TF activity can disrupt cellular development, homeostasis, or function, resulting in altered morphology (Gonen et al., 2018; Kvon et al., 2016), cellular transdifferentiation (Davis et al., 1987), or increased susceptibility to disease (Lee and Young, 2013). A better understanding of TF binding during development and homeostasis would provide insights into how cellular diversity arises and is maintained under normal and abnormal biological conditions.

Single-cell RNA sequencing (scRNA-seq) has emerged as the de facto approach for characterizing cellular diversity in complex tissues and organisms (Campbell et al., 2017; Cao et al., 2017; Fincher et al., 2018; Han et al., 2018; Karaiskos et al., 2017; Zeisel et al., 2015). Recently, multi-modal scRNA-seq technologies have emerged (Angermueller et al., 2016; Cao et al., 2018; Clark et al., 2018; Dey et al., 2015; Macaulay et al., 2015; Peterson et al., 2017; Stoeckius et al., 2017) linking transcriptional information to other genomic assays. These methods address the fact that, while scRNA-seq can describe the current state of a biological system, it alone cannot explain how that state arose. A notable lacuna in the single-cell repertoire is a method for jointly assaying transcriptome and TF binding. Such a method would lead to the genome-wide identification of TF binding sites across multiple cell types in complex tissues. Chromatin immunoprecipitation sequencing (ChIP-seq) is the most popular approach to studying TF binding (Johnson et al., 2007), and, while a number of antibody-based single-cell methods to detect DNA-protein contacts have been reported (Ai et al., 2019, Carter et al., 2019, Grosselin et al., 2019, Heiner et al., 2019, Harada et al., 2019, Kaya-Okur et al., 2019, Rotem et al., 2015, Wang et al., 2019), these techniques have generally mapped highly abundant proteins, such as modified histones and CTCF. DamID can recover TF binding sites by detecting nearby exogenously methylated adenines (Greil et al., 2006; Vogel et al., 2007), but in single cells it has only been used to study lamina-associated domains (Kind et al., 2013, 2015; Rooijers et al., 2019). A combined single-cell assay of DamID and transcriptome (scDam&T-seq) has been described (Rooijers et al., 2019) but is a plate-based assay that limits throughput. None of the other single-cell techniques that measure DNA-protein interactions simultaneously capture mRNA, restricting their use to predetermined cell types. Single-cell assays for transposase-accessible chromatin using sequencing (ATAC-seq; Buenrostro et al., 2015; Cao et al., 2018) could be used to identify nucleosome-free regions that may be bound by TFs, though they rely on motif inference to identify potential DNA binding proteins. These assays do not directly measure TF occupancy nor can they be used to study transcriptional regulators that bind DNA indirectly or non-specifically, such as chromatin remodelers.

We have previously developed transposon calling cards to assay TF binding (Wang et al., 2007, 2011, 2012a). This system relies on two components: a fusion between a TF and a transposase and a transposon carrying a reporter gene. The fusion transposase deposits transposons near TF binding sites, which are subsequently amplified from genomic DNA and sequenced. Thus, the redirected transposase leaves "calling cards" at the genomic locations it has visited, which can be identified later in time. The result is a genome-wide assay of all binding sites for that particular TF. In mammalian cells, we have heterologously expressed the piggyBac transposase (Ding et al., 2005) fused to the TF SP1 and shown that the resulting pattern of insertions reflects SP1's binding preferences (Wang et al., 2012a). However, this method was only feasible in bulk preparations of thousands of cells.

Here, we present single-cell calling cards (scCC), an extension of transposon calling cards that simultaneously profiles mRNA content and TF binding at single-cell resolution. The key component of our work is the self-reporting transposon (SRT), a novel element whose genomic location can be mapped from mRNA. We show that the RNA-based calling card method is more efficient than our standard DNA-based protocol and can be used to map TF binding sites with a directed transposase. We also demonstrate that the unfused piggyBac transposase, through its native affinity for the bromodomain TF BRD4, can be used to identify BRD4-bound super-enhancers (SEs). We then present the scCC method, which allows cell-type-specific mapping of SRTs from scRNA-seq libraries. Thus, in one experiment, we can cluster cells by transcriptional identity and identify TF binding sites within those cell types. We highlight the range of this technology using a breadth of TFs in a variety of cell lines. We then use scCC to discover bromodomain-dependent cell-state dynamics in K562 cells. Finally, we identify cell-type-specific BRD4 binding sites in vivo in the postnatal mouse cortex. These results demonstrate that scCC could be a broadly applicable tool to study specific TF binding interactions across multiple cell types within heterogeneous systems.

Results

SRTs Can Be Mapped from mRNA Instead of Genomic DNA

To combine scRNA-seq with calling cards, we first developed a transposon whose genomic location could be determined from mRNA. We created a piggyBac SRT by removing the polyadenylation signal (PAS) downstream of the reporter gene (FIG. 2A; Supplemental Methods) in the transposon. RNA polymerase II (Pol II) transcribes the SRT reporter and continues through the terminal repeat (TR) into the flanking genomic sequence. Thus, SRTs "self-report" their locations through the unique genomic sequence found in the 3' untranslated regions (UTRs) of the reporter gene transcripts. While previously published gene- or enhancer-trap transposons (Cadiñanos and Bradley, 2007) could also encode local positional information in RNA, they are resolution-limited to the nearest gene or enhancer, respectively.

In contrast, SRT-derived transcripts contain the transposon-genome junction, so insertions can be mapped with base-pair precision.

Figure 2A:
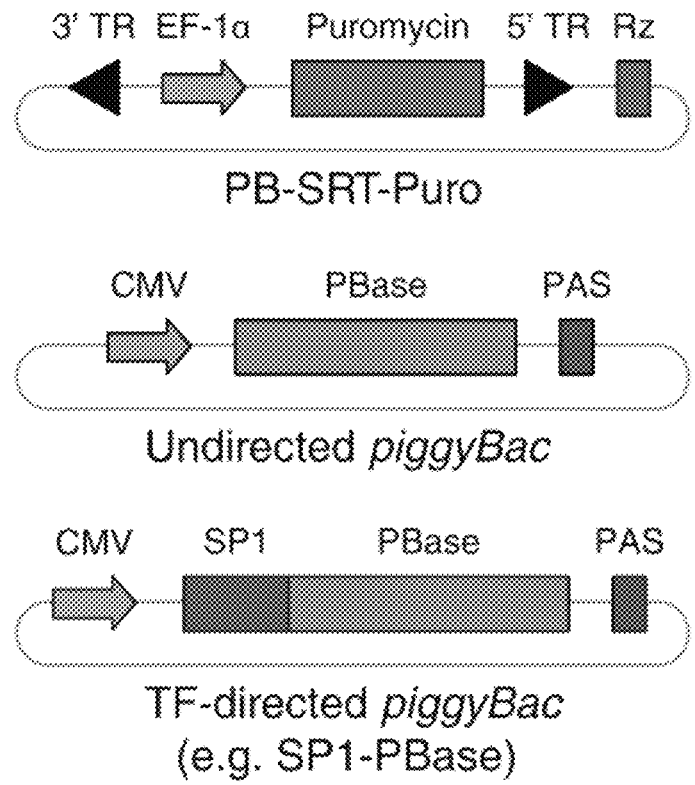
FIG. 2A-FIG. 2D. Self-Reporting Transposons Are Mapped More Efficiently from RNA Compared to DNA. (A) Schematics of a self-reporting piggyBac transposon with puromycin reporter gene (PB-SRT-Puro) and undirected (PBase) and SP1-directed (SP1-PBase) piggyBac transposases. (B) Molecular workflow for mapping SRTs from bulk RNA libraries. (C) Overlap of SRTs recovered by DNA- or RNA-based protocols in HCT-116 cells. (D) Distribution of insertions with respect to genetic annotation between SRT libraries prepared from either DNA or RNA. TR, terminal repeat; Puro, puromycin; PAS, polyadenylation signal.
Figure 2B:
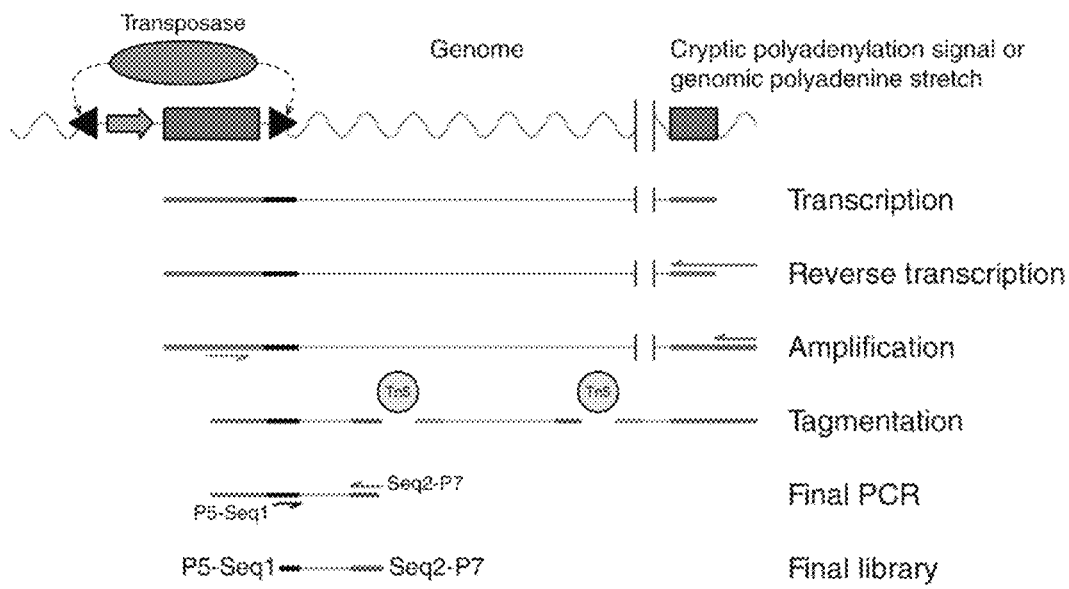

SRTs are mapped following reverse transcription (RT) and PCR amplification of self-reporting transcripts. These transcripts contain stretches of adenines that are derived from either cryptic PASs or templated propyladenine tracts in genomic DNA downstream of the SRT insertion site (FIG. 2B). We then use a modified tagmentation protocol to enrich for the transposon-genome junction (Methods). We confirmed SRTs generate reproducible libraries, require a functional transposase, and can be recovered from virtually any chromatin state (Supplemental Methods).

Figure 2C:
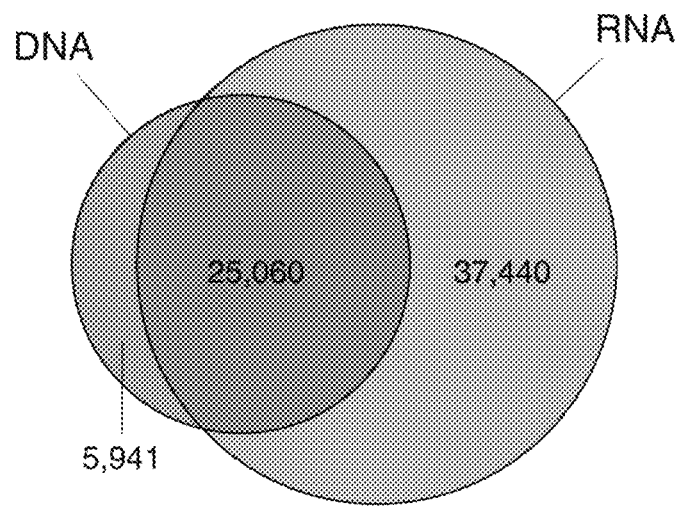
Figure 2D:
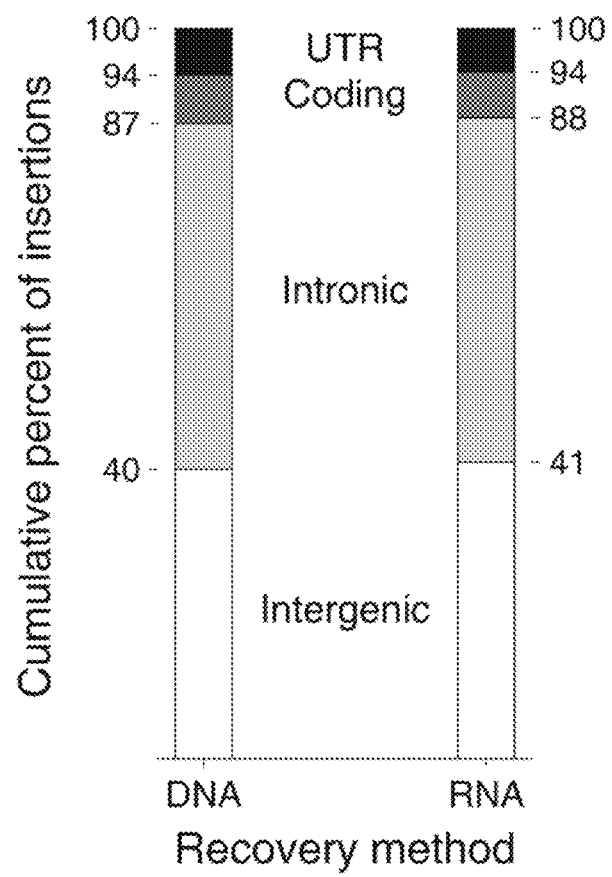

To compare how the new RNA-based approach fares against our standard DNA-based method (Wang et al., 2012a), we tested both protocols on the same population of cells. Our DNA-based library yielded 31,001 insertions, while the RNA-based protocol recovered 62,500 insertions (TABLE 1). Importantly, 80% of the insertions found by DNA calling cards were also recovered in the RNA-based library (25,060 insertions; FIG. 2C). Thus, at the level of individual transpositions, RNA-based mapping is highly sensitive. Moreover, the RNA protocol recovered a further 37,440 insertions that were not found in the DNA-based library. We analyzed the distribution of insertions by both genetic annotation (FIG. 2D) and chromatin state (Supplemental Methods) and found no appreciable differences in either case between the DNA and RNA libraries. Finally, we also confirmed that SRTs could still be used to study TF binding using established TF-piggyBac constructs and quantified the redirectability of these fusions (Supplemental Methods). Thus, RNA-based recovery of transposons appears to be unbiased with respect to our established, DNA-based protocol.

TABLE 1

Summary of bulk calling cards experiments, related to FIG. 2, FIG. 3, FIG. 5, FIG. 9 and Supplemental Methods.

| Sample | Construct | Modality | Replicates[a] | Insertions | Reads | Mean coverage |
|---|---|---|---|---|---|---|
| HCT-116 | SP1-PBase | DNA[b] | 1 | 31,001 | 21,975,948 | 708.9 |
| HCT-116 | SP1-PBase | RNA[b] | 1 | 62,500 | 14,993,901 | 239.9 |
| HCT-116 | PBase | RNA | 10 | 1,521,048 | 58,316,389 | 38.3 |
| HCT-116 | SP1-PBase | RNA | 10 | 410,588 | 35,526,586 | 86.5 |
| HCT-116 | HyPBase | RNA | 12 | 5,771,207 | 47,572,324 | 8.2 |
| HCT-116 | SP1-HyPBase | RNA | 11 | 2,029,931 | 40,214,827 | 19.8 |
| HCT-116 | SB100X | RNA | 12 | 26,515,072 | 67,650,985 | 2.6 |
| OCM-1A | HyPBase | RNA | 10 | 5,951,669 | 261,476,361 | 43.9 |
| OCM-1A | BAP1-HyPBase | RNA | 10 | 5,740,754 | 293,332,813 | 51.1 |

[a]Biological replicates.
[b]These experiments were used to assess DNA- vs. RNA-based recovery (FIG. 2C).

Clustering of Undirected piggyBac Insertions Identifies BRD4-Bound SEs

Previous studies have shown that undirected piggyBac preferentially inserts transposons near SEs (Yoshida et al., 2017), unique regulatory elements involved in regulating cell identity (Hnisz et al., 2013). SEs are enriched for the histone modification H3K27ac as well as Pol II and transcriptional coactivators like the mediator element MED1 and the bromodomain protein BRD4 (Hnisz et al., 2013; Lovén et al., 2013; Whyte et al., 2013). piggyBac has a strong biophysical affinity for BRD4, as these proteins can be co-immunoprecipitated (Gogol-Döring et al., 2016). Thus, we hypothesized that, given the millions of insertions recoverable by SRTs (TABLE 1), we would be able to identify BRD4-bound SEs simply from the localization of undirected piggyBac transpositions.

Figure 3A:
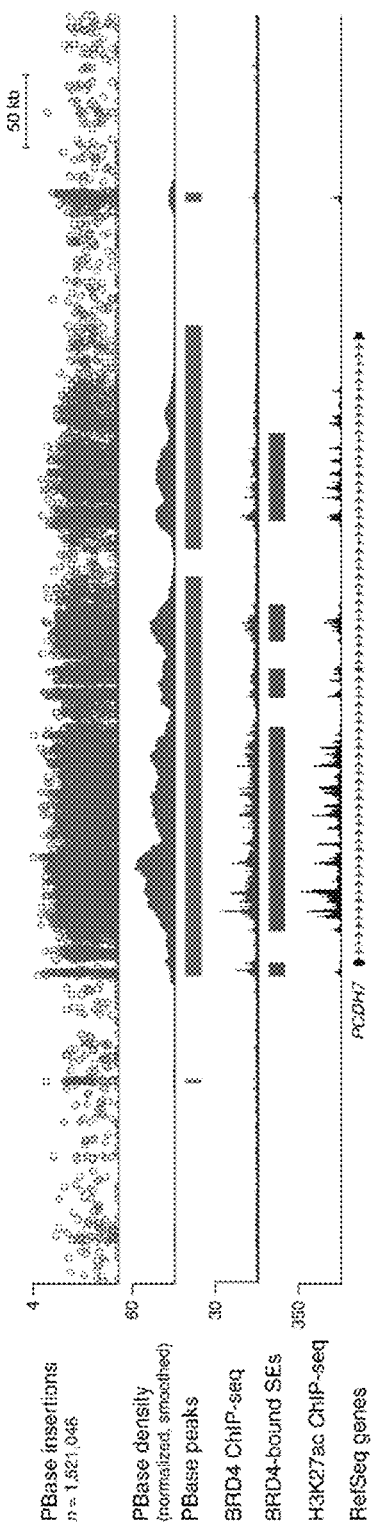
FIG. 3A-FIG. 3F. Undirected piggyBac SRTs Mark BRD4-Bound Super-enhancers. (A) Browser view of an undirected PBase insertions in HCT-116 cells at a SE alongside BRD4 and H3K27ac ChIP-seq data. (B) Reproducibility of normalized insertions at PBase peaks. (C) Mean BRD4 ChIP-seq signal at PBase peaks compared to permuted control set. (D) Heatmap of H3K27ac, H3K4me1, H3K9me3, and H3K27me3 ChIP-seq signal at PBase peaks. (E) Receiver-operator characteristic curve for SE detection using PBase peaks. (F) Precision-recall curve for SE detection using PBase peaks. See also FIG. 9. SE, super-enhancer; IPM, insertions per million mapped insertions; AUROC, area under receiver-operator curve; AUPRC, area under precision-recall curve; FC, fold change.
Figure 3B:
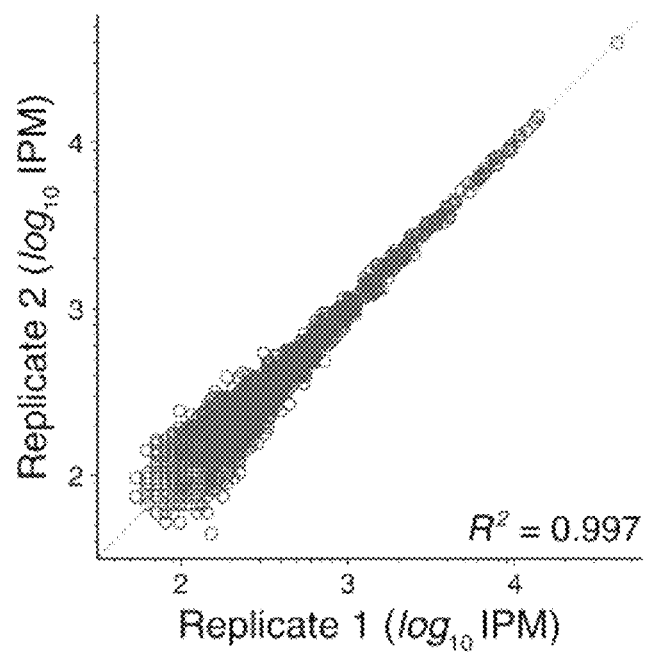
Figure 3C:
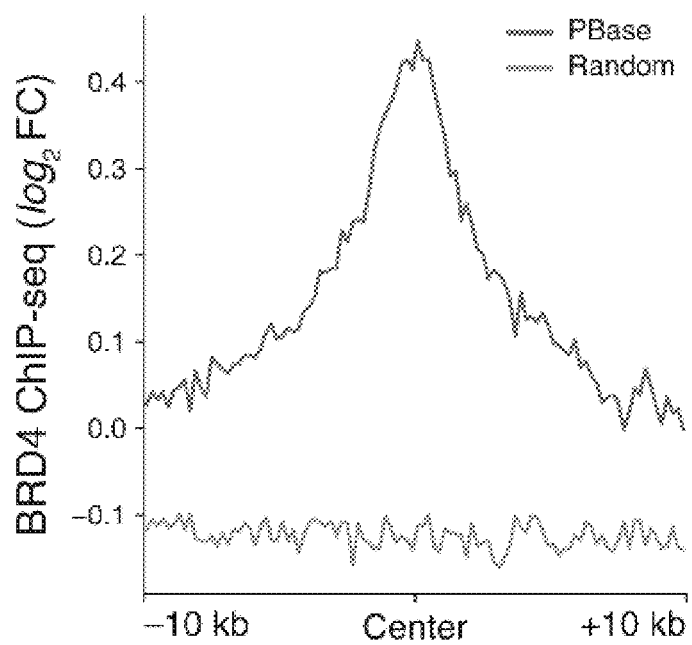
Figure 3D:
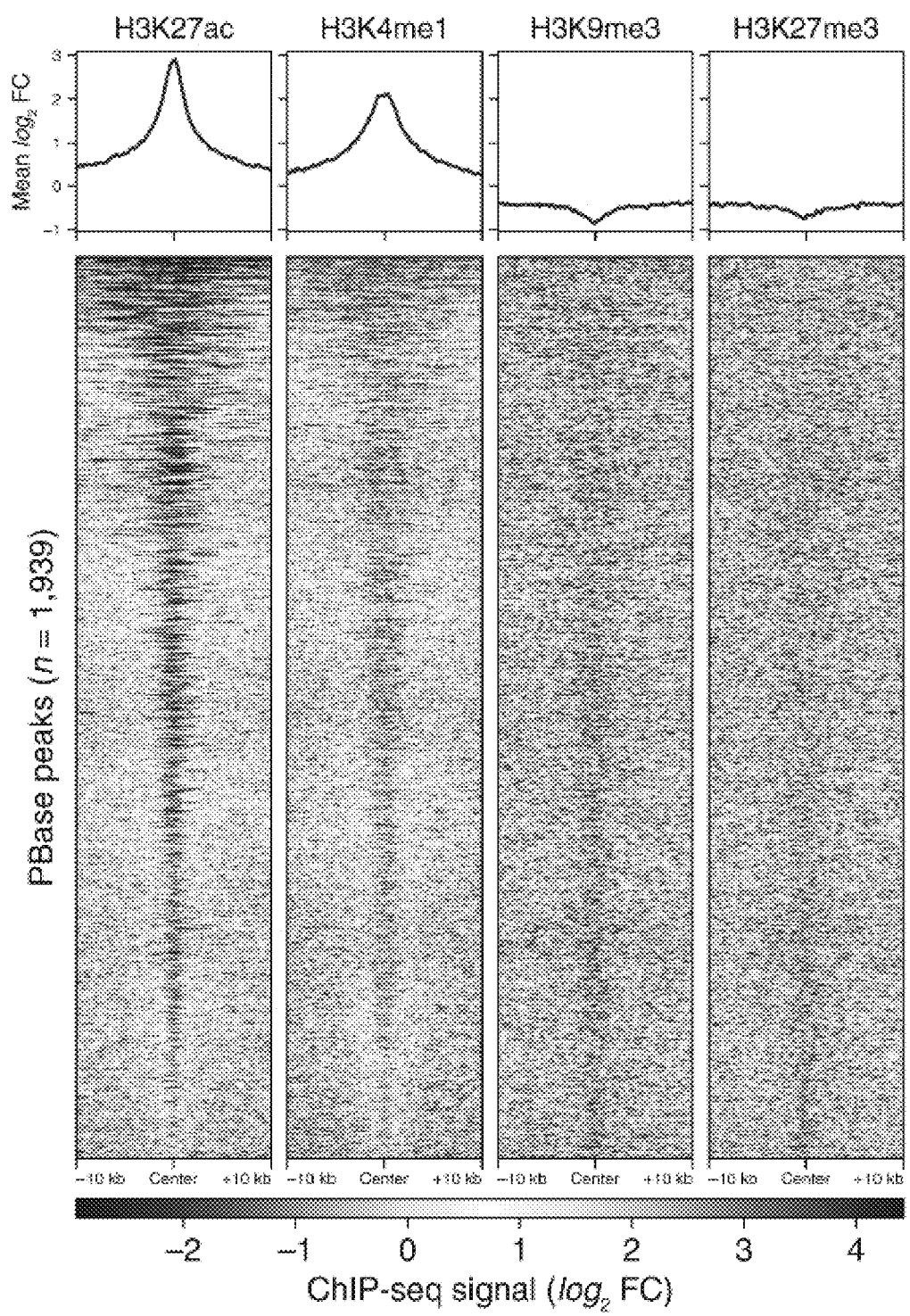

In HCT-116 cells, undirected piggyBac showed non-uniform densities of insertions at BRD4-bound loci (FIG. 3A; for guidance on interpreting a calling card track, see Methods). At statistically significant peaks of piggyBac calling cards, piggyBac showed high reproducibility of normalized insertions between biological replicates ($R^2 > 0.99$; FIG. 3B). We calculated the mean BRD4 enrichment, as assayed by ChIP-seq (McCleland et al., 2016), over all piggyBac peaks, which showed significantly increased BRD4 signal compared to a permuted control set (FIG. 3C; Kolmogorov-Smirnov [KS] test p<10$^{-9}$). Maximum BRD4 ChIP-seq signal was observed at calling card peak centers and decreased symmetrically in both directions. Moreover, piggyBac peaks showed striking overlap with ChIP-seq profiles for several histone modifications (Sloan et al., 2016; ENCODE Project Consortium, 2012), in particular, an enrichment for H3K27 acetylation (FIG. 3D). Since bromodomains bind acetylated histones, this observation further supports the notion that undirected piggyBac insertions can be used to map BRD4 binding. Peaks were also enriched in H3K4me1, another canonical enhancer mark, and depleted for H3K9me3 and H3K27me3, modifications associated with heterochromatin (Lawrence et al., 2016). In all, piggyBac insertion density is highly correlated with BRD4 binding throughout the genome and that regions enriched for undirected piggyBac insertions share features common to enhancers.

Figure 3E:
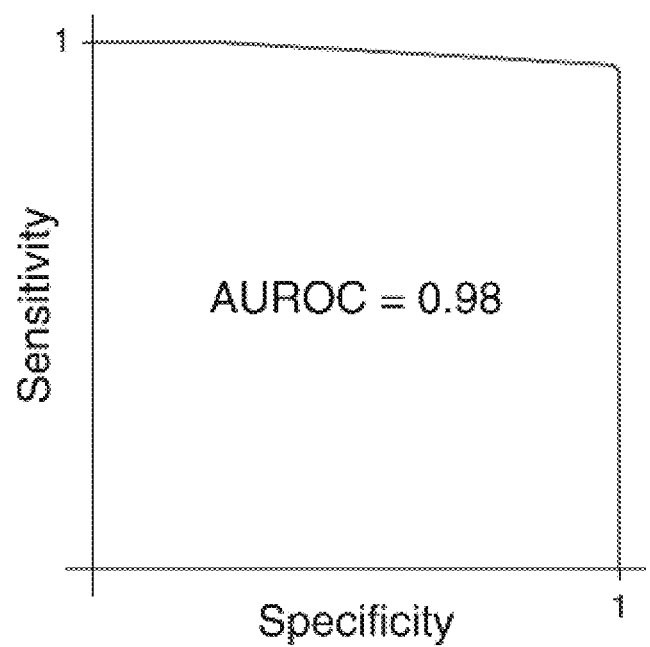
Figure 3F:
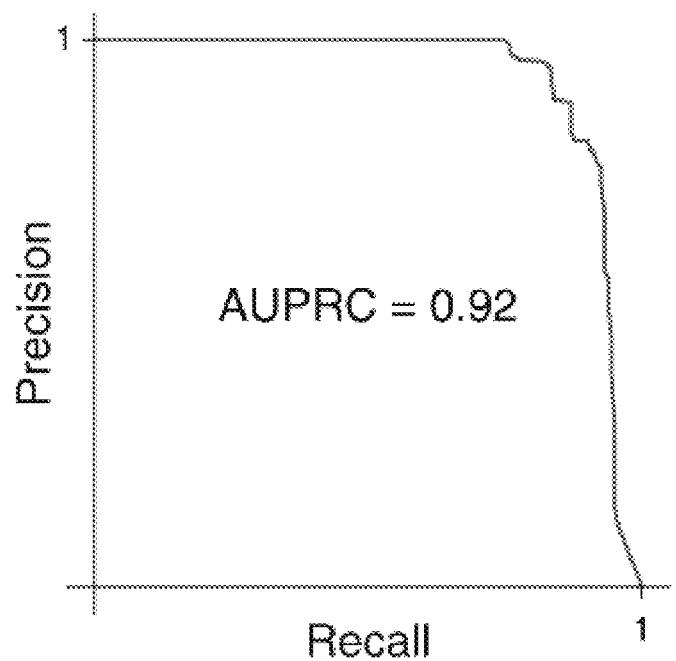

We next assessed whether undirected piggyBac peaks can be used to identify BRD4-bound SEs. We constructed receiver-operator characteristic curves based on our ability to detect SEs from piggyBac (FIG. 3E). The high area under the curve (0.98) indicates that we can robustly identify BRD4-bound SEs from piggyBac transpositions. Across a range of sensitivities, calling card peaks are highly specific and have high positive predictive value (AUPRC=0.92; FIG. 3F). These trends also hold true for the hyperactive piggyBac mutant (Supplemental Methods). Thus, undirected piggyBac transpositions can accurately assay BRD4-bound SEs.

Figure 4A:
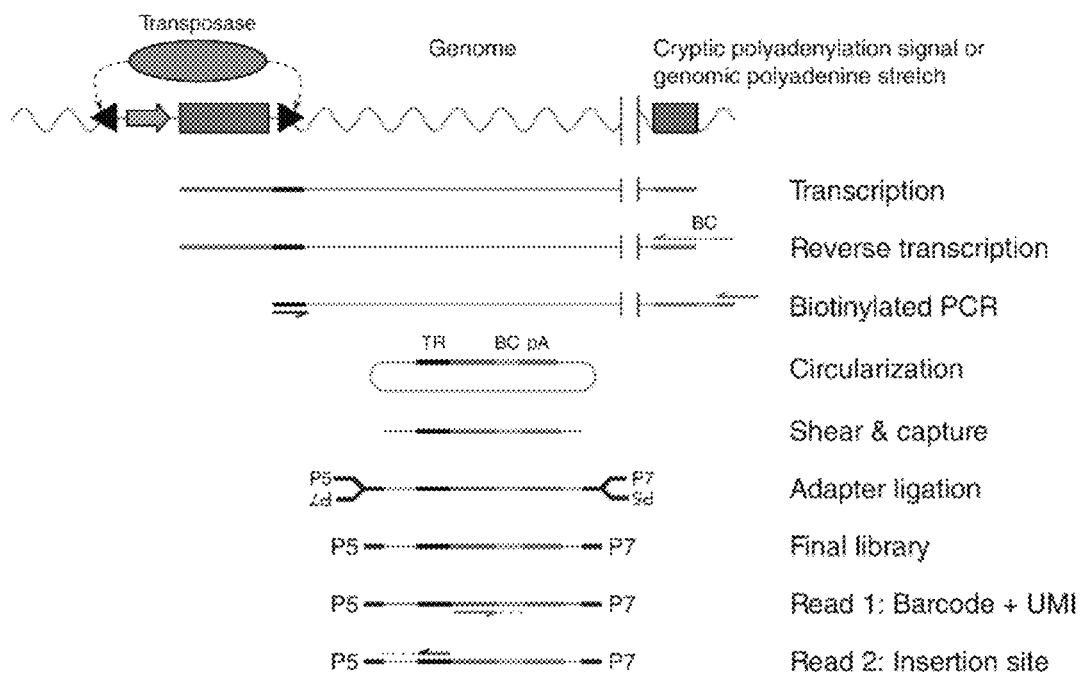
FIG. 4A-FIG. 4D. scCC Maps BRD4 Binding in Single Cells. (A) Schematic of the scCC library preparation strategy from scRNA-seq libraries. (B) Barnyard plot of scCC on a mixture of human HCT-116 and mouse N2a cells. (C) UMAP of scRNA-seq of a mixture of human HCT-116 and K562 cells. (D) Browser view of BRD4 peaks specific to HCT-116 and K562 cells deconvolved using scCC. See also FIG. 10 and FIG. 11. TR, terminal repeat; BC, barcode; pA, poly(A) sequence; UMI, unique molecular index.
Figure 9A:
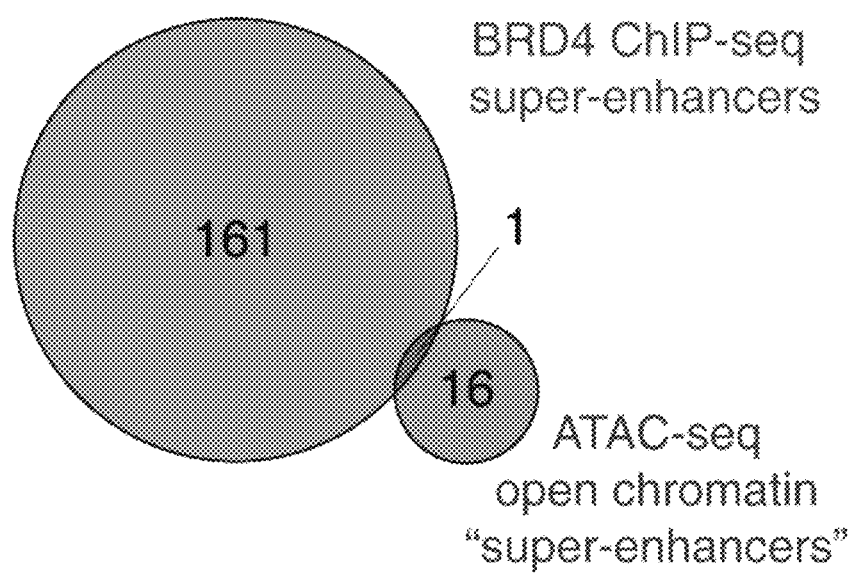
FIG. 9A-FIG. 9D. BRD4 Calling Cards with Undirected piggyBac Are Not Equivalent to ATAC-Seq, Related to FIG. 3. (A) Overlap of BRD4 super-enhancers, as inferred from BRD4 ChIP-seq, and "super-enhancers" inferred from open chromatin ATAC-seq peaks in HCT-116 cells. (B) Browser view of a BRD4 calling card peak that is not detected by ATAC-seq nor DNase-seq. (C) Comparison of transposase predilections for accessible chromatin. (D) Comparison of peak sizes and BRD4 ChIP-seq enrichment as called by DNase-seq, ATAC-seq, and undirected piggyBac calling cards, respectively. Peaks are scaled to the median peak width (denoted by the start and end ticks) and are flanked by 3 kb in either direction. SE: super-enhancer; DHS: DNaseI hypersensitivity site; FC: fold change; kb: kilobase.
Figure 9B:
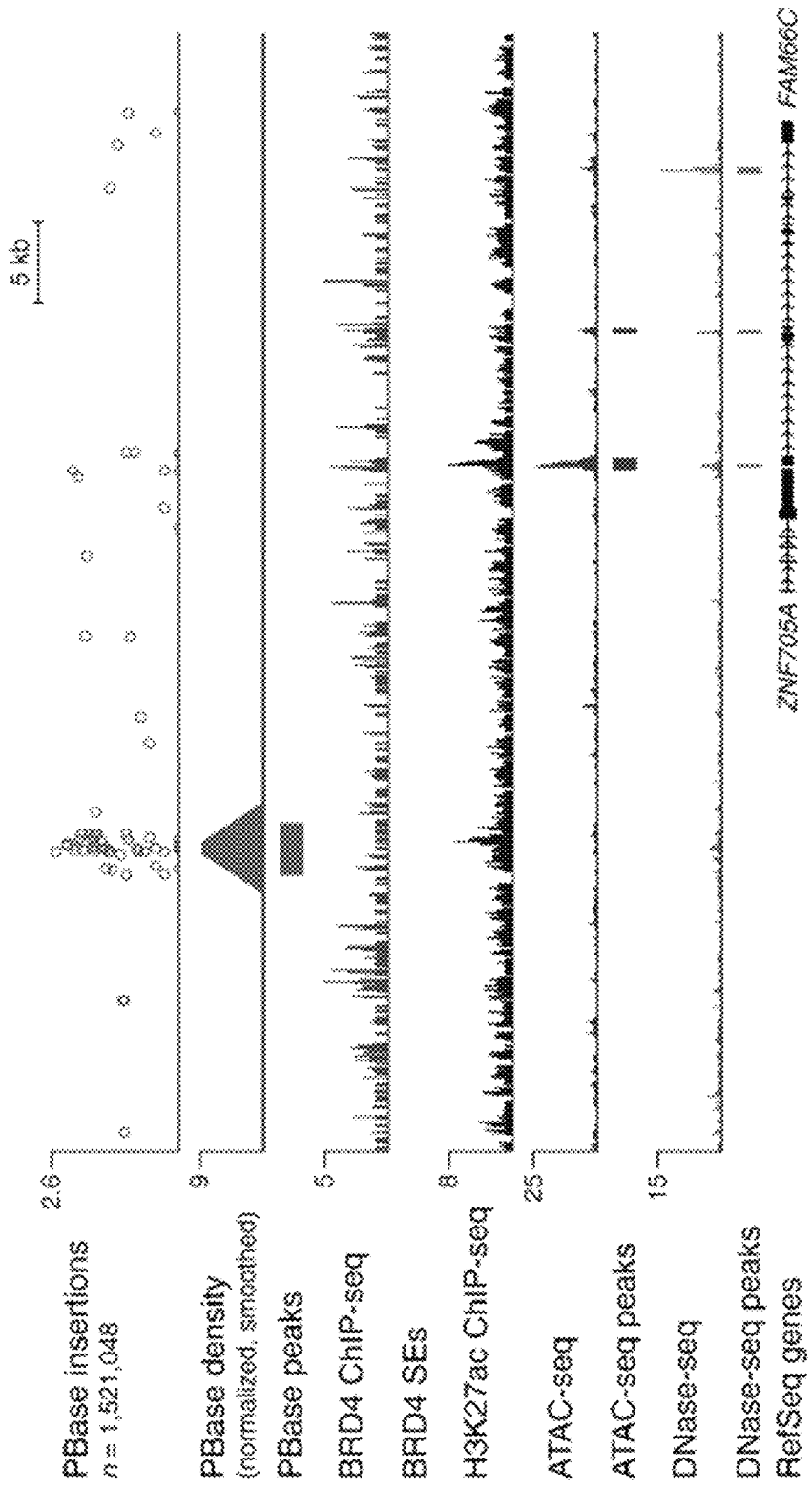
Figure 9C:
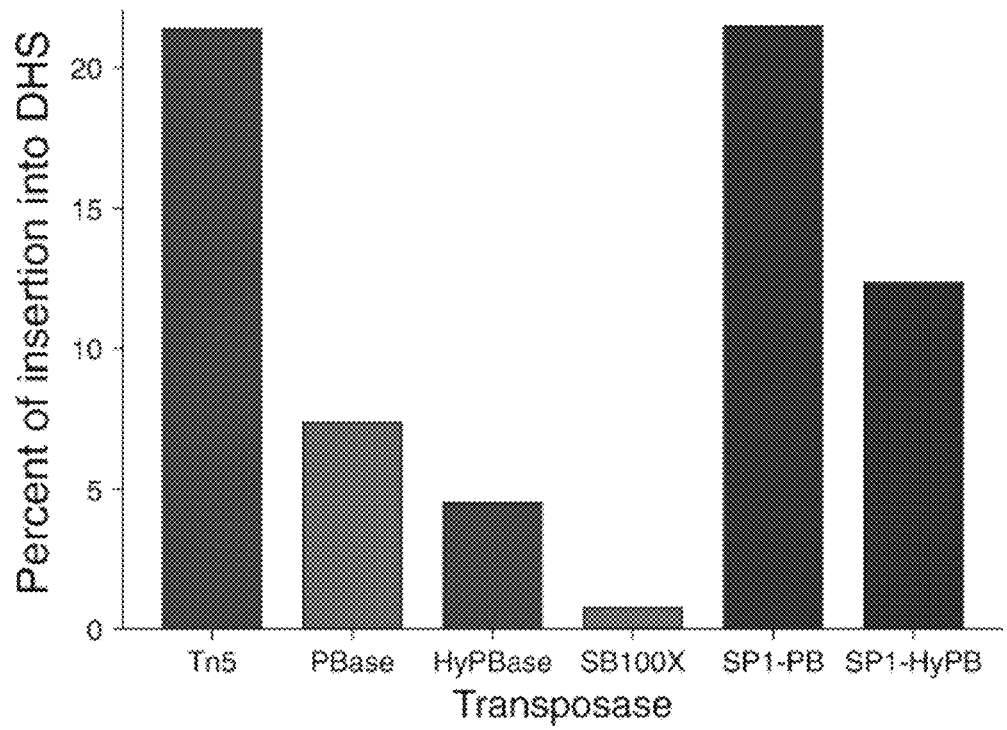
Figure 9D:
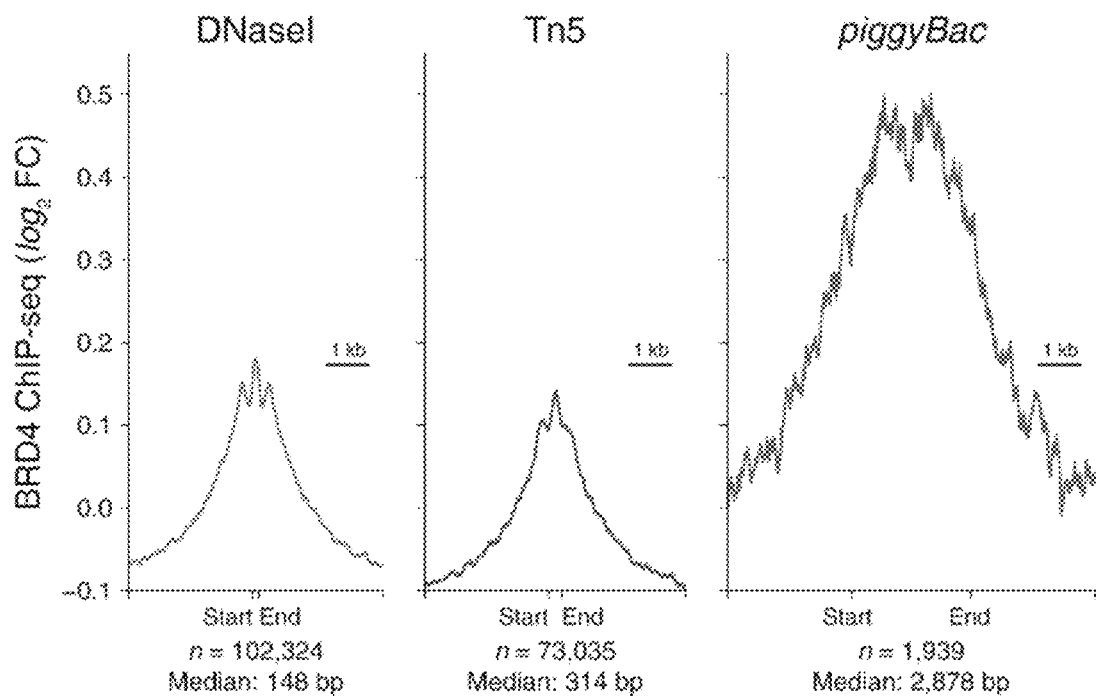

We also investigated how similar piggyBac transposition is to that of Tn5, the transposase used in ATAC-seq (Buenrostro et al., 2013, 2015) to identify open chromatin. Since BRD4 and H3K27ac co-occur at accessible loci, it may be that undirected calling cards and ATAC-seq provide redundant information. If that were the case, we should be able to identify BRD4-bound SEs with high sensitivity from ATAC-seq data alone, much as we have shown for piggyBac. We called SEs using publicly available ATAC-seq data from HCT-116 cells (Ponnaluri et al., 2017) in the same manner that we did for BRD4 ChIP-seq. We found almost no overlap between BRD4-bound SEs and these so-called SEs from ATAC-seq data (FIG. 9A). Moreover, there are a small number (4.3%) of piggyBac peaks that are not found in accessible chromatin (FIG. 9B), suggesting that there may be regulatory elements in closed chromatin that calling cards are better able to detect. Globally, over 20% of Tn5 insertions are directed to accessible sites, starkly higher than undirected piggyBac but comparable to TF-piggyBac fusions (FIG. 9C). That piggyBac's preference for targeting open chromatin can be markedly increased by a covalently linked TF highlights both piggyBac's baseline insensitivity for accessible sites and the efficacy of TF redirection. Finally, we find that piggyBac peaks are an order of magnitude larger than ATAC-seq peaks and, as a result, capture more BRD4 binding (FIG. 9D). We conclude that unfused piggyBac reflects BRD4's binding preferences whereas Tn5 reports on all accessible chromatin; as a result, undirected calling cards are not equivalent to ATAC-seq.

scCC Enables Simultaneous Identification of Cell Type and Cell-Type-Specific BRD4 Binding Sites We next sought to recover SRTs from scRNA-seq libraries, which would let us identify cell types from transcriptomic clustering and, using the same source material, simultaneously profile TF binding in those cell types. We adopted the 10× Chromium platform due to its high efficiency of cell and transcript capture as well as its ease of use (Zheng et al., 2017) but with a modified protocol (Methods). We split the first-strand synthesis product in two: one half is used to generate a scRNA-seq library, while the other half undergoes specific amplification for SRTs followed by circularization. The circularization step brings the cell barcode and unique molecular index (UMI), found at the 3' ends of each transcript, next to the transposon-genome junction. In this way, SRTs can be mapped and assigned to single cells using high-throughput short read sequencing (FIG. 4A). After sequencing, the cell barcodes shared between both libraries are used to connect individual insertions to specific cell types. We call this protocol scCC.

Figure 4B:
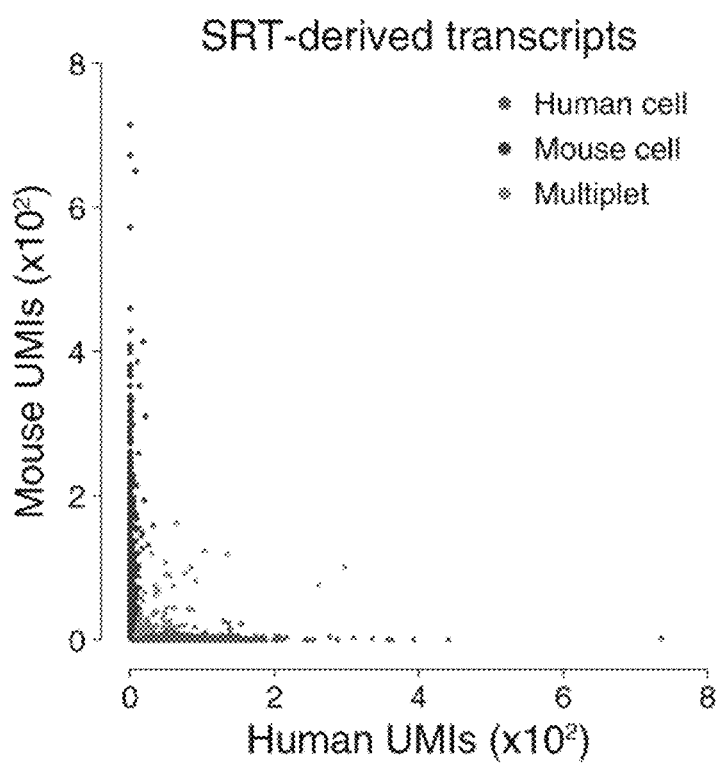
Figure 10A:
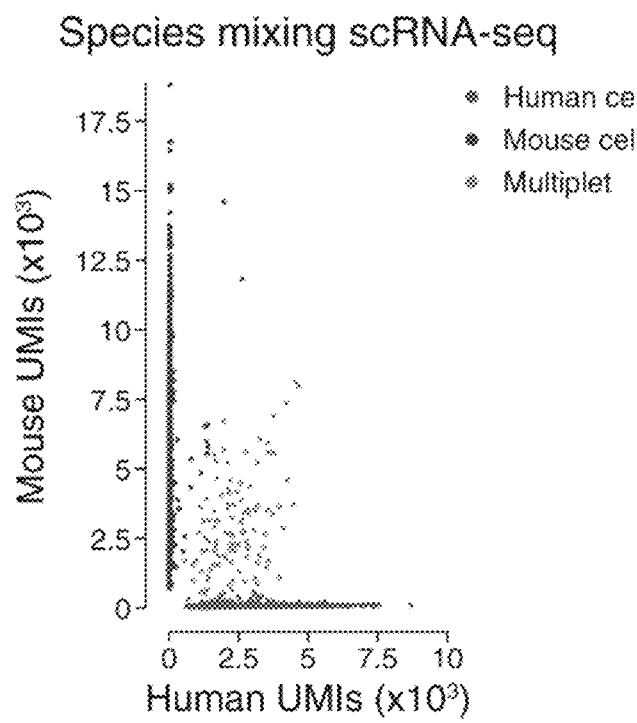
FIG. 10A-FIG. 10D. Filtering Single-Cell SRTs Reduce Intermolecular Artifacts, Related to FIG. 4. (A) Barnyard plot from scRNA-seq of human HCT-116 and mouse N2a cells. (B) Barnyard plot from scCC of HCT-116 and N2a cells without filtering (estimated multiplet rate of 25.1%). (C) Distribution of cell barcode purity from unfiltered scCC data. The x axis is the proportion of transcripts mapping to the human or mouse genomes. (D) Distribution of species purity after filtering scCC data. UMI: unique molecular indexes.
Figure 10B:
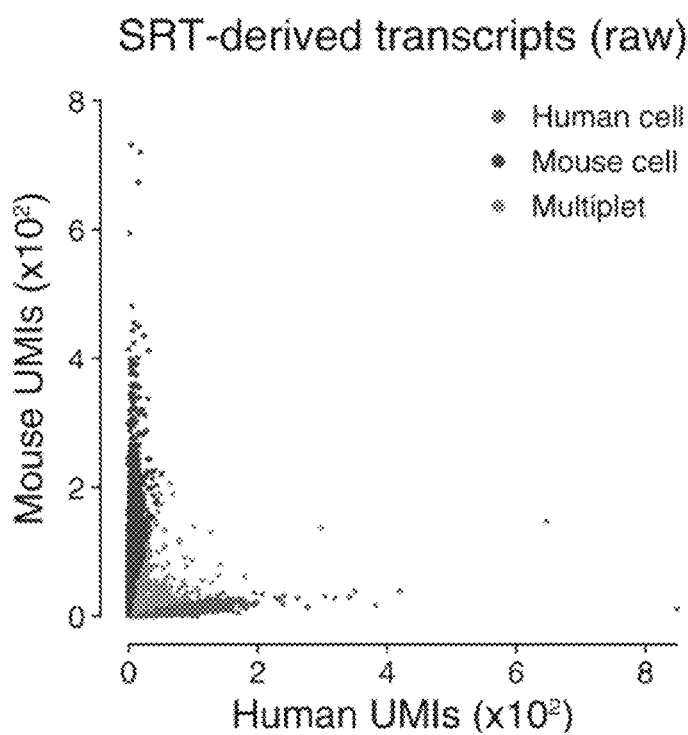
Figure 10C:
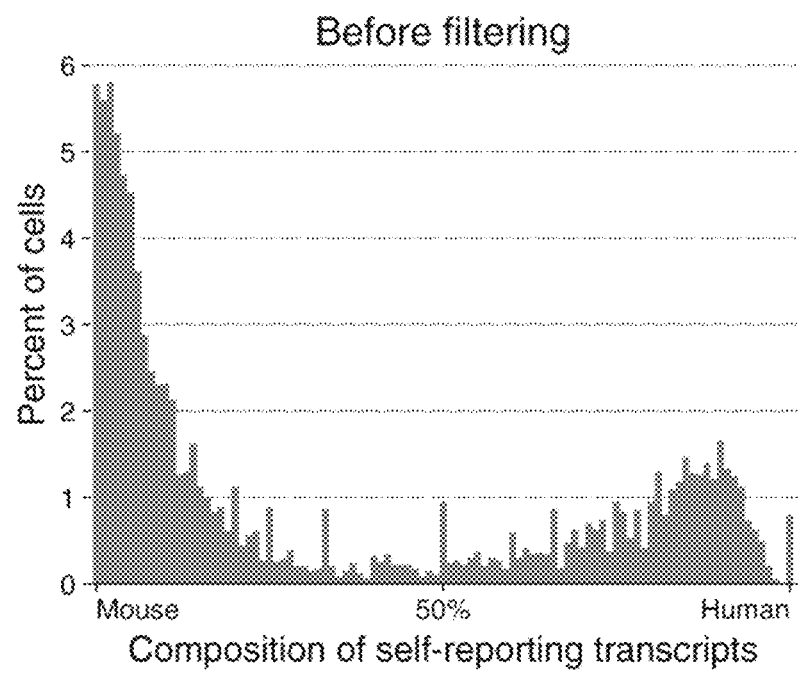
Figure 10D:
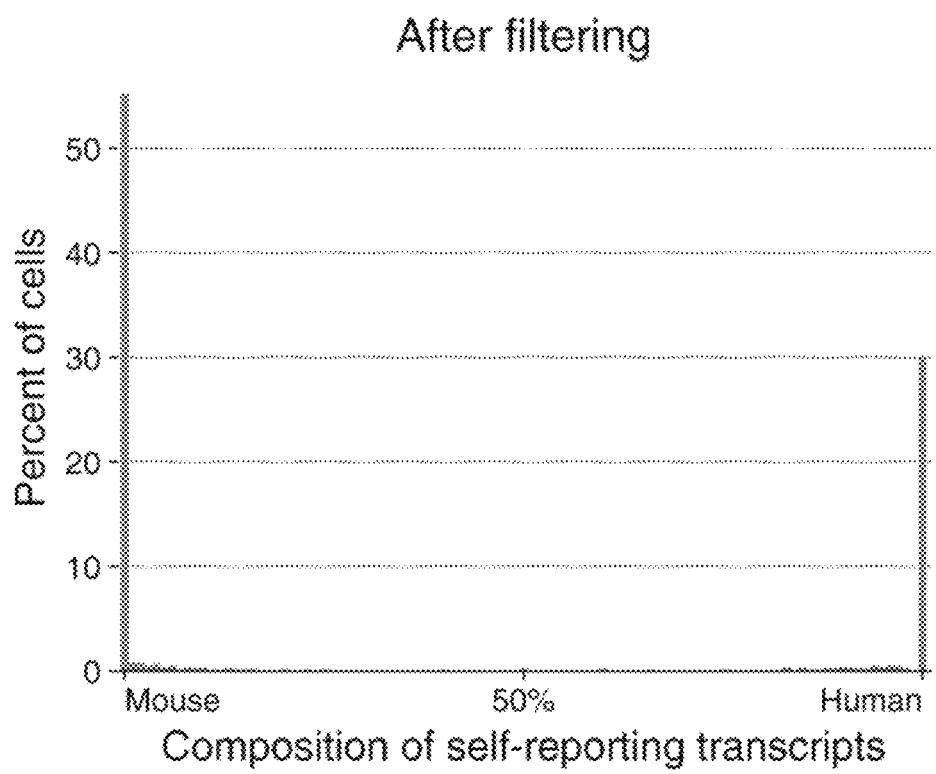

We first validated scCC by performing a species-mixing experiment with human HCT-116 cells and mouse N2a cells transfected with hyperactive piggyBac (HyPBase) and PB-SRT-Puro. The resulting scRNA-seq library showed strong species separation with an estimated multiplet rate of 3.2% (FIG. 10A). We restricted our calling card analysis to those insertions whose cell barcodes were observed in the scRNA-seq library (TABLE 2). The distribution of insertions across these cells reflected a continuum from pure mouse to pure human (FIG. 10B and FIG. 10C). Since intramolecular ligation in the circularization step or the subsequent PCR may introduce artifacts, such as the mis-assignment of a barcode from a mouse cell to an insertion site in a human cell, we required that a given insertion in a given cell must have at least two different UMIs associated with it. This filter greatly improved the number of pure mouse and human cells (FIG. 10D), yielding clear species separation with an estimated multiplet rate of 7.9% (FIG. 4B). Thus, scCC can accurately map SRT insertions in single cells.

TABLE 2

Summary of single cell calling cards experiments, related FIG. 4, FIG. 5, FIG. 6, FIG. 7, FIG. 8, FIG. 10, FIG. 11, FIG. 12, FIG. 13, FIG. 14, and FIG. 15.

| Sample | Construct | Libraries | Cells | Insertions | Reads | Mean coverage | Mean IPC | Median IPC | % cells with ≥1 insertion |
|---|---|---|---|---|---|---|---|---|---|
| HCT-116 & N2a | HyPBase | 1[a] | 6,068 | 33,223 | 1,710,525 | 51.5 | 5.4 | 4 | 91.8 |
| HCT-116 | HyPBase | 4[b] | 12,891 | 37,774 | 4,768,230 | 126.2 | 3.0 | 2 | 93.4 |
| K562 | HyPBase | 4[b] | 11,912 | 107,385 | 10,404,042 | 96.9 | 9.5 | 6 | 96.9 |
| HCT-116 | SP1-HyPBase | 4 | 30,411 | 77,210 | 9,874,157 | 127.9 | 2.6 | 2 | 83.8 |
| K562 | SP1-HyPBase | 4 | 21,554 | 327,465 | 44,851,070 | 137.0 | 15.3 | 9 | 95.8 |
| HepG2 | HyPBase | 3 | 17,195 | 144,176 | 20,035,606 | 139.0 | 8.4 | 6 | 96.1 |
| HepG2 | FOXA2-HyPBase | 3 | 16,623 | 105,000 | 15,677,152 | 149.3 | 6.3 | 4 | 96.0 |
| OCM-1A | HyPBase | 3 | 23,978 | 150,707 | 19,794,848 | 131.3 | 6.3 | 4 | 96.2 |

TABLE 2-continued

Summary of single cell calling cards experiments, related FIG. 4, FIG. 5, FIG. 6, FIG. 7, FIG. 8, FIG. 10, FIG. 11, FIG. 12, FIG. 13, FIG. 14, and FIG. 15.

| Sample | Construct | Libraries | Cells | Insertions | Reads | Mean coverage | Mean IPC | Median IPC | % cells with ≥1 insertion |
|---|---|---|---|---|---|---|---|---|---|
| OCM-1A | BAP1-HyPBase | 3 | 19,572 | 215,330 | 27,666,808 | 128.5 | 11.0 | 7 | 97.6 |
| Mouse cortex | HyPBase | 9[c] | 35,950 | 111,382 | 12,204,369 | 109.6 | 8.1 | 3 | 73.7 |

[a]This library was from a species-mixing experiment (FIG. 4B and FIG. 10).
[b]These libraries were demultiplexed from a cell line-mixing experiment (FIG. 4C-FIG. 4D and FIG. 11).
[c]This experiment is further stratified by cell type in TABLE 3.
IPC: insertions per cell.

Figure 4C:
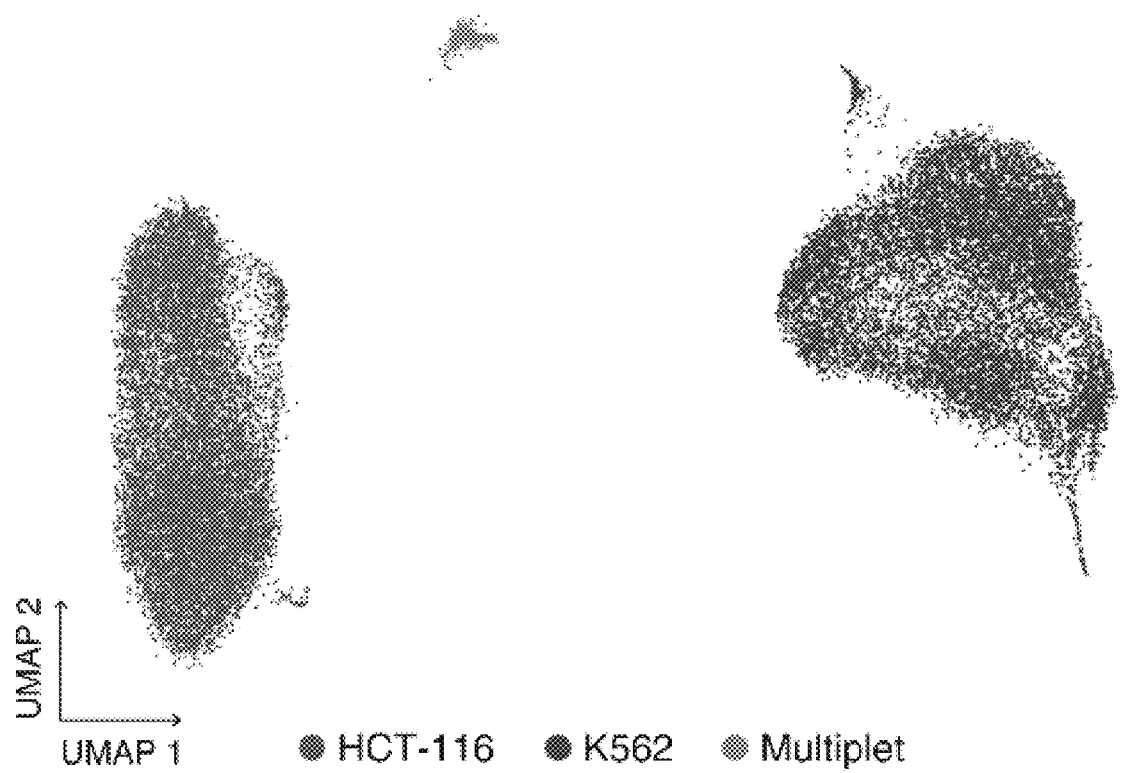
Figure 4D:
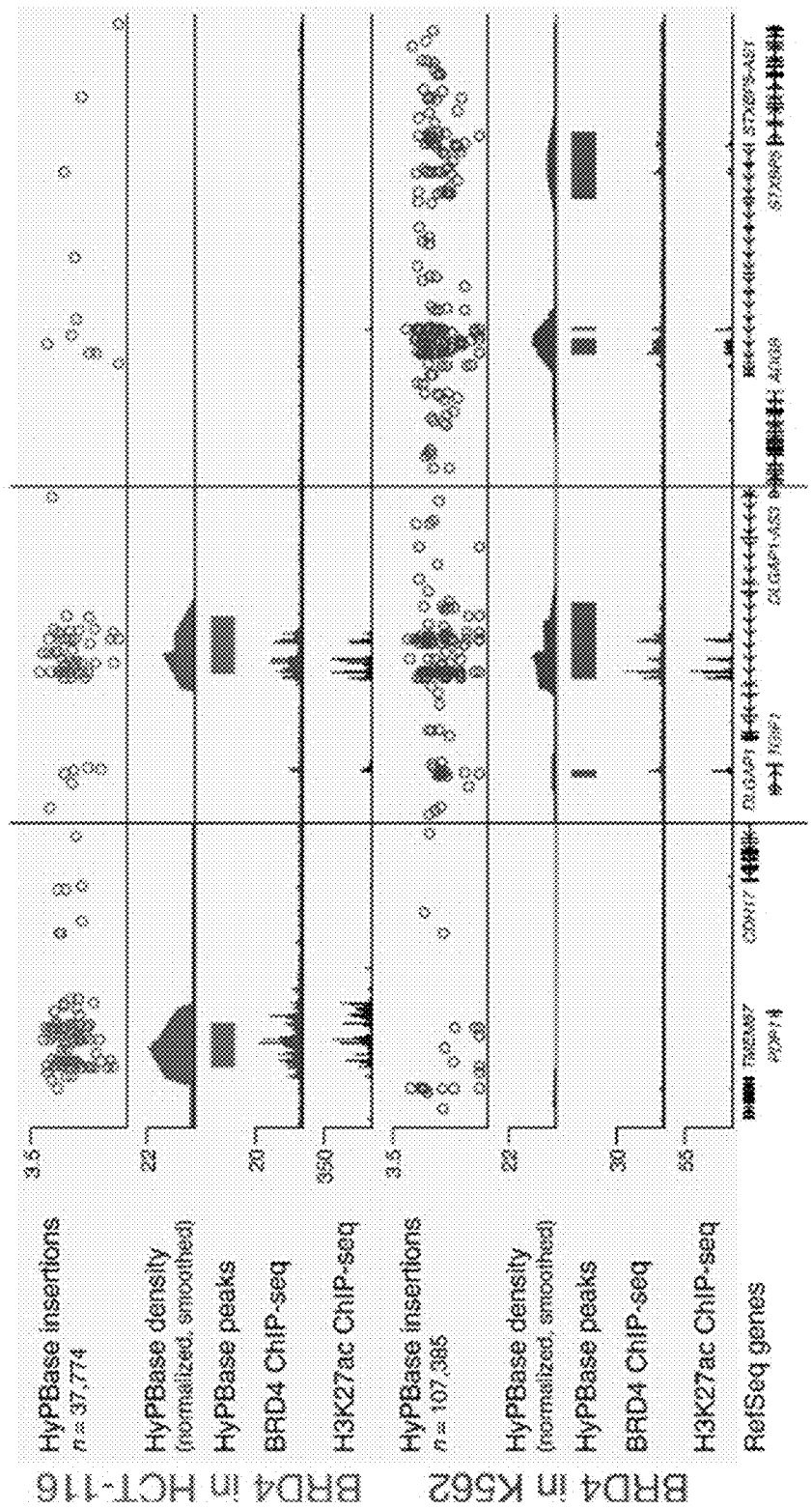
Figure 5A:
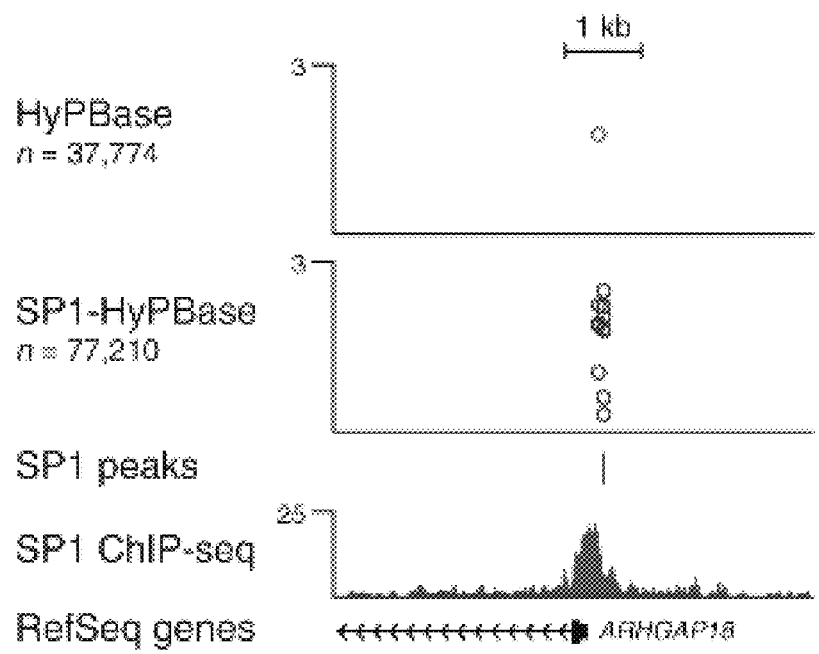
FIG. 5A-FIG. 5P. scCC Works with a Variety of Transcription Factors and Cell Lines. (A-D) scCC with SP1-HyPBase in HCT-116 cells reveal SP1 binding sites. (A) Browser view of a peak from SP1 scCC. (B) Mean SP1 ChIP-seq signal at scCC SP1 peaks. (C) Heatmap of SP1 ChIP-seq signal across all scCC SP1 peaks. (D) Core SP1 motif elicited from SP1 scCC peaks. (E-H) Same as (A)-(D) but in K562 cells. (I-L) scCC with FOXA2-HyPBase in HepG2 cells reveal FOXA2 binding sites. (I) Browser view of a peak from FOXA2 scCC. (J) Mean FOXA2 ChIP-seq signal at scCC FOXA2 peaks. (K) Heatmap of FOXA2 ChIP-seq signal across all scCC FOXA2 peaks. (L) Core FOXA2 motif elicited from FOXA2 scCC peaks. (M-P) scCC with BAP1-HyPB in OCM-1A cells reveal BAP1 binding sites. (M) Browser view of a peak from BAP1 scCC. (N) Mean bulk BAP1 calling cards signal at scCC BAP1 peaks. (O) Heatmap of bulk BAP1 calling cards signal across all scCC BAP1 peaks. (P) YY1 motif elicited from BAP1 scCC peaks. See also FIG. 12. FC, fold change.
Figure 5B:
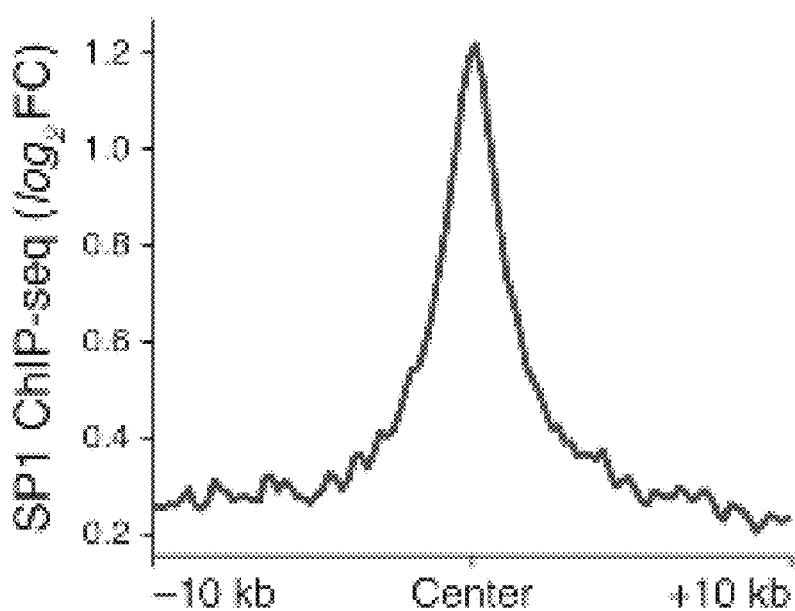
Figure 5C:
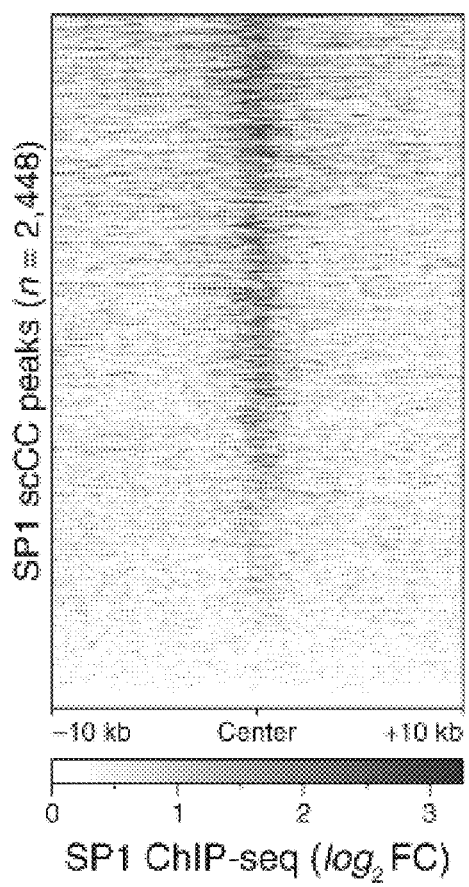
Figure 5D:
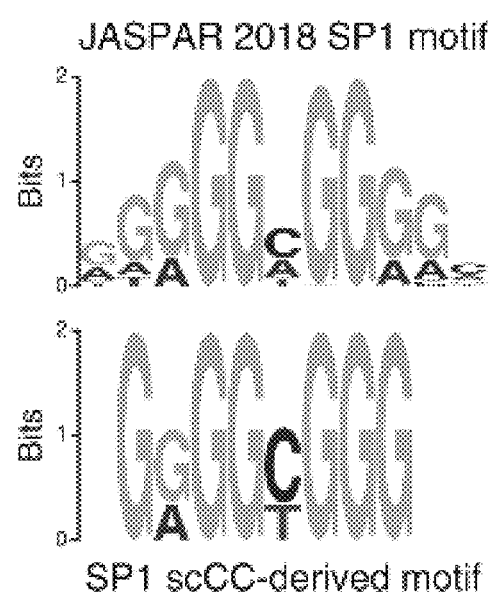
Figure 5E:
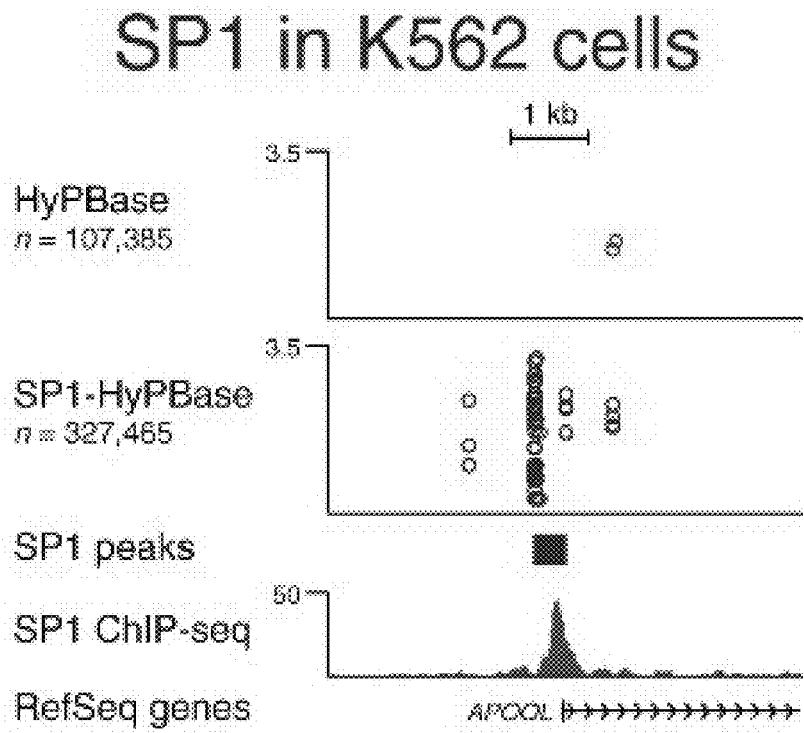
Figure 5F:
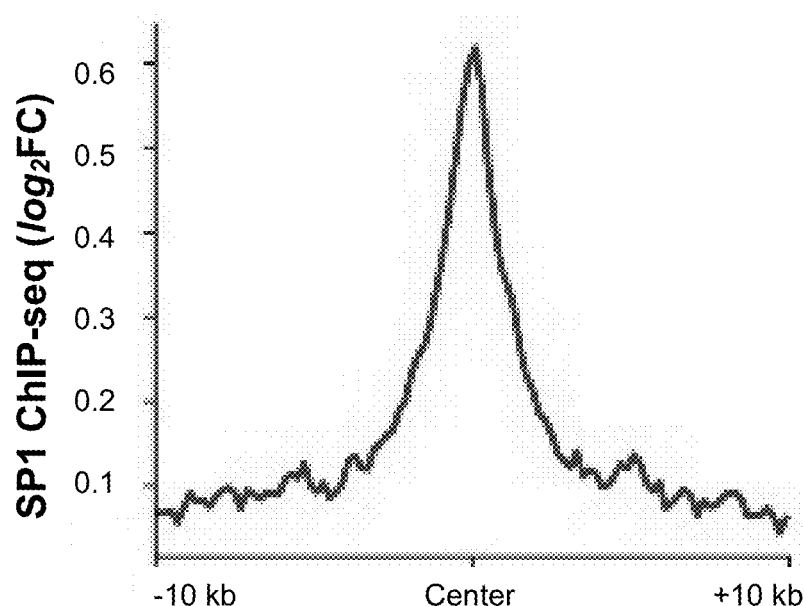
Figure 5G:
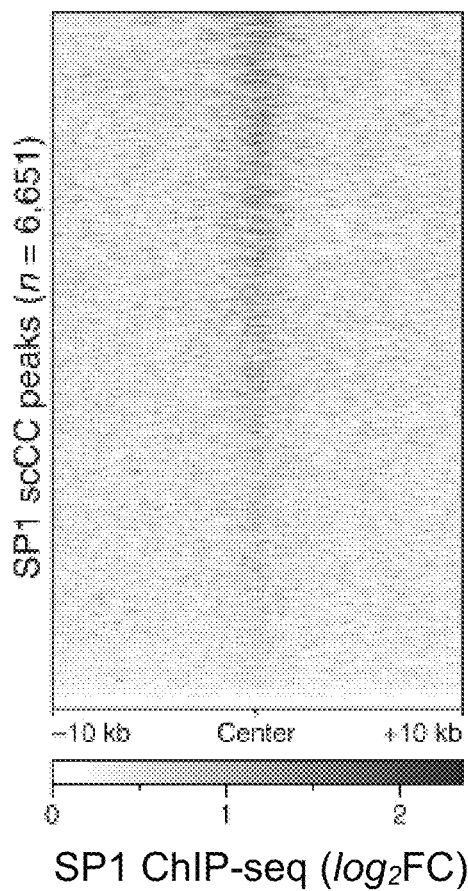
Figure 5H:
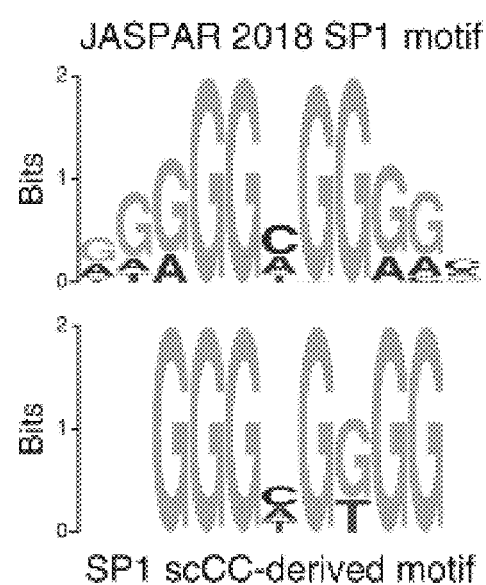
Figure 11A:
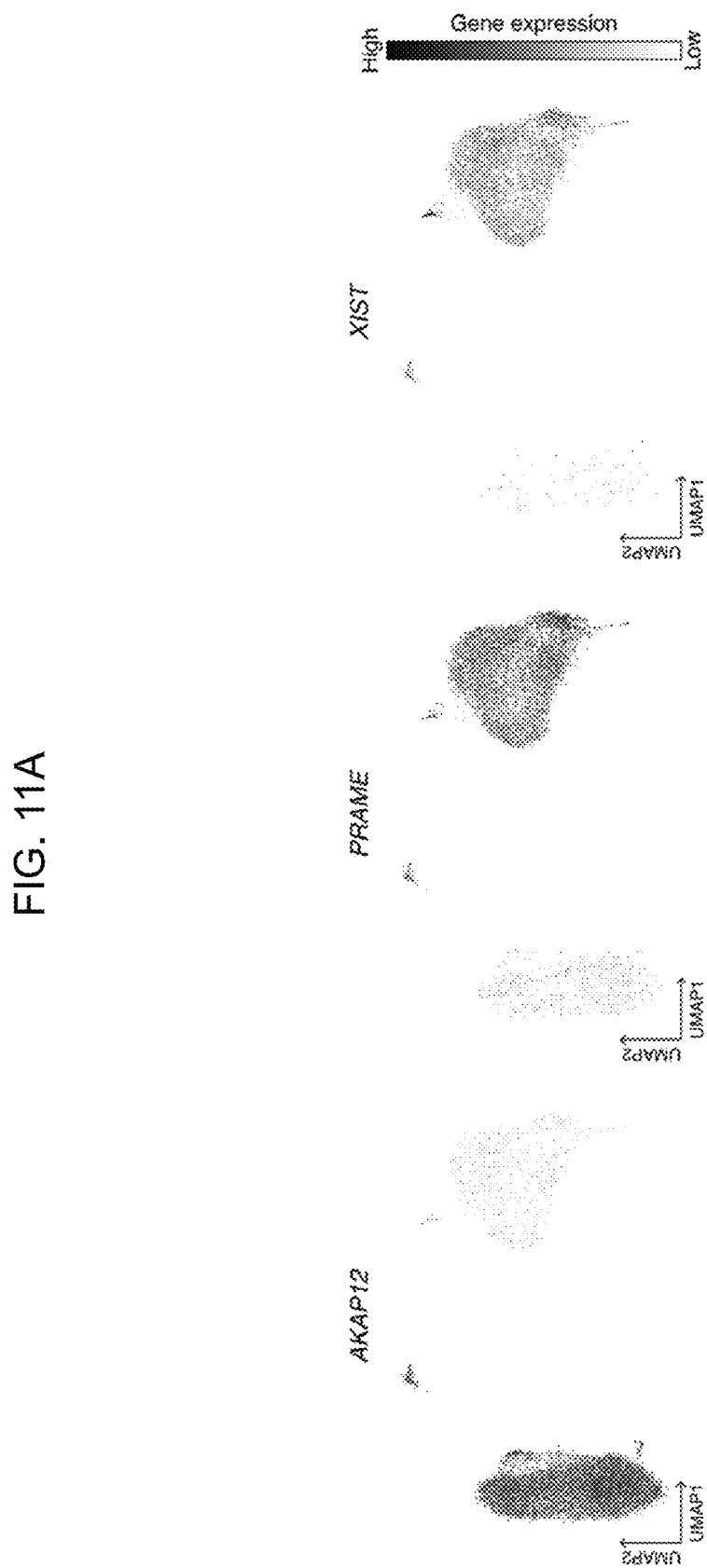
FIG. 11A-FIG. 11H. Validation and Performance of Undirected In Vitro scCC, Related to FIG. 4. (A) Single cell expression levels of three marker genes in a mixed scRNA-seq library of human HCT-116 and K562 cells. (B) Distributions of genes per cell by cell type. (C) Distributions of transcripts per cell by cell type. (D) Distributions of HyPBase insertions recovered per cell in HCT-116 and K562 cells. (E-F) Mean BRD4 ChIP-seq signal at HyPBase peaks in HCT-116 and K562 cells, respectively, compared to randomly permuted peaks (KS test $p<10^{-9}$ in each case). (G-H) Reproducibility of normalized insertions deposited by HyPBase and recovered by scCC at BRD4 binding sites in HCT-116 and K562 cells, respectively. KS: Kolmogorov-Smirnov.
Figure 11B:
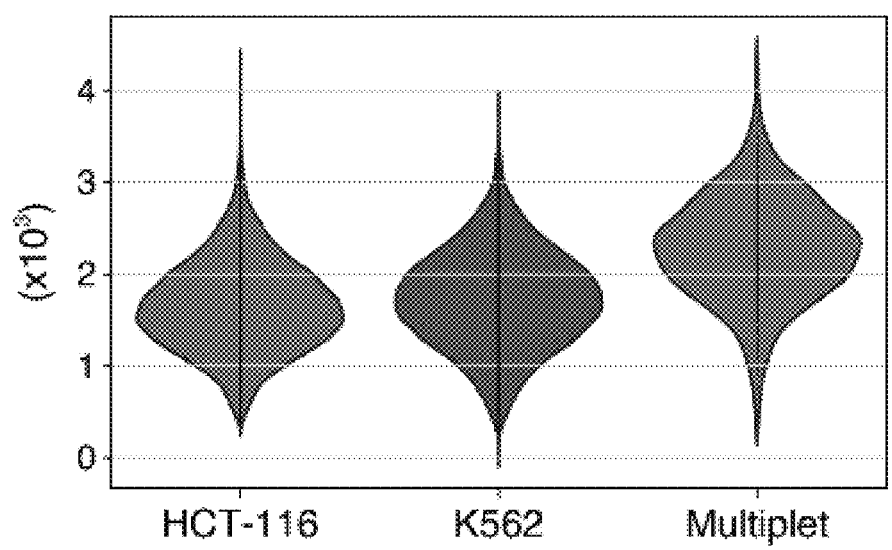
Figure 11C:
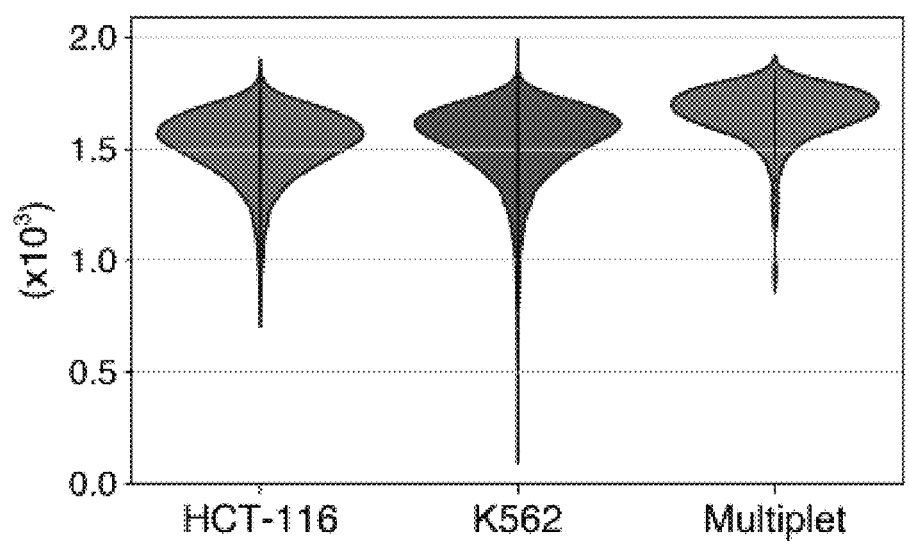
Figure 11D:
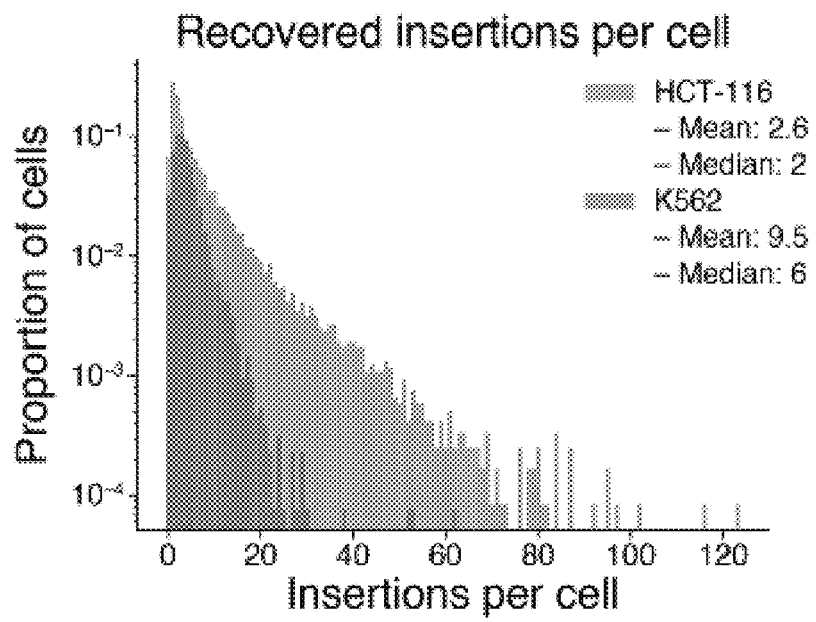
Figure 11E:
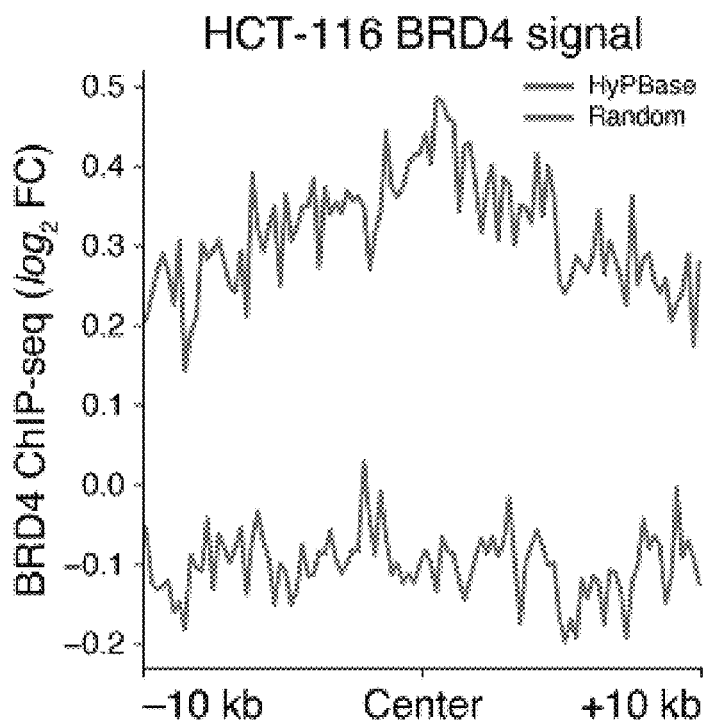
Figure 11F:
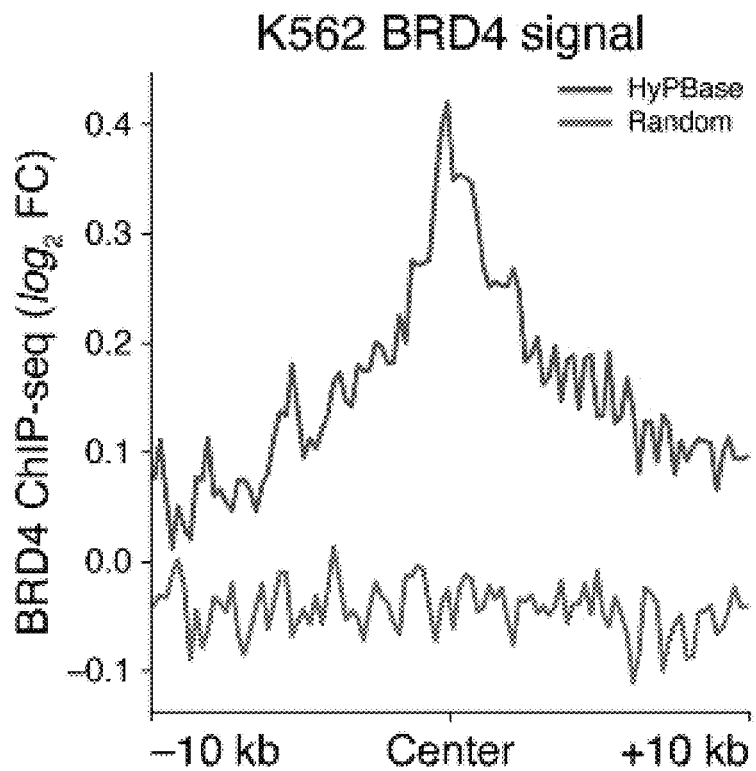
Figure 11G:
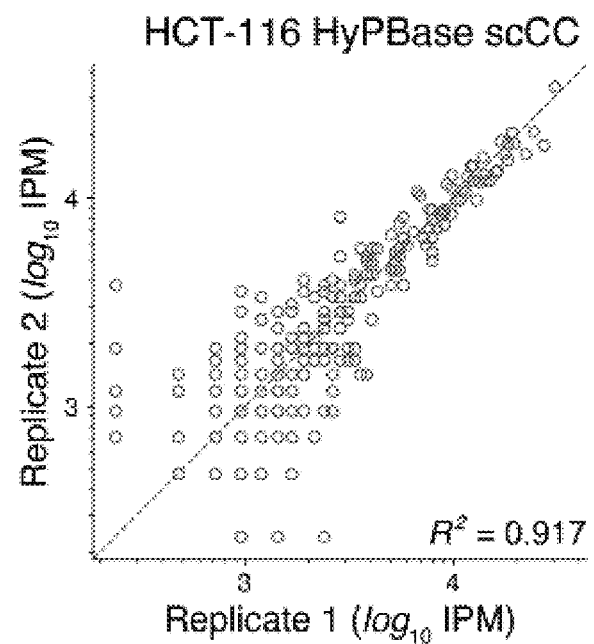
Figure 11H:
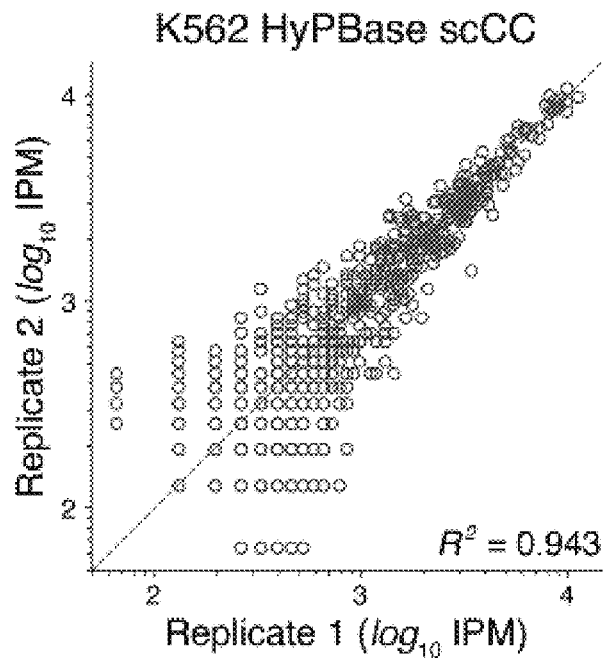
Figure 12A:
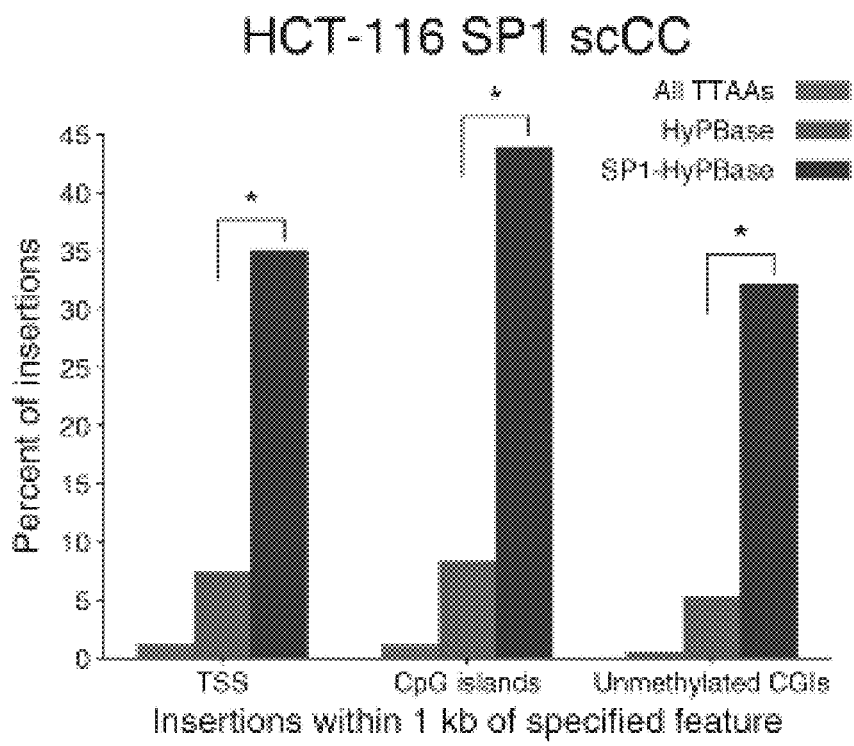
FIG. 12A-FIG. 12L. Validation and Performance of TF-Directed In Vitro scCC, Related to FIG. 5. (A-B) Enrichment of SP1-HyPBase-directed insertions to TSSs, CGIs, and unmethylated CGIs in single HCT-116 and K562 cells, respectively (G test of independence $p<10^{-9}$). (C) Enrichment of BAP1-HyPBase-directed insertions TSSs in single OCM-1A cells (G test of independence $p<10^{-9}$). (D) Percent of BAP1 targets that increase expression upon BAP1 KD stratified by binding site (Fisher's exact test $p<10^{-9}$). The dashed gray line represents the overall fraction of genes that increased expression upon KD. (E-H) Reproducibility of normalized insertions deposited by either HyPBase or TF-HyPBase fusions and recovered by scCC at TF binding sites, for the respective TF-cell line pair. (I-L) The distribution of recovered insertions per cell by construct (HyPBase versus TF-HyPBase) and cell type. TF: transcription factor; TSS: transcription start site; CGI: CpG island; KD: knockdown; IPM: insertions per million mapped insertions; n.s.: not significant.
Figure 12B:
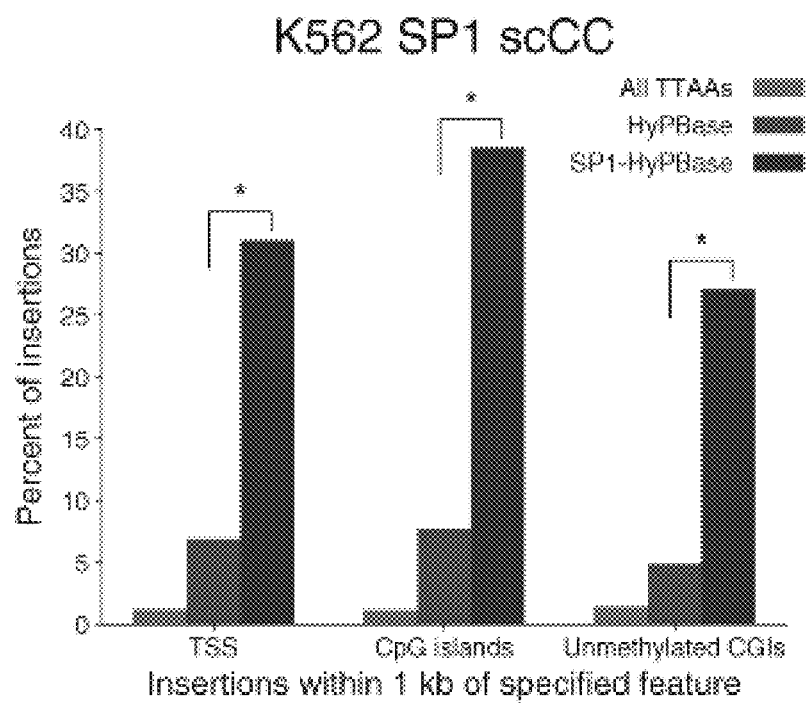
Figure 12C:
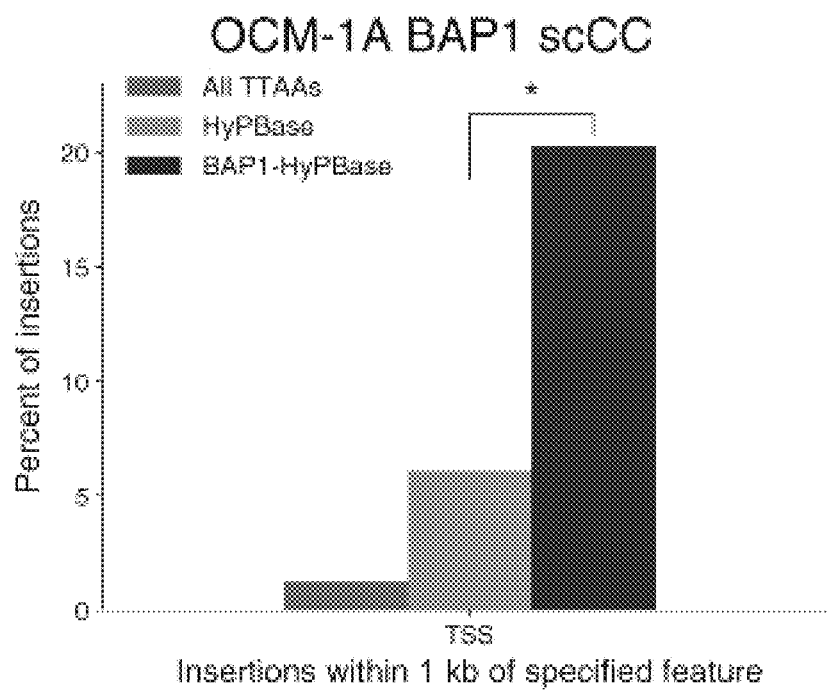
Figure 12D:
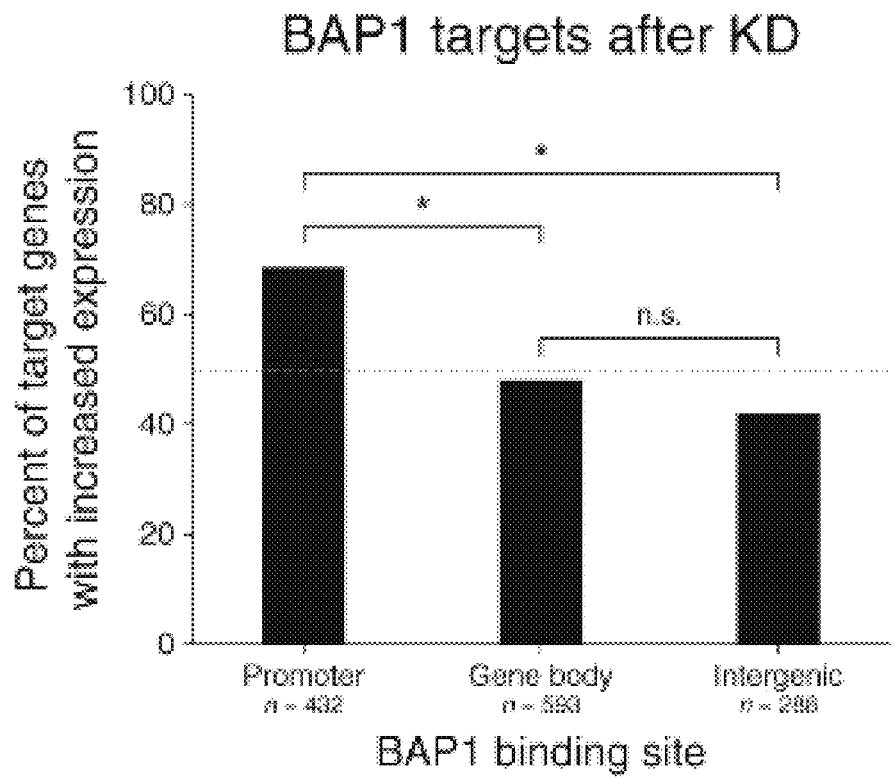
Figure 12E:
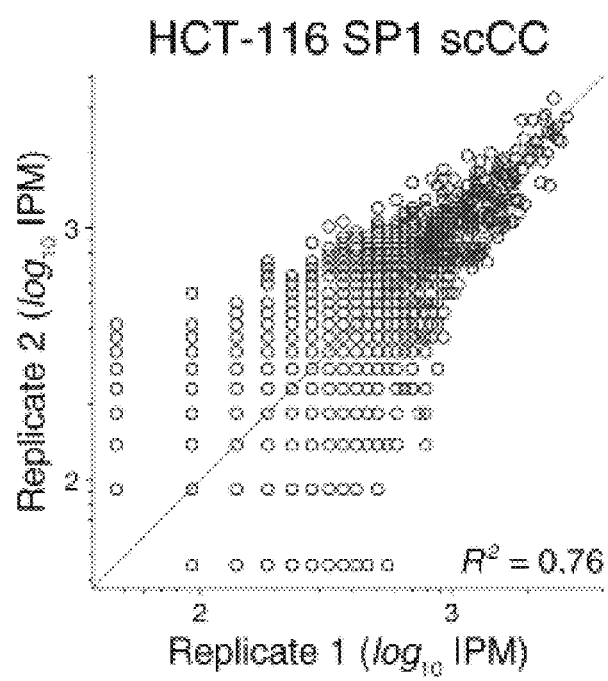
Figure 12F:
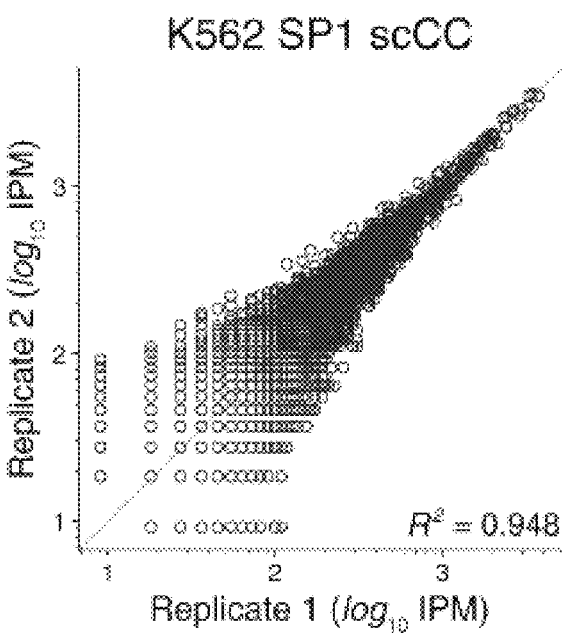
Figure 12G:
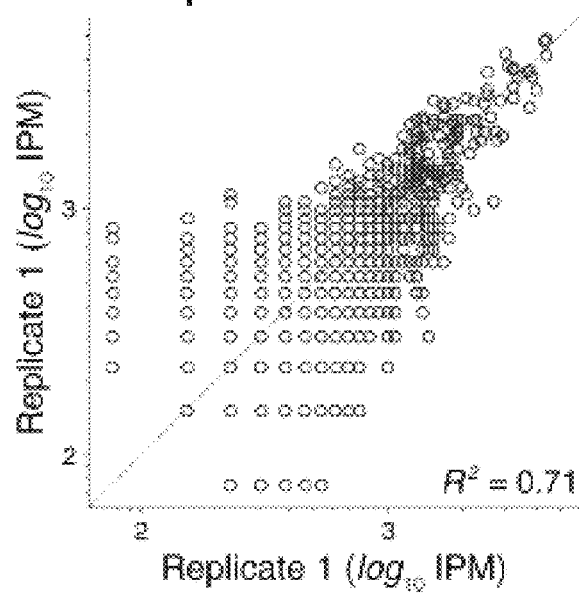
Figure 12H:
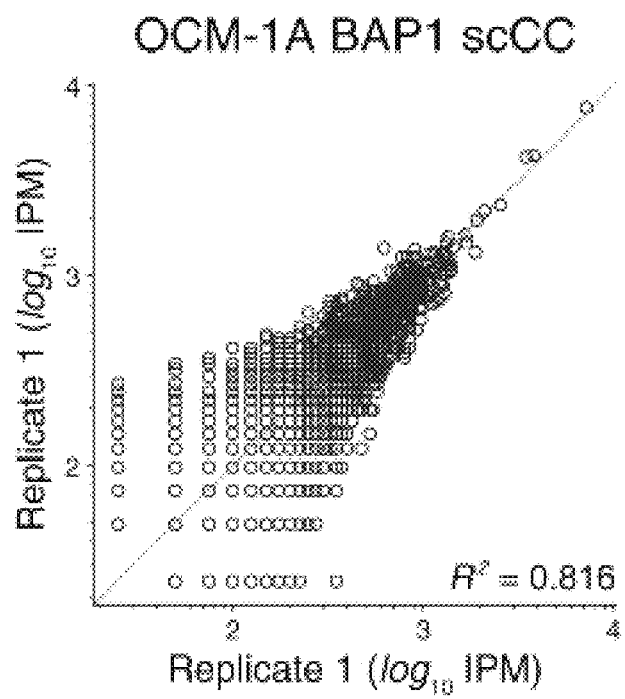
Figure 12I:
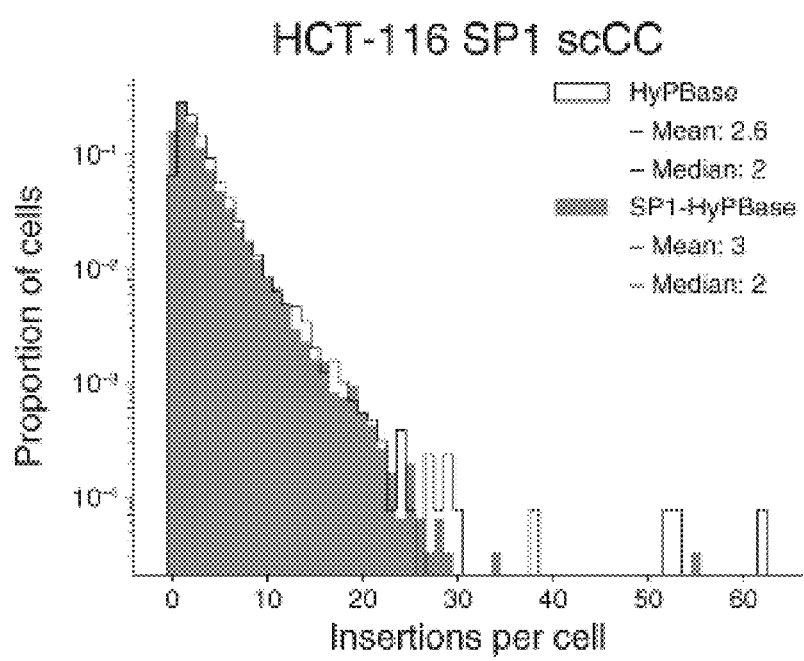
Figure 12J:
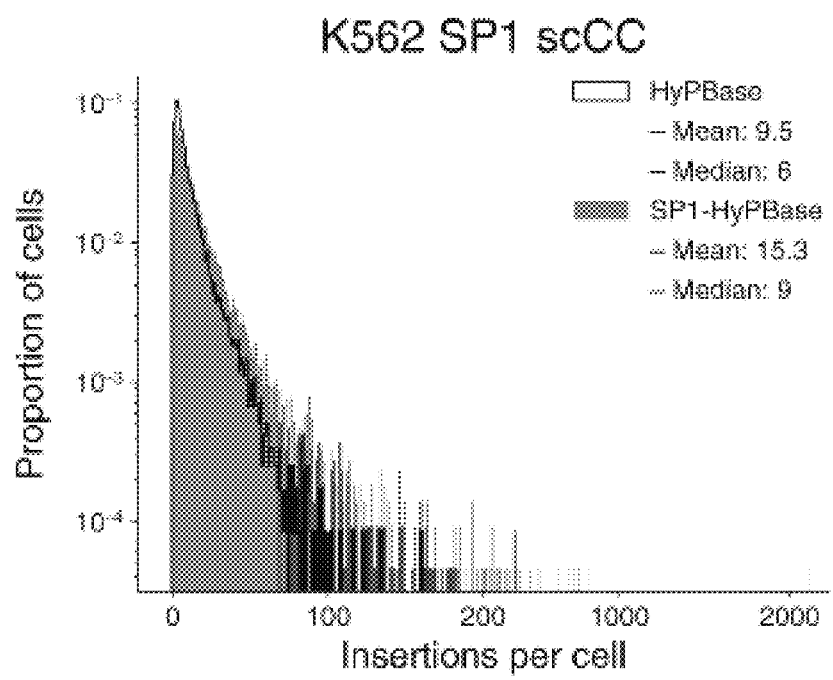
Figure 12K:
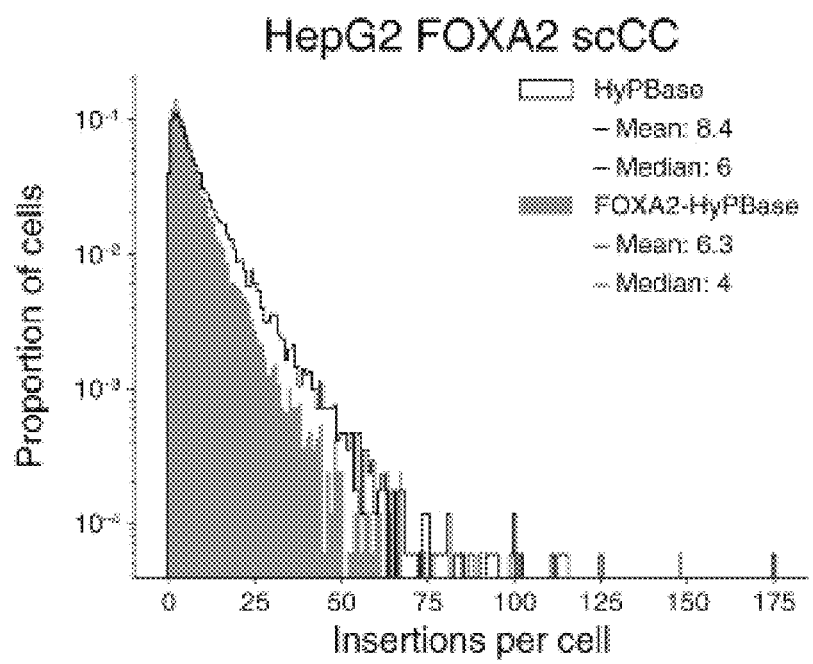
Figure 12L:
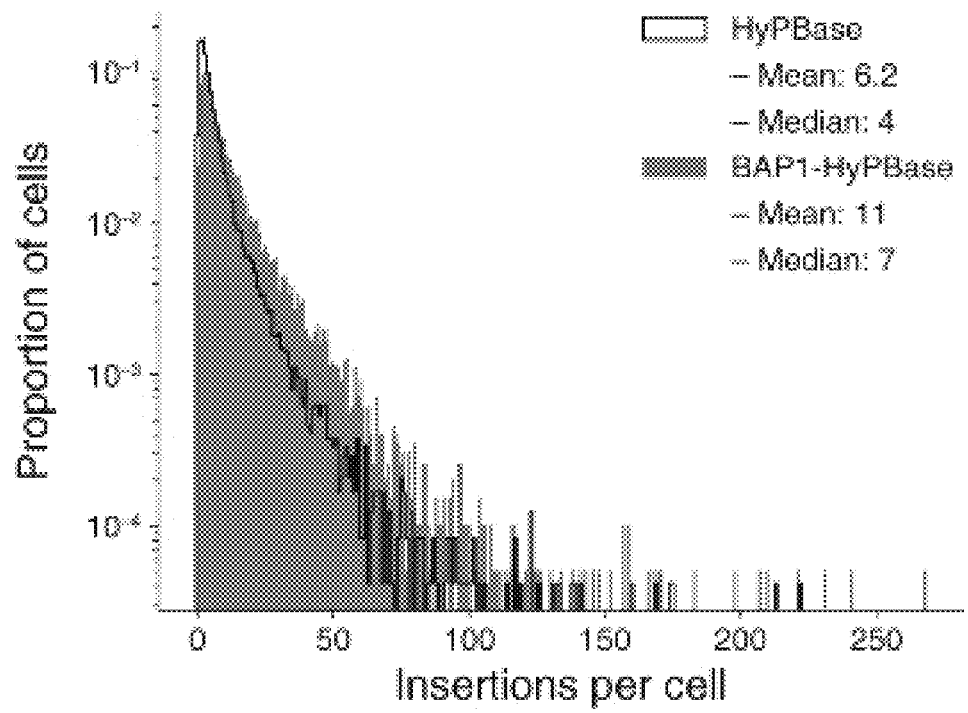

We then asked whether scCC could discern cell-type-specific BRD4 binding. We transfected two human cell lines, HCT-116 and K562, with HyPBase and PB-SRT-Puro and mixed them together. The resulting scRNA-seq libraries clearly distinguished these two cell types (FIG. 4C and FIG. 11A). We prepared scCC libraries from these cells and used the cell barcodes from the HCT-116 and K562 clusters to assign insertions to the two different cell types (TABLE 2). The distribution of insertions per cell varied by cell type (FIG. 11D) and was not explained by differences in total RNA content (FIG. 11B and FIG. 11C). Over 93% and 96% of HCT-116 and K562 cells, respectively, had at least one insertion event (TABLE 2). Using the scCC insertion data, we called peaks and successfully identified BRD4-bound loci that were specific to HCT-116 cells, shared between HCT-116 and K562, and specific to K562 cells, respectively (FIG. 4D). Both HCT-116 and K562 peaks showed statistically significant enrichment for BRD4 ChIP-seq signal over randomly permuted peaks (FIG. 11E and FIG. 11F, KS test $p<10^{-9}$ in both instances). Furthermore, 57% of HCT-116 peaks and 81% of K562 peaks were specifically bound in their respective cell type. We estimated that with a p value cutoff of $10^{-9}$, our sensitivity for detecting BRD4-bound SEs would be approximately 60% (Supplemental Methods), while the actual sensitivity at this level was 67%. Finally, at statistically significant peaks, normalized insertion counts were highly concordant between biological replicates in both cell types ($R^2=0.91$ and 0.94, respectively; FIG. 11G and S3H). In all, these experiments demonstrate that scCC can be used to identify and deconvolve cell-type-specific BRD4 binding sites.

scCC Identifies Binding Sites across a Spectrum of TFs and in a Variety of Cell Types Our success mapping BRD4 SEs in single cells gave us confidence that we would also be able to map TF binding with scCC. We transfected HCT-116 and K562 cells with an SP1 fusion construct (SP1-HyPBase) and performed scCC (TABLE 2). As was observed in bulk (Supplemental Methods), SP1-HyPBase-directed insertions recovered from single cells localized to SP1 binding sites in both HCT-116 and K562 cells (FIG. 5A and FIG. 5E). In both cell lines, we observed significant enrichment of SP1 ChIP-seq signal at scCC peaks (FIG. 5B and FIG. 5C and FIG. 5F and FIG. 5G) and motif analysis identified the SP1 DNA binding motif (FIG. 5D and FIG. 5H) ($p<10^{-30}$ in each instance). SP1 is known to preferentially bind near transcription start sites (TSSs) and is also thought to play a role in demethylating CpG islands (Brandeis et al., 1994; Macleod et al., 1994; Philipsen and Suske, 1999). Accordingly, we observed significant enrichments for insertions near TSSs, CpG islands, and unmethylated CpG islands in particular (FIG. 12A and FIG. 12B, G test of independence $p<10^{-9}$ in each instance).

Figure 5I:
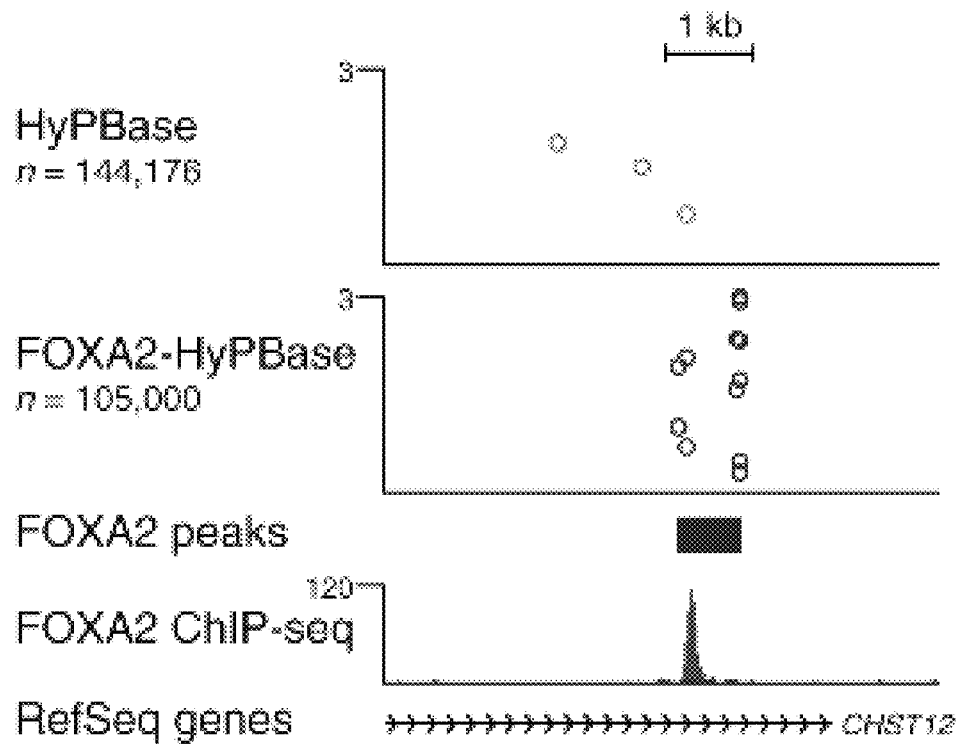
Figure 5J:
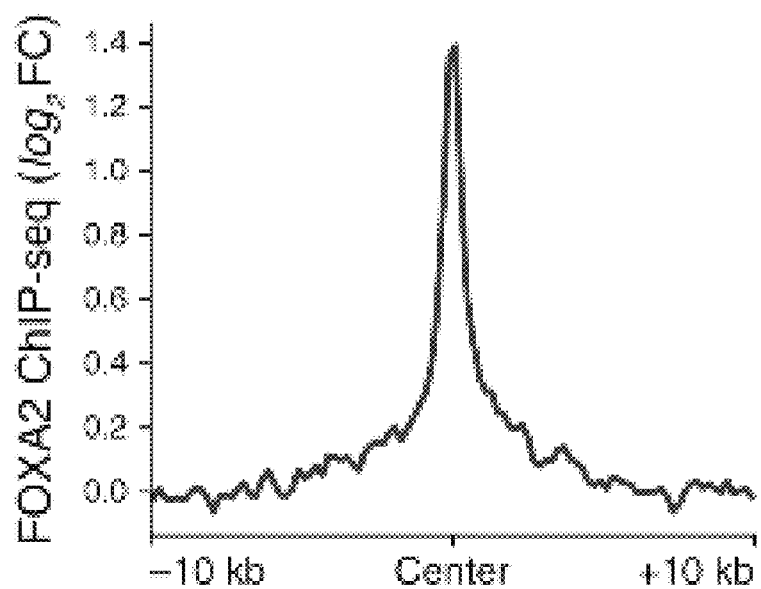
Figure 5K:
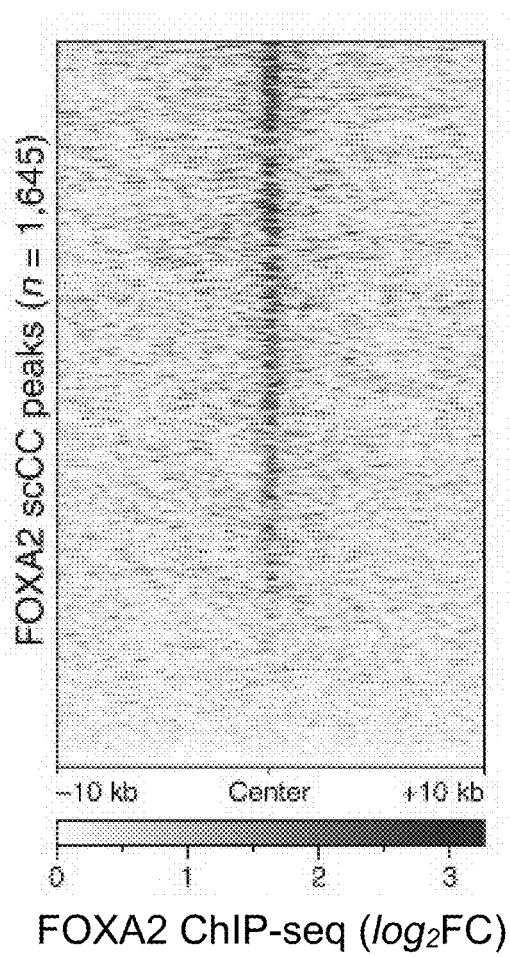
Figure 5L:
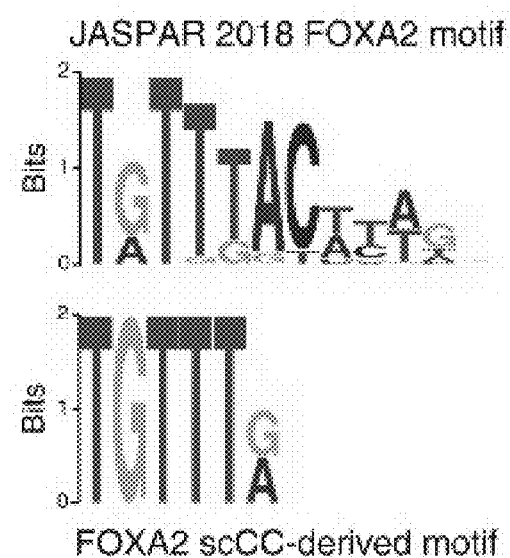

We next performed scCC in HepG2 cells with the pioneer factor FOXA2 (TABLE 2), which has been shown to be required for normal liver development and drives core transcriptional networks in cancer cells (Fournier et al., 2016; Lee et al., 2005). As with SP1, we observed a specific enrichment of insertions at FOXA2 binding sites (FIG. 5I). Peaks called from scCC FOXA2 data were enriched in FOXA2 ChIP-seq signal (FIG. 5J and FIG. 5K) and motif analysis was able to infer the core FOXA2 DNA binding motif (FIG. 5L).

Figure 5M:
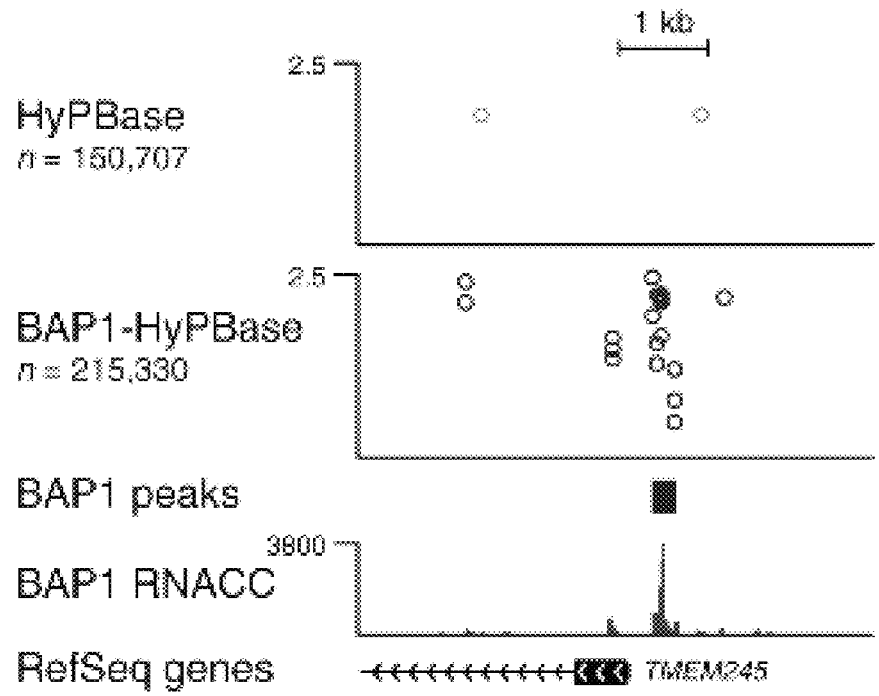
Figure 5N:
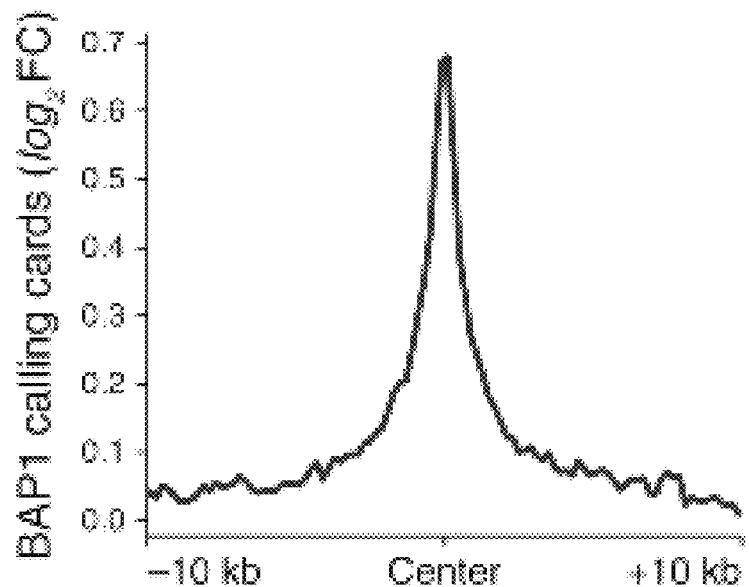
Figure 5O:
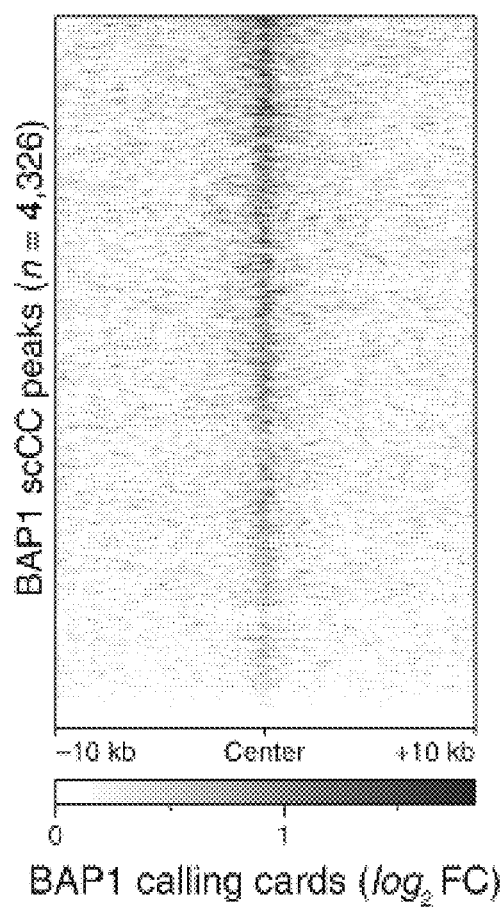
Figure 5P:
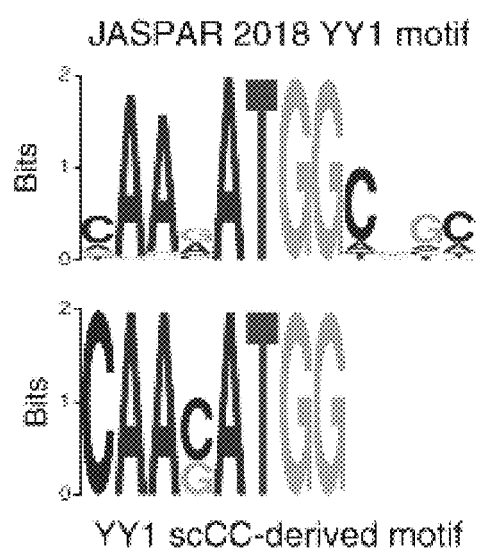

Last, we mapped the binding of BAP1 in the uveal melanoma cell line OCM-1A (Yen et al., 2018) using scCC (TABLE 2). Unlike SP1 and FOXA2, BAP1 does not bind DNA directly; instead, it is drawn to chromatin in a complex (Carbone et al., 2013; Yu et al., 2010) where it acts as a histone deubiquitinase. Despite this indirect interaction, we were able to resolve sharp BAP1-directed peaks (FIG. 5M). These peaks showed high concordance with bulk RNA calling card data that we also generated in this system (FIG. 5N and FIG. 5O; TABLE 1). Sequence analysis elicited the motif of YY1 (FIG. 5P), a DNA binding TF and known member of the BAP1 complex (Yu et al., 2010). BAP1 is known to preferentially bind promoters (Dey et al., 2012), and, as such, we observed a significant enrichment for BAP1-directed insertions near TSSs (FIG. 12C; G test of independence $p<10^{-9}$). While BAP1 is a member of the Polycomb repressive complex, there are conflicting reports as to its direct effects on gene expression (Campagne et al., 2019; Matatall et al., 2013; Yu et al., 2010). We cross-referenced our single-cell BAP1 peaks against published RNA-seq data in unperturbed and BAP1 knockdown OCM-1A cells (Yen et al., 2018). Genes where BAP1 is bound at the promoter, as opposed to in the gene body or at a nearby intergenic locus, are significantly more likely to have increased expression upon BAP1 knockdown (FIG. 12D; Fisher's exact test $p<10^{-9}$). This suggests that, in this model of uveal melanoma, promoter-bound BAP1 primarily acts as a repressor of gene expression.

Collectively, these results indicate that scCC can successfully map DNA-protein interactions for a range of TFs and in a variety of cell types. Furthermore, scCC showed high reproducibility in all four tested conditions ($R^2$ between 0.71 and 0.95; FIG. 12E-FIG. 12H). Although TF-piggyBac fusions have been previously reported to decrease transposase activity (Wu et al., 2006), our findings were more equivocal: some fusions showed less activity per cell than undirected HyPBase, while others were more efficient (FIG. 12I-FIG. 12L). Thus, there may be some variability in the number of recovered insertions depending on the TF and cell type of interest. Overall, however, the method is robust.

scCC Reveal Bromodomain-Dependent Cell-State Dynamics in K562 Cells

SEs and BRD4 are thought to mark genes important for specifying cell identity, and, while the strongest evidence for this comes from comparisons between organ systems or between sharply delineated disease states (Hnisz et al., 2013; Whyte et al., 2013), recent studies have shown that even closely related subpopulations of the same cell type can show subtle changes in BRD4 enrichment and enhancer utilization (Knoechel et al., 2014; Rathert et al., 2015). Recently, K562 cultures have been shown to be mixtures of a stem-like state characterized by high levels of the surface marker CD24, and a more differentiated, erythroleukemic state marked by low CD24 expression, with individual cells dynamically oscillating between these two extremes (Litzenburger et al., 2017). As we had profiled BRD4 binding in K562 cells with scCC, we wondered whether we could see evidence of these two states and, if so, whether there was differential utilization of BRD4 between them.

We first scored cells based on a principal-component analysis (PCA) of gene expression (FIG. 13A and FIG. 13B), which revealed a gradient of identities along a stem-like-to-differentiated cell-state axis (FIG. 6A). We then separated cells into $CD24^{high}$ nd $CD24^{low}$ clusters (FIG. 13C and FIG. 13D) and asked whether we could detect any differences in BRD4 binding between them in our scCC data. Indeed, we found multiple peaks that showed significant differential binding (FIG. 6B). We corroborated these hits by comparing our peak calls to bulk BRD4 and H3K27ac ChIP-seq data, as well as to RNA pol II ChIA-PET data, which connects putative enhancers to actively transcribed genes (Fullwood et al., 2009). We highlight two genes that showed both differential binding and expression: VMP1, bound more in the $CD24^{high}$ stem-like cells, and PVT1, bound more in the differentiated, $CD24^{low}$ cells (FIG. 13F and FIG. 13G). VMP1 overexpression is sufficient to induce autophagy (Ropolo et al., 2007), which is important for hematopoietic stem cell function (Folkerts et al., 2019; Ho et al., 2017) and may be one pathway recruited during these dynamic state transitions. PVT1 can act as both a tumor-suppressor and oncogene, in both instances acting on the MYC locus (Cho et al., 2018).

We next investigated whether the observed differences in BRD4 binding might be causally responsible for establishing these two cell states. Downregulating BRD4 has been shown to influence cell identity across a range of cell types (Di Micco et al., 2014; Kfoury et al., 2017; Najafova et al., 2017). Thus, we hypothesized that BRD4 inhibition would change the distribution of cells in the stem-like and differentiated states. Moreover, due to the asymmetric nature of significant hits (FIG. 6B), there is a subset of peaks specific to the $CD24^{high}$ state that are not shared by the $CD24^{low}$ state, suggesting that there may be a gene regulatory network that is recruited as cells transit from the differentiated to stem-like state and lost as they return. Hence, not only should the distribution of $CD24^{high}/CD24^{low}$ cells change upon BRD4 perturbation but the stem-like $CD24^{high}$ population should be more susceptible to such an intervention.

We tested this hypothesis by treating cells with JQ1, a small-molecule bromodomain inhibitor often used to disrupt BRD4 binding and alter target gene expression (Delmore et al., 2011; Garcia-Carpizo et al., 2018; Lovén et al., 2013; Sdelci et al., 2019). JQ1 treatment shifted the population from one containing equal proportions of $CD24^{high}/CD24^{low}$ cells to one composed of almost exclusively $CD2^{low}$ cells (>95%, FIG. 6C). This conversion took place rapidly over the first 2 days, plateaued by day 4, and remained stable 1 week after treatment. In contrast, the control cells remained evenly split between the two states at this time point (FIG. 6D; two-way ANOVA p<0.01). JQ1 was not selectively cytotoxic to $CD24^{high}$ cells as there were no significant differences in the levels of annexin V, an early marker of apoptosis, between $CD24^{high}$ and $CD24^{low}$ cells, regardless of whether they had been exposed to JQ1 or DMSO (FIG. 14A; three-way ANOVA p=0.84). Additionally, we examined whether CD24 is a direct target of BRD4, which would imply that the loss of CD24 staining was an unremarkable consequence of JQ1 treatment. We did not find evidence of BRD4 binding sites, either by ChIP-seq or calling cards, or of elevated H3K27 acetylation in the vicinity of CD24 (FIG. 14B). We also compared the relative changes in mRNA levels of MYC, a known BRD4 target (Knoechel et al., 2014; Lovén et al., 2013; Rathert et al., 2015; Zuber et al., 2011), to that of CD24 during the first 24 h of JQ1 exposure. While MYC levels fell within the first 3 h of exposure, transcript levels of CD24 decreased most precipitously between 3 and 9 h after JQ1 induction (FIG. 14C). This delayed response suggests a regulatory cascade rather than direct transcriptional control. Thus, JQ1 treatment does not trivially downregulate a cell-surface marker but rather likely perturbs gene regulatory networks that include CD24.

While JQ1 shows greatest affinity for BRD4, it does have some promiscuity toward other bromodomains, including the orthologs BRD2 and BRD3 (Filippakopoulos et al., 2010). To address whether off-target effects were responsible for the shift in cell states, we downregulated BRD4 expression with CRISPR interference (CRISPRi). We confirmed that our BRD4 guide RNA (gRNA) specifically reduced expression of BRD4 and not BRD2 nor BRD3 (FIG. 14D; Welch's t test p<0.05). As with JQ1, we observed a significant decrease in the proportion of $CD24^{high}$ cells with the BRD4 gRNA compared to the non-targeting (NT) gRNA (FIG. 6E; Welch's t test p<0.01), though not to the same levels as JQ1. This suggests that, while BRD4 is necessary for the observed cell-state dynamics between $CD24^{high}$ nd $CD24^{low}$ cells, it is likely that other bromodomains also play a role.

$CD24^{high}/CD24^{low}$ cells have been previously shown to have different chemosensitivities, with the latter population showing more apoptosis when exposed to imatinib (Litzenburger et al., 2017). Therefore, we asked whether BRD4 inhibition increases imatinib sensitivity in K562 cells. If so, it would imply that the observed state shift functionally alters K562 cells as opposed to simply modulating a cell-surface marker. We first pretreated K562 cells with either DMSO or JQ1 and then challenged each pretreatment group with either DMSO or imatinib and stained for apoptosis. In the DMSO pretreatment group, the percentage of $CD24^{high}$ cells rose to 54% on average, while for JQ1-pretreated cells the mean was 17% (FIG. 6F). When imatinib was added, a substantially greater fraction of JQ1-pretreated cells underwent apoptosis relative to DMSO-pretreated cells (FIG. 6F and FIG. 6G; two-way ANOVA p<0.01). Thus, JQ1 sensitizes K562 cells to imatinib. Furthermore, BRD4 CRISPRi partially phenocopied this sensitization (FIG. 14E and FIG. 14F; Tukey's honestly significant difference p=0.68). This phenomenon is likely dosage dependent: in our experiments, CRISPRi reduced BRD4 mRNA levels by less than 50% (FIG. 14D), whereas the JQ1 concentration we used is expected to almost completely abolish BRD4 activity (Filippakopoulos et al., 2010). Thus, while a mild knockdown can reduce CD24 expression, greater inhibition may be necessary to induce imatinib sensitivity. Nevertheless, these results establish that BRD4 inhibition functionally and phenotypically shifts the underlying cell state of K562 cells.

Finally, we examined whether the JQ1-induced K562 cell-state shift was a non-specific response to generic drug treatment. We treated K562 cultures with a panel of cell-cycle inhibitors, another class of commonly used antineoplastic agents. We first confirmed that all drugs altered the proportions of cells in either G1 or G2/M phase (FIG. 14G). Cultures remained under drug treatment until 5 days had elapsed, at which point we measured CD24 levels and stained for apoptosis (FIG. 14H). JQ1 caused the greatest reduction in $CD24^{high}$ cells (one-way ANOVA p<0.01) and induced significantly less apoptosis than lovastatin, its closest competitor (one-way ANOVA p<0.01). Thus, JQ1's effect on cell state appears to be mediated by a unique mechanism of action that is not readily replicated by cell-cycle perturbation.

scCC Deconvolves Cell-Type-Specific BRD4 Binding Sites in the Mouse Cortex

Figure 7A:
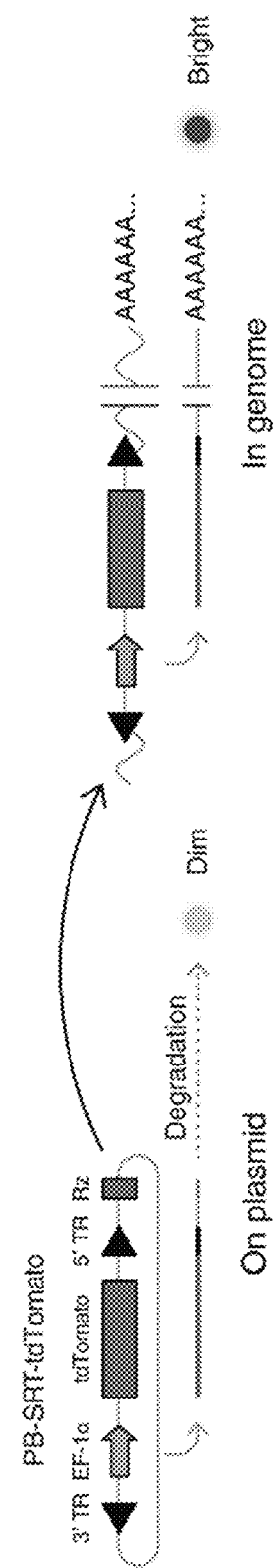
FIG. 7A-FIG. 7E. scCC Deconvolves BRD4-Bound Loci in the Mouse Cortex. (A) Schematic of PB-SRT-tdTomato. (B) Distribution of fluorescence intensity in K562 cells transfected with PB-SRT-tdTomato with and without piggyBac transposase. (C) Neuron and astrocyte clusters from scRNA-seq analysis of mouse cortex libraries transduced with AAV-HyPBase and AAV-PB-SRT-tdTomato. (D) Browser view of scCC HyPBase peaks in astrocytes and neurons alongside whole-cortex H3K27ac ChIP-seq. (E) Expression specificity distributions of genes overlapping astrocyte or neuron peaks; horizontal lines indicate medians of the distributions. See also FIG. 15. TR, terminal repeat; Rz, ribozyme.
Figure 7B:
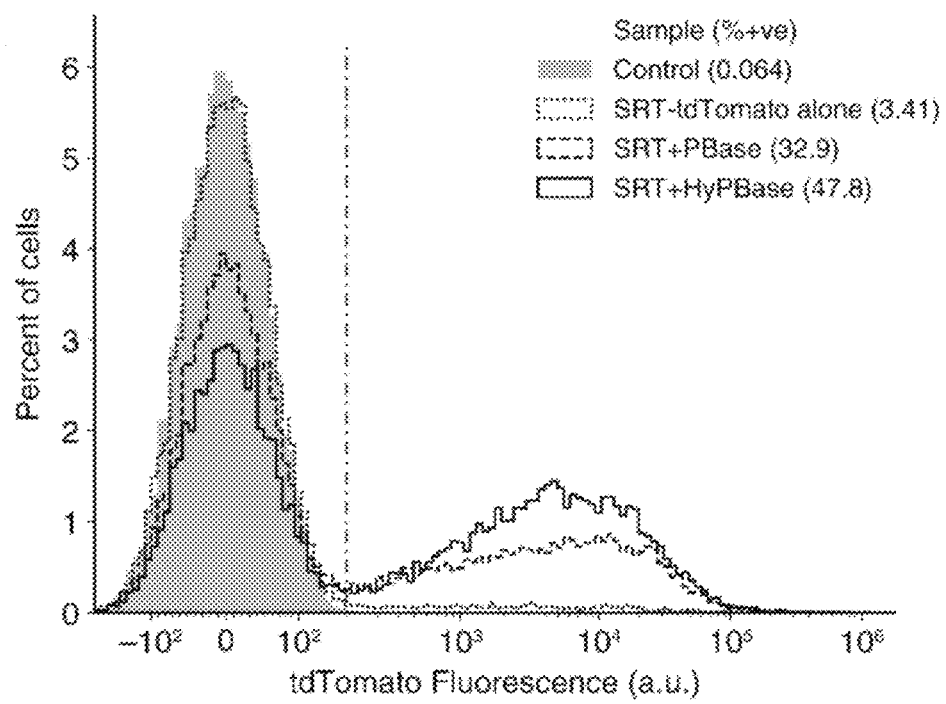

To establish broad utility for scCC, we sought to record TF binding in vivo. Since in vivo models preclude puromycin selection, we designed an SRT carrying a fluorescent reporter (FIG. 7A) and tested this reagent in cell culture. When this element was transfected without transposase, merely 3.4% of cells registered as positive, likely due to the action of the self-cleaving ribozyme downstream of the transposon. However, when the construct was co-transfected with piggyBac, this figure rose as high as 48%, a 16-fold increase in signal (FIG. 7B). Thus, this new construct, PB-SRT-tdTomato, allows us to collect cells carrying calling card insertions by fluorescence activated cell sorting (FACS).

Figure 7C:
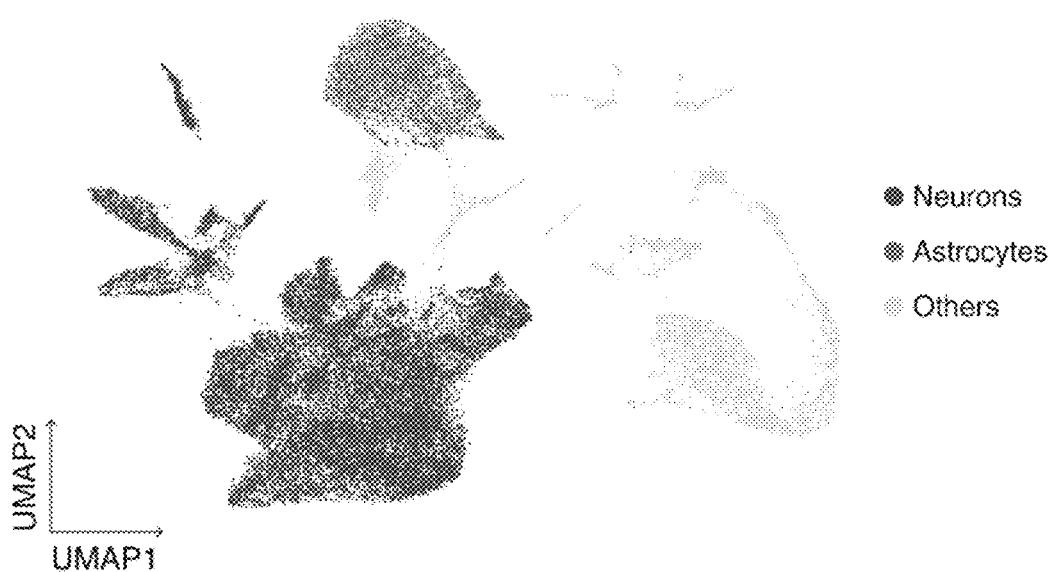
Figure 7D:
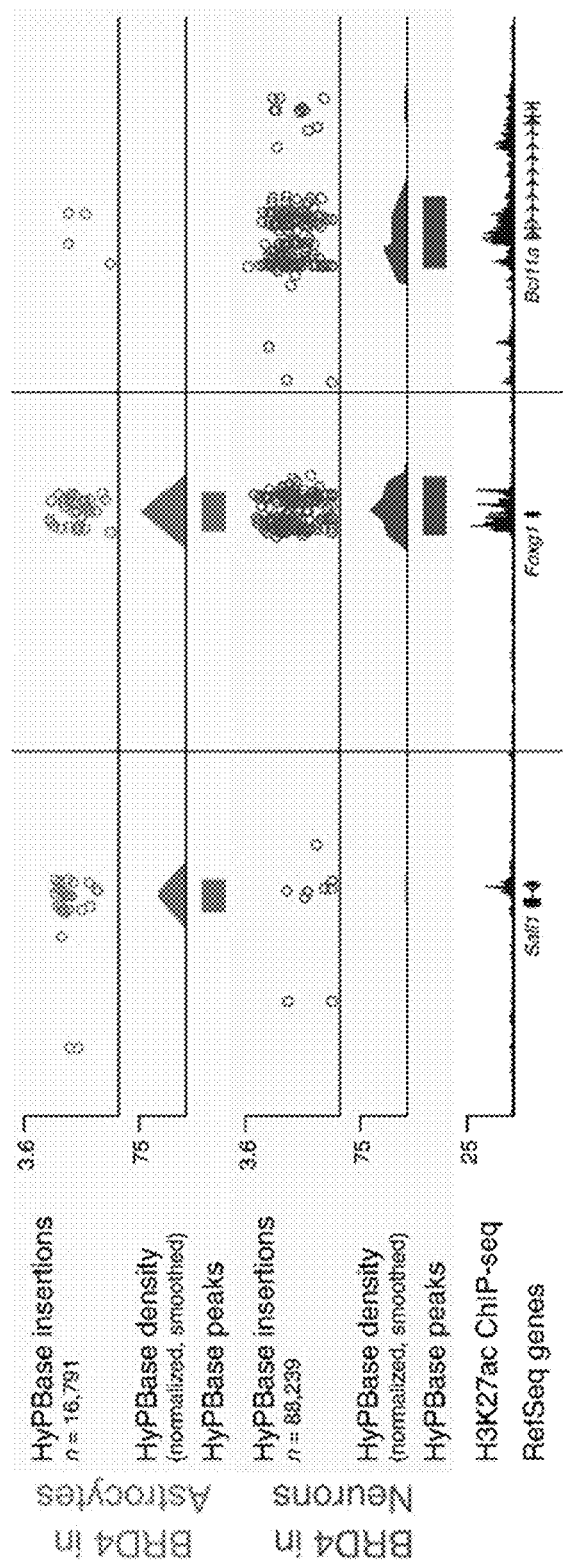
Figure 7E:
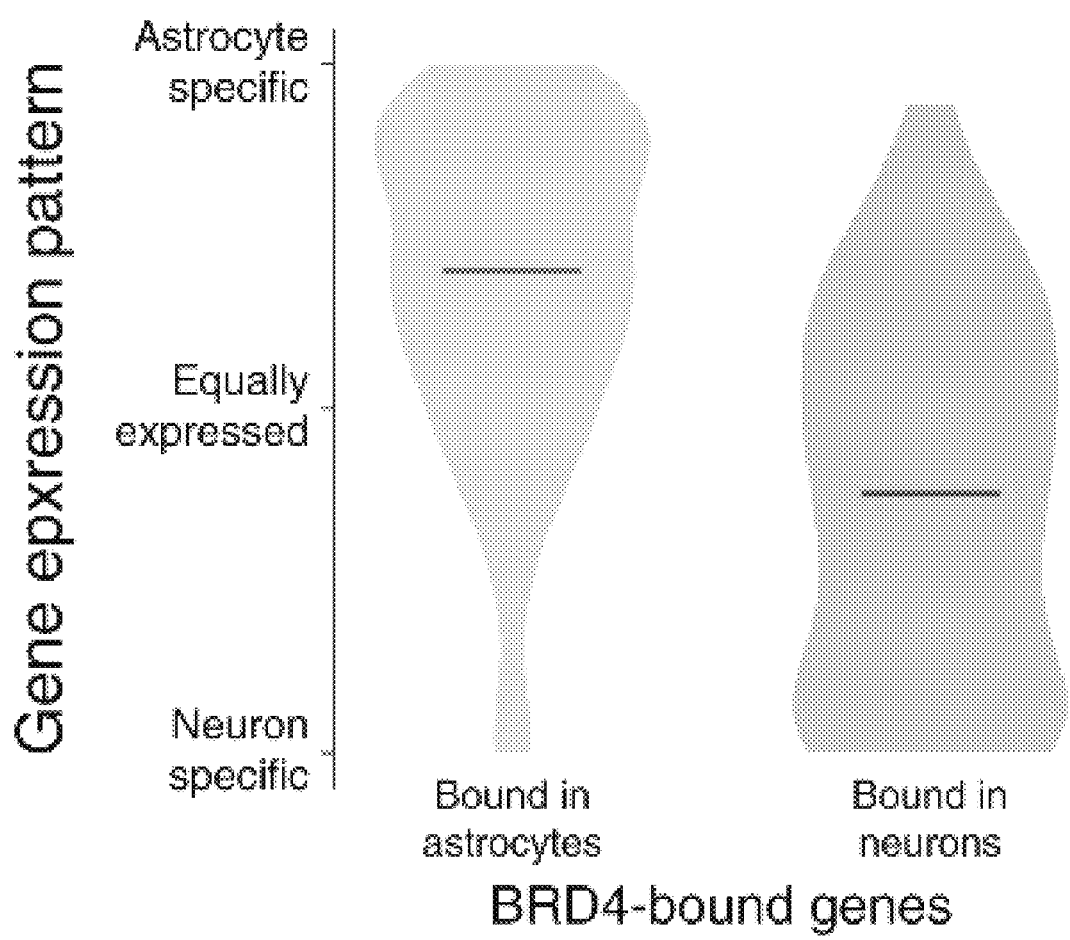
Figure 15A:
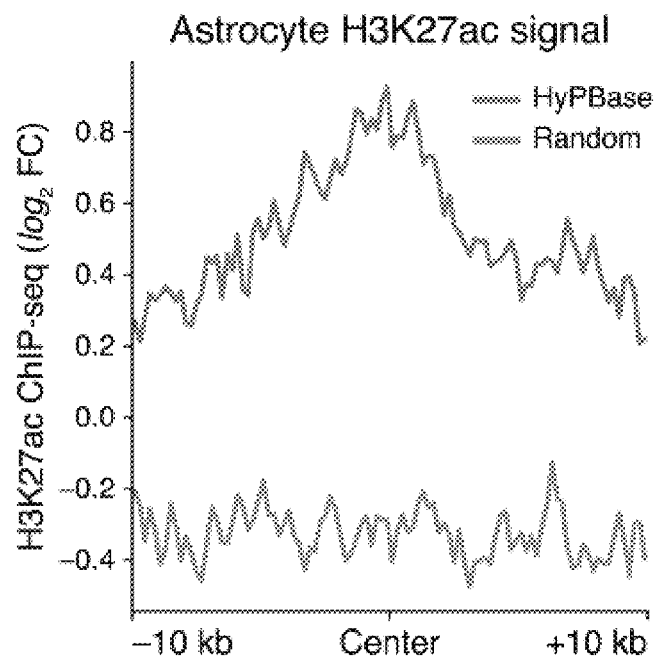
FIG. 15A-FIG. 15D. Validation of In Vivo BRD4 Binding in Astrocytes and Neurons, Related to FIG. 7. (A) Mean H3K27ac ChIP-seq signal at HyPBase peaks in astrocytes compared to randomly permuted peaks (KS test $p<10^{-9}$) (B) GO term enrichment analysis of genes near astrocytic BRD4 binding sites. (C) Mean H3K27ac ChIP-seq signal at HyPBase peaks in neurons compared to randomly permuted peaks (KS test $p<10^{-9}$). (D) GO term enrichment analysis of genes near neuronal BRD4 binding sites. (B and D) The white line indicates the Bonferroni-adjusted p value threshold at $\alpha=0.05$. GO: Gene Ontology; KS: Kolmogorov-Smirnov; FC: fold change.
Figure 15B:
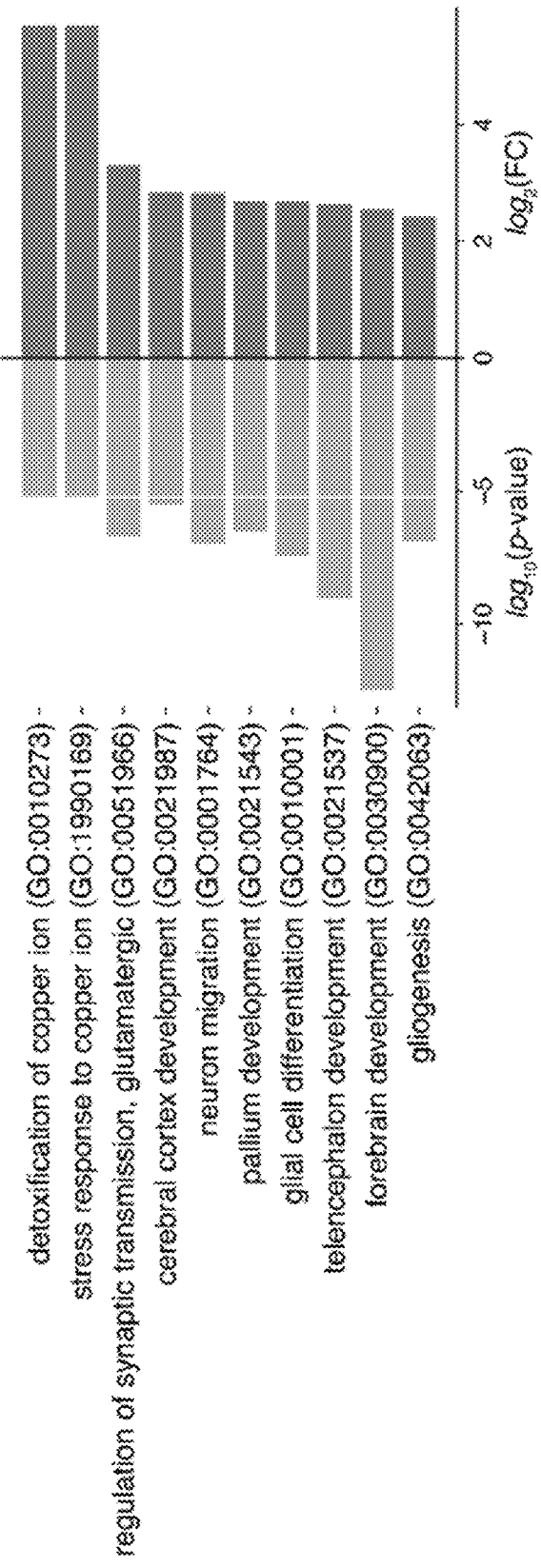
Figure 15C:
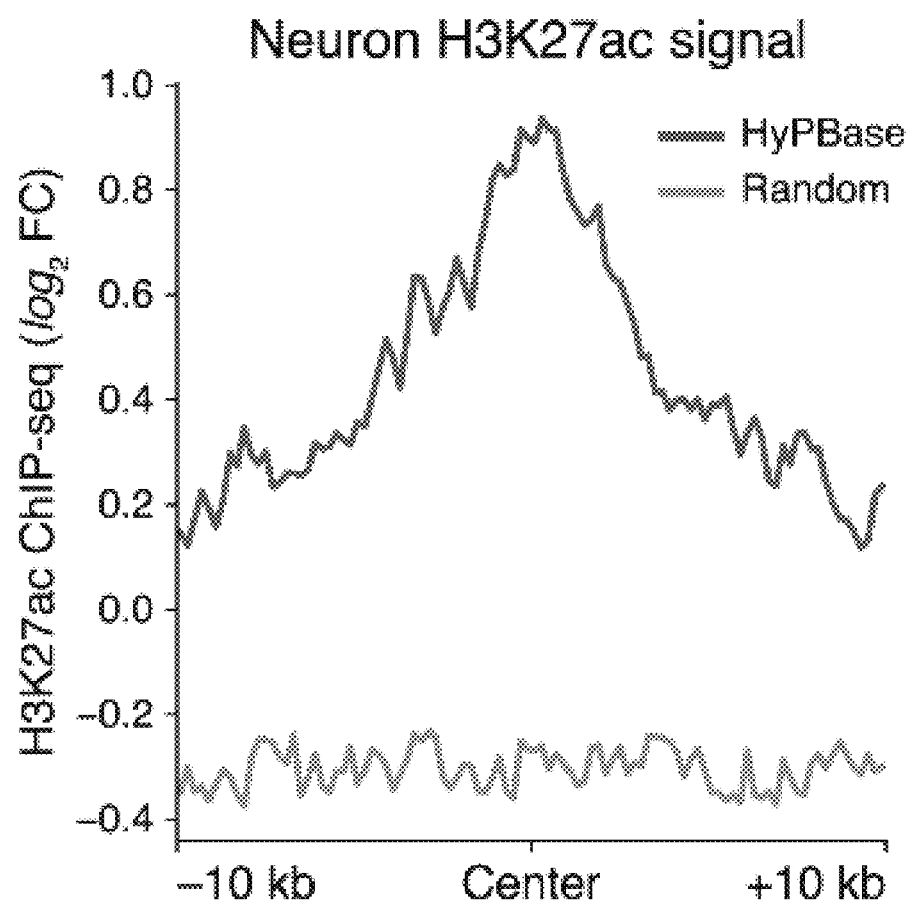
Figure 15D:
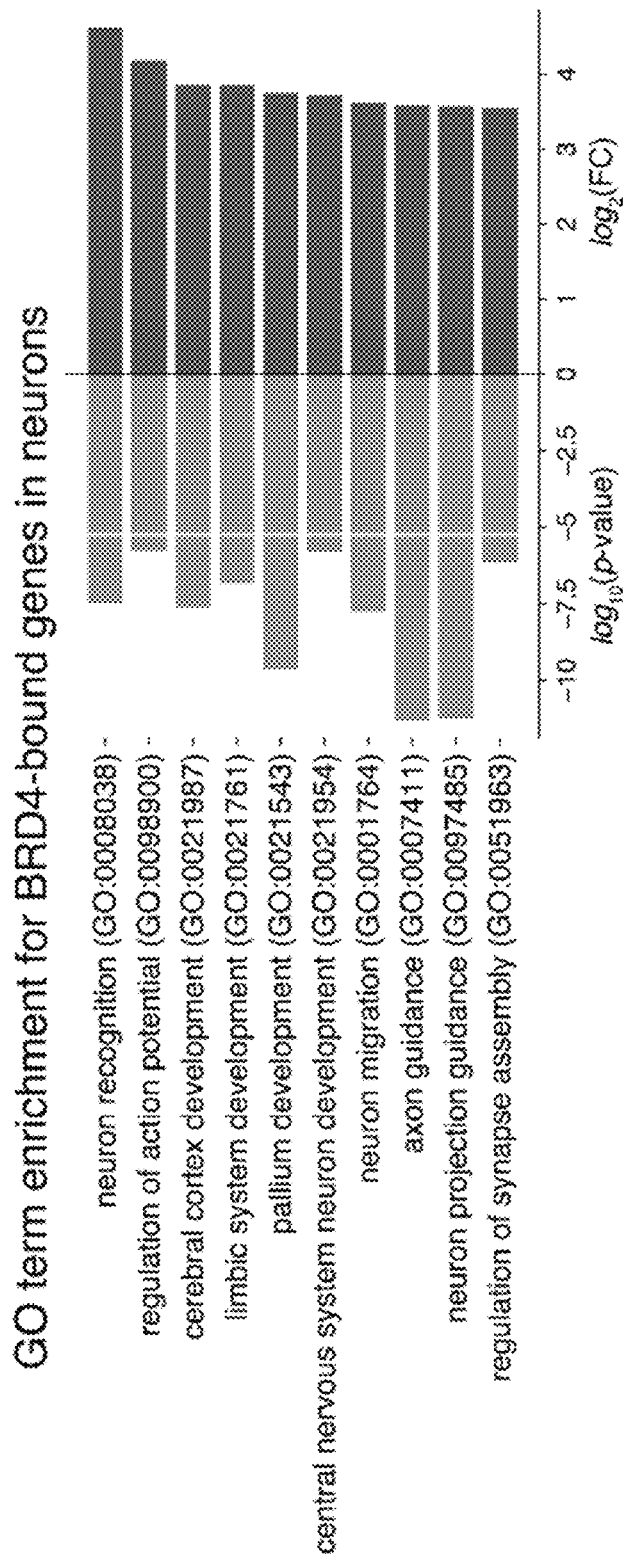

Next, we delivered PB-SRT-tdTomato and HyPBase to the postnatal mouse cortex by performing adeno-associated viral (AAV) transduction (Cammack et al., 2020) in P0-2 pups and then generating scRNA-seq and scCC libraries between P14 and P28. Most transduced cells were neurons or astrocytes (TABLE 2 and TABLE 3; FIG. 7C; Supplemental Methods), which is consistent with the known tropism of AAV9 (Cammack et al., 2020; Schuster et al., 2014). Therefore, we analyzed insertions in neurons (excluding neuroblasts and doublets) and astrocytes to determine whether scCC could recover biological differences between cell types in vivo. After calling peaks, we identified astrocyte-specific, neuron-specific, and shared BRD4 binding sites (FIG. 7D). Since BRD4 ChIP-seq has not yet been reported for the mouse brain, we compared our peak calls to a recent cortical H3K27ac ChIP-seq dataset (Stroud et al., 2017), and, while this dataset is a mélange of all cell types in the brain, scCC peaks in both astrocytes and neurons showed statistically significant enrichment of H3K27ac signal (FIG. 15A and FIG. 15C, KS test $p<10^{-9}$ in each case). Moreover, genes near astrocyte peaks were more likely to be specifically expressed in astrocytes and vice versa for genes near neuron peaks (FIG. 5E; Methods). Furthermore, Gene Ontology enrichment analysis (Mi et al., 2017) on the set of genes near astrocyte peaks included terms like "gliogenesis," and "glial cell differentiation," as well as copper metabolism (FIG. 15B), a known function of astrocytes (Scheiber and Dringen, 2013), while the set of genes near neuronal peaks was enriched for terms related to synapse assembly, axonal guidance, and neuron development (FIG. 15D). We conclude that scCC can accurately identify cell-type-specific BRD4 binding sites in vivo.

Figure 8A:
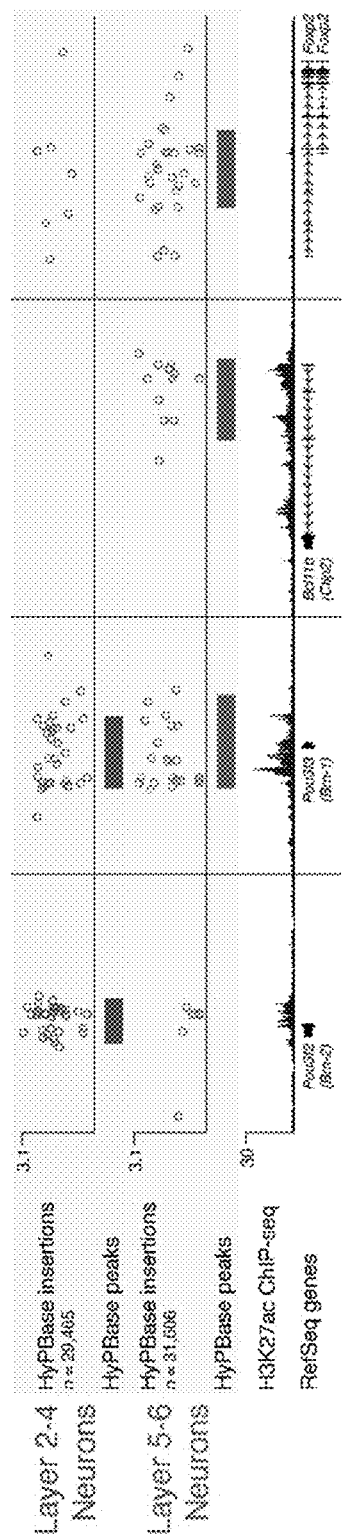
FIG. 8A-FIG. 8C. scCC Unmixes BRD4 Binding in Cortical Excitatory Neurons and Identifies Known Layer Markers. (A) Browser view of scCC HyPBase peaks in upper (layer 2-4) or lower (layer 5-6) cortical excitatory neurons alongside whole-cortex H3K27ac ChIP-seq. (B) Layer 2-4 and layer 5-6 cortical excitatory neurons highlighted among the scRNA-seq clusters. (C) Single-cell gene expression patterns of the four genes from (A).
Figure 8B:
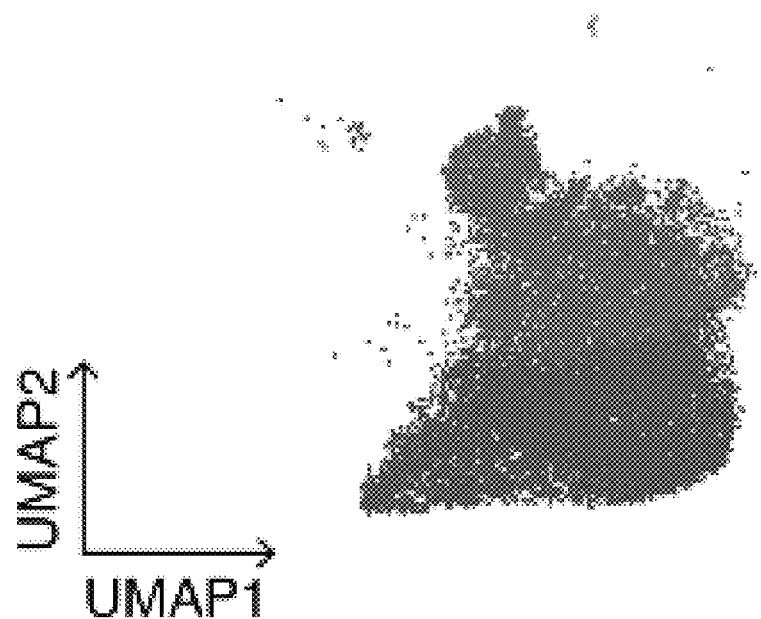
Figure 8C:
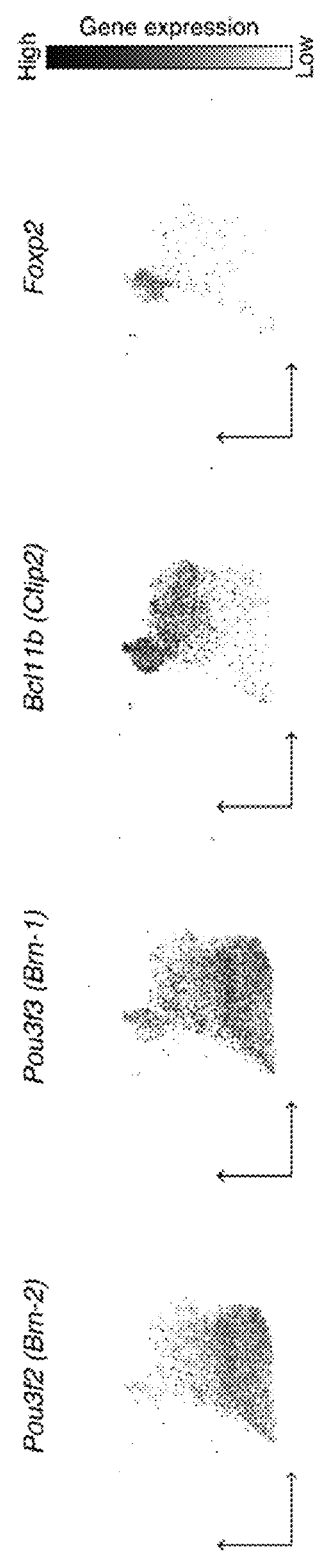

Last, we asked whether scCC in vivo could discriminate BRD4 binding between closely related cell types, much as we had shown in vitro with K562 cells. From our scRNA-seq data, we identified upper- and lower-layer cortical excitatory neurons (FIG. 8B; TABLE 3; Supplemental Methods) and compared HyPBase scCC data between them to identify shared and specific BRD4-bound loci. As a positive control, we found a shared BRD4 binding site at the Pou3f3 (Brn-1) locus (FIG. 8A), which was broadly expressed in both populations (FIG. 8C) and has been used to label layers 2-5 of the postnatal cortex (Molyneaux et al., 2007; Pucilowska et al., 2012). Differential binding analysis showed specific BRD4 enrichment at Pou3f2 (Brn-2) in upper-layer neurons, which is more restricted to layers 2-4 than Pou3f3 (Fan et al., 2008; Molyneaux et al., 2007), while lower cortical neurons showed BRD4 binding at Bcl11b (Ctip2) and Foxp2, common markers of layer 5 and layer 6 neurons, respectively (FIG. 8A; one-tailed Poisson $p<10^{-9}$ in each instance) (Molyneaux et al., 2007; Rašin et al., 2007). The expression patterns of these genes mirrored BRD4's binding specificity, with Pou3f2's expression mostly contained in the layer 2-4 cluster and the expression of Bcl11b and Foxp2 restricted to the layer 5-6 neuron population (FIG. 8C). Thus, scCC can identify differentially bound loci between very similar cell types in vivo.

TABLE 3

Breakdown of cortical cell types and scCC HyPBase insertions per cluster, related to FIG. 7, FIG. 8, and FIG. 15. IPC: insertions per cell.

| Cluster | Cells | Insertions | Mean IPC |
|---|---|---|---|
| Astrocyte | 4,727 | 16,791 | 3.6 |
| Astro_Neuron_Doublet | 394 | 1,653 | 4.2 |
| Ependymal | 107 | 153 | 1.4 |
| Microglia | 569 | 238 | 0.4 |
| Neuroblast_SVZ | 369 | 1,084 | 2.9 |
| Neuron_Cajal-Retzius | 552 | 4,363 | 7.9 |
| Neuron_Excit_AON | 1,939 | 8,190 | 4.2 |
| Neuron_Excit_Indeterminate | 3,660 | 6,377 | 1.7 |
| Neuron_Excit_L2-4 | 9,083 | 29,465 | 3.2 |
| Neuron_Excit_L5 | 5,544 | 26,437 | 4.8 |
| Neuron_Excit_L6 | 1,436 | 5,169 | 3.6 |
| Neuron_Granule_DG | 535 | 1,674 | 3.1 |
| Neuron_Inhibitory | 2,409 | 6,564 | 2.7 |
| Oligo_Mature | 2,740 | 1,729 | 0.6 |
| Oligo_NewlyForming | 959 | 674 | 0.7 |
| Oligo_Progenitor | 504 | 477 | 0.9 |
| Vascular_endothelial | 196 | 69 | 0.4 |
| Vascular_meningeal | 227 | 275 | 1.2 |

Discussion scCC enables simultaneous characterization of gene expression and TF binding in heterogeneous systems. The method is robust and flexible: we have demonstrated that it can map multiple kinds of DNA binding proteins—from sequence-specific TFs like SP1 and FOXA2, to indirect, chromatin-associated factors like BRD4 and BAP1—in a variety of in vitro systems and in vivo in the mouse cortex. Furthermore, our finding that cell-state transitions in K562 cells are mediated by bromodomain proteins including BRD4 demonstrates how scCC can lead to new hypotheses about transcriptional regulation in dynamic systems. Our approach fills a recognized void in the field (Shapiro et al., 2013; Shema et al., 2019) and is readily compatible with high-throughput droplet microfluidic platforms such as the 10× Chromium. We anticipate this technique will empower researchers to study TF binding in a variety of challenging ex vivo and in situ models.

The defining feature of scCC is the SRT. While here we have reported piggyBac and Sleeping Beauty SRTs (Supplemental Methods), the self-reporting paradigm may be broadly generalizable. Expanding the palette of SRT systems could yield further insight into chromatin dynamics (Yoshida et al., 2017). Moreover, SRTs may enable multiplexed studies of TF binding, either through the simultaneous expression of many TFs, each tagged to a different transposase, or through the use of multiple barcoded TF-piggyBac fusions expressed polyclonally in culture. Since SRTs can be widely dispersed through the genome, full-length sequencing of self-reporting transcripts may find new PASs (Supplemental Methods). Finally, SRTs could lead to new single-cell transposon-based assays. For example, just as CRISPR/Cas9 has been combined with scRNA-seq to assess the transcriptional effects of many single gene perturbations in parallel (Datlinger et al., 2017; Dixit et al., 2016), SRTs could enable massively multiplexed transposon mutagenesis screens to be read out by scRNA-seq.

One concern with calling cards is the potential for insertional mutagenesis of target genes leading to cell death and, consequently, false negatives. Previous work in diploid yeast found that calling cards are deposited into the promoters of essential and non-essential genes at comparable frequencies (Wang et al., 2011). Since mammalian genomes have much larger intergenic regions than yeast, human and mice genomes are likely also able to tolerate calling card transpositions. Long-term follow-up of mice transduced intracranially with AAV calling cards showed no significant tissue pathology, behavioral deficits, developmental defects, or metabolic dysregulation (Cammack et al., 2020). This suggests calling cards imposes, at most, a small mutagenic burden, though more studies are needed to verify this.

Another potential drawback of calling cards is that exogenous expression of a TF at supraphysiological levels may lead to ectopic binding and, consequently, false positives. We note that over 90% of our peaks from scCC of SP1 in HCT-116 cells and FOXA2 in HepG2 cells were within 1,000 bp of a ChIP-seq peak from the respective TF. This suggests that calling card peaks reflect endogenous binding, though this behavior may vary by factor. Overexpression might also alter the transcriptome of transfected cells. Comparing gene expression levels between cells treated with TF-piggyBac and the undirected piggyBac control cells can determine whether there is transcriptional perturbation and to what extent. Tagging the endogenous TF locus with piggyBac ensures native expression levels and would alleviate both concerns.

The relatively few insertions recovered on a per-cell basis inflates the number of cells that must be analyzed. We recommend processing enough cells to obtain at least 15,000 insertions to analyze BRD4-bound SEs with undirected piggyBac, and at least 30,000 insertions for both constructs in TF-directed experiments. This should achieve moderate sensitivities (~50%; Supplemental Methods) that can be increased by collecting more insertions. The scant data recovered on a per-cell level likely stem from limited transposase activity—up to 15-30 insertions per cell for PBase (Kettlun et al., 2011; Saridey et al., 2009; Wang et al., 2008; Wilson et al., 2007) and potentially up to 100 for HyPBase (Kalhor et al., 2018; Yusa et al., 2011)—and the low capture rate of mRNA transcripts in droplet scRNA-seq (Hwang et al., 2018). This sparsity precludes certain kinds of analyses, such as multimodal data integration. Moreover, piggyBac's strict preference for TTAA tetramers also contributes to broader peaks with lower spatial resolution. While we overcame the latter constraint by focusing on peak centers and narrow peaks, peak width is inversely correlated with the number of insertions analyzed; as such, improving recovery of SRTs from single cells should be prioritized. Some of these gains may come organically as the transcript capture rates of scRNA-seq technologies improve. Since the per-cell costs for scRNA-seq are falling exponentially (Svensson et al., 2018), combining scCC with sample multiplexing strategies like cell hashing (Stoeckius et al., 2018) or combinatorial barcoding (Rosenberg et al., 2018) may be an attractive approach to increase sensitivity.

Finally, calling card insertions, being integrated into the genome and preserved through mitosis, could serve as a molecular memory for recording TF binding events. The use of an inducible transposase (Qi et al., 2017) would enable the recording and identification of temporally restricted TF binding sites. This would help uncover the stepwise order of events underlying the regulation of specific genes and inform cell-fate decision making. More generally, transposon insertions could serve as barcodes of developmental lineage. Single transposition events have been used to delineate relationships during hematopoiesis (Rodriguez-Fraticelli et al., 2018; Sun et al., 2014). Multiplexing several SRTs across every cell in an organism could code lineage in a cumulative and combinatorially diverse fashion, generating high-resolution cellular phylogenies.

Key Resources Table

| REAGENT or RESOURCE | SOURCE | IDENTIFIER |
|---|---|---|
| Antibodies | | |
| Brilliant Violet 421 anti-human CD24 Antibody (clone ML5) | BioLegend | Cat# 311121; RRID: AB_10915556 |
| Brilliant Violet 421 Mouse IgG2a, κ Isotype Ctrl Antibody (clone MOPC-173) | BioLegend | Cat# 400259; RRID: AB_10895919 |
| APC anti-human CD24 Antibody (clone ML5) | BioLegend | Cat# 311117; RRID: AB_1877150 |
| APC Rat IgG2a, κ Isotype Ctrl (clone RTK2758) | BioLegend | Cat# 400511; RRID: AB_2814702 |
| Bacterial and Virus Strains | | |
| AAV9-PB-SRT-tdTomato | Joseph D. Dougherty | N/A |

-continued

| REAGENT or RESOURCE | SOURCE | IDENTIFIER |
|---|---|---|
| AAV9-HyPBase | (Cammack et al., 2020) Joseph D. Dougherty | N/A |
| Lenti-dCas9-KRAB | (Cammack et al., 2020) This study | N/A |
| Lenti-BRD4-CRISPRi | This study | N/A |
| Lenti-NT-CRISPRi | This study | N/A |

Chemicals, Peptides, and Recombinant Proteins

| | | |
|---|---|---|
| DMEM | GIBCO | Cat# 11965-084 |
| Antibiotic-Antimycotic (100X) | GIBCO | Cat# 15240-062 |
| FBS | Peak Serum | Cat# PS-FB3 |
| RPMI 1640 Medium | GIBCO | Cat# 11875-085 |
| Lipofectamine 3000 Transfection Reagent | Invitrogen | Cat# L3000015 |
| Trypsin-EDTA solution | Sigma-Aldrich | Cat# T4049 |
| DPBS, no calcium, no magnesium | GIBCO | Cat# 14190-136 |
| RNAprotect Cell Reagent | QIAGEN | Cat# 76526 |
| 2-Mercaptoethanol | GIBCO | Cat# 21985-023 |
| RNase-Free DNase Set | QIAGEN | Cat# 79254 |
| Maxima H Minus Reverse Transcriptase | Thermo Scientific | Cat# EP0752 |
| Advantage ® UltraPure PCR Deoxynucleotide Mix | Takara Bio | Cat# 639125 |
| RNaseOUT Recombinant Ribonuclease Inhibitor | Invitrogen | Cat# 10777019 |
| TransIT ®-LT1 Transfection Reagent | Mirus | Cat# MIR2304 |
| RNase H | New England BioLabs | Cat# M0297S |
| HiFi HotStart ReadyMix (2X) | Kapa Biosystems | Cat# KK2601 |
| AMPure XP beads | Beckman Coulter | Cat# A63880 |
| Puromycin dihydrochloride | Sigma-Aldrich | Cat# P8833 |
| Crystal violet | Sigma-Aldrich | Cat# C0775 |
| Methanol | Fisher Scientific | Cat# A452-4 |
| Formaldehyde | Fisher Scientific | Cat# BP531-500 |
| High Sensitivity D1000 Reagents | Agilent | Cat# 5067-5585 |
| Ficoll PM400 (Dry Powder) | GE Healthcare | Cat# 17030010 |
| NxGen ® RNase Inhibitor | Lucigen | Cat# 30281-1 |
| Dynabeads MyOne Silane | Life Technologies | Cat# 37002D |
| IDTE pH 8.0 (1X TE Solution) | IDT | Cat# 11-05-01-13 |
| High Sensitivity D5000 Reagents | Agilent | Cat# 5067-5593 |
| NEBuffer 2 | New England BioLabs | Cat# B7002S |
| Buffer EB | QIAGEN | Cat# 19086 |
| Hibernate-A Medium | GIBCO | Cat# A1247501 |

-continued

| REAGENT or RESOURCE | SOURCE | IDENTIFIER |
|---|---|---|
| D-(+)-Trehalose dihydrate | Sigma-Aldrich | Cat# T9531 |
| B-27 Supplement (50X), serum free | GIBCO | Cat# 17504044 |
| 0.5M EDTA, pH 8.0 | Corning | Cat# 46-034-CI |
| Papain, Lyophilized | Worthington Biochemical | Cat# LS003118 |
| Deoxyribonuclease I, Filtered | Worthington Biochemical | Cat# LS002060 |
| Trypsin Inhbitor, Ovomucoid | Worthington Biochemical | Cat# LS003087 |
| Bovine Serum Albumin | Sigma-Aldrich | Cat# A9418 |
| OptiPrep Density Gradient Medium | Sigma-Aldrich | Cat# D1556 |
| HBSS (10X) | GIBCO | Cat# 14185052 |
| Magnesium chloride | Sigma-Aldrich | Cat# M4880 |
| Magnesium sulfate | Sigma-Aldrich | Cat# M2643 |
| Calcium chloride dihydrate | Sigma-Aldrich | Cat# C7902 |
| D-(+)-Glucose | Sigma-Aldrich | Cat# G7021 |
| Dimethyl sulfoxide (DMSO) | Sigma-Aldrich | Cat# D2650 |
| Cell Staining Buffer | BioLegend | Cat# 420201 |
| Annexin V Binding Buffer | BioLegend | Cat# 422201 |
| SuperScript VILO cDNA Synthesis Kit | Invitrogen | Cat# 11754250 |
| PowerUp SYBR Green Master Mix | Applied Biosystems | Cat# 25742 |
| (+)-JQ1 | Selleck Chemicals | Cat# S7110 |
| Propidium iodide (PI) | Invitrogen | Cat# P3566 |
| Hoechst 33342 | Thermo Scientific | Cat# 62249 |
| Blasticidin S HCl | GIBCO | Cat# A1113903 |
| Lenti-X Concentrator | Takara Bio | Cat# 631232 |
| Lipofectamine 2000 Transfection Reagent | Invitrogen | Cat# 11668030 |
| Polybrene Infection/Transfection Reagent | Sigma-Aldrich | Cat# TR-1003 |
| Esp3I | New England BioLabs | Cat# R0734S |
| T4 DNA Ligase | New England BioLabs | Cat# M0202S |
| IMDM | GIBCO | Cat# 12440046 |
| Penicillin-streptomycin (10,000 U/mL) | GIBCO | Cat# 15140122 |
| Imatinib mesylate | Sigma-Aldrich | Cat# SML1027 |
| Lovastatin | Sigma-Aldrich | Cat# M2147 |
| Nocodazole | Sigma-Aldrich | Cat# M1404 |
| CVT-313 | Sigma-Aldrich | Cat# 238803 |
| RO-3306 | Sigma-Aldrich | Cat# SML0569 |
| Annexin V-FITC | BioLegend | Cat# 640905 |
| Commercial Assays | | |
| Neon Transfection System 100 µL Kit | Invitrogen | Cat# MPK10025 |
| RNeasy Plus Mini Kit | QIAGEN | Cat# 74134 |
| Qubit RNA HS Assay Kit | Invitrogen | Cat# Q32852 |
| Qubit dsDNA HS Assay Kit | Invitrogen | Cat# Q32851 |
| Nextera XT DNA Library Preparation Kit | Illumina | Cat# FC-131-1024 |

| REAGENT or RESOURCE | SOURCE | IDENTIFIER |
|---|---|---|
| High Sensitivity D1000 ScreenTape | Agilent | Cat# 5067-5584 |
| Chromium Single Cell 3' Library & Gel Bead Kit v2 | 10x Genomics | Cat# PN-120267 |
| High Sensitivity D5000 ScreenTape | Agilent | Cat# 5067-5592 |
| Nextera Mate Pair Library Prep Kit | Illumina | Cat# FC-132-1001 |
| Deposited Data | | |
| K562 CpG islands | Richard Myers | GEO: GSM1014203 |
| HCT-116 SP1 ChIP-seq | Richard Myers | ENCODE: ENCFF000PCT |
| HCT-116 CTCF ChIP-seq | Richard Myers | ENCODE: ENCFF000OZC |
| HCT-116 ChIP-seq input control (SP1, CTCF) | Richard Myers | ENCODE: ENCFF000PBO |
| HCT-116 BRD4 ChIP-seq | Ron Firestein | SRA: SRR2481799 |
| HCT-116 ChIP-seq input control (BRD4) | Ron Firestein | SRA: SRR2481800 |
| HCT-116 H3K27ac ChIP-seq | Bradley Bernstein | ENCODE: ENCFF082JPN, ENCFF176BXC |
| HCT-116 H3K4me1 ChIP-seq | Bradley Bernstein | ENCODE: ENCFF088BWP, ENCFF804MJI |
| HCT-116 H3K4me2 ChIP-seq | Bradley Bernstein | ENCODE: ENCFF936MMN, ENCFF937OOL |
| HCT-116 H3K4me3 ChIP-seq | Bradley Bernstein | ENCODE: ENCFF183OZI, ENCFF659FPR |
| HCT-116 H3K9me2 ChIP-seq | Bradley Bernstein | ENCODE: ENCFF760OZN, ENCFF565FDP |
| HCT-116 H3K9me3 ChIP-seq | Bradley Bernstein | ENCODE: ENCFF578MDZ, ENCFF033XOG |
| HCT-116 H3K27me3 ChIP-seq | Bradley Bernstein | ENCODE: ENCFF281SBT, ENCFF124GII |
| HCT-116 H3K36me3 ChIP-seq | Bradley Bernstein | ENCODE: ENCFF850EAH, ENCFF312RKB |
| HCT-116 H3K79me2 ChIP-seq | Bradley Bernstein | ENCODE: ENCFF865KPW, ENCFF947YPU |
| HCT-116 H4K20me1 ChIP-seq | Bradley Bernstein | ENCODE: ENCFF070JDY, ENCFF334HHB |
| HCT-116 ChIP-seq input control (H3K27ac, H3K4me1, H3K4me2, H3K4me3, H3K9me2, H3K9me3, H3K27me3, H3K36me3, H3K79me2, H4K20me1) | Bradley Bernstein | ENCODE: ENCFF048ZOQ, ENCFF827YXC |
| HCT-116 H3K9ac ChIP-seq | Bradley Bernstein | ENCODE: ENCFF408RRT |
| HCT-116 ChIP-seq input control (H3K9ac) | Bradley Bernstein | ENCODE: ENCFF413RQG |
| K562 BRD4 ChIP-seq | Bradley Bernstein | ENCODE: ENCFF335PHG |

-continued

| REAGENT or RESOURCE | SOURCE | IDENTIFIER |
| --- | --- | --- |
| K562 H3K27ac ChIP-seq | Bradley Bernstein | ENCODE: ENCFF000BXH |
| K562 ChIP-seq input control (BRD4, H3K27ac) | Bradley Bernstein | ENCODE: ENCFF000BWK |
| K562 SP1 ChIP-seq | Michael Snyder | ENCODE: ENCFF002DPL, ENCFF002EGC |
| K562 ChIP-seq input control (SP1) | Michael Snyder | ENCODE: ENCFF002EGI, ENCFF002EGA |
| HepG2 FOXA2 ChIP-seq | Richard Myers | ENCODE: ENCFF000PIX |
| HepG2 ChIP-seq input control (FOXA2) | Richard Myers | ENCODE: ENCFF000POV |
| OCM-1A HyPBase DNA calling cards | Michael Onken | https://doi.org/10.1186/s12920-018-0424-0 |
| OCM-1A BAP1-HyPBase DNA calling cards | Michael Onken | https://doi.org/10.1186/s12920-018-0424-0 |
| OCM-1A RNA-seq (BAP1 and control shRNA) | Michael Onken | GEO: GSE110193 |
| Mouse cortex H3K27ac ChIP-seq | Michael Greenberg | SRA: SRR6129714 |
| Mouse cortex ChIP-seq input control (H3K27ac) | Michael Greenberg | SRA: SRR6129695 |
| K562 RNA Pol II ChIA-PET | Yijun Ruan | ENCODE: ENCFF000KYH |
| HCT-116 DNase-seq | John Stamatoyannopoulos | ENCODE: ENCFF001DCK |
| HCT-116 ATAC-seq | Sriharsa Pradhan | SRA: SRR5453778 |
| HCT-116 ATAC-seq control | Michael Guertin | GEO: GSE92674 |
| HCT-116 CpG islands | Richard Myers | GEO: GSM1014209 |
| Sequencing data and processed output | This study | GEO: GSE148448 |
| Experimental Models: Cell Lines | | |
| Neuro-2a (N2a) | ATCC | Cat# CCL-131 |
| K-562 | ATCC | Cat# CCL-243 |
| Hep G2 | ATCC | Cat# HB-8065 |
| OCM-1A | Michael Onken (Yen et al., 2018) | N/A |
| HCT 116 | ATCC | Cat# CCL-247 |
| 293T/17 [HEK293T/17] | ATCC | Cat# CRL-11268 |
| Experimental Models: Organisms/Strains | | |
| Mouse: C57BL/6J | Joseph D. Dougherty (Cammack et al., 2020) | N/A |
| Oligonucleotides | | |
| Primers and oligonucleotides | This study, see TABLE 4 | N/A |
| Recombinant DNA | | |
| pRM1024: PBase | This study | N/A |
| PRM1114: HyPBase | This study | N/A |
| PRM1023: SP1-PBase | This study | N/A |
| PRM1677: SP1-HyPBase | This study | N/A |
| PRM1882: FOXA2-HyPBase | This study | N/A |
| PRM1863: BAP1-HyPBase | This study | N/A |

-continued

| REAGENT or RESOURCE | SOURCE | IDENTIFIER |
| --- | --- | --- |
| PRM1304: PB-SRT-Puro | This study | RRID: Addgene_154884 |
| PRM1535: PB-SRT-tdTomato | This study | RRID: Addgene_154885 |
| pCMV(CAT)T7-SB100 | Zsuzsanna Izsvák | RRID: Addgene_34879 |
| PRM1665: SP1-SB100X | This study | RRID: Addgene_154887 |
| PRM1668: SB-SRT-Puro | This study | RRID: Addgene_154888 |
| PRM1217: AAV-HyPBase | Joseph D. Dougherty (Cammack et al., 2020) | N/A |
| pRM1648: AAV-PB-SRT-tdTomato | Joseph D. Dougherty (Cammack et al., 2020) | RRID: Addgene_154889 |
| pUC19 Vector | New England BioLabs | Cat# N3041S |
| Lenti-dCas9-KRAB-blast | Gary Hon | RRID: Addgene_89567 |
| sgOpti | Eric Lander & David Sabatini | RRID: Addgene_85681 |
| pMD2.G | Didier Trono | RRID: Addgene_12259 |
| psPAX2 | Didier Trono | RRID: Addgene_12260 |
| PRM1889: BRD4 CRISPRi plasmid | This study | RRID: Addgene_154890 |
| PRM1890: Non-targeting CRISPRi plasmid | Robi D. Mitra (Lalli et al., 2019) | RRID: Addgene_154891 |
| Software and Algorithms | | |
| cutadapt 1.16 | Martin, 2011 | RRID: SCR_011841 |
| NovoAlign 3 | Novocraft Technologies | RRID: SCR_014818 |
| Cell Ranger 2.1.0 | 10x Genomics | RRID: SCR_017344 |
| scanpy 1.3.7 | Wolf et al., 2018 | RRID: SCR_018139 |
| Drop-seq tools 1.11 | Macosko et al., 2015 | RRID: SCR_018142 |
| astropy 3.2.1 | Robitaille et al., 2013 | RRID: SCR_018148 |
| WashU Human Epigenome Browser 46 | Zhou et al., 2011 | RRID: SCR_006208 |
| MEME-ChIP 4.11.2 | Machanick and Bailey, 2011 | RRID: SCR_001783 |
| Tomtom 5.1.0 | Gupta et al., 2007 | RRID: SCR_001783 |
| MACS 1.4.1 | Zhang et al., 2008 | RRID: SCR_013291 |
| BEDTools 2.27.1 | Quinlan and Hall, 2010 | RRID: SCR_006646 |
| NumPy 1.17.2 | Oliphant, 2015 | RRID: SCR_008633 |
| SciPy 1.4.1 | Virtanen et al., 2020 | RRID: SCR_008058 |
| statsmodels 0.10.1 | Seabold and Perktold, 2010 | RRID: SCR_016074 |
| matplotlib 3.0.3 | Hunter, 2007 | RRID: SCR_008624 |
| deeptools 3.0.1 | Ramírez et al., 2016 | RRID: SCR_016366 |
| ChromHMM 1.15 | Ernst et al., 2011 | RRID: SCR_018141 |
| liftOver | Hinrichs et al., 2006 | RRID: SCR_018160 |
| FlowCal 1.2.0 | Castillo-Hair et al., 2016 | RRID: SCR_018140 |
| PANTHER 14.0 | Mi et al., 2017 | RRID: SCR_004869 |
| ROSE 0.1 | Whyte et al., 2013 & Lovén et al., 2013 | RRID: SCR_017390 |
| FlowJo Software for Mac Version 10 | Becton, Dickson and Company | RRID: SCR_008520 |
| Multcomp 1.4-12 | Hothorn et al., 2008 | RRID: SCR_018255 |
| Custom calling card code | This study | https://github.com/arnavm/calling_cards |
| Other | | |
| Qubit ® 3.0 Fluorometer | Thermo Fisher | Cat# Q33216 |
| 4200 TapeStation System | Agilent | Cat# G2991AA |

-continued

| REAGENT or RESOURCE | SOURCE | IDENTIFIER |
|---|---|---|
| E220 Focused-ultrasonicator | Covaris | N/A |
| MasterCycler Pro PCR System | Eppendorf | Cat# 950030010 |
| Attune NxT Flow Cytometer | Thermo Fisher | N/A |
| CytoFLEX S | Beckman-Coulter | Cat# B75442 |
| QuantStudio | Applied Biosystems | Cat# A28567 |
| Protocol: Mammalian Calling Cards Quick Start Guide | This study | https://doi.org/10.17504/protocols.io.xurfnv6 |
| Protocol: Bulk Calling Cards Library Preparation | This study | https://doi.org/10.17504/protocols.io.xwhfpb6 |
| Protocol: Single Cell Calling Cards Library Preparation | This study | https://doi.org/10.17504/protocols.io.xwifpce |
| Protocol: Processing Bulk Calling Card Sequencing Data | This study | https://doi.org/10.17504/protocols.io.xwjfpcn |
| Protocol: Processing Single Cell Calling Card Sequencing Data | This study | https://doi.org/10.17504/protocols.io.4phgvj6 |
| Protocol: Calling Peaks on piggyBac Calling Card Data | This study | https://doi.org/10.17504/protocols.io.bb9xir7n |
| Protocol: Visualizing Calling Card Data on the WashU Epigenome Browser | This study | https://doi.org/10.17504/protocols.io.bca8ishw |

Resource Availability

Materials Availability

Plasmids generated in this study have been deposited to Addgene, where possible, and are available to the community. Plasmids encoding the piggyBac transposase are not available through Addgene due to licensing restrictions. These plasmids are available upon request to the Lead Contact.

Data and Code Availability

Data generated in this study have been submitted to the Gene Expression Ominbus (GEO) with accession number GSE148448. All code used to analyze the data is available online at https://github.com/arnavm/calling_cards.

Experimental Model and Subject Details

HCT-116, N2a, HEK293T, and HepG2 cells were cultured in Dulbecco's Modified Eagle Medium (DMEM) supplemented with 10% fetal bovine serum (FBS) and 1% of either penicillin-streptomycin or antibiotic-antimycotic. K562 (unless otherwise indicated) and OCM-1A cells were grown under the same conditions as described above, replacing DMEM with RPMI 1640 Medium. Cells were grown at 37° C. with 5% carbon dioxide ($CO_2$). Media was replenished every 2 days. HepG2 cells were a gift from the Genome Engineering iPSC Center (GEiC) at Washington University in St. Louis School of Medicine. OCM-1A cells were a gift from Dr. Michael Onken. For the $CD24^{high}/CD24^{low}$ cell state analyses, K562 cells were grown in IMDM containing 10% v/v FBS and 1% penicillin-streptomycin at 37° C. with 5% $CO_2$. Frozen aliquots were thawed and passaged every 48 hours until they reached a maximum concentration of 800,000 cells/ml. For experiments, cells were seeded at mid-log phase concentrations, around 400,000 cells/ml. At this point, ratio of $CD24^{high}/CD24^{low}$ cells was approximately 1:1, as determined by flow cytometry.

All mouse experiments were done following procedures described in (Cammack et al., 2020). In brief, we cloned the PB-SRT-tdTomato and HyPBase constructs into AAV vectors. The Hope Center Viral Vectors Core at Washington University in St. Louis packaged each construct in AAV9 capsids. Titers for each virus ranged between $1.1 \times 10^{13}$ and $2.2 \times 10^{13}$ viral genomes/ml. We mixed equal volumes of each virus and performed intracranial cortical injections of the mixture into newborn wild-type C57BL/6J pups (P0-2). As a gating control, we injected one litter-matched animal with AAV9-PB-SRT-tdTomato only. After 2 to 4 weeks, we sacrificed mice and dissected the cortex (8 libraries) or hippocampus (1 library). The sex of mice was not taken into consideration. All animal practices and procedures were approved by the Washington University in St. Louis Institutional Animal Care and Use Committee (IACUC) in accordance with National Institutes of Health (NIH) guidelines.

Method Details

DNA-Versus RNA-Based Recovery

Approximately 500,000 HCT-116 cells were plated in a single well of a 6-well plate. Cells were transfected with 2.5 μg of the SP1-PBase plasmid and 2.5 μg of the PB-SRT-Puro plasmid using Lipofectamine 3000 following manufacturer's instructions. After 24 hours, cells were split and plated 1:10 in each of three 10 cm dishes. Puromycin was then added to a final concentration of 2 µg/ml and colonies were grown under selection for two weeks. We obtained approximately 2,300 colonies. All cells were pooled together and split into two populations. One half was subjected to DNA extraction, self-ligation, and inverse PCR, as described previously (Wang et al., 2012a), with the following modification: digestion with MspI was not performed as the SRT construct contained an second MspI cut site near the terminal repeat. The other half of cells underwent RNA extraction and SRT library preparation (see below).

In Vitro Bulk Calling Card Experiments

We cotransfected 10-12 replicates of HCT-116 cells with 5 µg of PB-SRT-Puro plasmid and 5 µg PBase plasmid via Neon electroporation Each replicate contained $2\times10^6$ cells. As a negative control, we transfected one replicate of HCT-116 cells with 5 µg PB-SRT-Puro plasmid only. We used the following settings—pulse voltage: 1,530 V; pulse width: 20 ms; pulse number: 1. We used the same experimental setup for experiments with PB-SRT-Puro and each of SP1-PBase, HyPBase, and SP1-HyPBase plasmids, as well as with SB-SRT-Puro and SB100X (the latter a gift from Dr. Zsuzsanna Izsvák, Mátés et al., 2009) plasmids. After transfection, each replicate was plated into a 10 cm dish. For the OCM-1A library, we transfected 1.25 µg of PB-SRT-Puro and 1.25 µg of either HyPBase or BAP1-HyPBase (the latter a gift from Dr. Michael Onken; Yen et al., 2018) using the TransIT-LT1 transfection reagent following manufacturer's protocol for 6-well plates. Puromycin was added after 24 hours to a final concentration of 2 µg/ml. Cells were grown under selection for one week, by which time almost all negative control transfectants were dead. After 7 days, we dissociated each replicate with trypsin-EDTA and created single cell suspensions in phosphate-buffered saline (PBS). Aliquots of each replicate were cryopreserved in cell culture media (see above) supplemented with 5% DMSO. The remaining cells were pelleted by centrifugation at 300 g for 5 minutes. Cell pellets were either processed immediately or kept at −80° C. in RNAProtect Cell Reagent.

Isolation and RT of Bulk RNA

Total RNA was isolated from each replicate using the RNEasy Plus Mini Kit following manufacturer's instructions. Briefly, cell pellets were resuspended in 600 µl of Buffer RLT Plus with 1% 2-mercaptoethanol. Cells were homogenized by vortexing. DNA was removed by running lysate through gDNA Eliminator spin columns, while RNA was bound by passing the flow-through over RNEasy spin columns. An on-column treatment with DNaseI was also performed. After washing, RNA was eluted in 40 µl RNase-free $H_2O$. RNA was quantitated using the Qubit RNA HS Assay Kit.

We performed first strand synthesis on each replicate with Maxima H Minus Reverse Transcriptase. We mixed 2 µg of total RNA with 1 µl 10 mM dNTPs and 1 µl of 50 µM SMART_dT18VN primer (for a complete list of oligonucleotides, see TABLE 4), brought the total volume up to 14 µl, and incubated it at 65° C. for 5 minutes. After transferring to ice and letting rest for 1 minute, we added 4 µl 5× Maxima RT Buffer, 1 µl RNaseOUT, and 1 µl of 1:1 Maxima H Minus Reverse Transcriptase diluted in 1× RT Buffer (100 U). The solution was mixed by pipetting and incubated at 50° C. for 1 hour followed by heat inactivation at 85° C. for 10 minutes. Finally, we digested with 1 µl RNaseH at 37° C. for 30 minutes. cDNA was stored at −20° C.

TABLE 4

Oligonucleotides referenced in this work, related to Methods.

| Name | Sequence | Purification | Notes |
|---|---|---|---|
| SMART_dT18VN | AAGCAGTGGTATCAACGCAGAGTACGTTTTTTTTTTTTTTTTTTTTTTTTTTTTTVN | Standard desalt | RT primer for bulk RNA calling card recovery |
| SMART | AAGCAGTGGTATCAACGCAGAGT | Standard desalt | PCR primer for bulk RNA calling card amplification |
| SRT_PAC_F1 | CAACCTCCCCTTCTACGAGC | Standard desalt | Puromycin marker in SRT |
| SRT_tdTomato_F1 | TCCTGTACGGCATGGACGAG | Standard desalt | tdTomato marker in SRT |
| Raff_ACTB_F | CCTCGCCTTTGCCGATCCG | Standard desalt | Human ACTB primer (for RT control) |
| Raff_ACTB_R | GGATCTTCATGAGGTAGTCAGTCAGGTCC | Standard desalt | Human ACTB primer (for RT control) |
| OM-PB-ACG | AATGATACGGCGACCACCGAGATCTACACTCTTTCCCTACACGACGCTCTTCCGATCT<u>ACG</u>TTTACGCAGACTATCTTTCTAG | Standard desalt | For use with piggyBac SRTS |
| OM-PB-CTA | AATGATACGGCGACCACCGAGATCTACACTCTTTCCCTACACGACGCTCTTCCGATCT<u>CTA</u>TTTACGCAGACTATCTTTCTAG | Standard desalt | For use with piggyBac SRTs |
| OM-PB-GAT | AATGATACGGCGACCACCGAGATCTACACTCTTTCCCTACACGACGCTCTTCCGATCT<u>GAT</u>TTTACGCAGACTATCTTTCTAG | Standard desalt | For use with piggyBac SRTs |

TABLE 4-continued

Oligonucleotides referenced in this work, related to Methods.

| Name | Sequence | Purification | Notes |
| --- | --- | --- | --- |
| OM-PB-TGC | AATGATACGGCGACCACCGAGATCTACACTCTTTCCCTACACGACGCTCTTCCGATCTTGCTTTACGCAGACTATCTTTCTAG | Standard desalt | For use with piggyBac SRTs |
| OM-PB-TAG | AATGATACGGCGACCACCGAGATCTACACTCTTTCCCTACACGACGCTCTTCCGATCTTAGTTTACGCAGACTATCTTTCTAG | Standard desalt | For use with piggyBac SRTs |
| OM-PB-ATC | AATGATACGGCGACCACCGAGATCTACACTCTTTCCCTACACGACGCTCTTCCGATCTATCTTTACGCAGACTATCTTTCTAG | Standard desalt | For use with piggyBac SRTs |
| OM-PB-CGT | AATGATACGGCGACCACCGAGATCTACACTCTTTCCCTACACGACGCTCTTCCGATCTCGTTTTACGCAGACTATCTTTCTAG | Standard desalt | For use with piggyBac SRTs |
| OM-PB-GCA | AATGATACGGCGACCACCGAGATCTACACTCTTTCCCTACACGACGCTCTTCCGATCTGCATTTACGCAGACTATCTTTCTAG | Standard desalt | For use with piggyBac SRTs |
| OM-SB-ACG | AATGATACGGCGACCACCGAACACTCTTTCCCTACACGACGCTCTTCCGATCTACGTAAGTGTATGTAAACTTCCGACTTCAA | Standard desalt | For use with Sleeping Beauty SRTs |
| OM-SB-CTA | AATGATACGGCGACCACCGAACACTCTTTCCCTACACGACGCTCTTCCGATCTCTATAAGTGTATGTAAACTTCCGACTTCAA | Standard desalt | For use with Sleeping Beauty SRTs |
| OM-SB-GAT | AATGATACGGCGACCACCGAACACTCTTTCCCTACACGACGCTCTTCCGATCTGATTAAGTGTATGTAAACTTCCGACTTCAA | Standard desalt | For use with Sleeping Beauty SRTs |
| OM-SB-TGC | AATGATACGGCGACCACCGAACACTCTTTCCCTACACGACGCTCTTCCGATCTTGCTAAGTGTATGTAAACTTCCGACTTCAA | Standard desalt | For use with Sleeping Beauty SRTs |
| OM-SB-TAG | AATGATACGGCGACCACCGAACACTCTTTCCCTACACGACGCTCTTCCGATCTTAGTAAGTGTATGTAAACTTCCGACTTCAA | Standard desalt | For use with Sleeping Beauty SRTs |
| OM-SB-ATC | AATGATACGGCGACCACCGAACACTCTTTCCCTACACGACGCTCTTCCGATCTATCTAAGTGTATGTAAACTTCCGACTTCAA | Standard desalt | For use with Sleeping Beauty SRTs |
| OM-SB-CGT | AATGATACGGCGACCACCGAACACTCTTTCCCTACACGACGCTCTTCCGATCTCGTTAAGTGTATGTAAACTTCCGACTTCAA | Standard desalt | For use with Sleeping Beauty SRTs |
| OM-SB-GCA | AATGATACGGCGACCACCGAACACTCTTTCCCTACACGACGCTCTTCCGATCTGCATAAGTGTATGTAAACTTCCGACTTCAA | Standard desalt | For use with Sleeping Beauty SRTs |
| N7 indexed primer | CAAGCAGAAGACGGCATACGAGAT[index]GTCTCGTGGGCTCGG | Standard desalt | Uniquely identifies each bulk RNA calling card library in conjunction with barcoded transposon primer |
| 10x_TSO | AAGCAGTGGTATCAACGCAGAGTACATrGrGrG | Standard desalt | For continuing 10x scRNA-seq prep after splitting first RT product in half |
| Bio_Illumina_Seq1_scCC_10X_3xPT | /5Phos/ACACTCTTTCCC/iBiodT/ACACGACGCTCTTCCGA*T*C*T | HPLC | Single cell calling card primer for use with 10x Chromium 3' v2 kit |
| Bio_Long_PB_LTR_3xPT | /5Phos/GCGTCAATTTTACGCAGAC/iBiodT/ATCTTTC*T*A*G | HPLC | Single cell calling card primer for use with piggyBac SRTs |
| scCC_P5_adapter | AATGATACGGCGACCACCGAGATCTTCACTCATTCCACACGACTCCTTGCCAGTCTC*T | Standard desalt | Adapter for scCC (needs to be pre-annealed with scCC_P7_adapter) |

TABLE 4-continued

Oligonucleotides referenced in this work, related to Methods.

| Name | Sequence | Purification | Notes |
|---|---|---|---|
| scCC_P7_adapter | /5Phos/GAGACTGGCAAGTACACGTCGCACTCACCATGA[index]ATCTCGTATGCCGTCTTCTGCTTG | Standard desalt | Adapter for scCC (needs to be pre-annealed with scCC_P5_adapter) |
| scCC_P5_primer | AATGATACGGCGACCACCGAGATC | Standard desalt | For final scCC library PCR |
| scCC_P7_primer | CAAGCAGAAGACGGCATACGAGAT | Standard desalt | For final scCC library PCR |
| ScCC_PB_CustomRead2 | CGTGTAGGGAAAGAGTGTGCGTCAATTTTACGCAGACTATCTTTCTAG | PAGE | For custom sequencing of piggyBac scCC libraries; read 2 should begin with GGTTAA |
| scCC_CustomIndex1 | GAGACTGGCAAGTACACGTCGCACTCACCATGA | PAGE | For custom sequencing of scCC libraries |
| ACTB_PrimerBank_F | CATGTACGTTGCTATCCAGGC | Standard desalt | For qRT-PCR |
| ACTB_PrimerBank_R | CTCCTTAATGTCACGCACGAT | Standard desalt | For qRT-PCR |
| CD24_PrimerBank_F | CTCCTACCCACGCAGATTTATTC | Standard desalt | For qRT-PCR |
| CD24_PrimerBank_F | AGAGTGAGACCACGAAGAGAC | Standard desalt | For qRT-PCR |
| MYC_PrimerBank_F | GTCAAGAGGCGAACACACAAC | Standard desalt | For qRT-PCR |
| MYC_PrimerBank_R | TTGGACGGACAGGATGTATGC | Standard desalt | For qRT-PCR |
| BRD2_PrimerBank_F | AATGGCACAAACGCTGGAAAA | Standard desalt | For qRT-PCR |
| BRD2_PrimerBank_R | CACTGGTAACACTGCCCTG | Standard desalt | For qRT-PCR |
| BRD3_PrimerBank_F | TGCAAGCGAATGTATGCAGGA | Standard desalt | For qRT-PCR |
| BRD3_PrimerBank_R | CATCTGGGCCACTTTTTGTAGAA | Standard desalt | For qRT-PCR |
| BRD4_PrimerBank_F | GAGCTACCCACAGAAGAAACC | Standard desalt | For qRT-PCR |
| BRD4_PrimerBank_R | GAGTCGATGCTTGAGTTGTGTT | Standard desalt | For qRT-PCR |
| BRD4 CRISPRi gRNA | GCGGCTGCCGGCGGTGCCCG | N/A | For knockdown of BRD4 with CRISPRi |
| NT CRISPRi gRNA | GGAGGCGAGGTAAGACGCGG | N/A | Control non-targeting gRNA for CRISPRi |

Amplifying Self-Reporting Transcripts from RNA

The PCR conditions for amplifying self-reporting transcripts (i.e., transcripts derived from self-reporting transposons) involved mixing 1 µl cDNA template with 12.5 µl Kapa HiFi HotStart ReadyMix, 0.5 µl 25 µM SMART primer, and either 1 µl of 25 µM SRT_PAC_F1 primer (in the case of puromycin selection) or 0.5 µl of 25 µM SRT_tdTomato_F1 primer (in the case of tdTomato screening). The mixture was brought up to 25 µl with ddH₂O. Thermocycling parameters were as follows: 95° C. for 3 minutes; 20 cycles of: 98° C. for 20 s—65° C. for 30 s—72° C. for 5 minutes; 72° C. for 10 minutes; hold at 4° C. forever. As a control, cDNA quality can be assessed with exon-spanning primers for β-actin [see TABLE 4 for examples of human primers (Raff et al., 1997))] under the same thermocycling settings.

PCR products were purified using AM Pure XP beads. 12 µl of resuspended beads were added to the 25 µl PCR product and mixed homogenously by pipetting. After a 5-minute incubation at room temperature, the solution was placed on a magnetic rack for 2 minutes. The supernatant was aspirated and discarded. The pellet was washed twice with 200 µl of 70% ethanol (incubated for 30 s each time), discarding the supernatant each time. The pellet was left to dry at room temperature for 2 minutes. To elute, we added 20 µl ddH$_2$O to the pellet, resuspended by pipetting, incubated at room temperature for 2 minutes, and placed on a magnetic rack for one minute. Once clear, the solution was transferred to a clean 1.5 mL tube. DNA concentration was measured on the Qubit 3.0 Fluorometer using the dsDNA High Sensitivity Assay Kit.

Generation of Bulk RNA Calling Card Libraries

Calling card libraries from bulk RNA were generated using the Nextera XT DNA Library Preparation Kit. One nanogram of PCR product was resuspended in 5 µl ddH$_2$O. To this mixture we added 10 µl Tagment DNA (TD) Buffer and 5 µl Amplicon Tagment Mix (ATM). After pipetting to mix, we incubated the solution in a thermocycler preheated to 55° C. The tagmentation reaction was halted by adding 5 µl Neutralization Tagment (NT) Buffer and was kept at room temperature for 5 minutes. The final PCR was set up by adding 15 µl Nextera PCR Mix (NPM), 8 µl ddH2O, 1 µl of 10 µM transposon primer (e.g., OM-PB-NNN) and 1 µl Nextera N7 indexed primer. The transposon primer anneals to the end of the transposon terminal repeat—piggyBac, in the case of OM-PB primers, or Sleeping Beauty, in the case of OM-SB primers—and contains a 3 base pair barcode sequence. Every N7 primer contains a unique index sequence that is demultiplexed by the sequencer. Each replicate was assigned a unique combination of barcoded transposon primer and indexed N7 primer, enabling precise identification of each library's sequencing reads.

The final PCR was run under the following conditions: 95° C. for 30 s, 13 cycles of: 95° C. for 10 s—50° C. for 30 s—72° C. for 30 s, 72° C. for 5 minutes; hold at 4° C. forever. After PCR, the final library was purified using 30 µl (0.6×) AMPure XP beads, as described above. The library was eluted in 11 µl ddH$_2$O and quantitated on an Agilent TapeStation 4200 System using the High Sensitivity D1000 ScreenTape.

Colony Formation Assay

For the piggyBac transfectants, we electroporated 500,000 HCT-116 cells with 750 ng of PB-SRT-Puro and 750 ng of either HyPBase or SP1-HyPBase plasmid using the aforementioned Neon settings. For the SRT-only conditions, cells received 750 ng of PB-SRT-Puro. We used the same design for the Sleeping Beauty transfectants, replacing the transposases with either SB100X or SP1-SB100X and using SB-SRT-Puro as the transposon. Each set of 500,000 cells were plated in a single well of a 6-well plate and allowed to recover overnight. We then added puromycin to a final concentration of 2 µg/ml. We cultured cells under selection for one week. Colonies were visualized using a solution comprising 1×PBS, 1% formaldehyde, 1% methanol, and 0.05% w/v crystal violet. After aspirating median, we covered cells with this solution, staining plates for 20 minutes washing under cold water and air drying.

In Vitro single Cell Calling Card Experiments

All cell lines (HCT-116, K562, N2a, HepG2, and OCM-1A) were cultured as described above. HCT-116 cells were transfected using Neon electroporation with the aforementioned settings. K562 cells were electroporated with the following settings—pulse voltage: 1,450 V; pulse width: 10 ms; pulse number: 3. N2a cells were electroporated with the following settings—pulse voltage: 1,050 V; pulse width: 30 ms; pulse number: 2. HepG2 cells were electroporated with the following settings—pulse voltage: 1,200 V; pulse width: 50 ms; pulse number: 1. Each replicate for electroporation was comprised of 2×10$^6$ cells. All cells were allowed to recover for 24 hours before undergoing puromycin selection. A negative control replicate, transfected only with PB-SRT-Puro, was treated identically in parallel. Replicates were harvested once the negative control cells had died. For the species mixing experiment, we transfected one replicate each of HCT-116 and N2a cells with 5 µg PB-SRT-Puro and 5 µg HyPBase. For the cell line mixing experiment, we transfected four replicates each of HCT-116 and K562 cells with 5 µg PB-SRT-Puro and 5 µg HyPBase. In all cases, cells were cultured independently and mixed immediately prior to generating single cell emulsions. For single cell calling cards analysis of SP1 binding in HCT-116 and K562 cells, we transfected four replicates each with 5 µg PB-SRT-Puro and 5 µg SP1-HyPBase. These libraries were not mixed. We used the demultiplexed data from the cell line mixing experiment with HyPBase as controls. For single cell calling cards analysis of FOXA2 binding in HepG2 cells, we transfected six replicates each with 5 µg PB-SRT-Puro; three of these replicates were co-transfected with 5 µg HyPBase, while the other three were co-transfected with 5 µg FOXA2-HyPBase. We used the mouse ortholog of FOXA2, which has 97% primary sequence identity with human FOXA2. For single cell calling cards analysis of BAP1 binding in OCM-1A cells, we lipofected (as described above) six replicates each with 1.25 µg PB-SRT-Puro; three of these replicates were co-transfected with 1.25 µg HyPBase, while the other three were co-transfected with 1.25 µg BAP1-HyPBase.

Single Cell RNA-Seq Library Preparation

Single cell RNA-seq libraries were prepared using 10× Genomics' Chromium Single Cell 3' Library and Gel Bead Kit. Each replicate was targeted for recovery of 6,000 cells. Library preparation followed a modified version of the manufacturer's protocol. We prepared the Single Cell Master Mix without RT Primer, replacing it with an equivalent volume of Low TE Buffer. Gel-in-emulsion (GEM) generation and GEM-RT incubation proceeded as instructed. At the end of Post GEM-RT cleanup, we added 36.5 µl Elution Solution I and transferred 36 µl of the eluted sample to a new tube (instead of 35.5 µl and 35 µl, respectively). The eluate was split into two 18 µl aliquots and kept at −20° C. until ready for further processing. One fraction was kept for single cell calling cards library preparation (see next section), while the other half was further processed into a single cell RNA-seq library.

We then added the RT Primer sequence to the products in the scRNA-seq aliquot. We created an RT master mix by adding 20 µl of Maxima 5×RT Buffer, 20 µl of 20% w/v Ficoll PM-400, 10 µl of 10 mM dNTPs, 2.5 µl RNase Inhibitor and 2.5 µl of 100 µM 10×_TSO. To this solution we added 18 µl of the first RT product and 22 µl of ddH$_2$O. Finally, we added 5 µl Maxima H Minus Reverse Transcriptase, mixed by flicking, and centrifuged briefly. This reaction was incubated at 25° C. for 30 minutes followed by 50° C. for 90 minutes and heat inactivated at 85° C. for 5 minutes.

The solution was purified using DynaBeads MyOne Silane following 10× Genomics' instructions, beginning at "Post GEM-RT Cleanup-Silane DynaBeads" step D. The remainder of the single cell RNA-seq protocol, including purification, amplification, fragmentation, and final library amplification, followed manufacturer's instructions.

Single Cell Calling Cards Library Preparation

To amplify self-reporting transcripts from single cell RNA-seq libraries, we took 9 µl of RT product (the other half was kept in reserve) and added it to 25 µl Kapa HiFi HotStart ReadyMix and 15 µl ddH$_2$O. We then prepared a PCR primer cocktail comprising 5 µl of 100 µM Bio_Illumina_Seq1_scCC_10×_3×PT primer, 5 µl of 100

µM Bio_Long_PB_LTR_3×PT, and 10 µl of 10 mM Tris-HCl, 0.1 mM EDTA buffer. One µl of this cocktail was added to the PCR mixture and placed in a thermocycler. Thermocycling settings were as follows: 98° C. for 3 minutes; 20-22 cycles of 98° C. for 20 s—67° C. for 30 s—72° C. for 5 minutes; 72° C. for 10 minutes; 4° C. forever. PCR purification was performed with 30 µl AMPure XP beads (0.6× ratio) as described previously. The resulting library was quantitated on an Agilent TapeStation 4200 System using the High Sensitivity D5000 ScreenTape.

Single cell calling card library preparation was performed using the Nextera Mate Pair Sample Prep Kit with modifications to the manufacturer's protocol. The library was circularized by bringing 300 fmol (approximately 200 ng) of DNA up to a final volume of 268 µl with ddH$_2$O, then adding 30 µl Circularization Buffer 10× and 2 µl Circularization Ligase (final concentration: 1 nM). This reaction was incubated overnight (12-16 hours) at 30° C. After removal of linear DNA (following manufacturer's instructions), we sheared the library on a Covaris E220 Focused-ultrasonicator with the following settings—peak power intensity: 200; duty factor: 20%; cycles per burst: 200; time: 40 s, temperature: 6° C.

The library preparation was performed per manufacturer's instructions until adaptor ligation. We designed custom adapters (TABLE 4) so that the standard Illumina sequencing primers would not interfere with our library. Adapters were prepared by combining 4.5 µl of 100 µM scCC_P5_adapter, 4.5 µl of 100 µM scCC_P7_adapter, and 1 µl of NEBuffer 2, then heating in a thermocycler at 95° C. for 5 minutes, then holding at 70° C. for 15 minutes, then ramping down at 1% until it reached 25° C., holding at that temperature for 5 minutes, before keeping at 4° C. forever. One microliter of this custom adaptor mix was used in place of the manufacturer's recommended DNA Adaptor Index. The ligation product was cleaned per manufacturer's instructions. For the final PCR, the master mix was created by combining 20 µl Enhanced PCR Mix with 28 µl of ddH$_2$O and 1 µl each of 25 µM scCC_P5_primer and 25 µM scCC_P7_primer. This was then added to the streptavidin bead-bound DNA and amplified under the following conditions: 98° C. for 30 s, 15 cycles of: 98° C. for 10 s—60° C. for 30 s—72° C. for 2 minutes; 72° C. for 5 minutes; 4° C. forever. All of the PCR supernatant was transferred to a new tube and purified with 35 µl (0.7×) AMPure XP beads following manufacturer's instructions. The final library was eluted in 25 µl Elution Buffer and quantitated on an Agilent TapeStation 4200 System using the High Sensitivity D1000 ScreenTape.

Staining Protocols for K562 Cells

CD24 surface protein was quantified using monoclonal human antibodies. Cells were spun down at 300 g for 3 minutes and washed twice with 1 mL of Cell Staining Buffer. The cell pellet was then resuspended in 50 µl of Cell Staining Buffer containing 0.2 µg of either CD24-APC or CD24-BV421. The tube was rotated at 4° C. in the dark for 30 minutes. After, cells were washed twice (as before) and finally resuspended in 200 µl of Cell Staining Buffer. Cells were excited with 450/45 and 660/20 lasers (wavelength/filter bandwidth, both in nm). For concomitant analysis of DNA content, we used CD24-APC. Cells were incubated with 10 µg/ml Hoechst 33342 in 5 mL of growth medium for 30 minutes prior to the staining protocol. For simultaneous assessment of apoptosis, cells were stained with CD24-BV421. After the final wash, instead of resuspending in 200 µl of Cell Staining Buffer, cells were washed twice with Annexin V Staining Buffer. Cells were then incubated in 50 µl Annexin V Staining Buffer containing 0.2 µg Annexin V-FITC and 100 µg/ml propidium iodide (PI). The reaction was incubated for 15 minutes at room temperature in the dark. Afterward, we added 150 µl of Annexin V Staining Buffer and proceeded to flow cytometry. All samples were measured on a Beckman-Coulter CytoFLEX S flow cytometer. Cells were excited with 450/45, 525/40, and 610/20 lasers. We collected 10,000 events per sample. The resulting data were processed with FlowJo Software for Mac Version 10.

JQ1 Treatment of K562 Cells

For the longitudinal treatment of K562 cells with JQ1, we seeded cells at log phase growth and treated them with growth medium containing DMSO (~0.4% final concentration) or 250 nM JQ1 (dissolved in DMSO). Medium was replaced every 48 hours without splitting. On days 1, 2, 3, 4, and 7, cells were split in half: one half was stained for CD24 and DNA content, while the other half was stained for CD24 and apoptosis (both described above). Experiments were performed with three biological replicates.

For qRT-PCR, we cultured K562 cells in either DMSO or 250 nM JQ1, in triplicate, and collected cells at 0, 3, 6, 9, 12, and 24 hours of treatment. Cells were pelleted, resuspended in 300 µl of RNA CellProtect, and stored at −80° C. When we were ready to extract RNA, we thawed cells, prepared samples using QIAGEN RNEasy Plus Mini Kit, and quantitated with the Qubit RNA High Sensitivity kit. We reverse transcribed 500 ng of RNA with the SuperScript VILO cDNA Synthesis Kit in a 20 µl reaction, with the following thermocycling parameters: 25° C. for 10 minutes; 42° C. for 2 hours; 85° C. for 5 minutes. We then performed PCR with 2 µl of the RT product as template, 1 µl each of forward and reverse primer (10 µM), 6 µl ddH$_2$O, and 10 µl PowerUp SYBR Green Master Mix. We ran the PCR on an ABI QuantStudio 3 with the following settings: 2 minutes at 50° C., then 2 minutes at 95° C. (hot start); 45 cycles of 95° C. for 15 s followed by 60° C. for 1 minute. We generated melt curves after each PCR and all samples yielded a single peak. Gene-specific primers were obtained from PrimerBank (Wang et al., 2012b). Data were normalized to the levels of δ-actin.

BRD4 CRISPRi of K562 Cells

For CRISPRi, we first made lentivirus expressing dCas9-KRAB (Fulco et al., 2016; Xie et al., 2017) from Addgene plasmid #89567, a gift from Gary Hon, packaged in HEK293T cells along with pMD2.G (Addgene plasmid #12259) and psPAX2 (Addgene plasmid #12260), both gifts from Didier Trono. We cloned a BRD4 guide RNA, selected from the Dolcetto collection (Sanson et al., 2018), into the sgOpti plasmid (Addgene plasmid #85681, a gift from Eric Lander & David Sabatini) using Golden Gate assembly with Esp3I. We used an in-house pipeline to design a non-targeting gRNA sequence, which was cloned into CROPseq-opti (Lalli et al., 2019). Plasmids were transfected into HEK293T cells using Lipofectamine 2000. Media was collected after 24 and 48 hours, and subsequently concentrated using Lenti-X Concentrator. Viral titers were functionally assed on HEK293T cells using the appropriate antibiotic (blasticidin or puromycin).

Next, we generated a polyclonal pool of dCas9-KRAB-expressing K562 cells. We seeded each well of a 6-well plate with 200,000 cells each containing 2 mL of growth media supplemented with 4 µg/ml polybrene and 1,000,000 infectious lentiviral particles for an estimated multiplicity of infection (MOI) of 5. Plates were centrifuged at 2,000 g for 30 minutes and returned to the incubator. After 48 hours, cells were split to mid-log phase concentration (~400,000 cells/nil) and selected on blasticidin (10 µg/ml) for 48 hours. We made frozen stocks from these cells.

For the knockdown experiments, cells were thawed and allowed to recover for 4 days. We confirmed that the proportions of CD24$^{high}$/CD24$^{low}$ was approximately equal at this point. We then seeded 200,000 cells into each well of a 6-well plate. Three wells received the BRD4 gRNA lentivirus, while the other three received the non-targeting gRNA lentivirus, at MOI 2.5. We followed the same transduction protocol described above. After 48 hours of incubation, puromycin was added to the medium at a final concentration of 2 µg/ml. After a further 48 hours, cells were passaged 1:1 into 10 cm dishes containing 10 mL of growth medium. The surviving cells were allowed to expand for a further 5 days before being stained for CD24 (nine days after gRNA transduction.)

The BRD4 gRNA was validated by performing qRT-PCR on RNA samples from treated cells with primers for either BRD2, BRD3, or BRD4, as described above.

Imatinib Treatments of K562 Cells

Cells were challenged with imatinib either after JQ1 treatment or BRD4 CRISPRi. For the former, we plated 200,000 cells each well of a 6-well plate with 2 mL of growth medium. Half of the wells received DMSO while the other half received 250 nM JQ1. Cells were incubated for 5 days, with fresh media changes on days 1, 2, and 3. On day 5, a portion of each well was stained for CD24. The remaining cells in each well were split between two new wells. One well continued to receive medium supplemented with DMSO, while the other was treated with medium containing imatinib mesylate at a concentration of 1 µM. After 48 hours, every well was stained for CD24 as well as annexin V and propidium iodide, for apoptotic activity. Cells undergoing BRD4 or non-targeted CRISPRi were split in two and treated with either DMSO or imatinib (1 µM) as described and in triplicate. The resulting data were processed with FlowJo. We set gates such that we could exclude debris but that we would capture both live and dying cells. This gate was used to calculate levels of annexin V and PI.

Cell Cycle Perturbation of K562 Cells

We perturbed the cell cycle with lovastatin and nocodazole, two drugs classically used to synchronize cells in culture (Jackman and O'Connor, 2001), as well as the cyclin-dependent kinase inhibitors CVT-313 (Brooks et al., 1997) and RO-3306 (Vassilev et al., 2006). All drugs were dissolved in DMSO except nocodazole, which was dissolved in ethanol. We treated 200,000 cells per well in 6-well plates with either DMSO, ethanol (~0.4% final concentration), 250 nM JQ1, 12 µM lovastatin, 40 ng/µl nocodazole (in ethanol), 2 µM CVT-313, or 4.5 µM RO-3306. Media was refreshed every 48 hours. After 36 hours of treatment, we stained for CD24 levels and nuclear DNA content. We gated for live, single cells using the forward scatter (FSC) and side scatter channels (SSC). Univariate cell cycle analysis was performed with FlowJo. We confirmed that all drugs perturbed cell cycle by altering the proportions of cells in either G1 or G2/M phase (FIG. 14G). CVT-313 caused a significant increase in G1 arrest cells (one-way ANOVA $p<0.05$) and both nocodazole and RO-3306 caused significant G2 arrest (one-way ANOVA $p<0.01$). While lovastatin has been reported to arrest cells in G1, in our hands it caused a significant decrease in G1 phase K562 cells (one-way ANOVA $p<0.01$). Cultures remained under drug treatment until five days had elapsed, at which point we measured CD24 levels and stained for apoptosis (FIG. 14H). As before, we set gates to exclude debris to quantitate annexin V and PI, and measured CD24 in live cells gated on FSC and SSC. The G2 inhibitors, in particular, had very few cells in the FSC/SSC gate (typically below 5%).

SRT-td Tomato Fluorescence Validation

To test the fluorescence properties of the SRT-tdTomato construct, we transfected K562 cells as previously described with either 1 µg of pUC19 plasmid; 0.5 µg of PB-SRT-tdTomato plasmid and 0.5 µg pUC19; 0.5 µg of PB-SRT-tdTomato and 0.5 µg pBase plasmid; and 0.5 µg of PB-SRT-tdTomato and 0.5 µg HyPBase plasmid. Cells were allowed to expand for 8 days, after which fluorescence activity was assayed on an Attune NxT Flow Cytometer with an excitation wavelength of 561 nm. Flow cytometry data were visualized using FlowCal (Castillo-Hair et al., 2016). We also performed bulk RNA calling cards on HEK293T cells transfected with SRT-tdTomato with or without HyPBase plasmid. While these cells were not sorted based on fluorescence activity, the SRT library from cells transfected with both SRT and transposase were more complex and contained many more insertions than the library from cells receiving SRT alone (Supplemental Methods).

In Vivo scCC Experiments

We separately packaged the PB-SRT-tdTomato and HyPBase constructs in AAV9 viral particles (Cammack et al., 2020) and delivered mixtures of both viruses to the developing mouse cortex via intracranial injections at P1. After 2-4 weeks, we dissected the cortex, dissociated it to a single cell suspension, performed FACS to isolate tdTomato-positive cells, and generated both scRNA-seq and scCC libraries.

Mouse cortical tissues were dissociated to single suspensions following a modification of previously published methods (Avey et al., 2018; Saxena et al., 2012). We incubated samples in a papain solution containing Hibernate-A with 5% v/v trehalose, 1×B-27 Supplement, 0.7 mM EDTA, 70 µM 2-mercaptoethanol, and 2.8 mg/ml papain. After incubation at 37° C., cells were treated with DNaseI, triturated through increasingly narrow fire-polished pipettes, and passed through a 40-micron filter prewetted with resuspension solution: Hibernate-A containing 5% v/v trehalose, 0.5% Ovomucoid Trypsin Inhibitor, 0.5% Bovine Serum Albumin (BSA), 33 µg/ml DNaseI (Worthington), and 1×B-27 Supplement. The filter was washed with 6 mL of resuspension solution. The resulting suspension was centrifuged for 4 minutes at 250 g. The supernatant was discarded. The pellet was then resuspended in 2 mL of resuspension solution and resuspended by gentle pipetting.

We eliminated subcellular debris using gradient centrifugation. We first prepared a working solution of 30% w/v OptiPrep Density Gradient Medium mixed with an equal volume of 1× Hank's Balanced Salt Solution (HBSS) with 0.5% BSA. We then prepared solutions of densities 1.057, 1.043, 1.036, and 1.029 g/ml using by combining the working solution with resuspension solution at ratios of 0.33:0.67, 0.23:0.77, 0.18:0.82, and 0.13:0.87, respectively. We layered 1 mL aliquots of each solution in a 15 mL conical tube beginning with the densest solution on the bottom. The cell suspension was added last to the tube and centrifuged for 20 minutes at 800 g at 12° C. The top layer was then aspirated and purified cells were isolated from the remaining layers. These cells were then resuspended in FACS buffer: 1×HBSS, 2 mM $MgCl_2$, 2 mM $MgSO_4$, 1.25 mM $CaCl_2$, 1 mM D-glucose, 0.02% BSA, and 5% v/v trehalose. Cells were centrifuged for 4 minutes at 250 g, the supernatant was discarded, and the pellet was resuspended in FACS buffer by gentle pipetting.

Cells were then sorted based on fluorescence activity. As a gating control, we analyzed cells from cortices injected with AAV9-PB-SRT-tdTomato only. We then collected cells from brains transfected with AAV9-PB-SRT-tdTomato and AAV9-HyPBase whose fluorescence values exceeded the gate. After sorting, cells were centrifuged for 3 minutes at 250 g. The supernatant was discarded and cells were resuspended in FACS buffer at a concentration appropriate for 10× Chromium 3' scRNA-seq library preparation.

Quantification and Statistical Analysis

Statistical analyses were performed in Python 3.7.3 using SciPy (Virtanen et al., 2020) and statsmodels (Seabold and Perktold, 2010) as well as R 3.5.3 using the multcomp package (Hothorn et al., 2008). Flow cytometry figures were created with FlowJo. All other figures were created with Python using matplotlib (Hunter, 2007). Statistical details for individual experiments have been provided in the main text, figure legends, and Method Details. In general, we used 10-12 replicates for bulk RNA calling cards experiments; at least three separate libraries for single cell calling cards experiments; and three biological replicates for the K562 cell state experiments.

Interpreting Calling Card Tracks

Calling card tracks depict recovered transposons as discrete data points. Each circle in the track is an independent transposition event whose genomic coordinate is along the x axis. The y axis is the number of reads supporting each insertion on a $log_{10}$ scale. The total, genome-wide library size is shown at left (n). To better compare transpositions across libraries with different numbers of insertions, we also plotted the normalized local insertion rate as a density track.

Sequencing and Analysis: Bulk DNA CC Libraries

DNA calling card libraries were sequenced on the Illumine HiSeq 2500 platform. To increase the complexity of the library, PhiX was added at a final loading concentration of 50%. Reads were demultiplexed by the 3 base-pair barcode TAG followed by the end of the transposon terminal repeat, culminating with the piggyBac insertion site motif TTAA. Reads that had exact matches to these sequences were hard trimmed using cutadapt (Martin, 2011) with the following settings: -g "/\Calling Card Sequence"—minimum-length 1—discard-untrimmed -e 0—no-indels. Reads passing this filter were then trimmed of vector sequence along read 2 using cutadapt with the following settings: -g "/\ATCACTTAAGCCGGTAC'"—minimum-length 1—discard-untrimmed -e 0—no-indels. The remaining reads were aligned to the human genome (build hg38) with NovoAlign and the following settings: -n 40 -o SAM -o SoftClip. Aligned reads were validated by confirming that they mapped adjacent to the insertion site motif. Successful reads were then converted to calling card format (.ccf.; see http://wiki.wubrowse.org/Calling_card) using custom programs (available at https://github.com/arnavm/calling_cards) and visualized on the WashU Epigenome Browser v46 (Zhou et al., 2011) (http://epigenomegateway.wustl.edu/legacy/).

Sequencing and Analysis: Bulk RNA CC Libraries

Multiple calling card libraries were pooled together for sequencing on the Illumina HiSeq 2500 platform with 50% phiX. Reads were demultiplexed by the N7 index sequences added during the final PCR. Read 1 began with the 3 base-pair barcode followed by the end of the transposon terminal repeat, culminating with the insertion site motif (TTAA in the case of piggyBac; TA in the case of Sleeping Beauty) before entering the genome. piggyBac reads were checked for exact matches to the barcode, transposon sequence, and insertion site at the beginning of reads before being hard trimmed using cutadapt with the following settings: -g "/\NNNGCGTCAATTTTACGCAGAC-TATCTTTCTAGGGTTAA"—minimum-length 1—discard-untrimmed -e 0—no-indels, where NNN is replaced with the primer barcode. Sleeping Beauty libraries were trimmed with the following settings: -g "/\NNN-TAAGTGTATGTAAACTTCCGACTTCAACTGTA"—minimum-length 1—discard-untrimmed -e 0—no-indels. Reads passing this filter were then trimmed of any trailing Nextera adaptor sequence, again using cutadapt and the following settings: -a "CTGTCTCTTATACA-CATCTCCGAGCCCACGA-GACTNNNNNNNNNNTCTCGT ATGCCGTCTTCTGCTTG"—minimum-length 1. The remaining reads were aligned to the human genome (build hg38) with NovoAlign and the following settings: -n 40 -o SAM -o SoftClip. Aligned reads were validated by confirming that they mapped adjacent to the insertion site motif. Successful reads were then converted to calling card format (.ccf.) and visualized on the WashU Epigenome Browser v46 (Zhou et al., 2011) (http://epigenomegateway.wustl.edu/legacy/).

Sequencing and Analysis: scRNA-seq Libraries scRNA-seq libraries were sequenced on either Illumina HiSeq 2500 or NovaSeq machines. Reads were analyzed using 10× Genomics' Cell Ranger with the following settings: —expect-cells=6000—chemistry=SC3Pv2—local-cores=16—localmem=30. The digital gene expression matrices from 10× were then further processed with scanpy (Wolf et al., 2018) for identification of highly variable genes, batch correction, dimensionality reduction, and Louvain clustering. Processed scRNA-seq datasets were stored as .loom files (http://loompy.org). We cross-referenced gene expression data with published datasets (Rosenberg et al., 2018; Rouillard et al., 2016; Saunders et al., 2018; Tasic et al., 2018; Zeisel et al., 2018) to assign cell types. The species mixing analysis was performed using Drop-seq_tools (Macosko et al., 2015).

Sequencing and Analysis: scCC Libraries scCC libraries were sequenced on Illumina NextSeq 500 machines (v2 Reagent Cartridges) with 50% PhiX. We used the standard Illumina primers for read 1 and index 2 (BP10 and BP14, respectively), and custom primers for read 2 and index 1 (TABLE 4). Read 1 sequenced the cell barcode and unique molecular index of each self-reporting transcript. Read 2 began with GGTTAA (end of the piggyBac terminal repeat and insertion site motif) before continuing into the genome. Reads containing this exact hexamer were trimmed using cutadapt with the following settings: -g "/\GGT-TAA"—minimum-length 1—discard-untrimmed -e 0—no-indels. Reads passing this filter were then trimmed of any trailing P7 adaptor sequence, again using cutadapt and with the following settings: -a "AGAGACTGGCAAGTA-CACGTCGCACTCACCATGANNNNNNNNATCTCGT ATGCCGTCTTCTGCTTG"—minimum-length 1. Reads passing these filters were aligned using 10× Genomics' cellranger with the following settings:—expect-cells=6000—nosecondary—chemistry=SC3Pv2—local-cores=16—localmem=30. This workflow also managed barcode validation and collapsing of UMIs. Aligned reads were validated by verifying that they mapped adjacent to TTAA tetramers. Reads were then converted to calling card format (.ccf.). Finally, to minimize the presence of intermolecular artifacts, we required that each insertion must have been tagged by at least two different UMIs. We used the set of validated cell barcodes from each scRNA-seq library to demultiplex library-specific barcoded insertions from the scCC data. This approach requires no shared cell barcodes between individual scCC (and scRNA-seq) libraries. As a result, we excluded insertions from non-unique cell barcodes, which represented a very small number of total cells lost (<1% per multiplexed library). More details on these steps are also provided in the associated protocols. For the species mixing experiment, cells were classified as either human or mouse if at least 80% of self-reporting transcripts in that cell mapped to the human or mouse genome, respectively, and as a multiplet. The estimated multiplet rate was calculated by doubling the observed percentage of human-mouse multiplet, to account for human-human and mouse-mouse doublets.

Peak Calling on Calling Card Data

We called peaks in calling card data using Bayesian blocks (Scargle et al., 2013), a noise-tolerant algorithm for segmenting discrete, one-dimensional data, using the astropy implementation (Robitaille et al., 2013; The Astropy Collaboration et al., 2018). Bayesian blocks segments the genome into non-overlapping blocks where the density of calling card insertions is uniform. By comparing the segmentation against a background model, we were able to use Poisson statistics to assess whether a given block shows statistically significant enrichment for insertions. Let $$B=\{b_1, b_2, \ldots b_n\}$$

represent the set of blocks found by performing Bayesian block segmentation on all insertions from a TF-directed experiment (e.g., SP1-PBase). For each block $b_i$, let $x_i$ be the number of insertions in that block in the TF-directed experiment. Similarly, let $y'_i$ be the number of insertions in that block in the undirected experiment (e.g., PBase) normalized to the total number of insertions found in the TF-directed experiment. Then, for each block we calculated the Poisson p value of observing at least $x_i$ insertions assuming a Poisson distribution with expectation $$y'_i : P(k \geq x_i | \lambda = y'_i).$$

We accepted all blocks that were significant beyond a particular p value threshold.

For the analysis of TF-directed insertions, either in bulk or in single cells, we added a pseudocount of 1 to $y'_i$, the number of insertions in block $b_i$ in the undirected experiment. We selected all blocks whose p values were significant at a Benjamini-Hochberg false discovery rate of 5% (Benjamini and Hochberg, 1995). We polished peak calls by merging statistically significant blocks that were within 250 bases of each other and by aligning block edges to coincide with TTAAs.

To identify BRD4 binding sites from undirected piggyBac insertions, we segmented those insertions using Bayesian blocks. For each block $b_i$, we let $x'_i$ denote the number of undirected insertions in that block. We also calculated $x'_i$, the expected number of insertions in block $b_i$ assuming piggyBac insertions were distributed uniformly across the genome. We did this by dividing the total number of TTAAs in the genome by the total number of undirected insertions, then multiplying this value by the number of TTAAs in block. Then, for each block we calculated the Poisson p value $$p(k \geq x_i | \lambda = x'_i).$$

We accepted all blocks that were significant beyond a particular p value threshold. Finally, we merged statistically-significant blocks that were within 12,500 bases of each other (Pott and Lieb, 2015; Whyte et al., 2013).

For the bulk PBase and HyPBase analysis, we used p value cutoffs of $10^{-30}$ and $10^{-62}$, respectively. (We chose these stringent thresholds to better resolve super-enhancers, which is our primary focus here.) For both in vitro and in vivo single cell HyPBase analyses, we used a p value cutoff of $10^{-9}$. To identify the differentially-bound loci between $CD24^{high}/CD24^{ow}$ K562 cells, as well as between upper and lower cortical layer neurons (i.e., Pou3f2/Brn-2, Bcl11b/Ctip2, and Foxp2), we used the same framework as described above for TF-directed analysis but did reciprocal enrichment analyses, where one dataset was used as the "experiment" track and the other as the "control" track, and vice-versa. This results in two one-sided hypothesis tests. When analyzing differential binding between upper and lower cortical layer neurons, we used a p value cutoff of $10^{-9}$. For the $CD24^{high}/CD24^{low}$ K562 analysis, we restricted our hypothesis testing to BRD4-bound peaks found in the cell line mixing experiment that had at least 20 insertions between both groups. For each peak, we normalized the number of insertions from each population by a library-specific scaling factor and calculated the fold change in binding as $\log_2$(Normalized $CD24^{high}$ insertions/Normalized $CD24^{low}$ insertions)|. We then took the smaller of the two p values and adjusted for multiple hypotheses at a Benjamini-Hochberg false discovery rate of 10%. This was plotted against the fold-change values to generate the volcano plot (colored circles indicate significant peaks after FDR correction). Data points were annotated when peaks overlapped or were near a single gene.

Density tracks were generated by taking the Bayesian blocks segmentation of each calling card dataset and, for each block, calculating the normalized number of insertions and dividing by the length of the block in kilobases (insertions per kilobase per million mapped insertions, or IPKM). This was plotted as a bedgraph file with smoothing applied in the WashU Epigenome Browser (25 pixel windows).

Custom code to facilitate these analyses is available online (https://github.com/arnavm/calling_cards). Detailed instructions on how to analyze calling card data are provided in the linked protocols.

TF Binding Analysis

We compared our TF-directed calling card peaks to publicly available ChIP-seq datasets. See below for more details on aligning and analyzing ChIP-seq data. We collated a list of unique transcription start sites (TSSs) by taking the 5'-most coordinates of RefSeq Curated genes in the hg38 build (UCSC Genome Browser). A list of CpG islands in HCT-116 and K562 cells and their methylation statuses were derived from previously-published Methyl-seq data (Brunner et al., 2009). We used the liftOver tool (Hinrichs et al., 2006) to convert coordinates from hg18 to hg38. We tested for enrichment in SP1-directed insertions at TSSs, CpG islands, and unmethylated CpG islands with the G test of independence. We used the same test when testing enrichment of BAP1-directed insertions at TSSs. For motif discovery, we restricted our analysis to peaks less than 5,000 bp in length. We then used MEME-ChIP (Machanick and Bailey, 2011) with a dinucleotide shuffled control and the following settings: -dna -nmeme 600 -seed 0 -ccut 250 -meme-mod zoops -meme-minw 4 -meme-nmotifs 10. Motifs were aligned on the web version of Tomtom (Gupta et al., 2007) querying the "Vertebrates (In vivo and in silico)" database. We cross-referenced BAP1 scCC binding sites with publicly available BAP1 shRNA data (Yen et al., 2018), focusing on genes that showed a significant change in gene expression (adjusted p value <0.05).

BRD4 Sensitivity, Specificity, and Precision

We used a published BRD4 ChIP-seq dataset (McCleland et al., 2016) to identify BRD4-bound super-enhancers in HCT-116 cells, following previously-described methods (Lovén et al., 2013; Whyte et al., 2013). We first called peaks using MACS 1.4.1 (Zhang et al., 2008) at $p<10^{-9}$ (using the parameters -p 1e-9—keep-dup="auto" -f BAM -g hs -w -S—space=50), then fed this into ROSE. We discarded artifactual loci less than 2,000 bp in size, yielding a final list of 162 super-enhancers. To evaluate sensitivity, we used BEDtools (Quinlan and Hall, 2010) to ask what fraction of piggyBac peaks, at various p value thresholds, overlapped the set of BRD4-bound super-enhancers. To measure specificity, we created a list of regions predicted to be insignificantly enriched (p>0.1) for BRD4 ChIP-seq signal. We then sampled bases from this region such that the distribution of peak sizes was identical to that of the 162 super-enhancers. We sampled to 642× coverage, sufficient to cover each base with one peak, on average. We then asked what fraction of our piggyBac peaks overlapped these negative peaks and subtracted that value from 1 to obtain specificity. Finally, we calculated precision, or positive predictive value, by dividing the total number of detected super-enhancer peaks by the sum of the super-enhancer peaks and the false positive peaks.

Downsampling and Replication Analysis

When performing downsampling analyses on calling card insertions, we randomly sampled insertions without replacement and in proportion to the number of reads supporting each insertion. Peaks were called on the downsampled insertions at a range of p value cutoffs. Linear interpolation was performed using NumPy (Oliphant, 2015) and visualized using matplotlib (Hunter, 2007). Replication was assessed by splitting calling card insertions into two, approximately equal, files based on their barcode sequences. Each new file was treated as a single biological experiment. For each peak called from the joint set of all insertions, we plotted the number of normalized insertions (IPM) in one replicate on the x axis and the other replicate on y axis.

Analysis of External Datasets

For ChIP-seq, ATAC-seq, and DNase-seq data, we aligned raw reads using Novoalign with the following settings for single-end datasets: -o SAM -o SoftClip; while paired-end datasets were mapped with the additional flag -i PE 200-500. To calculate and visualize the fold enrichment in ChIP-seq signal at calling card peaks, we used deeptools (Ramirez et al., 2016). We tested for significant mean enrichment in BRD4 ChIP-seq signal at piggyBac peaks over randomly shuffled control peaks with the Kolmogorov-Smirnov test. Chromatin state analysis was performed using ChromHMM as previously described (Ernst et al., 2011). For each chromatin state, we plotted the mean and standard deviation of the rate of normalized insertions (IPKM). We called peaks on SP1 ChIP-seq, DNase- and ATAC-seq data using MACS 2 with the following settings: -q 0.05—keep-dup="auto." For the analysis of "super-enhancers" from ATAC-seq data, we used control data derived from ATAC-seq on deproteinized human genomic DNA (Martins et al., 2018) and followed the same steps for calling super-enhancers from BRD4 ChIP-seq data (above). If necessary, files were converted to hg38 using liftOver (Hinrichs et al., 2006).

Cell State Analyses of K562: scRNA-seq and scCC

Cell state analysis was performed on batch-corrected K562 scRNA-seq data derived from the HyPBase cell line mixing experiment. Principal components analysis (PCA) of single cell gene expression FIG. 13A) revealed CD24 as one of the top genes in PC1, while PC2 was enriched in hemoglobin genes, particularly the fetal-specific markers HBE1 and HBZ. Furthermore, the expression of top PC1 and PC2 genes appear to be anticorrelated: cells that strongly expressed CD24 are not likely to express HBZ, and vice-versa (FIG. 13B), suggesting mutually exclusive states. We then scored cells based on the expression of VIM, TMSB4X, HBG1, and HBG2, revealing a gradient of cell states along a stem-like-to-differentiated axis (FIG. 6A). We then modeled the distribution of this state score as a 3 component Gaussian mixture model, drawing cutoffs where adjacent Gaussian distributions intersected (FIG. 13C). These cutoffs were then used to label cells as either stem-like ($CD24^{high}$), differentiated ($CD24^{low}$), or intermediate (FIG. 13D). The expression levels of CD24 and HBZ, which were not used to score cells, showed high specificity for the stem-like and differentiated clusters (FIG. 13E). Differentially bound peaks were called as described above.

Analysis of K562 Experiments

We analyzed the JQ1 time course experiment using a two-way ANOVA with treatment and day as the independent variables and the percentage of $CD24^{low}$ cells as the dependent variable. For the analysis of annexin V levels in either JQ1- or DMSO-treated $CD24^{high}$ and $CD24^{low}$ cells, we used a three-way ANOVA with treatment, cell state, and day as independent variables. The imatinib experiments following either JQ1 or BRD4 CRISPRi pretreatment were analyzed using a two-way ANOVA with pretreatment (JQ1/DMSO or NT/BRD4 gRNA) and treatment as the independent variables. Multiple hypothesis correction was performed using Tukey's honestly significant difference. For the cell cycle inhibitor experiment, data were analyzed using a one-way ANOVA with Dunnett's post hoc test using either DMSO or EtOH (for RO-3306) as controls.

In Vivo scCC Analysis and Validation

Single cell RNA-seq and single cell calling card libraries were prepared, sequenced, and analyzed as described above. Cell types were assigned based on the expression of key marker genes and cross-referenced with recent cortical scRNA-seq datasets (Rosenberg et al., 2018; Saunders et al., 2018; Tasic et al., 2018; Zeisel et al., 2018). BRD4-bound peak calls were validated by comparing to a previously published cortical H3K27ac ChIP-seq dataset (Stroud et al., 2017). Read alignment and statistical analysis were performed as described above.

The specificity of BRD4-bound gene expression in astrocytes and neurons was analyzed by first identifying all genes within 10,000 bases of astrocyte and neuronal BRD4 peaks. Although assigning an enhancer to its target gene is a difficult problem, using the nearest gene is common practice (Gasperini et al., 2019). To control for sensitivity of gene detection, we downsampled the neuron insertions to the same number of astrocyte insertions, then called peaks and identified nearby genes in this subset. We used gene expression data from a bulk RNA-seq dataset (Zhang et al., 2014) to compute the specificity of gene expression between astrocytes and neurons. We first discarded genes whose expression was not measured, and then set the value for genes with 0.1 FPKM to zero (to better distinguish non-expressed genes from lowly-expressed genes). Finally, for each gene $g_i$, we calculated the specificity as AstrocyteFPKM(gi)=[AstrocyteFPKM](gi)+NeuronFPKM(gi).

Thus, a value of 0 denotes a gene purely expressed in neurons, a value of 0.5 for a gene equally expressed in both cell types, and a value of 1 for a gene purely expressed in astrocytes. After accounting for differences in library size, we identified 383 genes near astrocyte peaks and 184 genes near neuron peaks, with 46 genes found in both datasets. We plotted the distributions of gene expression specificity for these gene sets. (FIG. 5E). Gene Ontology analysis was performed on the same sets of genes using PANTHER (Mi et al., 2017) on the "GO biological process complete" database. Fisher's exact test was used to compute p values, which were then subject to Bonferroni correction.

Additional Resources

We have created a number of protocols describing how to perform all aspects of bulk and single cell calling cards, from molecular biology and sequencing through data analysis and visualization. While these are listed in the Key Resources Table, we have also created a publicly accessible portal for easy access to all our workflows: https://www.protocols.io/groups/calling-cards/. Moving forward, this resource should contain the most up-to-date information.

Molecular Biology of Self-Reporting Transposons (SRTs)

Self-reporting transposons (SRTs) are synthetic constructs that generate transcripts whose 3' untranslated regions (UTRs) contain the genomic sequence identifying the SRT's insertion site. These transcripts can be recovered using a poly(T) reverse transcription (RT) primer tailed with a universal priming site at one end of the transcripts. It is unclear whether self-reporting transcripts are truly polyadenylated like protein-coding mRNA (i.e. contain non-templated 3' adenines added by poly(A) polymerase after cleavage from RNA polymerase II) or contain templated stretches of adenine to which the RT primer can internally hybridize. Regardless, transcripts are amplified after first-strand synthesis. We then perform a pair of nested PCRs with an intermediate tagmentation step (Picelli et al., 2014) to recover the transposon-genome junction. After adapter trimming and alignment, the 5' coordinates of these reads specify the genomic locations of insertions in the library (FIG. 2A).

Supplemental Methods

Additional Validation of SRTs

Figure 16A:
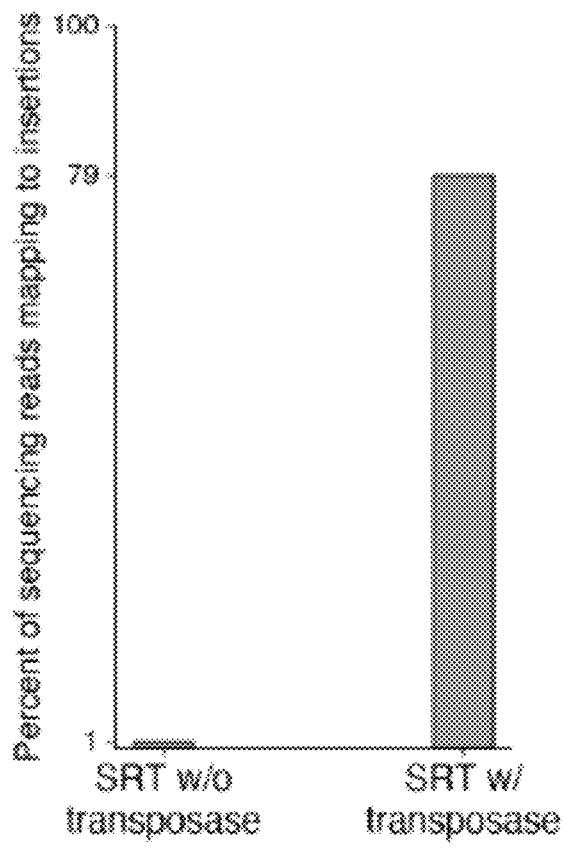
FIG. 16A-FIG. 16D. Properties of self-reporting transposons (SRTs). (A) Efficiencies of bulk RNA calling card libraries prepared from HEK293T cells transfected with PB-SRT-tdTomato with or without HyPBase transposase. (B) Overlap of SRTs recovered by two technical replicates of bulk RNA calling cards in HCT-116 cells transfected with PB-SRT-Puro and SP1-PBase. (C) Distribution of insertions with respect to chromatin state between SRT libraries prepared from either DNA or RNA. (D) Breakdown of sequencing reads mapping to the genome or plasmid from SRT libraries prepared from either DNA or RNA.
Figure 16B:
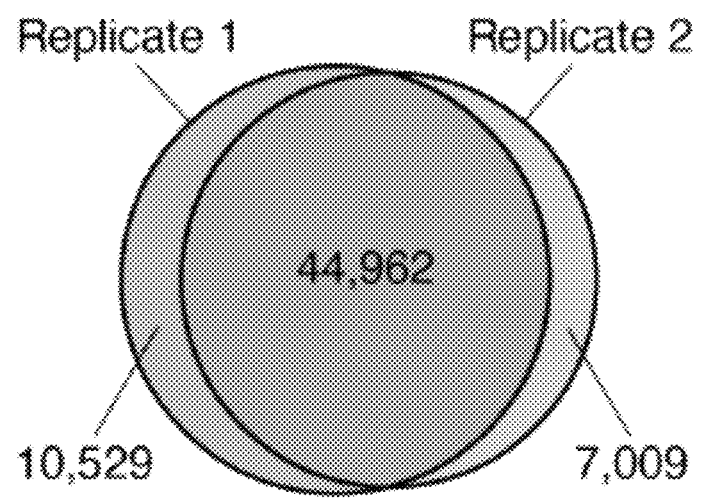
Figure 16C:
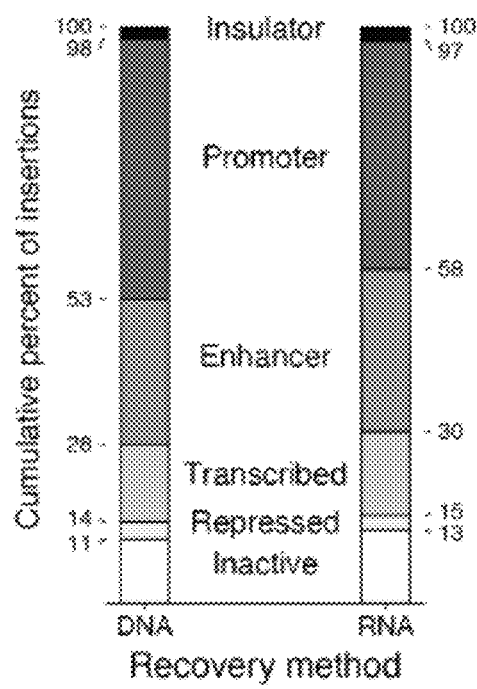
Figure 16D:
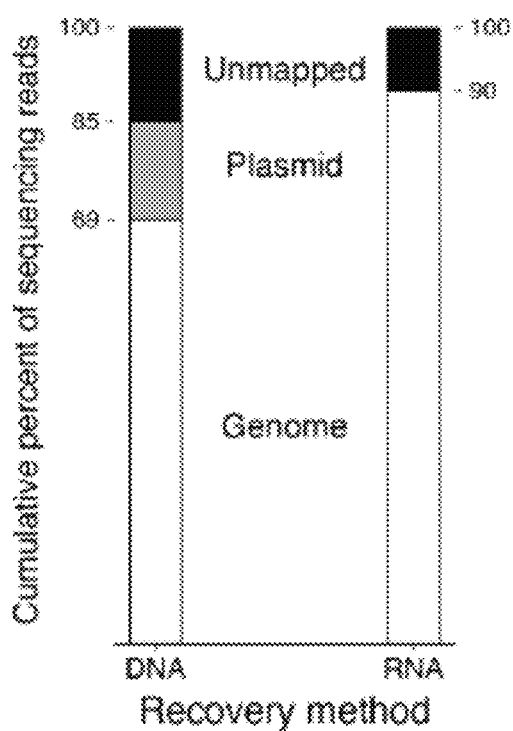

To confirm that our molecular protocol was specific for transposed SRTs (as opposed to the original plasmid copy), we generated libraries from cells transfected with either piggyBac SRTs alone or SRTs alongside piggyBac transposase. Libraries generated without transposase yielded very few reads mapping to the genome; however, protocol is highly efficient when transposase is added (FIG. 16A). Thus, a functional transposase is required to successfully map SRTs. This is likely due to the inclusion of a self-cleaving hammerhead ribozyme downstream of the SRT on the plasmid (below). We also found that technical replicates of the bulk SRT protocol showed high reproducibility, with over 80% concordance at the level on individual transpositions (FIG. 16B). To further compare the recovery of SRTs between the DNA- and RNA-based protocols, we generated chromatin state annotations based on epigenomic ChIP-seq data in HCT-116 cells (Methods, FIG. 17, and TABLE 5). We observed that the distribution of insertions with respect to chromatin state was highly concordant between the DNA and RNA libraries (FIG. 16C).

TABLE 5

ChromHMM chromatin state annotations in HCT-116 cells.

| Emission | CTCF | H3K9me2 | H3k9me3 | H3k27me3 | H3k36me3 | H4K20me1 | H3K4me1 |
|---|---|---|---|---|---|---|---|
| 1 | 86 | 1 | 1 | 1 | 1 | 2 | 13 |
| 2 | 23 | 1 | 1 | 2 | 0 | 1 | 38 |
| 3 | 25 | 0 | 0 | 0 | 2 | 1 | 35 |
| 4 | 14 | 0 | 1 | 0 | 2 | 1 | 89 |
| 5 | 3 | 2 | 2 | 1 | 1 | 2 | 59 |
| 6 | 3 | 1 | 2 | 0 | 14 | 9 | 77 |
| 7 | 1 | 1 | 4 | 0 | 13 | 10 | 11 |
| 8 | 0 | 1 | 3 | 0 | 14 | 5 | 4 |
| 9 | 5 | 0 | 2 | 0 | 32 | 8 | 16 |
| 13 | 0 | 3 | 6 | 1 | 1 | 3 | 4 |
| 12 | 0 | 1 | 19 | 1 | 1 | 3 | 3 |
| 15 | 0 | 2 | 3 | 30 | 0 | 5 | 3 |
| 11 | 0 | 0 | 0 | 0 | 0 | 0 | 0 |
| 14 | 0 | 1 | 1 | 1 | 0 | 1 | 2 |
| 10 | 3 | 48 | 69 | 30 | 54 | 36 | 28 |

Chromatin mark observation frequency (%)

| Emission | H3K4me2 | H3K4me3 | H3K27ac | H3K9ac | H3K79me2 | Candidate State Annotation |
|---|---|---|---|---|---|---|
| 1 | 21 | 1 | 5 | 0 | 1 | Insulator |
| 2 | 97 | 87 | 20 | 29 | 3 | Promote |
| 3 | 100 | 100 | 96 | 98 | 37 | |
| 4 | 98 | 36 | 95 | 41 | 4 | Enhancer |
| 5 | 57 | 1 | 9 | 1 | 3 | |
| 6 | 90 | 27 | 53 | 22 | 92 | |
| 7 | 1 | 0 | 5 | 0 | 85 | Transcribed |
| 8 | 0 | 0 | 2 | 0 | 12 | |
| 9 | 5 | 0 | 65 | 1 | 36 | |
| 13 | 0 | 0 | 0 | 0 | 2 | |
| 12 | 0 | 1 | 0 | 0 | 1 | Repressed |
| 15 | 0 | 0 | 0 | 0 | 1 | |
| 11 | 0 | 0 | 0 | 0 | 0 | Inactive |
| 14 | 0 | 0 | 0 | 0 | 0 | |
| 10 | 21 | 34 | 21 | 15 | 28 | |

Chromatin mark observation frequency (%)

Noise Reduction

A common artifact observed in DNA-based transposon recovery is a large fraction of reads aligning to the donor transposon plasmid instead of the genome. Although this can be mitigated by long selection times or by digestion with the methyladenine-sensitive enzyme DpnI (Wang et al., 2012a), these methods do not completely eliminate background and are not compatible with all experimental paradigms (e.g. viral transduction). To reduce this artifact, we included a hammerhead ribozyme (Yen et al., 2004) in the SRT plasmid downstream of the 5' terminal repeat (TR). Before transposition, the ribozyme will cleave the nascent transcript originating from the marker gene, thus preventing RT. Transposition allows the SRT to escape the downstream ribozyme, leading to recovery of the self-reporting transcript. In our comparison of DNA- and RNA-based recovery, about 15% of reads from the DNA library aligned to the plasmid, compared to fewer than 1% of reads from the RNA library (FIG. 9D). Thus, the addition of a self-cleaving ribozyme virtually eliminated recovery of un-excised transposons.

Uniform Recovery of SRTs

Figure 17A:
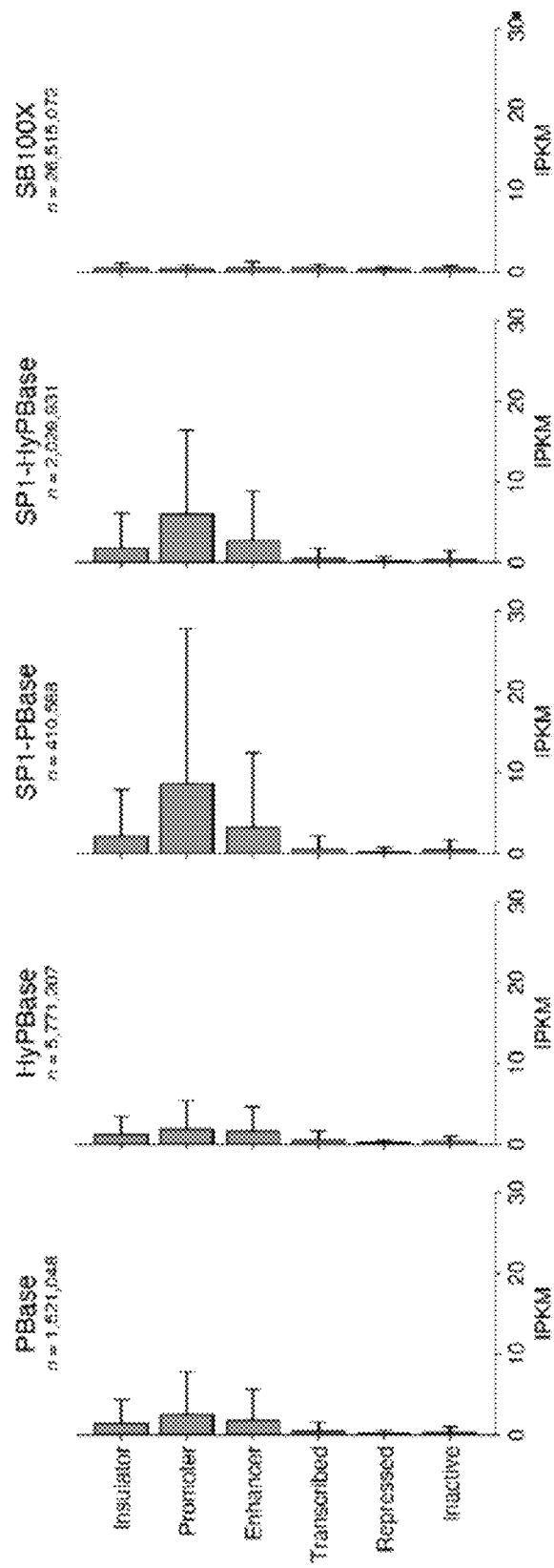
FIG. 17A-FIG. 17B. piggyBac, SP1-piggyBac fusions, and Sleeping Beauty display different local transposition rates depending on chromatin state. (A) Chromatin state analysis on the local rates of transposition of undirected piggyBac, SP1-piggyBac fusions, and Sleeping Beauty transposases in HCT-116 cells. (B) Same data as (A) but with different x-axes for each graph. IPKM: insertions per kilobase per million mapped insertions.
Figure 17B:
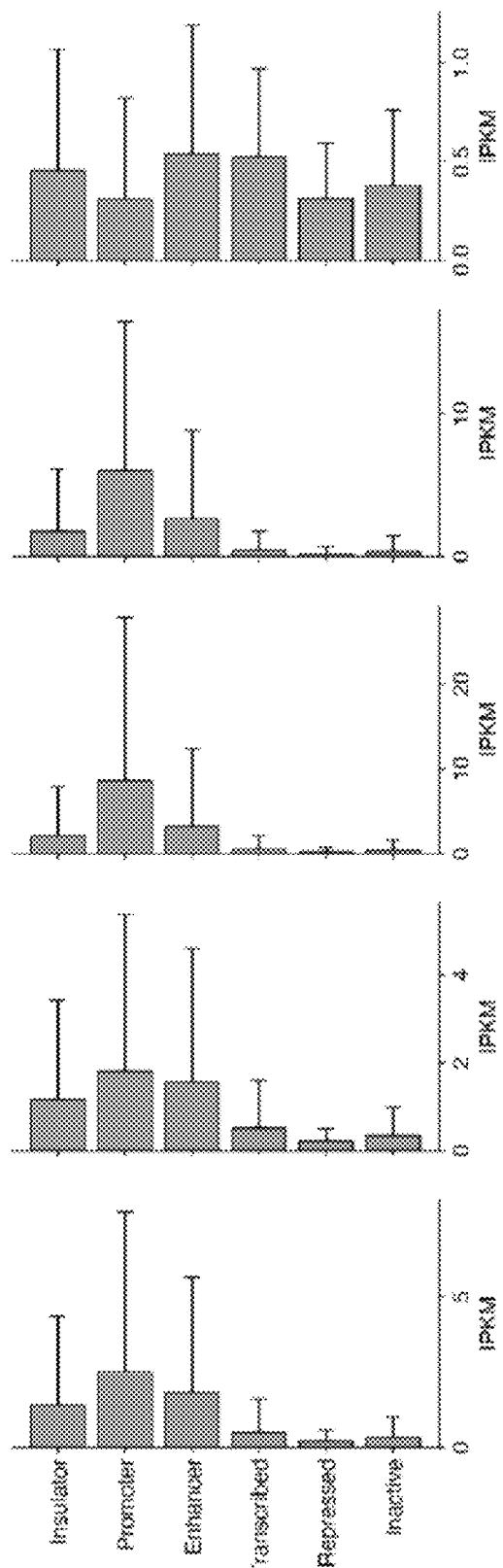

Since SRT recovery relies on transcription, we wondered if SRTs deposited in euchromatic regions were recovered more efficiently than SRTs in less permissive chromatin states, which might lead to biases when mapping TF binding. As piggyBac is known to preferentially insert near active chromatin (Yoshida et al., 2017), this question cannot be easily answered using this transposon. Prior studies have shown that the Sleeping Beauty transposase (Ivics et al., 1997; Mates et al., 2009) has very little preference for chromatin state (Yoshida et al., 2017). Therefore, we created a self-reporting Sleeping Beauty transposon and compared its genome-wide distribution to that of SRTs deposited by wild-type piggyBac (TABLE 1; FIG. 17A-FIG. 17B). Undirected piggyBac transposases appeared to modestly prefer transposing into promoter and enhancers, which is consistent with previous reports (Gogol-Döring et al., 2016; Yoshida et al., 2017) (TABLE 5). By contrast, Sleeping Beauty showed largely uniform rates of insertions across all chromatin states, including repressed and inactive chromatin (FIG. 17B). These results affirm that while RNA-based recovery is more efficient, it still preserves the underlying genomic distributions of insertions. Furthermore, because SRTs can be recovered from virtually any chromatin state, RNA-based calling card recovery can be employed to analyze a variety of TFs with broad chromatin-binding preferences.

SRTs are Compatible with TF-Directed Calling Cards

Since the SRT is a new reagent, we sought to confirm that bulk RNA calling cards can, like DNA calling cards (Wang et al., 2012a), be used to identify TF binding sites. We transfected 10-12 replicates of HCT-116 cells with plasmids containing the PB-SRT-Puro donor transposon and SP1 fused to either piggyBac (SP1-PBase) or a hyperactive variant of piggyBac (Yusa et al., 2011) (SP1-HyPBase). As controls, we also transfected a similar number of replicates with undirected PBase or HyPBase, respectively. We obtained 410,588 insertions from SP1-PBase and 1,521,048 insertions from PBase; similarly, we obtained 2,029,931 SP1-HyPBase insertions and 5,771,207 insertions from HyPBase (TABLE 1).

Figure 18A:
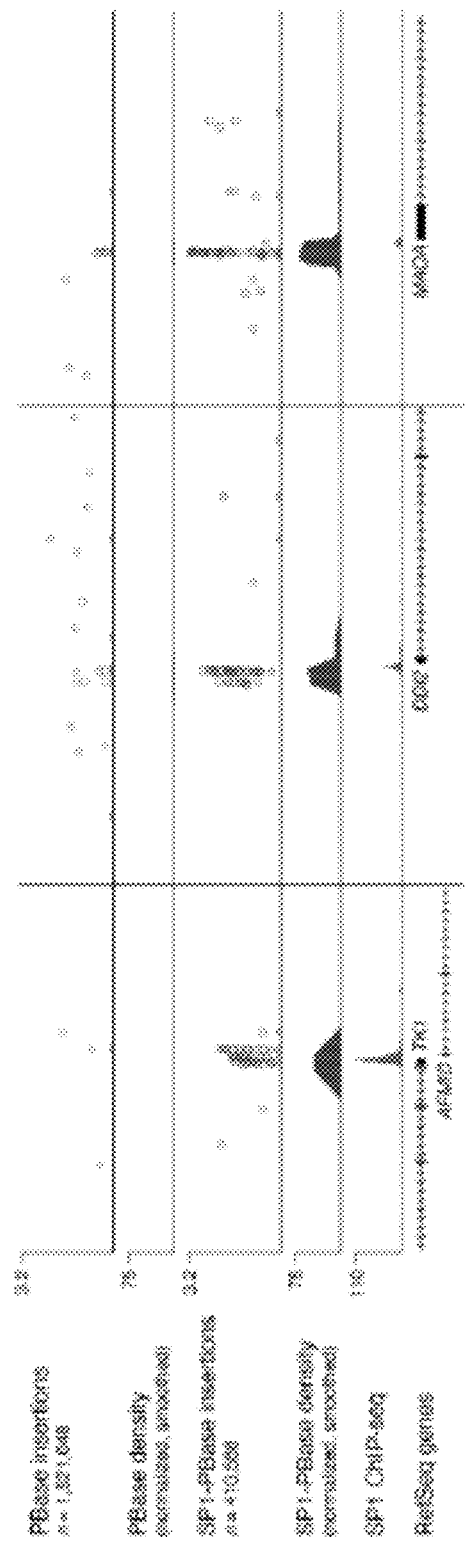
FIG. 18A-FIG. 18F. SP1 fused to piggyBac (SP1-PBase) redirects SRTs to SP1 binding sites. (A) Browser view of bulk SP1-PBase calling cards in HCT-116 cells. (B) Reproducibility of normalized insertions at bulk SP1-PBase peaks. (C) Mean SP1 ChIP-seq signal at bulk SP1-PBase peaks. (D) Heatmap of SP1 ChIP-seq signal at bulk SP1-PBase peaks. (E) Enrichment of SP1-PBase-directed insertions to TSSs, CGIs, and unmethylated CGIs (G test of independence $p<10^{-9}$). (F) SP1 core motif elicited from bulk SP1-PBase peaks. IPM: insertions per million mapped insertions; FC: fold change; TSS: transcription start sites; CGI: CpG island.
Figure 18B:
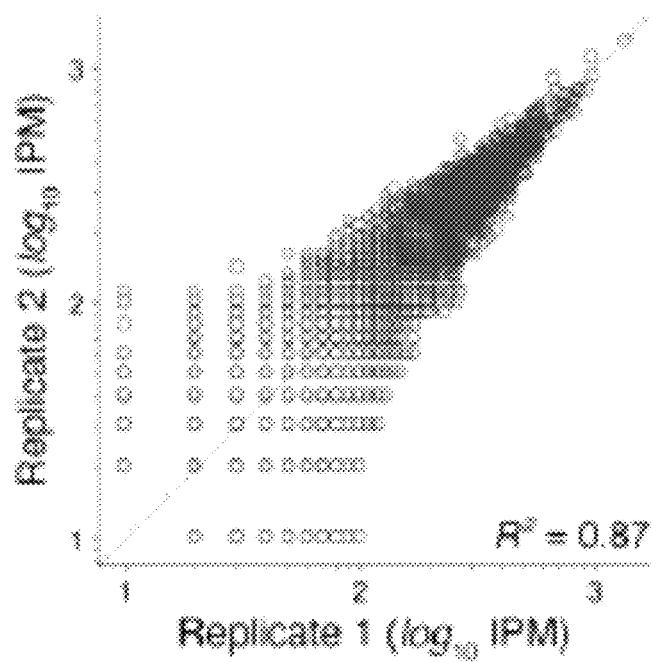
Figure 18C:
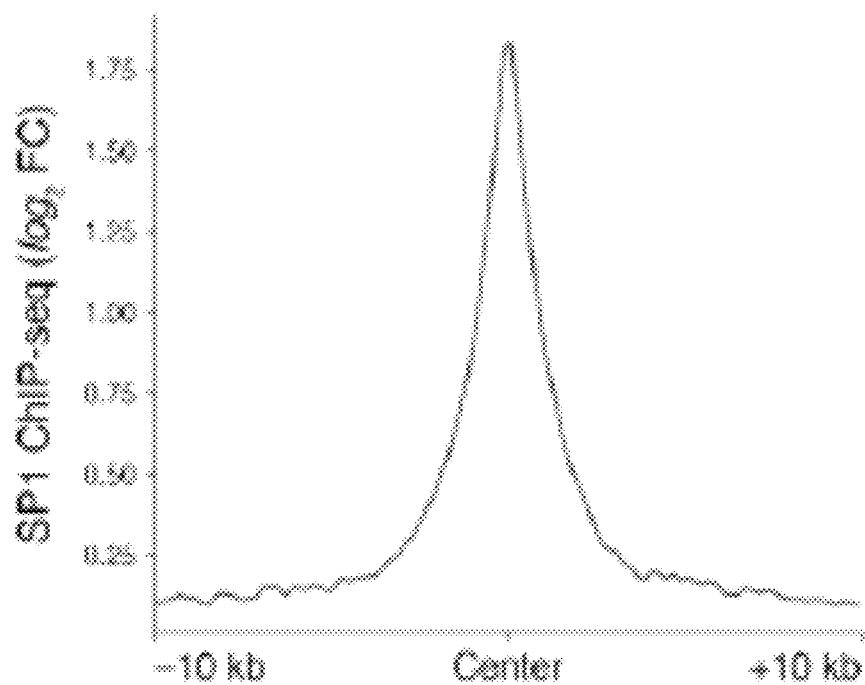
Figure 18D:
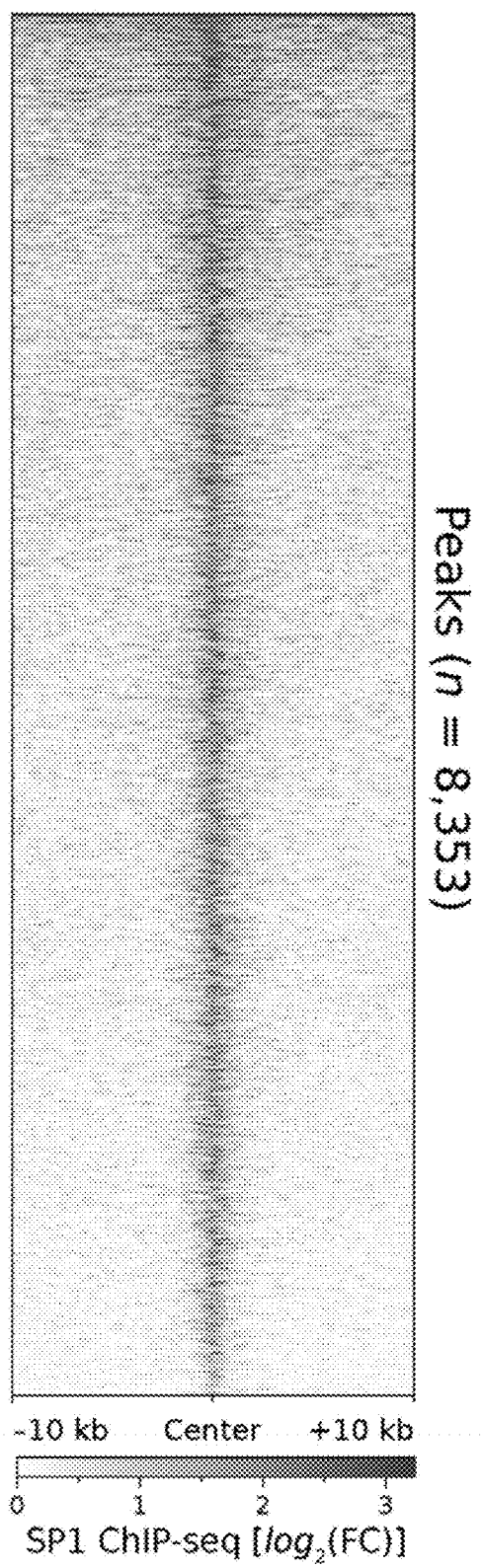
Figure 19A:
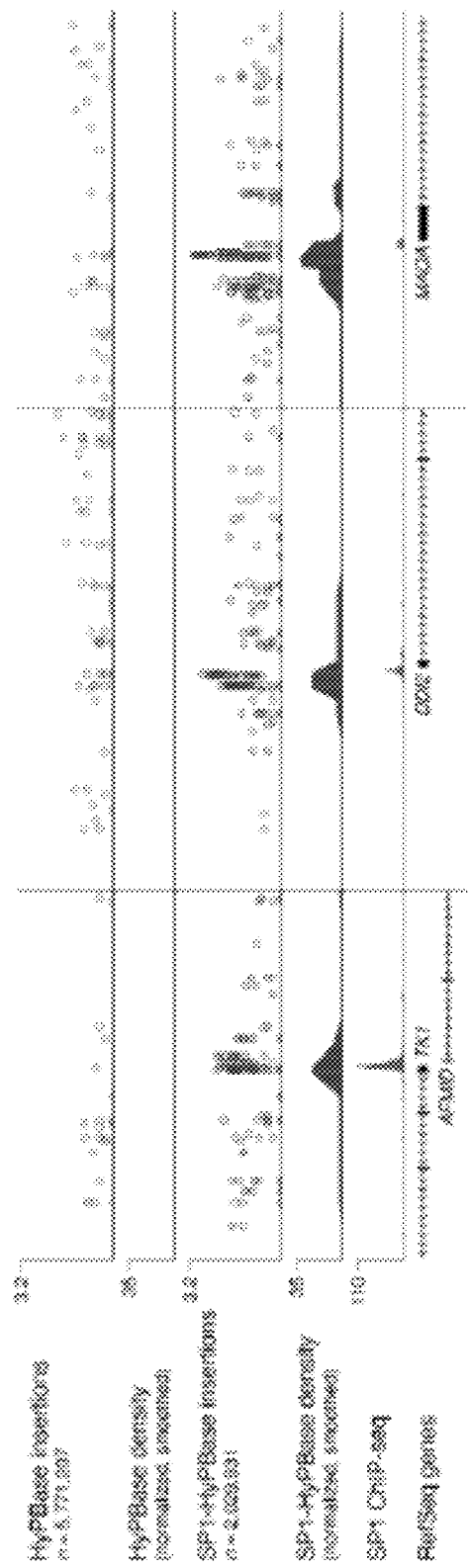
FIG. 19A-FIG. 19F. SP1 fused to hyperactive piggyBac (SP1-HyPBase) also redirects SRTs to SP1 binding sites. (A) Browser view of bulk SP1-HyPBase calling cards in HCT-116 cells. (B) Reproducibility of normalized insertions at bulk SP1-HyPBase peaks. (C) Mean SP1 ChIP-seq signal at bulk SP1-HyPBase peaks. (D) Heatmap of SP1 ChIP-seq signal at bulk SP1-HyPBase peaks. (E) Enrichment of SP1-HyPBase-directed insertions to TSSs, CGIs, and unmethylated CGIs (G test of independence $p<10^{-9}$). (F) SP1 core motif elicited from bulk SP1-HyPBase peaks. IPM: insertions per million mapped insertions; FC: fold change; TSS: transcription start sites; CGI: CpG island.
Figure 19B:
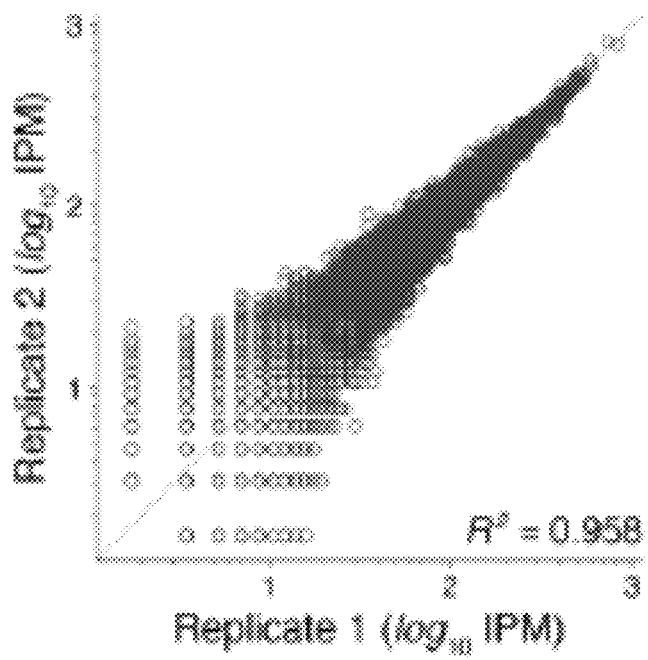
Figure 19C:
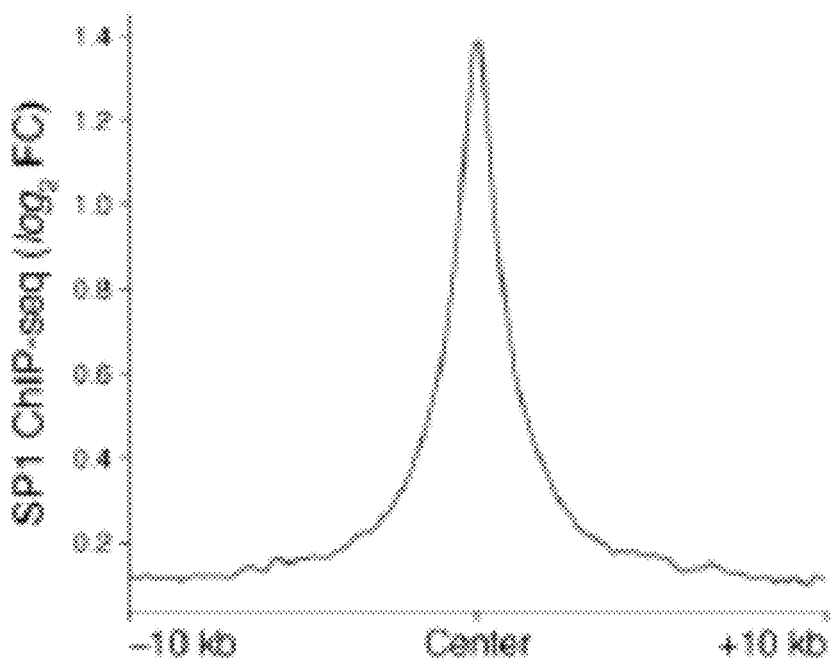
Figure 19D:
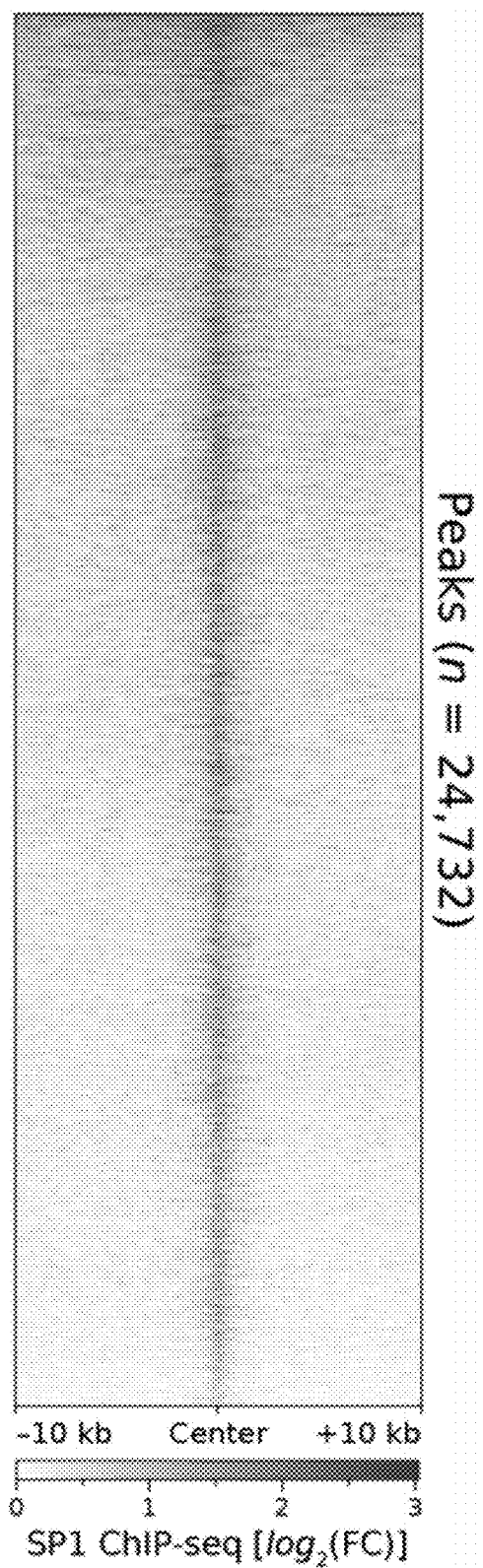

Just as we had observed previously with DNA calling cards (Wang et al., 2012a), RNA calling cards were also redirected by SP1-PBase and SP1-HyPBase to SP1-bound regions of the genome (FIG. 18A and FIG. 18A). All three of the loci shown in FIG. 18A and FIG. 19A show a specific enrichment of calling card insertions in the SP1 fusion experiments that is not observed in the undirected control libraries. Next, we called peaks at all genomic regions enriched for SP1-directed transposition. The number of insertions observed at significant peaks for both SP1-PBase and SP1-HyPBase was highly reproducible between biological replicates (R2=0.87 and 0.96, respectively; FIG. 18B and FIG. 19B). Furthermore, calling card peaks were highly enriched for SP1 ChIP-seq signal at their centers, both on average (FIG. 18C and FIG. 19C) and in aggregate (FIG. 18D and FIG. 19D).

Figure 18E:
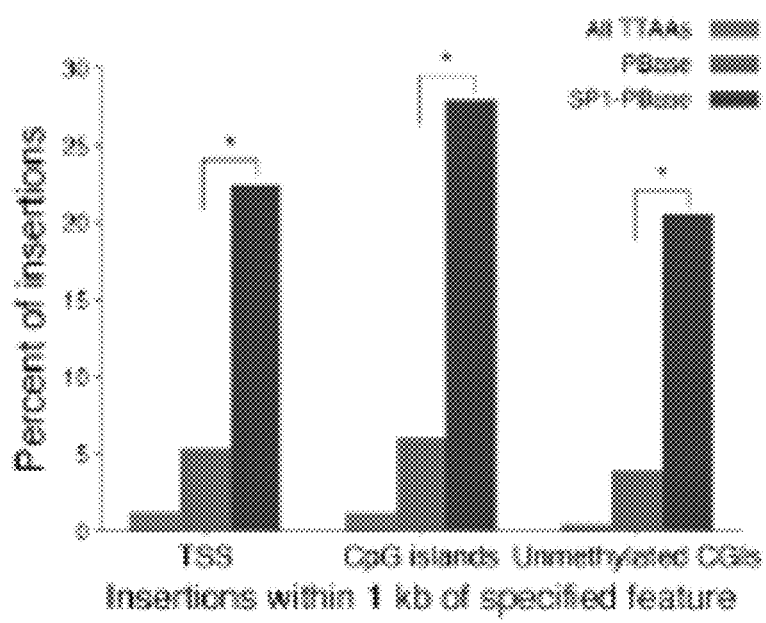
Figure 18F:
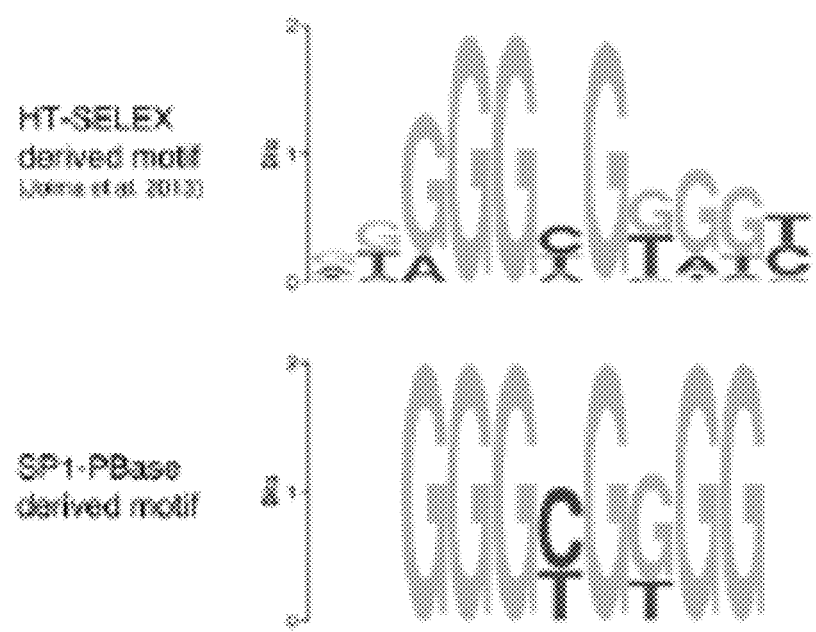
Figure 19E:
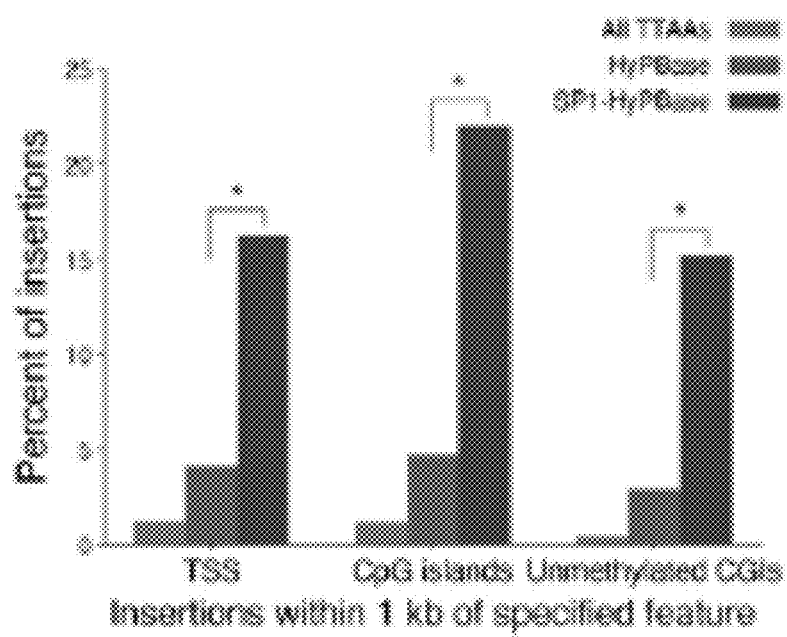
Figure 19F:
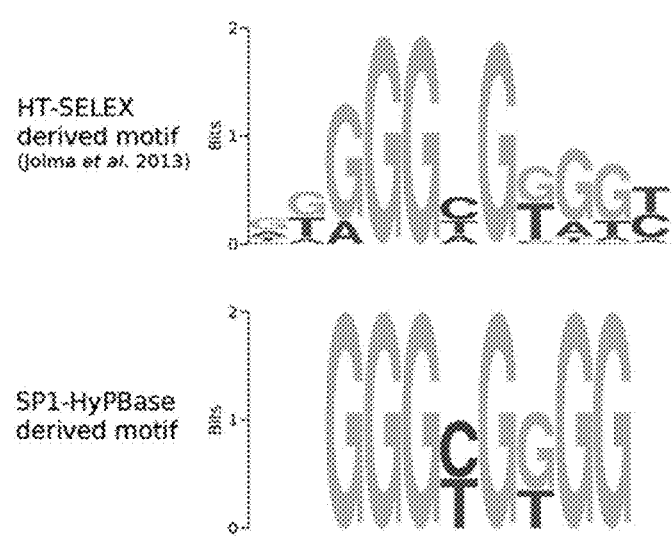

SP1 is known to preferentially bind near transcription start sites (TSSs) and is also thought to play a role in demethylating CpG islands (Brandeis et al., 1994; Macleod et al., 1994; Philipsen and Suske, 1999). We confirmed that the SP1-directed transposases preferentially inserted SRT calling cards near TSSs, CpG islands, and unmethylated CpG islands at statistically significant frequencies ($p<10^{-9}$ in each instance, G test of independence; FIG. 18E and FIG. 19E). Moreover, compared to undirected piggyBac, SP1-directed piggyBac showed a striking preference for depositing insertions into promoters (FIG. 17A-B). Lastly, regions targeted by SP1-PBase and SP1-HyPBase were enriched for the core SP1 DNA binding motif ($p<10^{-79}$ in each instance; FIG. 18F and SM4F). Taken together, these results indicate that the genome-wide binding of SP1 can be accurately mapped using piggyBac SRTs.

Hyperactive piggyBac Insertions Identify BRD4-Bound Super-Enhancers

Figure 20A:
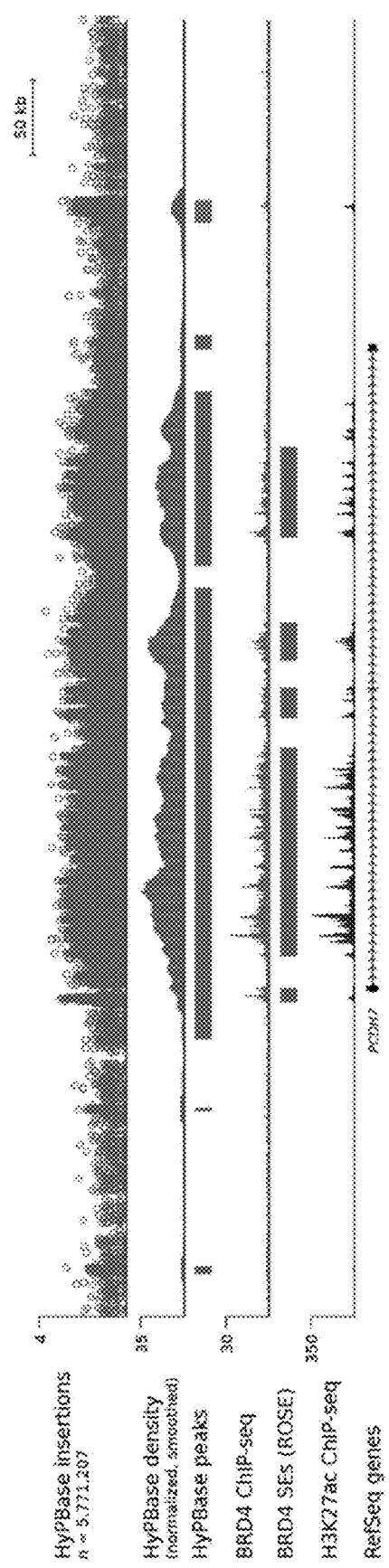
FIG. 20A-FIG. 20F. Undirected hyperactive piggyBac (HyPBase) SRTs also mark BRD4-bound superenhancers. (A) Browser view of undirected HyPBase insertions at a SE alongside BRD4 and H3K27ac ChIP-seq data in HCT-116 cells. (B) Reproducibility of normalized insertions at HyPBase peaks. (C) Mean BRD4 ChIP-seq signal at HyPBase peaks compared to permuted control set. (D) Heatmap of H3K27ac, H3K4me1, H3K9me3, and H3K27me3 ChIP-seq signal at HyPBase peaks. (E) Receiver-operator characteristic curve for SE detection using HyPBase peaks. (F) Precision-recall curve for SE detection using HyPBase peaks. SE: super-enhancer; IPM: insertions per million mapped insertions; AUROC: area under receiver-operator curve; AUPRC: area under precision-recall curve; FC: fold change.
Figure 20B:
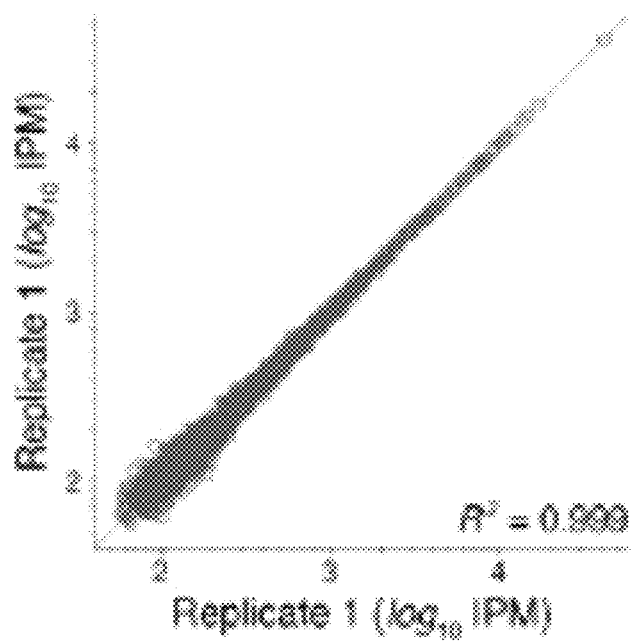
Figure 20C:
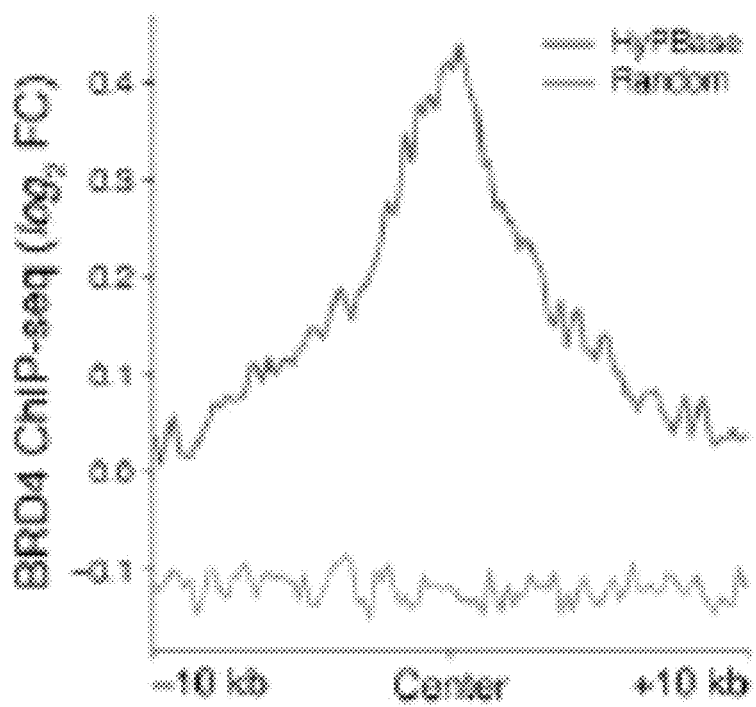
Figure 20D:
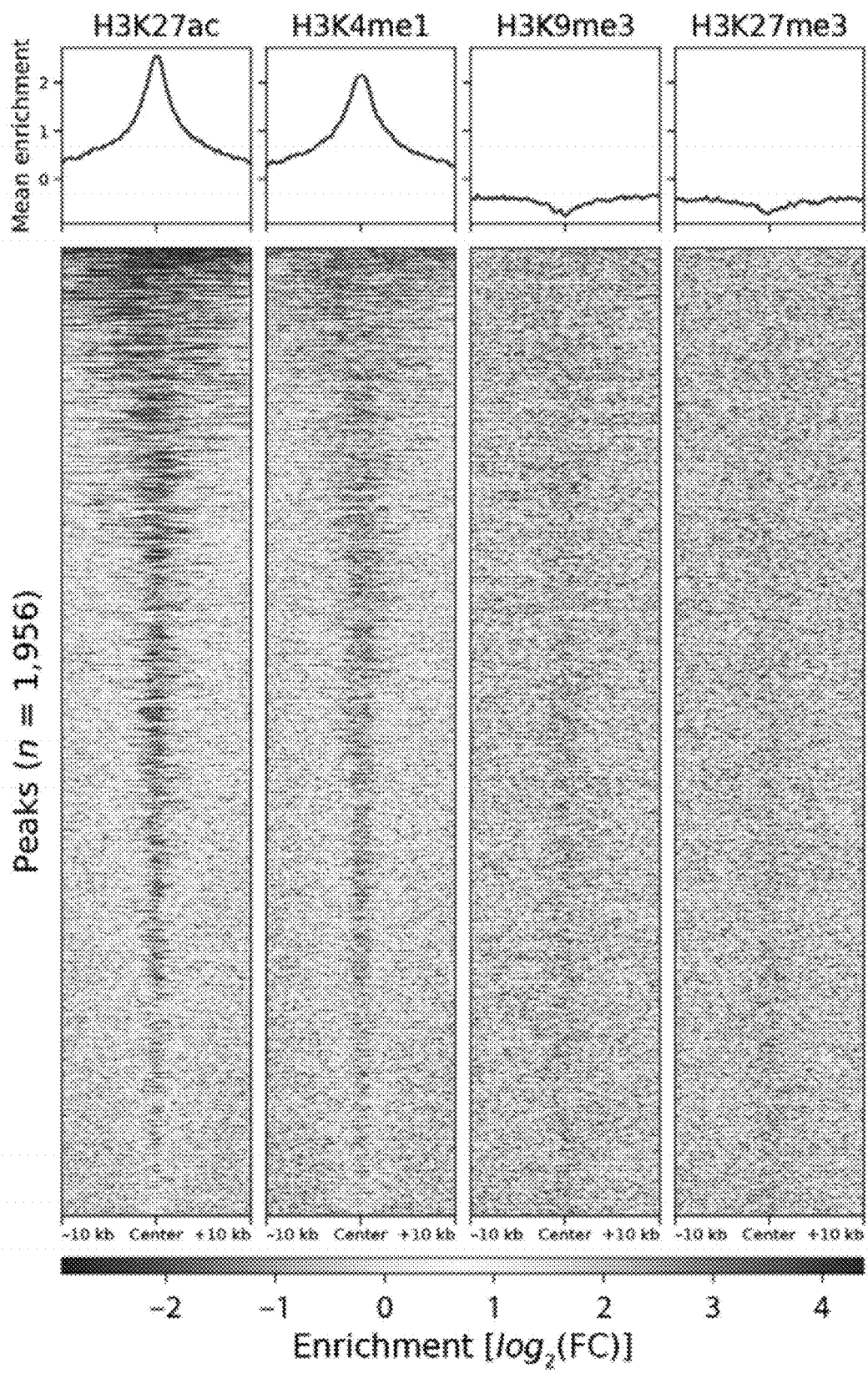
Figure 20E:
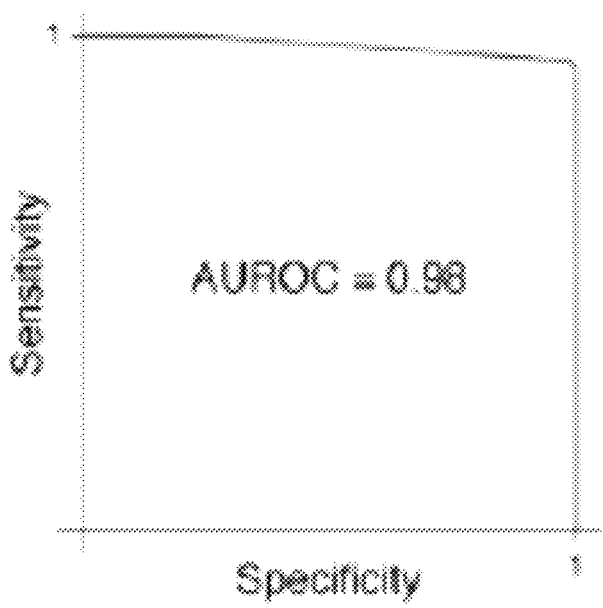
Figure 20F:
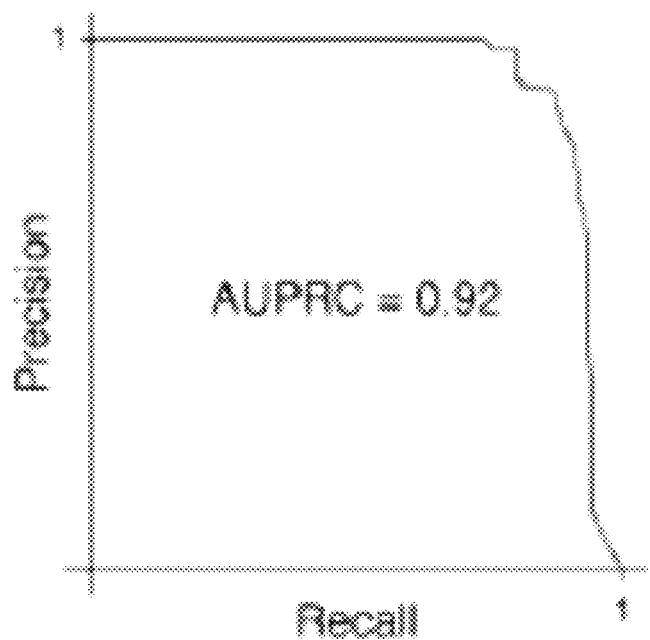
Figure 23:
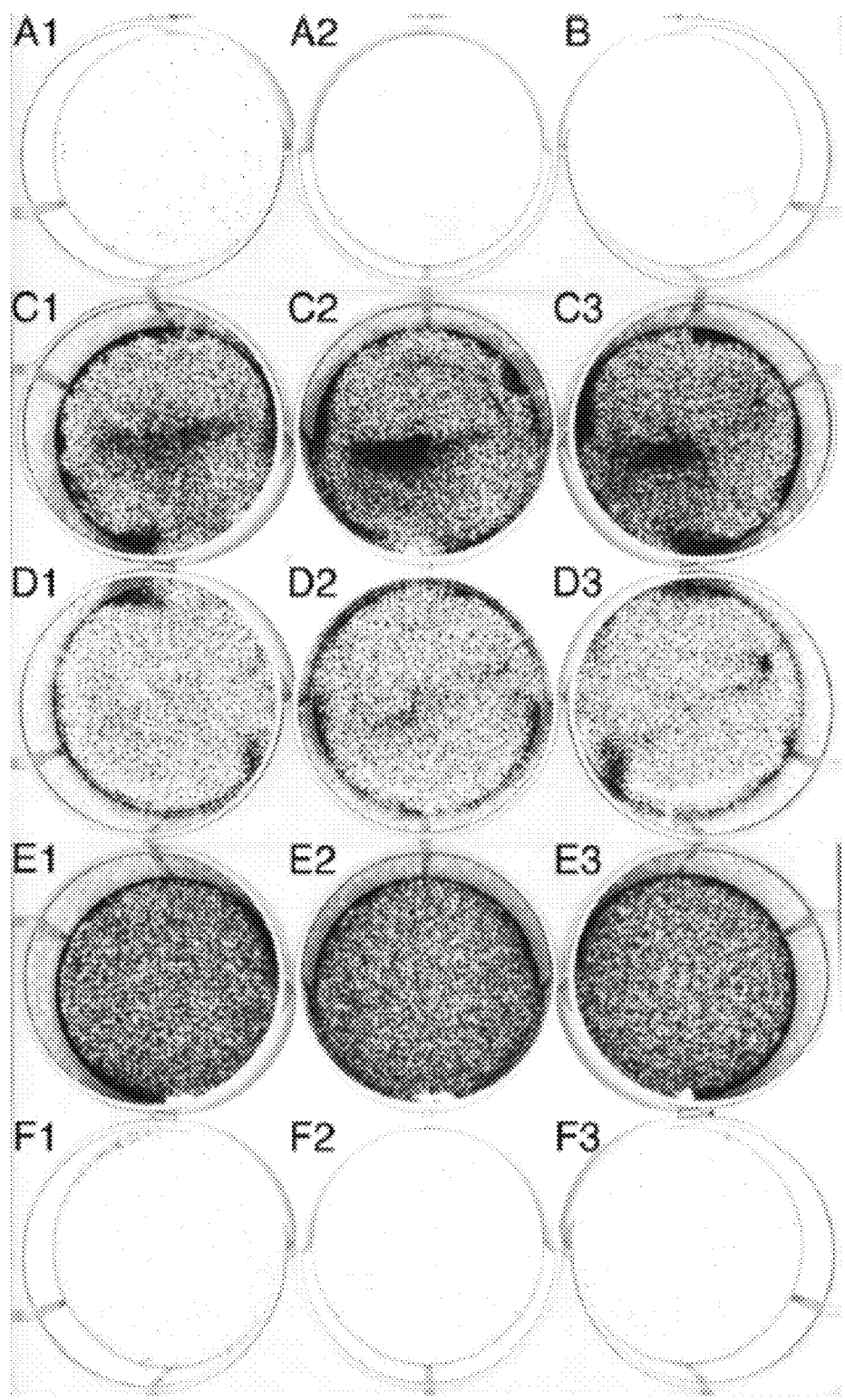
FIG. 23. piggyBac is more tolerant of transcription factor fusions than Sleeping Beauty. Colony formation assays of HCT-116 cells transfected with the specified construct(s), selected with puromycin, and stained with crystal violet. Numbers indicate biological replicates. (A) PB-SRT-Puro (B) Untransfected (no DNA). (C) PB-SRT-Puro and hyperactive piggyBac transposase (HyPBase). (D) PB-SRT-Puro and SP1 fused to hyperactive piggyBac (SP1-HyPBase). (E) SB-SRT-Puro and hyperactive Sleeping Beauty (SB100X). (F) SB-SRT-Puro and SP1 fused to hyperactive Sleeping Beauty 00X).

We analyzed hyperactive piggyBac transposase (HyPBase) data in identical fashion to the standard piggyBac transposase (PBase). Undirected HyPBase showed non-uniform densities of insertions at BRD4-bound loci (FIG. 20A and FIG. 23). At statistically significant peaks, HyPBase showed high reproducibility of normalized insertions between biological replicates ($R_2>0.99$; FIG. 20B). We calculated the mean BRD4 enrichment, as assayed by ChIP-seq (McCleland et al., 2016), over all HyPBase peaks, which showed significantly increased BRD4 signal compared to a permuted control set ($p<10^{-9}$, Kolmogorov-Smirnov test; FIG. 20C). Maximum BRD4 ChIP-seq signal was observed at calling card peak centers and decreased symmetrically in both directions. Furthermore, HyPBase peaks showed striking overlap with ChIP-seq profiles for several histone modifications (Sloan et al., 2016; The ENCODE Project Consortium, 2012), in particular an enrichment for the enhancer-associated acetylated H3K27 and monomethylated H4K4; and depletion for the heterochromatin marks H3K9me3 and H3K27me3 (Lawrence et al., 2016) (FIG. 20D). Finally, HyPBase-derived peaks showed high sensitivity, specificity, and precision for BRD4-bound super-enhancers (SEs; FIG. 20E-FIG. 20F).

Figure 21A:
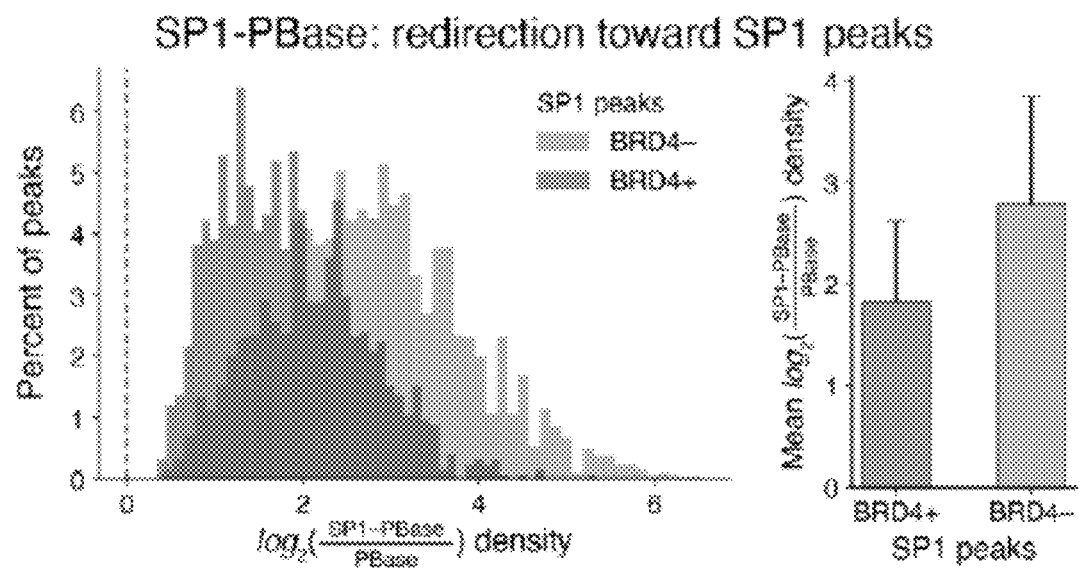
FIG. 21A-FIG. 21D. Redirectability of SP1-piggyBac fusion constructs. (A) Left: distribution of insertion densities at SP1-PBase peaks that either overlap, or do not overlap, BRD4-directed PBase peaks (BRD4+ and BRD4−, respectively) in HCT-116 cells. Right: mean and SD of distributions. (B) Left: distribution of insertion densities at BRD4-directed, PBase peaks that either overlap, or do not overlap, SP1-Pbase peaks (SP1+ and SP1−, respectively). Right: mean and SD of distributions. (C-D) Similar analysis as (A-B) applied to the SP1-HyPBase and HyPBase datasets, respectively. SD: standard deviation.
Figure 21B:
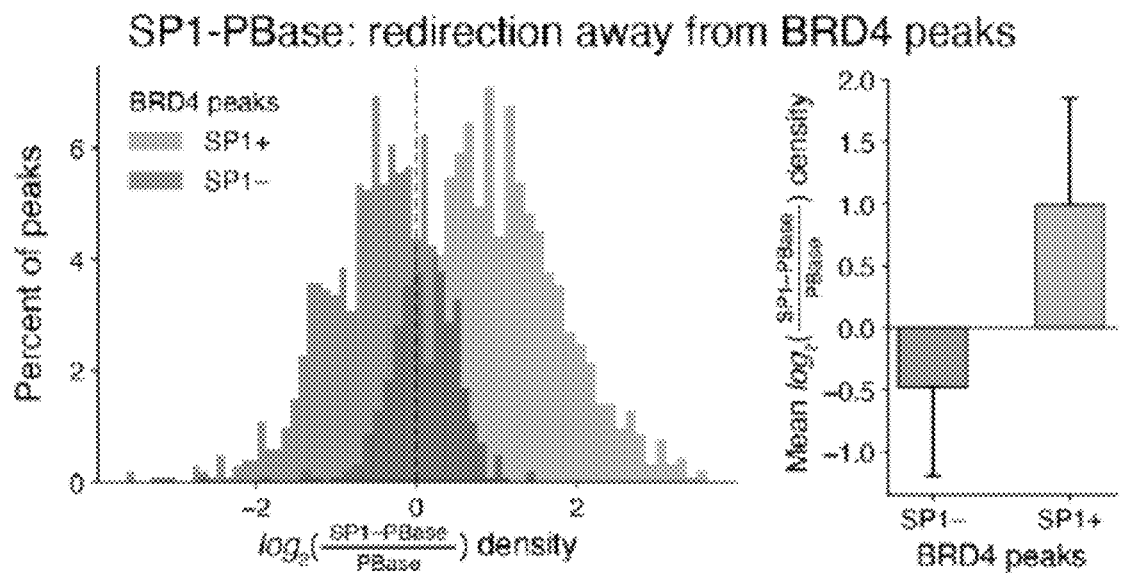
Figure 21C:
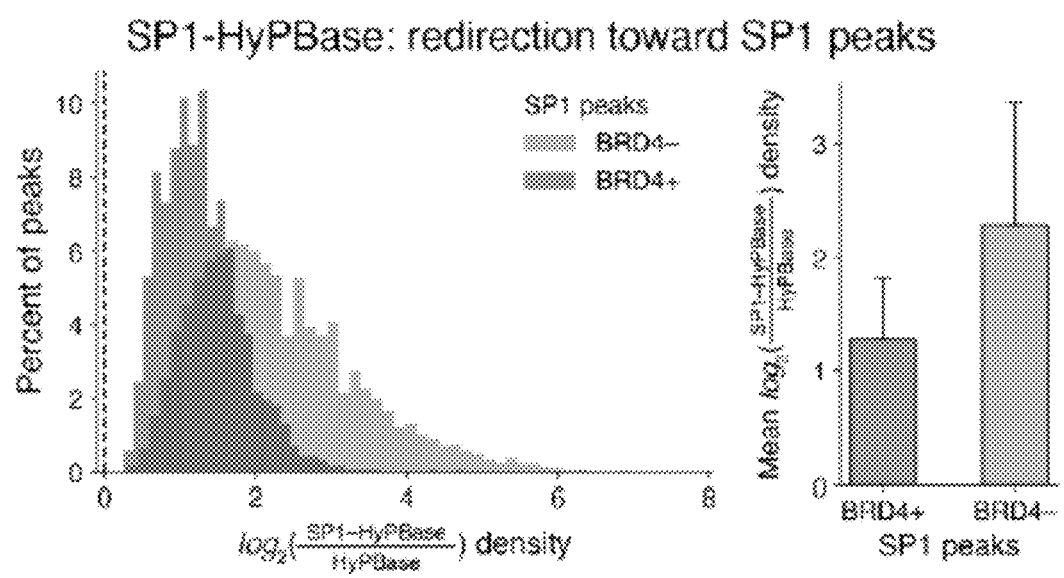
Figure 21D:
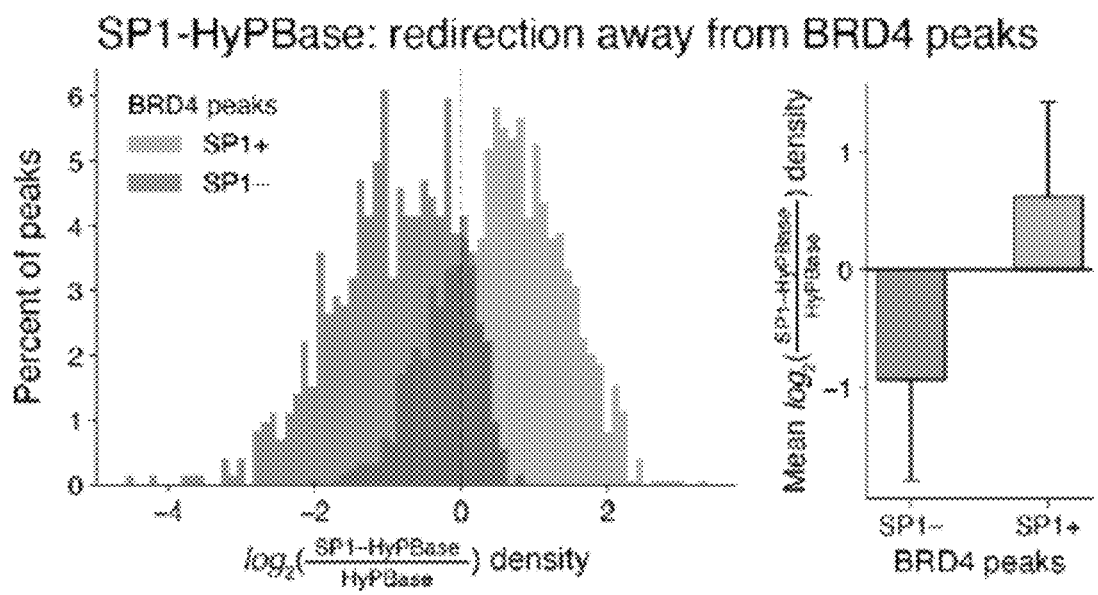
Figure 22:
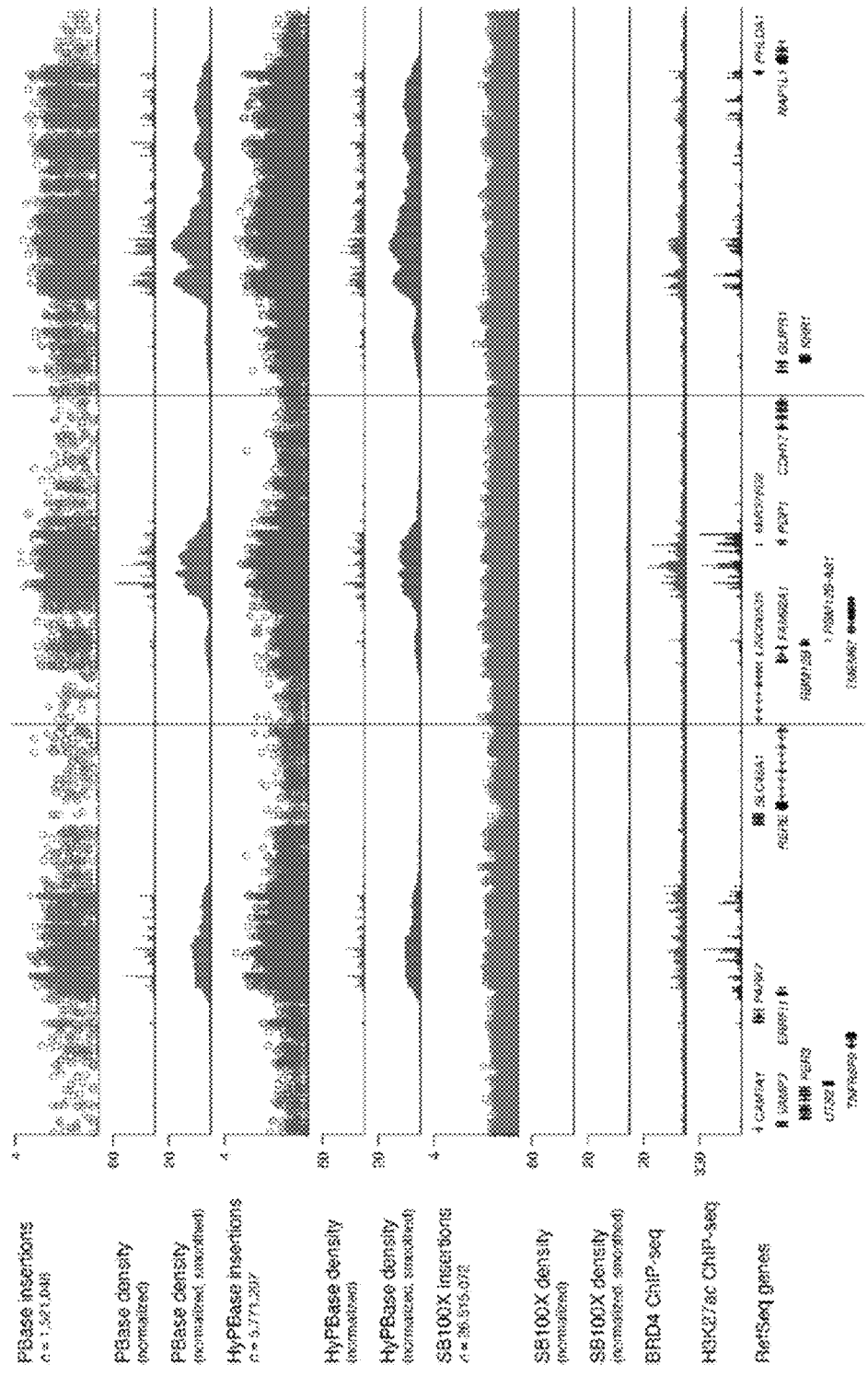
FIG. 22. Examples of BRD4-bound super-enhancers identified by bulk PBase and HyPBase calling cards in HCT-116 cells. Three different loci exhibiting non-uniform densities of piggyBac insertions correlated with BRD4 and H3K27ac ChIP-seq data. Sleeping Beauty insertions at those same loci are more uniformly distributed. Density tracks are shown before and after smoothing.

Redirectability of piggyBac piggyBac's baseline preference for BRD4 raises questions about how efficiently TF-piggyBac fusions can redirect insertions near TF binding sites. We further analyzed the bulk SP1-directed experiments and found that SP1-piggyBac increased insertion density at SP1-bound, BRD4-depleted regions by five- to seven-fold, on average (FIG. 21A and FIG. 21C). We also saw a decrease in insertion density at non-SP1-bound BRD4 peaks on the order of 30 to 50 percent (FIG. 21B and FIG. 21D). This suggests that, while the reduction of signal at BRD4-bound loci may be modest, the redirection to TF binding sites can be quite stark, explaining how TF binding sites can be accurately identified (Wang et al., 2012a). In contrast to piggyBac, Sleeping Beauty has a more uniform background distribution of insertions (FIG. 22), which suggests that the latter transposon system might be even more redirectable and allow us to perform TF-directed calling cards without the need for an undirected transposase control. Unfortunately, direct fusions of TFs to Sleeping Beauty almost completely abolish transposase activity (Wu et al., 2006). We confirmed this in a colony formation assay with SP1 fused to either piggyBac or Sleeping Beauty. The SP1-Sleeping Beauty fusion had virtually undetectable levels of transposition, whereas the SP1-piggyBac construct was still enzymatically functional (FIG. 23). Currently, piggyBac remains the practical choice for mammalian calling cards, but the prospect of a background-free calling card strategy should motivate future research.

Downsampling Analysis

Figures 24A, 24B:
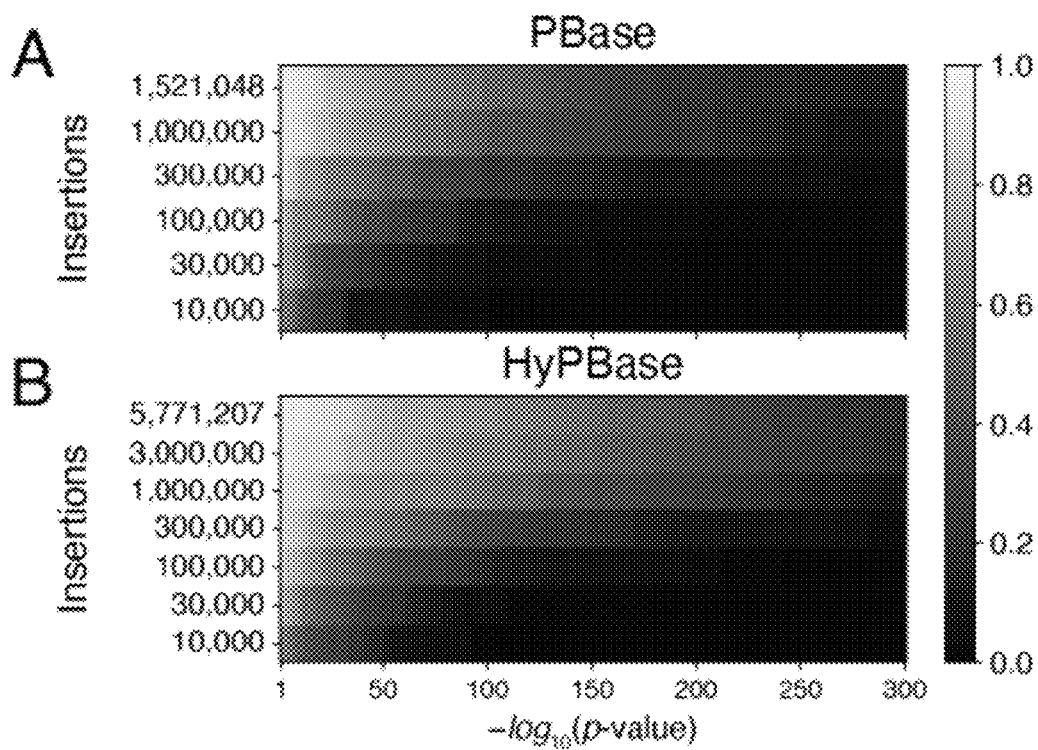
FIG. 24A-FIG. 24F. Downsampling undirected and directed piggyBac insertions simulates assay performance. (A) Downsampling analysis of BRD4-bound SE detection by PBase insertions (in HCT-116 cells) at various p-value thresholds. (B) Downsampling analysis in (A) applied to HyPBase insertions. (C) Linear interpolation applied to (A) to predict SE sensitivity across a range of insertions. (D) Linear interpolation applied to (B). (E) Reproducibility of bulk SP1 calling card peaks at various numbers of HyPBase and SP1-HyPBase insertions, relative to the full dataset (top right corner). (F) Linear interpolation applied to (E) to predict peak reproducibility across a range of experimental and control insertions.

To project how transposon calling cards would scale to single cell experiments, where molecular techniques show broadly reduced sensitivity compared their bulk counterparts, we simulated assay performance under increasingly sparse conditions. We quantified the relationship between SE sensitivity and the number of insertions recovered in undirected calling cards experiments by downsampling the data from the PBase and HyPBase experiments in half-log increments and calculating sensitivity (FIG. 24A-FIG. 24B). These heatmaps show that sensitivity increases with the total number of insertions recovered. Since we cannot predict how many, or few, insertions will be recovered in future experiments, we also performed linear interpolation on the downsampled data.

Figures 24C, 24D:
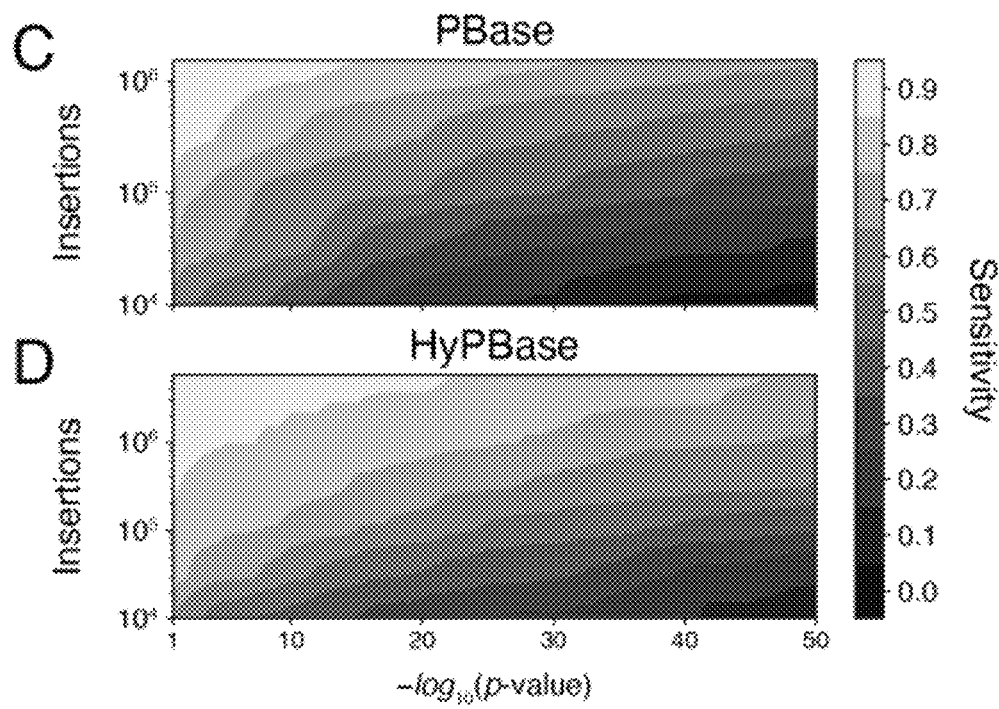
Figure 24E:
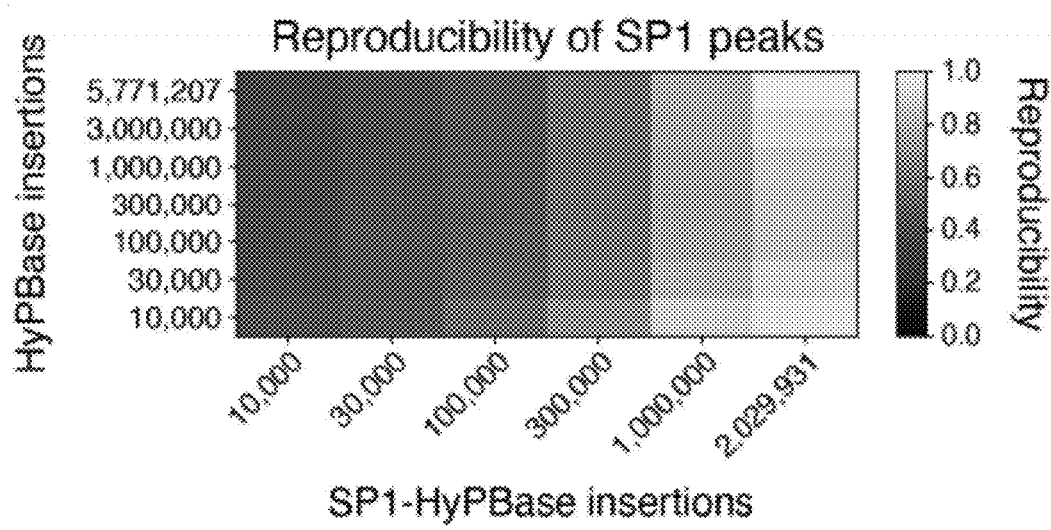
Figure 24F:
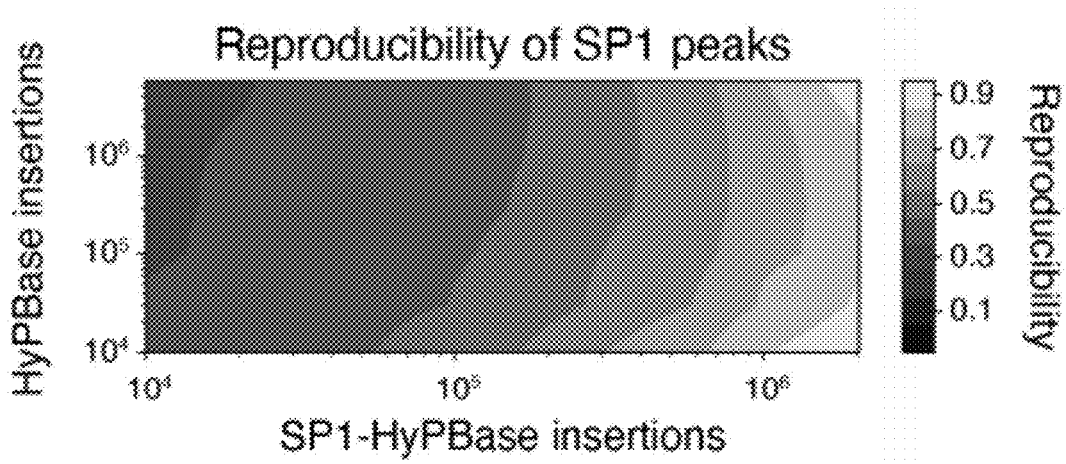

The resulting contour plots (FIG. 24C-FIG. 24D) indicate the approximate sensitivity of BRD4-bound SE detection in HCT-116 cells. Our analysis suggests that even with as few as 10,000 insertions, we can still obtain sensitivities around 50%. Similarly, we investigated the reproducibility of SP1-directed peaks at a various downsampled numbers of insertions, using the peaks obtained from our bulk SP1-HyPBase experiment in HCT-116 cells as our reference set (FIG. 24E-FIG. 24F). We found that peak detection is directly proportional to the number of SP1-directed insertions recovered. At a lower limit of 10,000 insertions in both the experimental and control datasets, there was 40% overlap with peaks called from our bulk dataset. Together, these analyses provide a guide for how well calling cards will perform in the limit of insertion recovery.

Molecular Biology of Single Cell Calling Cards

Single cell calling cards (scCC) uses a modified version of the bulk SRT amplification protocol since the cell barcode and transposon-genome junction may be too far to sequence with short-read technology. To overcome this, we amplify with primers that bind to the universal priming sequence next to the cell barcode and the terminal sequence of the piggyBac TR. These primers are biotinylated and carry a 5' phosphate group (TABLE 4). The PCR products of this amplification are diluted and allowed to circularize overnight. They are then sheared and captured with streptavidin-coated magnetic beads (Methods). The rest of the library is prepared on-bead and involves end repair, A-tailing, and adapter ligation (Methods). A final PCR step adds the required Illumina sequences for high-throughput sequencing (Methods). The standard Illumina read 1 primer sequences the cell barcode and UMI, while a custom read 2 primer, annealing to the end of the piggyBac 5' TR, sequences into the genome. Thus, we collect both the location of a piggyBac insertion as well as its cell of origin. Cells undergo droplet encapsulation and barcoding using the 10× Chromium protocol, with the omission of the template switch oligonucleotide (TSO; Methods) from the RT step. The resulting product is then split in two: one half is used to generate the scRNA-seq library (including adding back the TSO) while the other half undergoes the scCC protocol. After sequencing, the shared cell barcodes between both libraries are used to connect individual insertions to specific cell types.

Single Cell RNA-seq of the Mouse Cortex

Figure 25A:
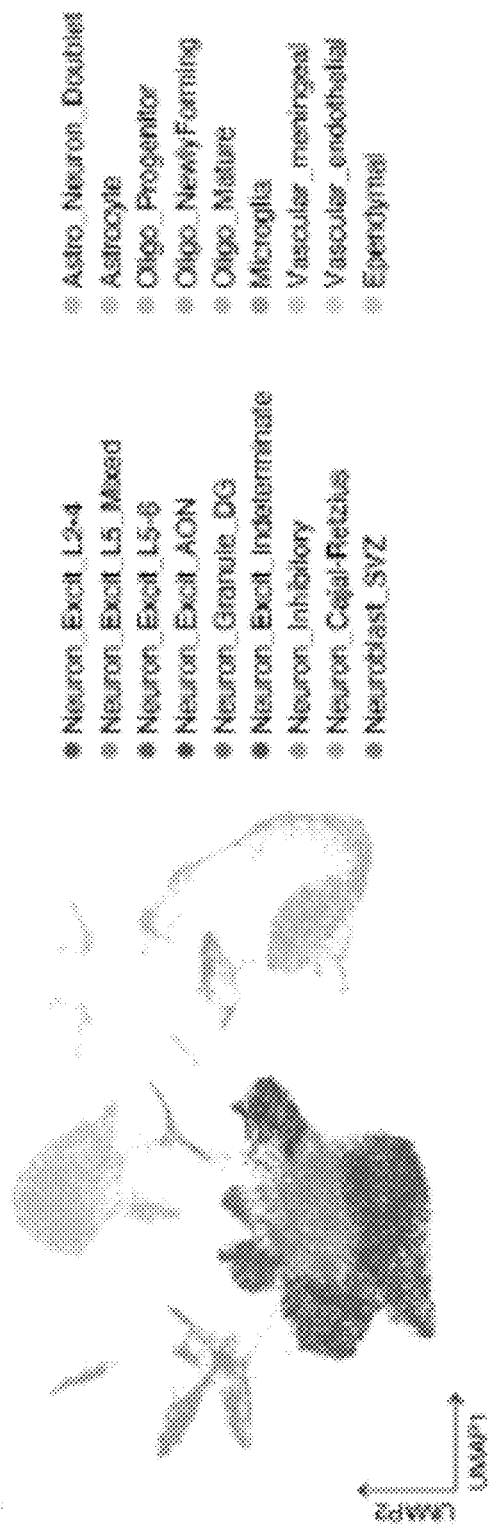
FIG. 25A-FIG. 25B. Clustering of SRT-treated cortical cells and associated marker genes. (A) Two-dimensional UMAP embedding of nine mouse brain (P14-28; 8 cortical, 1 hippocampal) scRNA-seq libraries transduced with AAV9-PB-SRT-tdTomato and AAV9-HyPBase at P0-2. Louvain clustering analysis identified 18 populations. (B) Expression profiles of selected marker genes used to identify individual cell types. Excit: excitatory; oligo: oligodendrocytes; SVZ: sub-ventricular zone; AON: anterior olfactory nucleus; DG: dentate gyrus; L2-4: layer 2-4; L5-6: layer 5-6.
Figure 25B:
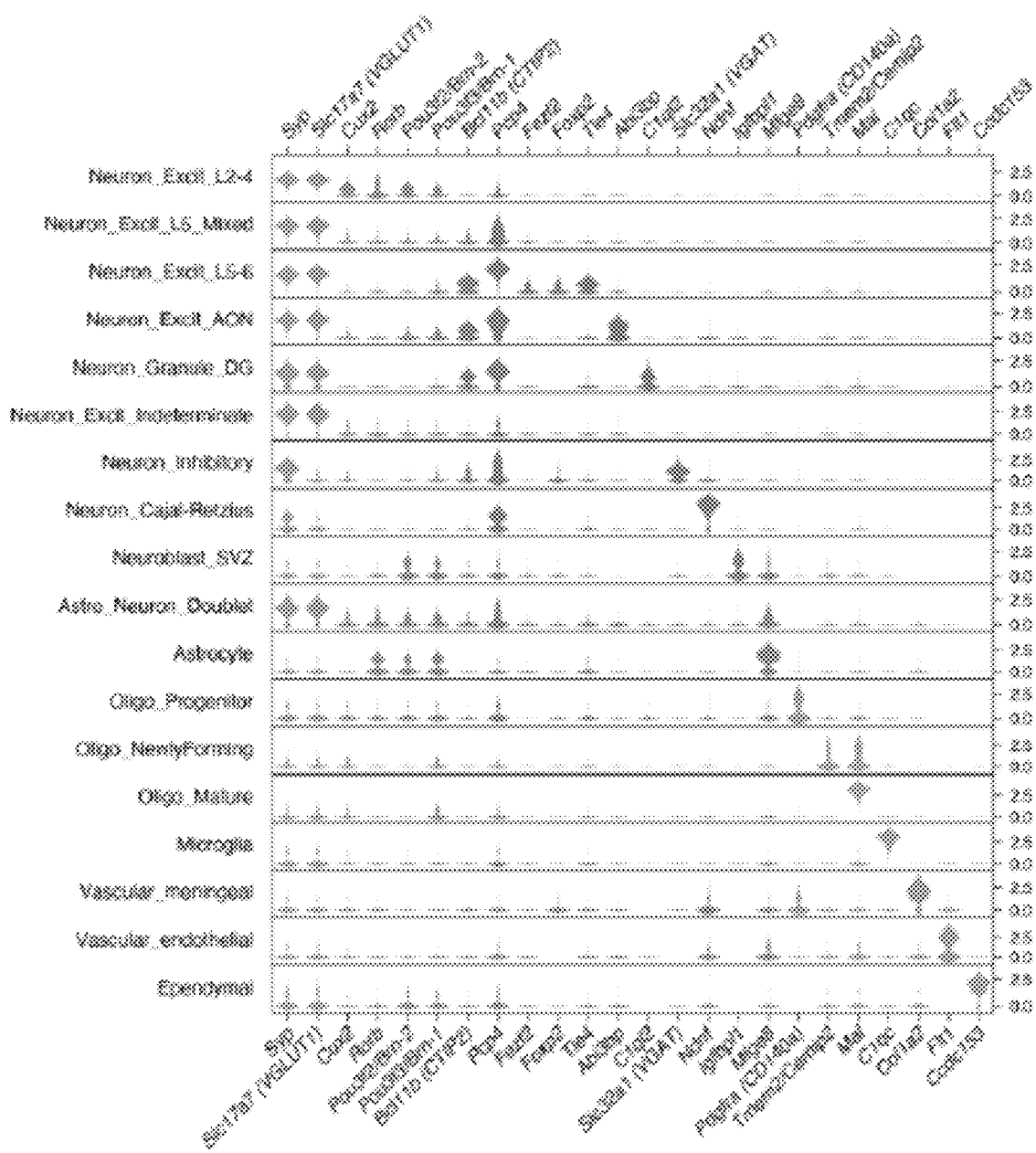

We chose the mouse cortex for our in vivo proof-of-concept because it is a heterogeneous tissue that has been the focus of several recent single cell studies (Rosenberg et al., 2018; Saunders et al., 2018; Tasic et al., 2018; Zeisel et al., 2015, 2018). We collected nine scRNA-seq libraries from P14-P28 mice, encompassing 35,950 cells and 111,382 insertions (TABLE 2). We clustered cells by their mRNA profiles and used established marker genes to classify different cell types (FIG. 25A-FIG. 25B) (Saunders et al., 2018; Tasic et al., 2018; Zeisel et al., 2018). Neurons and astrocytes were the two major cell populations we recovered, which is consistent with the known tropism of AAV9 (Cammack et al., 2020; Schuster et al., 2014), though we also identified a spectrum of differentiating oligodendrocytes and trace amounts of microglial, vascular, and ependymal cells (TABLE 3).

Discussion on SRT Recovery and Polyadenylation Signals

Mapping SRTs using cellular RNA appears to be substantially more efficient than the DNA-based inverse PCR method, but the reasons for this are unclear. Some efficiency is likely gained by eliminating self-ligation, as well as having multiple mRNA copies of each insertion to buffer against PCR artifacts. It is also unknown what fraction of self-reporting transcripts are actually polyadenylated as opposed to merely containing A-rich genomic tracts. Non-genic polyadenylation signals (PASs) prevent anti-sense transcription (Chiu et al., 2018), which suggests that PASs may be more common in the genome than previously appreciated. Targeted 3'-end sequencing (Chen et al., 2017; Zheng et al., 2016) of SRT libraries should help resolve this question, while long-read sequencing of self-reporting transcripts may identify non-canonical PASs.

Discussion on piggyBac's Affinity for BRD4

The natural affinity of piggyBac for BRD4 makes it ideal for studying BRD4-bound SEs, which play important regulatory roles in development and disease (Hnisz et al., 2013; Lovén et al., 2013; Whyte et al., 2013). It is unclear why piggyBac has this predilection. BRD4 has an intrinsically disordered region and cooperative interactions between BRD4 and coactivators like MED1 may mediate the formation of intranuclear condensates (Sabari et al., 2018) at SEs. One hypothesis is that piggyBac has a similarly disordered domain that allows it to preferentially enter condensates and enrich SEs with insertions. If such a domain exists, mutating it may make unfused piggyBac more uniform in its insertion profile, improving its utility for TF-directed calling cards.

Discussion on Designing TF-piggyBac Fusions

Although we exclusively used N-terminal fusions in this study, calling cards can also work with C-terminal fusions (Yen et al., 2018). For viral constructs where space is limited, we have also had success fusing a TF's binding domain to piggyBac (Cammack et al., 2020). In general, multiple fusion strategies should be tested to empirically determine the optimal construct, particularly if the binding domain lies near one of the termini. Finally, some TFs may not bind when fused to piggyBac and thus would not work with calling cards, though in our experience this is uncommon (less than 25% of the time or so).

Supporting Citations

The following references appear in the Supplemental Information: Chen et al., 2017, Chiu et al., 2018, Ivics et al., 1997, Picelli et al., 2014, Sabari et al., 2018, Yen et al., 2004, Zheng et al., 2016.

REFERENCES

S. Ai, H. Xiong, C. C. Li, Y. Luo, Q. Shi, Y. Liu, X. Yu, C. Li, A. He Profiling chromatin states using single-cell itChIP-seq Nat. Cell Biol., 21 (2019), pp. 1164-1172

C. Angermueller, S. J. Clark, H. J. Lee, I. C. Macaulay, M. J. Teng, T. X. Hu, F. Krueger, S. Smallwood, C. P. Ponting, T. Voet, et al. Parallel single-cell sequencing links transcriptional and epigenetic heterogeneity Nat. Methods, 13 (2016), pp. 229-232

D. Avey, S. Sankararaman, A. K. Y. Yim, R. Barve, J. Milbrandt, R. D. Mitra
Single-Cell RNA-Seq Uncovers a Robust Transcriptional Response to Morphine by Glia Cell Rep., 24 (2018), pp. 3619-3629

Y. Benjamini, Y. Hochberg Controlling the False Discovery Rate: A Practical and Powerful Approach to Multiple Testing. J. R. Stat Soc. Ser. B Methodol., 57 (1995), pp. 289-300

M. Brandeis, D. Frank, I. Keshet, Z. Siegfried, M. Mendelsohn, A. Nemes, V. Temper, A. Razin, H. Cedar Sp1 elements protect a CpG island from de novo methylation Nature, 371 (1994), pp. 435-438

E. E. Brooks, N. S. Gray, A. Joly, S. S. Kerwar, R. Lum, R. L. Mackman, T. C. Norman, J. Rosete, M. Rowe, S. R. Schow, et al. CVT-313, a specific and potent inhibitor of CDK2 that prevents neointimal proliferation J. Biol. Chem., 272 (1997), pp. 29207-29211

A. L. Brunner, D. S. Johnson, S. W. Kim, A. Valouev, T. E. Reddy, N. F. Neff, E. Anton, C. Medina, L. Nguyen, E. Chiao, et al. Distinct DNA methylation patterns characterize differentiated human embryonic stem cells and developing human fetal liver Genome Res., 19 (2009), pp. 1044-1056

J. D. Buenrostro, P. G. Giresi, L. C. Zaba, H. Y. Chang, W. J. Greenleaf Transposition of native chromatin for fast and sensitive epigenomic profiling of open chromatin, DNA-binding proteins and nucleosome position Nat. Methods, 10 (2013), pp. 1213-1218

J. D. Buenrostro, B. Wu, U. M. Litzenburger, D. Ruff, M. L. Gonzales, M. P. Snyder, H. Y. Chang, W. J. Greenleaf Single-cell chromatin accessibility reveals principles of regulatory variation Nature, 523 (2015), pp. 486-490

J. Cadiñanos, A. Bradley Generation of an inducible and optimized piggyBac transposon system Nucleic Acids Res., 35 (2007) e87-e87

A. J. Cammack, A. Moudgil, J. Chen, M. J. Vasek, M. Shabsovich, K. McCuHough, A. Yen, T. Lagunas, S. E. Maloney, J. He, et al. A viral toolkit for recording transcription factor-DNA interactions in live mouse tissues Proc. Natl. Acad. Sci. USA, 117 (2020), pp. 10003-10014

A. Campagne, M.-K. Lee, D. Zielinski, A. Michaud, S. Le Corre, F. Dingli, H. Chen, L. Z. Shahidian, I. Vassilev, N. Servant, et al. BAP1 complex promotes transcription by opposing PRC1-mediated H2A ubiquitylation Nat. Commun., 10 (2019), p. 348

J. N. Campbell, E. Z. Macosko, H. Fenselau, T. H. Pers, A. Lyubetskaya, D. Tenen, M. Goldman, A. M. J. Verstegen, J. M. Resch, S. A. McCarroll, et al. A molecular census of arcuate hypothalamus and median eminence cell types Nat. Neurosci., 20 (2017), pp. 484-496

J. Cao, J. S. Packer, V. Ramani, D. A. Cusanovich, C. Huynh, R. Daza, X. Qiu, C. Lee, S. N. Furlan, F. J. Steemers, et al. Comprehensive single-cell transcriptional profiling of a multicellular organism Science, 357 (2017), pp. 661-667

J. Cao, D. A. Cusanovich, V. Ramani, D. Aghamirzaie, H. A. Pliner, A. J. Hill, R. M. Daza, J. L. McFaline-Figueroa, J. S. Packer, L. Christiansen, et al. Joint profiling of chromatin accessibility and gene expression in thousands of single cells Science, 361 (2018), pp. 1380-1385

M. Carbone, H. Yang, H. I. Pass, T. Krausz, J. R. Testa, G. Gaudino BAP1 and cancer Nat. Rev. Cancer, 13 (2013), pp. 153-159

B. Carter, W. L. Ku, J. Y. Kang, G. Hu, J. Perrie, Q. Tang, K. Zhao Mapping histone modifications in low cell number and single cells using antibody-guided chromatin tagmentation (ACT-seq) Nat. Commun., 10 (2019), p. 3747

S. M. Castillo-Hair, J. T. Sexton, B. P. Landry, E. J. Olson, O. A. Igoshin, J. J. Tabor FlowCal: A User-Friendly, Open Source Software Tool for Automatically Converting Flow Cytometry Data from Arbitrary to Calibrated Units ACS Synth. Biol., 5 (2016), pp. 774-780

W. Chen, Q. Jia, Y. Song, H. Fu, G. Wei, T. Ni Alternative Polyadenylation: Methods, Findings, and Impacts Genomics Proteomics Bioinformatics, 15 (2017), pp. 287-300

A. C. Chiu, H. I. Suzuki, X. Wu, D. B. Mahat, A. J. Kriz, P. A. Sharp Transcriptional Pause Sites Delineate Stable Nucleosome-Associated Premature Polyadenylation Suppressed by U1 snRNP Mol. Cell, 69 (2018), pp. 648-663

S. W. Cho, J. Xu, R. Sun, M. R. Mumbach, A. C. Carter, Y. G. Chen, K. E. Yo st, J. Kim, J. He, S. A. Nevins, et al. Promoter of lncRNA Gene PVT1 Is a Tumor-Suppressor DNA Boundary Element Cell, 173 (2018), pp. 1398-1412

S. J. Clark, R. Argelaguet, C.-A. Kapourani, T. M. Stubbs, H. J. Lee, C. Alda-Catelines, F. Krueger, G. Sanguinetti, G. Kelsey, J. C. Marioni, et al. scNMT-seq enables joint profiling of chromatin accessibility DNA methylation and transcription in single cells Nat. Commun., 9 (2018), p. 781

P. Datlinger, A. F. Rendeiro, C. Schmidl, T. Krausgruber, P. Traxler, J. Klu ghammer, L. C. Schuster, A. Kuchler, D. Alper, C. Bock Pooled CRISPR screening with single-cell transcriptome readout Nat. Methods, 14 (2017), pp. 297-301

R. L. Davis, H. Weintraub, A. B. Lassar Expression of a single transfected cDNA converts fibroblasts to myoblasts Cell, 51 (1987), pp. 987-1000

J. E. Delmore, G. C. Issa, M. E. Lemieux, P. B. Rahl, J. Shi, H. M. Jacobs, E. Kastritis, T. Gilpatrick, R. M. Paranal, J. Qi, et al. BET bromodomain inhibition as a therapeutic strategy to target c-Myc Cell, 146 (2011), pp. 904-917

A. Dey, D. Seshasayee, R. Noubade, D. M. French, J. Liu, M. S. Chaurushi ya, D. S. Kirkpatrick, V. C. Pham, J. R. Lill, C. E. Bakalarski, et al. Loss of the tumor suppressor BAP1 causes myeloid transformation Science, 337 (2012), pp. 1541-1546

S. S. Dey, L. Kester, B. Spanjaard, M. Bienko, A. van Oudenaarden Integrated genome and transcriptome sequencing of the same cell Nat. Biotechnol., 33 (2015), pp. 285-289

R. Di Micco, B. Fontanals-Cirera, V. Low, P. Ntziachristos, S. K. Yuen, C. D. Lovell, I. Dolgalev, Y. Yonekubo, G. Zhang, E. Rusinova, et al. Control of embryonic stem cell identity by BRD4-dependent transcriptional elongation of super-enhancer-associated pluripotency genes Cell Rep., 9 (2014), pp. 234-247

S. Ding, X. Wu, G. Li, M. Han, Y. Zhuang, T. Xu Efficient transposition of the piggyBac (PB) transposon in mammalian cells and mice Cell, 122 (2005), pp. 473-483

A. Dixit, O. Parnas, B. Li, J. Chen, C. P. Fulco, L. Jerby-Arnon, N. D. Marjanovic, D. Dionne, T. Burks, R. Raychowdhury, et al. Perturb-Seq: Dissecting Molecular Circuits with Scalable Single-Cell RNA Profiling of Pooled Genetic Screens Cell, 167 (2016), pp. 1853-1866.e17

ENCODE Project Consortium An integrated encyclopedia of DNA elements in the human genome Nature, 489 (2012), pp. 57-74

J. Ernst, P. Kheradpour, T. S. Mikkelsen, N. Shoresh, L. D. Ward, C. B. Epstein, X. Zhang, L. Wang, R. Issner, M. Coyne, et al. Mapping and analysis of chromatin state dynamics in nine human cell types Nature, 473 (2011), pp. 43-49

X. Fan, H.-J. Kim, D. Bouton, M. Warner, J.-Å. Gustafsson Expression of liver X receptor β is essential for formation of superficial cortical layers and migration of later-born neurons Proc. Natl. Acad. Sci. USA, 105 (2008), pp. 13445-13450

P. Filippakopoulos, J. Qi, S. Picaud, Y. Shen, W. B. Smith, O. Fedorov, E. M. Morse, T. Keates, T. T. Hickman, I. Felletar, et al. Selective inhibition of BET bromodomains Nature, 468 (2010), pp. 1067-1073

C. T. Fincher, O. Wurtzel, T. de Hoog, K. M. Kravarik, P. W. Reddien Cell type transcriptome atlas for the planarian Schmidtea mediterranean Science, 360 (2018) eaaq1736-e1757

N. M. E. Fogarty, A. McCarthy, K. E. Snijders, B. E. Powell, N. Kubikova, P. Blakeley, R. Lea, K. Elder, S. E. Wamaitha, D. Kim, et al. Genome editing reveals a role for OCT4 in human embryogenesis Nature, 550 (2017), pp. 67-73

H. Folkerts, A. T. Wierenga, F. A. van den Heuvel, R. R. Woldhuis, D. S. Kluit, J. Jaques, J. J. Schuringa, E. Vellenga Elevated VMP1 expression in acute myeloid leukemia amplifies autophagy and is protective against venetoclax-induced apoptosis Cell Death Dis., 10 (2019), p. 421

M. Fournier, G. Bourriquen, F. C. Lamaze, M. C. Côté, É. Fournier, C. Joly-Beauparlant, V. Caron, S. Gobeil, A. Droit, S. Bilodeau FOXA and master transcription factors recruit Mediator and Cohesin to the core transcriptional regulatory circuitry of cancer cells Sci. Rep., 6 (2016), p. 34962

C. P. Fulco, M. Munschauer, R. Anyoha, G. Munson, S. R. Grossman, E. M. Perez, M. Kane, B. Cleary, E. S. Lander, J. M. Engreitz Systematic mapping of functional enhancer-promoter connections with CRISPR interference Science, 354 (2016), pp. 769-773

M. J. Fullwood, M. H. Liu, Y. F. Pan, J. Liu, H. Xu, Y. B. Mohamed, Y. L. Orlov, S. Velkov, A. Ho, P. H. Mei, et al. An oestrogen-receptor-α-bound human chromatin interactome Nature, 462 (2009), pp. 58-64

V. Garcia-Carpizo, S. Ruiz-Llorente, J. Sarmentero, O. Graña-Castro, D. G. Pisano, M. J. Barrero CREBBP/EP300 bromodomains are critical to sustain the GATA1/MYC regulatory axis in proliferation Epigenetics Chromatin, 11 (2018), p. 30

M. Gasperini, A. J. Hill, J. L. McFaline-Figueroa, B. Martin, S. Kim, M. D. Zhang, D. Jackson, A. Leith, J. Schreiber, W. S. Noble, et al. A Genome-wide Framework for Mapping Gene Regulation via Cellular Genetic Screens Cell, 176 (2019), pp. 377-390

A. Gogol-Ddring, I. Ammar, S. Gupta, M. Bunse, C. Miskey, W. Chen, W. Uckert, T. F. Schulz, Z. Izsvák, Z. Ivics Genome-wide Profiling Reveals Remarkable Parallels Between Insertion Site Selection Properties of the MLV Retrovirus and the piggyBac Transposon in Primary Human CD4(+) T Cells Mol. Ther., 24 (2016), pp. 592-606

N. Gonen, C. R. Futtner, S. Wood, S. A. Garcia-Moreno, I. M. Salamone, S. C. Samson, R. Sekido, F. Poulat, D. M. Maatouk, R. L ovell-Badge Sex reversal following deletion of a single distal enhancer of Sox9 Science, 360 (2018), pp. 1469-1473

F. Greil, C. Moorman, B. van Steensel DamID: Mapping of In Vivo Protein—Genome Interactions Using Tethered DNA Adenine Methyltransferase Methods Enzymol., 410 (2006), pp. 342-359

K. Grosselin, A. Durand, J. Marsolier, A. Poitou, E. Marangoni, F. Nemati, A. Dahmani, S. Lameiras, F. Reyal, O. Frenoy, et al. High-throughput single-cell ChIP-seq identifies heterogeneity of chromatin states in breast cancer Nat. Genet., 51 (2019), pp. 1060-1066

S. Gupta, J. A. Stamatoyannopoulos, T. L. Bailey, W. S. Noble Quantifying similarity between motifs Genome Biol., 8 (2007), p. R24

J. B. Gurdon Cell Fate Determination by Transcription Factors Curr. Top. Dev. Biol., 116 (2016), pp. 445-454

B. P. Hafler, N. Surzenko, K. T. Beier, C. Punzo, J. M. Trimarchi, J. H. Kong, C. L. Cepko Transcription factor Olig2 defines subpopulations of retinal progenitor cells biased toward specific cell fates Proc. Natl. Acad. Sci. USA, 109 (2012), pp. 7882-7887

S. J. Hainer, A. Botkovit, K. N. McCannell, O. J. Rando, T. G. Fazzio Profiling of Pluripotency Factors in Single Cells and Early Embryos Cell, 177 (2019), pp. 1319-1329

X. Han, R. Wang, Y. Zhou, L. Fei, H. Sun, S. Lai, A. Saadatpour, Z. Zhou, H. Chen, F. Ye, et al. Mapping the Mouse Cell Atlas by Microwell-Seq Cell, 172 (2018), pp. 1091-1107

A. Harada, K. Maehara, T. Handa, Y. Arimura, J. Nogami, Y. Hayashi-Takanaka, K. Shirahige, H. Kurumizaka, H. Kimura, Y. Ohkawa A chromatin integration labelling method enables epigenomic profiling with lower input Nat. Cell Biol., 21 (2019), pp. 287-296

A. S. Hinrichs, D. Karolchik, R. Baertsch, G. P. Barber, G. Bejerano, H. Clawson, M. Diekhans, T. S. Furey, R. A. Harte, F. Hsu, et al. The UCSC Genome Browser Database: update 2006 Nucleic Acids Res., 34 (2006), pp. D590-D598

D. Hnisz, B. J. Abraham, T. I. Lee, A. Lau, V. Saint-André, A. A. Sigova, H. A. Hoke, R. A. Young Super-enhancers in the control of cell identity and disease Cell, 155 (2013), pp. 934-947

T. T. Ho, M. R. Warr, E. R. Adelman, O. M. Lansinger, J. Flach, E. V. Verovs kaya, M. E. Figueroa, E. Passegué Autophagy maintains the metabolism and function of young and old stem cells Nature, 543 (2017), pp. 205-210

T. Hothorn, F. Bretz, P. Westfall Simultaneous inference in general parametric models Biom. J., 50 (2008), pp. 346-363

J. D. Hunter Matplotlib: A 2D Graphics Environment Comput. Sci. Eng., 9 (2007), pp. 90-95

B. Hwang, J. H. Lee, D. Bang Single-cell RNA sequencing technologies and bioinformatics pipelines Exp. Mol. Med., 50 (2018), p. 96

Z. Ivics, P. B. Hackett, R. H. Plasterk, Z. Izsvák Molecular reconstruction of Sleeping Beauty, a Tc1-like transposon from fish, and its transposition in human cells Cell, 91 (1997), pp. 501-510

J. Jackman, P. M. O'Connor Methods for Synchronizing Cells at Specific Stages of the Cell Cycle Curr. Protoc. (2001), 10.1002/0471143030.cb0803s00 Published online May 1, 2001

D. S. Johnson, A. Mortazavi, R. M. Myers, B. Wold Genome-wide mapping of in vivo protein-DNA interactions Science, 316 (2007), pp. 1497-1502

R. Kalhor, K. Kalhor, L. Mejia, K. Leeper, A. Graveline, P. Mali, G. M. Church Developmental barcoding of whole mouse via homing CRISPR Science, 361 (2018), p. eaat9804

N. Karaiskos, P. Wahle, J. Alles, A. Boltengagen, S. Ayoub, C. Kipar, C. Kocks, N. Rajewsky, R. P. Zinzen The Drosophila embryo at single-cell transcriptome resolution Science, 358 (2017), pp. 194-199

H. S. Kaya-Okur, S. J. Wu, C. A. Codomo, E. S. Pledger, T. D. Bryson, J. G. Henikoff, K. Ahma d, S. Henikoff CUT&Tag for efficient epigenomic profiling of small samples and single cells Nat. Commun., 10 (2019), p. 1930

C. Kettlun, D. L. Galvan, A. L. George Jr., A. Kaja, M. H. Wilson Manipulating piggyBac transposon chromosomal integration site selection in human cells Mol. Ther., 19 (2011), pp. 1636-1644

N. Kfoury, Z. Qi, M. Wilkinson, L. Broestl, K. Berrett, A. Moudgil, S. Sanka raraman, X. Chen, J. Gertz, R. Mitra, et al. Brd4-bound enhancers drive critical sex differences in glioblastoma bioRxiv (2017), 10.1101/199059

J. Kind, L. Pagie, H. Ortabozkoyun, S. Boyle, S. S. de Vries, H. Janssen, M. Amendola, L. D. Nolen, W. A. Bickmore, B. van Steensel Single-cell dynamics of genome-nuclear lamina interactions Cell, 153 (2013), pp. 178-192

J. Kind, L. Pagie, S. S. de Vries, L. Nahidiazar, S. S. Dey, M. Bienko, Y. Zhan, B. Lajoie, C. A. de Graaf, M. Amendola, et al. Genome-wide maps of nuclear lamina interactions in single human cells Cell, 163 (2015), pp. 134-147

B. Knoechel, J. E. Roderick, K. E. Williamson, J. Zhu, J. G. Lohr, M. J. Cotton, S. M. Gillespie, D. Fernandez, M. Ku, H. Wang, et al. An epigenetic mechanism of resistance to targeted therapy in T cell acute lymphoblastic leukemia Nat. Genet., 46 (2014), pp. 364-370

E. Z. Kvon, O. K. Kamneva, U. S. Melo, I. Barozzi, M. Osterwalder, B. J. Mannion, V. Tissières, C. S. Pickle, I. Plajzer-Frick, E. A. Lee, et al. Progressive Loss of Function in a Limb Enhancer during Snake Evolution Cell, 167 (2016), pp. 633-642

M. A. Lalli, D. Avey, J. D. Dougherty, J. Milbrandt, R. D. Mitra High-throughput single-cell functional elucidation of neurodevelopmental disease-associated genes reveals convergent mechanisms altering neuronal differentiation bioRxiv (2019), 10.1101/862680

M. Lawrence, S. Daujat, R. Schneider Lateral Thinking: How Histone Modifications Regulate Gene Expression Trends Genet., 32 (2016), pp. 42-56

T. I. Lee, R. A. Young Transcriptional regulation and its misregulation in disease Cell, 152 (2013), pp. 1237-1251

C. S. Lee, J. R. Friedman, J. T. Fulmer, K. H. Kaestner The initiation of liver development is dependent on Foxa transcription factors Nature, 435 (2005), pp. 944-947

U. M. Litzenburger, J. D. Buenrostro, B. Wu, Y. Shen, N. C. Sheffield, A. Kathiria, W. J. Greenleaf, H. Y. Chang Single-cell epigenomic variability reveals functional cancer heterogeneity Genome Biol., 18 (2017), p. 15

X. Liu, J. Huang, T. Chen, Y. Wang, S. Xin, J. Li, G. Pei, J. Kang Yamanaka factors critically regulate the developmental signaling network in mouse embryonic stem cells Cell Res., 18 (2008), pp. 1177-1189

J. Lovén, H. A. Hoke, C. Y. Lin, A. Lau, D. A. Orlando, C. R. Vakoc, J. E. Bra dner, T. I. Lee, R. A. Young Selective inhibition of tumor oncogenes by disruption of super-enhancers Cell, 153 (2013), pp. 320-334

I. C. Macaulay, W. Haerty, P. Kumar, Y. I. Li, T. X. Hu, M. J. Teng, M. Goolam, N. Saurat, P. Coupland, L. M. Shirley, et al. G&T-seq: parallel sequencing of single-cell genomes and transcriptomes Nat. Methods, 12 (2015), pp. 519-522

P. Machanick, T. L. Bailey MEME-ChIP: motif analysis of large DNA datasets Bioinformatics, 27 (2011), pp. 1696-1697

D. Macleod, J. Charlton, J. Mullins, A. P. Bird Sp1 sites in the mouse aprt gene promoter are required to prevent methylation of the CpG island Genes Dev., 8 (1994), pp. 2282-2292

E. Z. Macosko, A. Basu, R. Satija, J. Nemesh, K. Shekhar, M. Goldman, I. Tirosh, A. R. Bialas, N. Kamitaki, E. M. Martersteck, et al. Highly Parallel Genome-wide Expression Profiling of Individual Cells Using Nanoliter Droplets Cell, 161 (2015), pp. 1202-1214

M. Martin Cutadapt removes adapter sequences from high-throughput sequencing reads EMBnet. J., 17 (2011), pp. 10-12

A. L. Martins, N. M. Walavalkar, W. D. Anderson, C. Zang, M. J. Guertin Universal correction of enzymatic sequence bias reveals molecular signatures of protein/DNA interactions Nucleic Acids Res., 46 (2018), p. e9

K. A. Matatall, O. A. Agapova, M. D. Onken, L. A. Worley, A. M. Bowcock, J. W. Harbour BAP1 deficiency causes loss of melanocytic cell identity in uveal melanoma BMC Cancer, 13 (2013), p. 371

L. Mátés, M. K. L. Chuah, E. Belay, B. Jarchow, N. Manoj, A. Acosta-Sanchez, D. P. Grzela, A. Schmitt, K. Becker, J. Matrai, et al. Molecular evolution of a novel hyperactive Sleeping Beauty transposase enables robust stable gene transfer in vertebrates Nat. Genet., 41 (2009), pp. 753-761

M. L. McCleland, K. Mesh, E. Lorenzana, V. S. Chopra, E. Segal, C. Watan abe, B. Haley, O. Mayba, M. Yaylaoglu, F. Gnad, R. Firestein CCAT1 is an enhancer-templated RNA that predicts BET sensitivity in colorectal cancer J. Clin. Invest., 126 (2016), pp. 639-652

H. Mi, X. Huang, A. Muruganujan, H. Tang, C. Mills, D. Kang, P. D. Thoma PANTHER version 11: expanded annotation data from Gene Ontology and Reactome pathways, and data analysis tool enhancements Nucleic Acids Res., 45 (D1) (2017), pp. D183-D189

R. Mizuguchi, M. Sugimori, H. Takebayashi, H. Kosako, M. Nagao, S. Yoshida, Y. Nabeshima, K. Shimamura, M. Nakafuku Combinatorial roles of olig2 and neurogenin2 in the coordinated induction of pan-neuronal and subtype-specific properties of motoneurons Neuron, 31 (2001), pp. 757-771

B. J. Molyneaux, P. Arlotta, J. R. L. Menezes, J. D. Macklis Neuronal subtype specification in the cerebral cortex Nat. Rev. Neurosci., 8 (2007), pp. 427-437

Z. Najafova, R. Tirado-Magallanes, M. Subramaniam, T. Hossan, G. Schmidt, S. Nagarajan, S. J. Baumgart, V. K. Mishra, U. Bedi, E. Hesse, et al. BRD4 localization to lineage-specific enhancers is associated with a distinct transcription factor repertoire Nucleic Acids Res., 45 (2017), pp. 127-141

T. E. Oliphant Guide to NumPy Continuum Press (2015)

V. M. Peterson, K. X. Zhang, N. Kumar, J. Wong, L. Li, D. C. Wilson, R. Moore, T. K. McClanahan, S. Sadekova, J. A. Klappenbach Multiplexed quantification of proteins and transcripts in single cells Nat. Biotechnol., 35 (2017), pp. 936-939

S. Philipsen, G. Suske A tale of three fingers: the family of mammalian Sp/XKLF transcription factors Nucleic Acids Res., 27 (1999), pp. 2991-3000

S. Picelli, A. K. Björklund, B. Reinius, S. Sagasser, G. Winberg, R. Sandberg Tn5 transposase and tagmentation procedures for massively scaled sequencing projects Genome Res., 24 (2014), pp. 2033-2040

V. K. C. Ponnaluri, G. Zhang, P.-O. Estève, G. Spracklin, S. Sian, S. Y. Xu, T. Benoukraf, S. Pradhan NicE-seq: high resolution open chromatin profiling Genome Biol., 18 (2017), p. 122

S. Pott, J. D. Lieb What are super-enhancers? Nat. Genet., 47 (2015), pp. 8-12

J. Pucilowska, P. A. Puzerey, J. C. Karlo, R. F. Galán, G. E. Landreth Disrupted ERK signaling during cortical development leads to abnormal progenitor proliferation, neuronal and network excitability and behavior, modeling human neuro-cardio-facial-cutaneous and related syndromes J. Neurosci., 32 (2012), pp. 8663-8677

Z. Qi, M. N. Wilkinson, X. Chen, S. Sankararaman, D. Mayhew, R. D. Mitra An optimized, broadly applicable piggyBac transposon induction system Nucleic Acids Res., 45 (2017), p. e55

A. R. Quinlan, I. M. Hall BEDTools: a flexible suite of utilities for comparing genomic features Bioinformatics, 26 (2010), pp. 841-842

T. Raff, M. van der Giet, D. Endemann, T. Wiederholt, M. Paul Design and testing of β-actin primers for RT-PCR that do not co-amplify processed pseudogenes Biotechniques, 23 (1997), pp. 456-460

F. Ramirez, D. P. Ryan, B. Grüning, V. Bhardwaj, F. Kilpert, A. S. Richter, S. Heyne, F. Dündar, T. Manke deepTools2: a next generation web server for deep-sequencing data analysis Nucleic Acids Res., 44 (W1) (2016), pp. W160-W165

M.-R. Rasin, V.-R. Gazula, J. J. Breunig, K. Y. Kwan, M. B. Johnson, S. Liu-Chen, H.-S. Li, L. Y. Jan, Y.-N. Jan, P. Rakic, N. Sestan Numb and Numbl are required for maintenance of cadherin-based adhesion and polarity of neural progenitors Nat. Neurosci., 10 (2007), pp. 819-827

P. Rathert, M. Roth, T. Neumann, F. Muerdter, J.-S. Roe, M. Muhar, S. Deswal, S. Cerny-Reiterer, B. Peter, J. Jude, et al. Transcriptional plasticity promotes primary and acquired resistance to BET inhibition Nature, 525 (2015), pp. 543-547

T. P. Robitaille, E. J. Tollerud, P. Greenfield, M. Droettboom, E. Bray, T. Aldcroft, M. Davis, A. Ginsburg, A. M. Price-Whelan, W. E. Kerzendorf, et al. Astropy: A community Python package for astronomy Astron. Astrophys., 558 (2013), p. A33

A. E. Rodriguez-Fraticelli, S. L. Wolock, C. S. Weinreb, R. Panero, S. H. Patel, M. Jankovic, J. Sun, R. A. Calogero, A. M. Klein, F. D. Camargo Clonal analysis of lineage fate in native haematopoiesis Nature, 553 (2018), pp. 212-216

K. Rooijers, C. M. Markodimitraki, F. J. Rang, S. S. de Vries, A. Chialastri, K. L. de Luca, D. Mooijman, S. S. Dey, J. Kind Simultaneous quantification of protein-DNA contacts and transcriptomes in single cells Nat. Biotechnol., 37 (2019), pp. 766-772

A. Ropolo, D. Grasso, R. Pardo, M. L. Sacchetti, C. Archange, A. Lo Re, M. Seux, J. Nowak, C. D. Gonzalez, J. L. Iovanna, M. I. Vaccaro The pancreatitis-induced vacuole membrane protein 1 triggers autophagy in mammalian cells J. Biol. Chem., 282 (2007), pp. 37124-37133

A. B. Rosenberg, C. M. Roco, R. A. Muscat, A. Kuchina, P. Sample, Z. Yao, L. T. Graybuck, D. J. Peeler, S. Mukherjee, W. Chen, et al. Single-cell profiling of the developing mouse brain and spinal cord with split-pool barcoding Science, 360 (2018), pp. 176-182

A. Rotem, O. Ram, N. Shoresh, R. A. Sperling, A. Goren, D. A. Weitz, B. E. Bernstein Single-cell ChIP-seq reveals cell subpopulations defined by chromatin state Nat. Biotechnol., 33 (2015), pp. 1165-1172

A. D. Rouillard, G. W. Gundersen, N. F. Fernandez, Z. Wang, C. D. Monteiro, M. G. McDermott, A. Ma'ayan The harmonizome: a collection of processed datasets gathered to serve and mine knowledge about genes and proteins Database (Oxford), 2016 (2016), p. baw100

B. R. Sabari, A. Dall'Agnese, A. Boija, I. A. Klein, E. L. Coffey, K. Shrinivas, B. J. Abraham, N. M. Hannett, A. V. Zamudio, J. C. Manteiga, et al. Coactivator condensation at super-enhancers links phase separation and gene control Science, 361 (2018), p. eaar3958

K. R. Sanson, R. E. Hanna, M. Hegde, K. F. Donovan, C. Strand, M. E. Sullender, E. W. Vaimberg, A. Goodale, D. E. Root, F. Piccioni, J. G. Doench Optimized libraries for CRISPR-Cas9 genetic screens with multiple modalities Nat. Commun., 9 (2018), p. 5416

S. K. Saridey, L. Liu, J. E. Doherty, A. Kaja, D. L. Galvan, B. S. Fletcher, M. H. Wilson PiggyBac transposon-based inducible gene expression in vivo after somatic cell gene transfer Mol. Ther., 17 (2009), pp. 2115-2120

A. Saunders, E. Z. Macosko, A. Wysoker, M. Goldman, F. M. Krienen, H. de Rivera, E. Bien, M. Baum, L. Bortolin, S. Wang, et al. Molecular Diversity and Specializations among the Cells of the Adult Mouse Brain Cell, 174 (2018), pp. 1015-1030

A. Saxena, A. Wagatsuma, Y. Noro, T. Kuji, A. Asaka-Oba, A. Watahiki, C. Gurnot, M. Fagiolini, T. K. Hensch, P. Carninci Trehalose-enhanced isolation of neuronal subtypes from adult mouse brain Biotechniques, 52 (2012), pp. 381-385

J. D. Scargle, J. P. Norris, B. Jackson, J. Chiang Studies in astronomical time series analysis. Vi. Bayesian block representationS Astrophys. J., 764 (2013), p. 167

I. F. Scheiber, R. Dringen Astrocyte functions in the copper homeostasis of the brain Neurochem. Int., 62 (2013), pp. 556-565

D. J. Schuster, J. A. Dykstra, M. S. Riedl, K. F. Kitto, L. R. Belur, R. S. McIvor, R. P. Elde, C. A. Fairbanks, L. Vulchanova Biodistribution of adeno-associated virus serotype 9 (AAV9) vector after intrathecal and intravenous delivery in mouse Front. Neuroanat., 8 (2014), p. 42

S. Sdelci, A. F. Rendeiro, P. Rathert, W. You, J. G. Lin, A. Ringler, G. Hofstätter, H. P. Moll, B. Gürtl, M. Farlik, et al. MTHFD1 interaction with BRD4 links folate metabolism to transcriptional regulation Nat. Genet., 51 (2019), pp. 990-998

S. Seabold, J. Perktold statsmodels: Econometric and statistical modeling with python Proceedings of the 9th Python in Science Conference, Vol. 57, SciPy Society (2010), p. 61

E. Shapiro, T. Biezuner, S. Linnarsson Single-cell sequencing-based technologies will revolutionize whole-organism science Nat. Rev. Genet., 14 (2013), pp. 618-630

E. Shema, B. E. Bernstein, J. D. Buenrostro Single-cell and single-molecule epigenomics to uncover genome regulation at unprecedented resolution Nat. Genet., 51 (2019), pp. 19-25

C. A. Sloan, E. T. Chan, J. M. Davidson, V. S. Malladi, J. S. Strattan, B. C. Hitz, I. Gabdank, A. K. Narayanan, M. Ho, B. T. Lee, et al. ENCODE data at the ENCODE portal Nucleic Acids Res., 44 (D1) (2016), pp. D726-D732

M. Stoeckius, C. Hafemeister, W. Stephenson, B. Houck-Loomis, P. K. Chattopadhyay, H. Swerdlow, R. Satija, P. Smibert Simultaneous epitope and transcriptome measurement in single cells Nat. Methods, 14 (2017), pp. 865-868

M. Stoeckius, S. Zheng, B. Houck-Loomis, S. Hao, B. Z. Yeung, W. M. Mauck 3rd, P. Smibert, R. Satija Cell Hashing with barcoded antibodies enables multiplexing and doublet detection for single cell genomics Genome Biol., 19 (2018), p. 224

H. Stroud, S. C. Su, S. Hrvatin, A. W. Greben, W. Renthal, L. D. Boxer, M. A. Nagy, D. R. Hochbaum, B. Kinde, H. W. Gabel, M. E. Greenberg Early-Life Gene Expression in Neurons Modulates Lasting Epigenetic States Cell, 171 (2017), pp. 1151-1164

J. Sun, A. Ramos, B. Chapman, J. B. Johnnidis, L. Le, Y.-J. Ho, A. Klein, O. Hofmann, F. D. Camargo Clonal dynamics of native haematopoiesis Nature, 514 (2014), pp. 322-327

V. Svensson, R. Vento-Tormo, S. A. Teichmann Exponential scaling of single-cell RNA-seq in the past decade Nat. Protoc., 13 (2018), pp. 599-604

K. Takahashi, S. Yamanaka Induction of pluripotent stem cells from mouse embryonic and adult fibroblast cultures by defined factors Cell, 126 (2006), pp. 663-676

B. Tasic, Z. Yao, L. T. Graybuck, K. A. Smith, T. N. Nguyen, D. Bertagnolli, J. Goldy, E. Garren, M. N. Economo, S. Viswanathan, et al. Shared and distinct transcriptomic cell types across neocortical areas Nature, 563 (2018), pp. 72-78

The Astropy Collaboration, A. M. Price-Whelan, B. M. Sipőcz, H. M. Günther, P. L. Lim, S. M. Crawford, S. Conseil, D. L. Shupe, M. W. Craig, N. Dencheva, et al. The Astropy Project: Building an inclusive, open-science project and status of the v2.0 core package Astron. J., 156 (2018), p. 123

L. T. Vassilev, C. Toyer, S. Chen, D. Knezevic, X. Zhao, H. Sun, D. C. Heimbrook, L. Chen Selective small-molecule inhibitor reveals critical mitotic functions of human CDK1 Proc. Natl. Acad. Sci. USA, 103 (2006), pp. 10660-10665

P. Virtanen, R. Gommers, T. E. Oliphant, M. Haberland, T. Reddy, D. Cournapeau, E. Burovski, P. Peterson, W. Weckesser, J. Bright, et al., SciPy 1.0 Contributors SciPy 1.0: fundamental algorithms for scientific computing in Python Nat. Methods, 17 (2020), pp. 261-272

M. J. Vogel, D. Peric-Hupkes, B. van Steensel Detection of in vivo protein-DNA interactions using DamID in mammalian cells Nat. Protoc., 2 (2007), pp. 1467-1478

H. Wang, M. Johnston, R. D. Mitra Calling cards for DNA-binding proteins Genome Res., 17 (2007), pp. 1202-1209

W. Wang, C. Lin, D. Lu, Z. Ning, T. Cox, D. Melvin, X. Wang, A. Bradley, P. Liu Chromosomal transposition of PiggyBac in mouse embryonic stem cells Proc. Natl. Acad. Sci. USA, 105 (2008), pp. 9290-9295

H. Wang, D. Mayhew, X. Chen, M. Johnston, R. D. Mitra Calling Cards enable multiplexed identification of the genomic targets of DNA-binding proteins Genome Res., 21 (2011), pp. 748-755

H. Wang, D. Mayhew, X. Chen, M. Johnston, R. D. Mitra "Calling cards" for DNA-binding proteins in mammalian cells Genetics, 190 (2012), pp. 941-949

X. Wang, A. Spandidos, H. Wang, B. Seed PrimerBank: a PCR primer database for quantitative gene expression analysis, 2012 update Nucleic Acids Res., 40 (2012), pp. D1144-D1149

Q. Wang, H. Xiong, S. Ai, X. Yu, Y. Liu, J. Zhang, A. He CoBATCH for High-Throughput Single-Cell Epigenomic Profiling Mol. Cell, 76 (2019), pp. 206-216.e7

W. A. Whyte, D. A. Orlando, D. Hnisz, B. J. Abraham, C. Y. Lin, M. H. Kagey, P. B. Rahl, T. I. Lee, R. A. Young Master transcription factors and mediator establish super-enhancers at key cell identity genes Cell, 153 (2013), pp. 307-319

M. H. Wilson, C. J. Coates, A. L. George Jr. PiggyBac transposon-mediated gene transfer in human cells Mol. Ther., 15 (2007), pp. 139-145

F. A. Wolf, P. Angerer, F. J. Theis SCANPY: large-scale single-cell gene expression data analysis Genome Biol., 19 (2018), p. 15

S. C.-Y. Wu, Y.-J. J. Meir, C. J. Coates, A. M. Handler, P. Pelczar, S. Moisyadi, J. M. Kaminski piggyBac is a flexible and highly active transposon as compared to sleeping beauty, Tol2, and Most in mammalian cells Proc. Natl. Acad. Sci. USA, 103 (2006), pp. 15008-15013

S. Xie, J. Duan, B. Li, P. Zhou, G. C. Hon Multiplexed Engineering and Analysis of Combinatorial Enhancer Activity in Single Cells Mol. Cell, 66 (2017), pp. 285-299.e5

L. Yen, J. Svendsen, J.-S. Lee, J. T. Gray, M. Magnier, T. Baba, R. J. D'Amato, R. C. Mulligan Exogenous control of mammalian gene expression through modulation of RNA self-cleavage Nature, 431 (2004), pp. 471-476

M. Yen, Z. Qi, X. Chen, J. A. Cooper, R. D. Mitra, M. D. Onken Transposase mapping identifies the genomic targets of BAP1 in uveal melanoma BMC Med. Genomics, 11 (2018), p. 97

J. Yoshida, K. Akagi, R. Misawa, C. Kokubu, J. Takeda, K. Horie Chromatin states shape insertion profiles of the piggyBac, Tol2 and Sleeping Beauty transposons and murine leukemia virus Sci. Rep., 7 (2017), p. 43613

H. Yu, N. Mashtalir, S. Daou, I. Hammond-Martel, J. Ross, G. Sui, G. W. Hart, F. J. Rauscher 3rd, E. Drobetsky, E. Milot, et al. The ubiquitin carboxyl hydrolase BAP1 forms a ternary complex with YY1 and HCF-1 and is a critical regulator of gene expression Mol. Cell. Biol., 30 (2010), pp. 5071-5085

K. Yusa, L. Zhou, M. A. Li, A. Bradley, N. L. Craig A hyperactive piggyBac transposase for mammalian applications Proc. Natl. Acad. Sci. USA, 108 (2011), pp. 1531-1536

A. Zeisel, A. B. Muñoz-Manchado, S. Codeluppi, P. Lönnerberg, G. La Manno, A. Juréus, S. Marques, H. Munguba, L. He, C. Betsholtz, et al. Brain structure. Cell types in the mouse cortex and hippocampus revealed by single-cell RNA-seq Science, 347 (2015), pp. 1138-1142

A. Zeisel, H. Hochgerner, P. Lönnerberg, A. Johnsson, F. Memic, J. van der Zwan, M. Häring, E. Braun, L. E. Borm, G. La Manno, et al. Molecular Architecture of the Mouse Nervous System Cell, 174 (2018), pp. 999-1014.e22

Y. Zhang, T. Liu, C. A. Meyer, J. Eeckhoute, D. S. Johnson, B. E. Bernstein, C. Nusbaum, R. M. Myers, M. Brown, W. Li, X. S. Liu Model-based analysis of ChIP-Seq (MACS) Genome Biol., 9 (2008), p. R137

Y. Zhang, K. Chen, S. A. Sloan, M. L. Bennett, A. R. Scholze, S. O'Keeffe, H. P. Phatnani, P. Guarnieri, C. Caneda, N. Ruderisch, et al. An RNA-sequencing transcriptome and splicing database of glia, neurons, and vascular cells of the cerebral cortex J. Neurosci., 34 (2014), pp. 11929-11947

D. Zheng, X. Liu, B. Tian 3′READS+, a sensitive and accurate method for 3′ end sequencing of polyadenylated RNA RNA, 22 (2016), pp. 1631-1639

G. X. Y. Zheng, J. M. Terry, P. Belgrader, P. Ryvkin, Z. W. Bent, R. Wilson, S. B. Ziraldo, T. D. Wheeler, G. P. McDermott, J. Zhu, et al. Massively parallel digital transcriptional profiling of single cells Nat. Commun., 8 (2017), p. 14049

X. Zhou, B. Maricque, M. Xie, D. Li, V. Sundaram, E. A. Martin, B. C. Koebe, C. Nielsen, M. Hirst, P. Farnham, et al. The Human Epigenome Browser at Washington University Nat. Methods, 8 (2011), pp. 989-990

X. Zhu, H. Zuo, B. J. Maher, D. R. Serwanski, J. J. LoTurco, Q. R. Lu, A. Nishiyama Olig2-dependent developmental fate switch of NG2 cells Development, 139 (2012), pp. 2299-2307

J. Zuber, J. Shi, E. Wang, A. R. Rappaport, H. Herrmann, E. A. Sison, D. Magoon, J. Qi, K. Blatt, M. Wunderlich, et al. RNAi screen identifies Brd4 as a therapeutic target in acute myeloid leukaemia Nature, 478 (2011), pp. 524-528

What is claimed is:

1. A method of sensitizing cancer cells to a chemotherapeutic agent or treating a subject having cancer cells, the method comprising:
   (i) administering an effective amount of a BET inhibiting agent to a subject or cancer cells, wherein the cancer cells comprise stem-like or CD24high cells regulated by BRD4, wherein the effective amount of the BET inhibiting agent converts the cancer cells into a more chemotherapeutically-sensitive state and reduces an amount of stem-like or CD24high cells, and wherein the BET inhibiting agent is selected from the group consisting of ABBV-075, BAY1238097, BI 894999, BMS-986158, CPI-0610, CPI203, FT-1101, GS-5829, GSK525762, GSK2820151, I-BET, I-BET762, I-BET151, INCB054329, JQ1, OTX015, MK-8628, MS417, PFI-1, PLX51107, RO6870810, RVX2135, TEN-010, and ZEN003694; and
   (ii) administering a chemotherapeutic agent to the cancer cells.

2. The method of claim 1, wherein the cancer cells have a high amount of chemoresistant, stem-like cells prior to administrating the BET inhibiting agent.

3. The method of claim 1, wherein the cancer cells have a greater than or equal amount stem-like or CD24high cells to differentiated or CD24low cells.

4. The method of claim 1, wherein the BET inhibiting agent is administered in an amount effective to decrease a percentage of chemoresistant, stem-like cells and increase a percentage of differentiated, chemosensitive cells.

5. The method of claim 1, wherein the BET inhibiting agent is administered in an amount effective to reduce an amount of chemoresistant, stem-like cells.

6. The method of claim 1, wherein the BET inhibiting agent is administered in an amount effective to sensitize cancer cells to treatment with a chemotherapeutic agent.

7. The method of claim 1, wherein the BET inhibiting agent is administered in an amount effective to increase potency of a chemotherapeutic agent, wherein the chemotherapeutic agent targets a differentiated cell state more efficiently than a stem-like cell state.

8. The method of claim 1, wherein the BET inhibiting agent is administered before the chemotherapeutic agent.

9. The method of claim 1, wherein the BET inhibiting agent and the chemotherapeutic agent are administered simultaneously.

10. The method of claim 1, wherein the BET inhibiting agent is administered after the chemotherapeutic agent.

11. The method of claim 1, wherein the chemotherapeutic agent is imatinib.

12. The method of claim 1, wherein the BET inhibiting agent is JQ1.

13. The method of claim 1, wherein the chemotherapeutic agent is selected from a chemotherapy agent that targets a differentiated cell state more efficiently than a stem-like cell state.

14. The method of claim 1, wherein the cancer cells are leukemia cells.

15. The method of claim 1, wherein the subject or cell is administered the BET inhibiting agent between about 1-10 days prior to being administered a chemotherapeutic agent.

* * * * *

SEQUENCE LISTING

```
<160> NUMBER OF SEQ ID NOS: 51

<210> SEQ ID NO 1
<211> LENGTH: 59
<212> TYPE: DNA
<213> ORGANISM: Artificial Sequence
<220> FEATURE:
<223> OTHER INFORMATION: SMART_dT18VN RT primer for bulk RNA calling
      card recovery
<220> FEATURE:
<221> NAME/KEY: misc_feature
<222> LOCATION: (59)..(59)
<223> OTHER INFORMATION: n is a, c, g, or t

<400> SEQUENCE: 1
aagcagtggt atcaacgcag agtacgtttt tttttttttt tttttttttt tttttttvn      59

<210> SEQ ID NO 2
<211> LENGTH: 23
<212> TYPE: DNA
<213> ORGANISM: Artificial Sequence
<220> FEATURE:
<223> OTHER INFORMATION: SMART primer PCR primer for bulk RNA calling
      card amplification

<400> SEQUENCE: 2
aagcagtggt atcaacgcag agt                                             23

<210> SEQ ID NO 3
<211> LENGTH: 20
<212> TYPE: DNA
<213> ORGANISM: Artificial Sequence
<220> FEATURE:
<223> OTHER INFORMATION: SRT_PAC_F1

<400> SEQUENCE: 3
caacctcccc ttctacgagc                                                 20

<210> SEQ ID NO 4
<211> LENGTH: 28
<212> TYPE: DNA
<213> ORGANISM: Artificial Sequence
<220> FEATURE:
<223> OTHER INFORMATION: SRT_tdTomato_F1
<220> FEATURE:
<221> NAME/KEY: misc_feature
<222> LOCATION: (24)..(24)
<223> OTHER INFORMATION: n is a, c, g, or t

<400> SEQUENCE: 4
tcctgtacgg catggacgag standard                                        28
```

-continued

```
<210> SEQ ID NO 5
<211> LENGTH: 19
<212> TYPE: DNA
<213> ORGANISM: Artificial Sequence
<220> FEATURE:
<223> OTHER INFORMATION: Raff_ACTB_F

<400> SEQUENCE: 5
cctcgccttt gccgatccg                                                   19

<210> SEQ ID NO 6
<211> LENGTH: 29
<212> TYPE: DNA
<213> ORGANISM: Artificial Sequence
<220> FEATURE:
<223> OTHER INFORMATION: Raff_ACTB_R

<400> SEQUENCE: 6
ggatcttcat gaggtagtca gtcaggtcc                                        29

<210> SEQ ID NO 7
<211> LENGTH: 83
<212> TYPE: DNA
<213> ORGANISM: Artificial Sequence
<220> FEATURE:
<223> OTHER INFORMATION: OM-PB-ACG

<400> SEQUENCE: 7
aatgatacgg cgaccaccga gatctacact ctttccctac acgacgctct tccgatctac      60
gtttacgcag actatctttc tag                                              83

<210> SEQ ID NO 8
<211> LENGTH: 83
<212> TYPE: DNA
<213> ORGANISM: Artificial Sequence
<220> FEATURE:
<223> OTHER INFORMATION: OM-PB-CTA

<400> SEQUENCE: 8
aatgatacgg cgaccaccga gatctacact ctttccctac acgacgctct tccgatctct      60
atttacgcag actatctttc tag                                              83

<210> SEQ ID NO 9
<211> LENGTH: 83
<212> TYPE: DNA
<213> ORGANISM: Artificial Sequence
<220> FEATURE:
<223> OTHER INFORMATION: OM-PB-GAT

<400> SEQUENCE: 9
aatgatacgg cgaccaccga gatctacact ctttccctac acgacgctct tccgatctga      60
ttttacgcag actatctttc tag                                              83

<210> SEQ ID NO 10
<211> LENGTH: 83
<212> TYPE: DNA
<213> ORGANISM: Artificial Sequence
<220> FEATURE:
<223> OTHER INFORMATION: OM-PB-TGC

<400> SEQUENCE: 10
aatgatacgg cgaccaccga gatctacact ctttccctac acgacgctct tccgatcttg      60
ctttacgcag actatctttc tag                                              83
```

```
<210> SEQ ID NO 11
<211> LENGTH: 83
<212> TYPE: DNA
<213> ORGANISM: Artificial Sequence
<220> FEATURE:
<223> OTHER INFORMATION: OM-PB-TAG

<400> SEQUENCE: 11
aatgatacgg cgaccaccga gatctacact ctttccctac acgacgctct tccgatctta    60
gtttacgcag actatctttc tag                                            83

<210> SEQ ID NO 12
<211> LENGTH: 83
<212> TYPE: DNA
<213> ORGANISM: Artificial Sequence
<220> FEATURE:
<223> OTHER INFORMATION: OM-PB-ATC

<400> SEQUENCE: 12
aatgatacgg cgaccaccga gatctacact ctttccctac acgacgctct tccgatctat    60
ctttacgcag actatctttc tag                                            83

<210> SEQ ID NO 13
<211> LENGTH: 83
<212> TYPE: DNA
<213> ORGANISM: Artificial Sequence
<220> FEATURE:
<223> OTHER INFORMATION: OM-PB-CGT

<400> SEQUENCE: 13
aatgatacgg cgaccaccga gatctacact ctttccctac acgacgctct tccgatctcg    60
ttttacgcag actatctttc tag                                            83

<210> SEQ ID NO 14
<211> LENGTH: 83
<212> TYPE: DNA
<213> ORGANISM: Artificial Sequence
<220> FEATURE:
<223> OTHER INFORMATION: OM-PB-GCA

<400> SEQUENCE: 14
aatgatacgg cgaccaccga gatctacact ctttccctac acgacgctct tccgatctgc    60
atttacgcag actatctttc tag                                            83

<210> SEQ ID NO 15
<211> LENGTH: 83
<212> TYPE: DNA
<213> ORGANISM: Artificial Sequence
<220> FEATURE:
<223> OTHER INFORMATION: OM-SB-ACG

<400> SEQUENCE: 15
aatgatacgg cgaccaccga acactctttc cctacacgac gctcttccga tctacgtaag    60
tgtatgtaaa cttccgactt caa                                            83

<210> SEQ ID NO 16
<211> LENGTH: 83
<212> TYPE: DNA
<213> ORGANISM: Artificial Sequence
<220> FEATURE:
<223> OTHER INFORMATION: OM-SB-CTA
```

<400> SEQUENCE: 16
aatgatacgg cgaccaccga acactctttc cctacacgac gctcttccga tctctataag    60
tgtatgtaaa cttccgactt caa    83

<210> SEQ ID NO 17
<211> LENGTH: 83
<212> TYPE: DNA
<213> ORGANISM: Artificial Sequence
<220> FEATURE:
<223> OTHER INFORMATION: OM-SB-GAT

<400> SEQUENCE: 17
aatgatacgg cgaccaccga acactctttc cctacacgac gctcttccga tctgattaag    60
tgtatgtaaa cttccgactt caa    83

<210> SEQ ID NO 18
<211> LENGTH: 83
<212> TYPE: DNA
<213> ORGANISM: Artificial Sequence
<220> FEATURE:
<223> OTHER INFORMATION: OM-SB-TGC

<400> SEQUENCE: 18
aatgatacgg cgaccaccga acactctttc cctacacgac gctcttccga tcttgctaag    60
tgtatgtaaa cttccgactt caa    83

<210> SEQ ID NO 19
<211> LENGTH: 83
<212> TYPE: DNA
<213> ORGANISM: Artificial Sequence
<220> FEATURE:
<223> OTHER INFORMATION: OM-SB-TAG

<400> SEQUENCE: 19
aatgatacgg cgaccaccga acactctttc cctacacgac gctcttccga tcttagtaag    60
tgtatgtaaa cttccgactt caa    83

<210> SEQ ID NO 20
<211> LENGTH: 83
<212> TYPE: DNA
<213> ORGANISM: Artificial Sequence
<220> FEATURE:
<223> OTHER INFORMATION: OM-SB-ATC

<400> SEQUENCE: 20
aatgatacgg cgaccaccga acactctttc cctacacgac gctcttccga tctatctaag    60
tgtatgtaaa cttccgactt caa    83

<210> SEQ ID NO 21
<211> LENGTH: 83
<212> TYPE: DNA
<213> ORGANISM: Artificial Sequence
<220> FEATURE:
<223> OTHER INFORMATION: OM-SB-CGT

<400> SEQUENCE: 21
aatgatacgg cgaccaccga acactctttc cctacacgac gctcttccga tctcgttaag    60
tgtatgtaaa cttccgactt caa    83

<210> SEQ ID NO 22
<211> LENGTH: 83
<212> TYPE: DNA
<213> ORGANISM: Artificial Sequence
<220> FEATURE:
<223> OTHER INFORMATION: OM-SB-GCA

<400> SEQUENCE: 22
aatgatacgg cgaccaccga acactctttc cctacacgac gctcttccga tctgcataag    60
tgtatgtaaa cttccgactt caa                                           83

<210> SEQ ID NO 23
<211> LENGTH: 39
<212> TYPE: DNA
<213> ORGANISM: Artificial Sequence
<220> FEATURE:
<223> OTHER INFORMATION: N7 indexed primer

<400> SEQUENCE: 23
caagcagaag acggcatacg agatgtctcg tgggctcgg                           39

<210> SEQ ID NO 24
<211> LENGTH: 27
<212> TYPE: DNA
<213> ORGANISM: Artificial Sequence
<220> FEATURE:
<223> OTHER INFORMATION: 10x_TSO

<400> SEQUENCE: 24
aagcagtggt atcaacgcag agtacat                                       27

<210> SEQ ID NO 25
<211> LENGTH: 32
<212> TYPE: DNA
<213> ORGANISM: Artificial Sequence
<220> FEATURE:
<223> OTHER INFORMATION: Bio_Illumina_Seq1_scCC_10X_3xPT

<400> SEQUENCE: 25
acactctttc ccacacgacg ctcttccgat ct                                 32

<210> SEQ ID NO 26
<211> LENGTH: 29
<212> TYPE: DNA
<213> ORGANISM: Artificial Sequence
<220> FEATURE:
<223> OTHER INFORMATION: Bio_Long_PB_LTR_3xPT

<400> SEQUENCE: 26
gcgtcaattt tacgcagaca tctttctag                                     29

<210> SEQ ID NO 27
<211> LENGTH: 58
<212> TYPE: DNA
<213> ORGANISM: Artificial Sequence
<220> FEATURE:
<223> OTHER INFORMATION: scCC_P5_adapter

<400> SEQUENCE: 27
aatgatacgg cgaccaccga gatcttcact cattccacac gactccttgc cagtctct     58

<210> SEQ ID NO 28
<211> LENGTH: 57
<212> TYPE: DNA
<213> ORGANISM: Artificial Sequence

```
<220> FEATURE:
<223> OTHER INFORMATION: scCC_P7_adapter

<400> SEQUENCE: 28
gagactggca agtacacgtc gcactcacca tgaatctcgt atgccgtctt ctgcttg      57

<210> SEQ ID NO 29
<211> LENGTH: 24
<212> TYPE: DNA
<213> ORGANISM: Artificial Sequence
<220> FEATURE:
<223> OTHER INFORMATION: scCC_P5_primer

<400> SEQUENCE: 29
aatgatacgg cgaccaccga gatc                                          24

<210> SEQ ID NO 30
<211> LENGTH: 24
<212> TYPE: DNA
<213> ORGANISM: Artificial Sequence
<220> FEATURE:
<223> OTHER INFORMATION: scCC_P7_primer

<400> SEQUENCE: 30
caagcagaag acggcatacg agat                                          24

<210> SEQ ID NO 31
<211> LENGTH: 48
<212> TYPE: DNA
<213> ORGANISM: Artificial Sequence
<220> FEATURE:
<223> OTHER INFORMATION: scCC_PB_CustomRead2

<400> SEQUENCE: 31
cgtgtaggga aagagtgtgc gtcaatttta cgcagactat ctttctag                48

<210> SEQ ID NO 32
<211> LENGTH: 33
<212> TYPE: DNA
<213> ORGANISM: Artificial Sequence
<220> FEATURE:
<223> OTHER INFORMATION: scCC_CustomIndex1

<400> SEQUENCE: 32
gagactggca agtacacgtc gcactcacca tga                                33

<210> SEQ ID NO 33
<211> LENGTH: 21
<212> TYPE: DNA
<213> ORGANISM: Artificial Sequence
<220> FEATURE:
<223> OTHER INFORMATION: ACTB_PrimerBank_F

<400> SEQUENCE: 33
catgtacgtt gctatccagg c                                             21

<210> SEQ ID NO 34
<211> LENGTH: 21
<212> TYPE: DNA
<213> ORGANISM: Artificial Sequence
<220> FEATURE:
<223> OTHER INFORMATION: ACTB_PrimerBank_R

<400> SEQUENCE: 34
ctccttaatg tcacgcacga t                                             21
```

<210> SEQ ID NO 35
<211> LENGTH: 23
<212> TYPE: DNA
<213> ORGANISM: Artificial Sequence
<220> FEATURE:
<223> OTHER INFORMATION: CD24_PrimerBank_F

<400> SEQUENCE: 35 ctcctacccca cgcagattta ttc                                    23

<210> SEQ ID NO 36
<211> LENGTH: 21
<212> TYPE: DNA
<213> ORGANISM: Artificial Sequence
<220> FEATURE:
<223> OTHER INFORMATION: CD24_PrimerBank_F

<400> SEQUENCE: 36
agagtgagac cacgaagaga c                                       21

<210> SEQ ID NO 37
<211> LENGTH: 21
<212> TYPE: DNA
<213> ORGANISM: Artificial Sequence
<220> FEATURE:
<223> OTHER INFORMATION: MYC_PrimerBank_F

<400> SEQUENCE: 37
gtcaagaggc gaacacacaa c                                       21

<210> SEQ ID NO 38
<211> LENGTH: 21
<212> TYPE: DNA
<213> ORGANISM: Artificial Sequence
<220> FEATURE:
<223> OTHER INFORMATION: MYC_PrimerBank_R

<400> SEQUENCE: 38
ttggacggac aggatgtatg c                                       21

<210> SEQ ID NO 39
<211> LENGTH: 21
<212> TYPE: DNA
<213> ORGANISM: Artificial Sequence
<220> FEATURE:
<223> OTHER INFORMATION: BRD2_PrimerBank_F

<400> SEQUENCE: 39
aatggcacaa acgctggaaa a                                       21

<210> SEQ ID NO 40
<211> LENGTH: 19
<212> TYPE: DNA
<213> ORGANISM: Artificial Sequence
<220> FEATURE:
<223> OTHER INFORMATION: BRD2_PrimerBank_R

<400> SEQUENCE: 40
cactggtaac actgccctg                                          19

<210> SEQ ID NO 41
<211> LENGTH: 21
<212> TYPE: DNA
<213> ORGANISM: Artificial Sequence
<220> FEATURE:
<223> OTHER INFORMATION: BRD3_PrimerBank_F

```
<400> SEQUENCE: 41
tgcaagcgaa tgtatgcagg a                                              21

<210> SEQ ID NO 42
<211> LENGTH: 23
<212> TYPE: DNA
<213> ORGANISM: Artificial Sequence
<220> FEATURE:
<223> OTHER INFORMATION: BRD3_PrimerBank_R

<400> SEQUENCE: 42
catctgggcc acttttttgta gaa                                           23

<210> SEQ ID NO 43
<211> LENGTH: 21
<212> TYPE: DNA
<213> ORGANISM: Artificial Sequence
<220> FEATURE:
<223> OTHER INFORMATION: BRD4_PrimerBank_F

<400> SEQUENCE: 43
gagctaccca cagaagaaac c                                              21

<210> SEQ ID NO 44
<211> LENGTH: 22
<212> TYPE: DNA
<213> ORGANISM: Artificial Sequence
<220> FEATURE:
<223> OTHER INFORMATION: BRD4_PrimerBank_R

<400> SEQUENCE: 44
gagtcgatgc ttgagttgtg tt                                             22

<210> SEQ ID NO 45
<211> LENGTH: 20
<212> TYPE: DNA
<213> ORGANISM: Artificial Sequence
<220> FEATURE:
<223> OTHER INFORMATION: BRD4 CRISPRi gRNA

<400> SEQUENCE: 45
gcggctgccg gcggtgcccg                                                20

<210> SEQ ID NO 46
<211> LENGTH: 20
<212> TYPE: DNA
<213> ORGANISM: Artificial Sequence
<220> FEATURE:
<223> OTHER INFORMATION: NT CRISPRi gRNA

<400> SEQUENCE: 46
ggaggcgagg taagacgcgg                                                20

<210> SEQ ID NO 47
<211> LENGTH: 17
<212> TYPE: DNA
<213> ORGANISM: Artificial Sequence
<220> FEATURE:
<223> OTHER INFORMATION: Calling card sequence

<400> SEQUENCE: 47
atcacttaag ccggtac                                                   17
```

```
<210> SEQ ID NO 48
<211> LENGTH: 36
<212> TYPE: DNA
<213> ORGANISM: Artificial Sequence
<220> FEATURE:
<223> OTHER INFORMATION: Calling Card Sequence

<400> SEQUENCE: 48
gcgtcaattt tacgcagact atctttctag ggttaa                            36

<210> SEQ ID NO 49
<211> LENGTH: 32
<212> TYPE: DNA
<213> ORGANISM: Artificial Sequence
<220> FEATURE:
<223> OTHER INFORMATION: Calling Card Sequence

<400> SEQUENCE: 49
taagtgtatg taaacttccg acttcaactg ta                                32

<210> SEQ ID NO 50
<211> LENGTH: 58
<212> TYPE: DNA
<213> ORGANISM: Artificial Sequence
<220> FEATURE:
<223> OTHER INFORMATION: Calling Card Sequence

<400> SEQUENCE: 50
ctgtctctta tacacatctc cgagcccacg agacttctcg tatgccgtct tctgcttg    58

<210> SEQ ID NO 51
<211> LENGTH: 67
<212> TYPE: DNA
<213> ORGANISM: Artificial Sequence
<220> FEATURE:
<223> OTHER INFORMATION: Calling Card Sequence
<220> FEATURE:
<221> NAME/KEY: misc_feature
<222> LOCATION: (35)..(43)
<223> OTHER INFORMATION: n is a, c, g, or t

<400> SEQUENCE: 51
agagactggc aagtacacgt cgcactcacc atgannnnnn nnnatctcgt atgccgtctt  60
ctgcttg                                                           67
```